United States Patent
Nordkild et al.

(10) Patent No.: US 9,353,172 B2
(45) Date of Patent: May 31, 2016

(54) LONG ACTING BIOLOGICALLY ACTIVE LUTEINIZING HORMONE (LH) COMPOUND

(75) Inventors: Peter Nordkild, Gentofte (DK); Svend Lindenberg, Skodsborg (DK); Claus Yding Andersen, Hellerup (DK); Kim Vilbour Andersen, Brønshøj (DK)

(73) Assignee: ARTS BIOLOGICS A/S, Copenhagen ( * ) Notice: Subject to any disclaimer, the term of this patent is extended or adjusted under 35 U.S.C. 154(b) by 0 days.

(21) Appl. No.: 14/233,455

(22) PCT Filed: Jul. 9, 2012

(86) PCT No.: PCT/EP2012/063373
§ 371 (c)(1),
(2), (4) Date: Apr. 25, 2014

(87) PCT Pub. No.: WO2013/010840
PCT Pub. Date: Jan. 24, 2013

(65) Prior Publication Data
US 2014/0228292 A1    Aug. 14, 2014

Related U.S. Application Data

(60) Provisional application No. 61/639,268, filed on Apr. 27, 2012.

(30) Foreign Application Priority Data

Jul. 18, 2011 (EP) .................. 11174423
Aug. 30, 2011 (EP) .................. 11179410
Dec. 7, 2011 (DK) .................. 2011 70678

(51) Int. Cl.
*A61K 38/24* (2006.01)
*A61K 47/48* (2006.01)
*C07K 14/59* (2006.01)
*C07K 14/76* (2006.01)

(52) U.S. Cl.
CPC .............. *C07K 14/59* (2013.01); *A61K 38/24* (2013.01); *A61K 47/483* (2013.01); *A61K 47/48215* (2013.01); *A61K 47/48284* (2013.01); *A61K 47/48369* (2013.01); *C07K 14/76* (2013.01); *C07K 2319/31* (2013.01)

(58) Field of Classification Search
None
See application file for complete search history.

(56) References Cited

U.S. PATENT DOCUMENTS

| 4,179,337 | A | 12/1979 | Davis |
| 5,929,028 | A | 7/1999 | Skrabanja et al. |
| 2004/0126838 | A1 | 7/2004 | DeFrees |
| 2004/0248784 | A1 | 12/2004 | Filori |
| 2008/0108571 | A1 | 5/2008 | Filicori |
| 2009/0105140 | A1* | 4/2009 | Rosen et al. .................. 514/12 |
| 2010/0291079 | A1* | 11/2010 | Low .................. 424/134.1 |

FOREIGN PATENT DOCUMENTS

| WO | 9009800 A | 9/1990 |
| WO | 0067778 A | 11/2000 |
| WO | 0158493 A | 8/2001 |
| WO | 0179480 A | 10/2001 |
| WO | WO 01/79443 | * 10/2001 |
| WO | 03022302 A | 3/2003 |
| WO | 03022303 A | 3/2003 |
| WO | 03103770 A | 12/2003 |
| WO | 2005073383 A | 11/2005 |
| WO | 2009095479 A | 8/2009 |
| WO | 2010092135 A | 10/2010 |

OTHER PUBLICATIONS

Related PCT appln. No. PCT/EP2012/063373, 3rd Party Observation dated Jun. 9, 2015.
Related PCT appln. No. PCT/EP2012/063373, IPRP, dated Oct. 8, 2013.
Related PCT appln. No. PCT/EP2012/063373, Response to Written Opinion, dated May 27, 2013.
Related PCT appln. No. PCT/EP2012/063373, International Search Report and Written Opinion, dated Feb. 27, 2013.
Related EP Appln. No. EP 11 17 9410, European Search Report dated Jan. 5, 2012.
Glasier AF, Wickings EJ, Rodger, MW, Hillier, SG and Baird, DT; J Æ Endocrinology.1988; 119 A-159.
Schenker, J.G, Yarkoni, S, and Granat, M. Multiple pregnancies following induction of ovulation. Fertil Steril. 1981; 35: 105-123.
Al-Inany HG, Abou-Setta AM, Aboulghar MA, Mansour RT, Serour GI. Efficacy and safety of human menopausal gonadotrophins versus recombinant FSH: a meta-analysis. Reprod Biomed Online. 2008; 16: 81-8.
Al-Inany HG, Abou-Setta AM, Aboulghar MA, Mansour RT, Serour GI. Highly purified hMG achieves better pregnancy rates in IVF cycles but not ICSI cycles compared with recombinant FSH: a meta-analysis. Gynecol Endocrinol. 2009; 25:6, 372-8.
Amoss M S Jr, Monahan MW and Verlander MS "A Long-acting Polymer Coupled Luteinizing Hormone Releasing Factor Analogue", J Clin. Endocrin. and Metab., 1974; 1:187-190.

(Continued)

*Primary Examiner* — Christina Borgeest
(74) *Attorney, Agent, or Firm* — Cheryl H. Agris; Agris & von Natzmer, LLP

(57) ABSTRACT

The present invention relates to a long acting biologically active luteinizing hormone (LH) compound comprising an LH agonist linked to a pharmaceutically acceptable molecule providing an in vivo plasma half-life of the LH agonist or LH compound which is increased substantially compared to the in vivo plasma half-life of an LH agonist administered in the same manner as the LH compound. The present invention relates to methods for controlled ovarian stimulation which can be used in conjunction with assisted reproduction technologies such as in vitro fertilization, intra cytoplasmatic sperm injection, intra uterine insemination and in vitro maturation. In other aspects the invention relates to methods for inducing folliculogenesis and methods for providing luteal support for the corpora lutea.

5 Claims, 50 Drawing Sheets

(56) References Cited

OTHER PUBLICATIONS

Figure 1A:
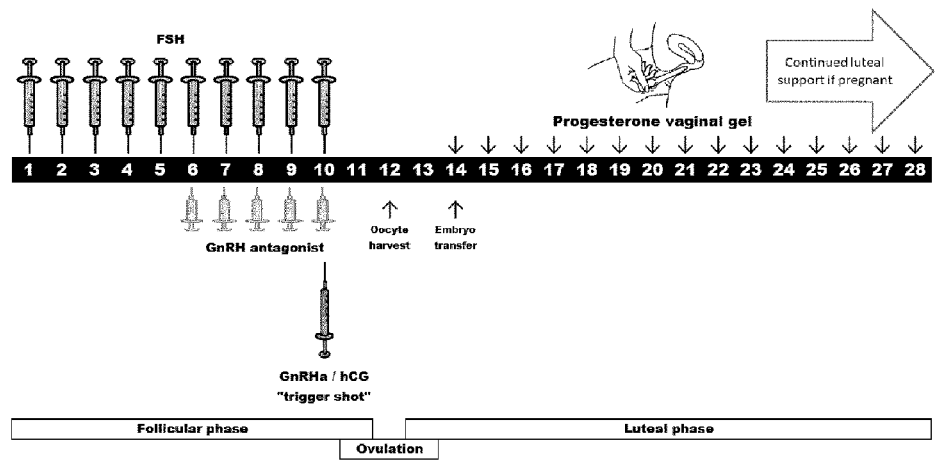

Barrios-De-Tomasi J, Timossi C, Merchant H, Quintanar A, Avalos JM, Andersen CY, Ulloa-Aguirre A. Assessment of the in vitro and in vivo biological activities of the human follicle-stimulating isohormones. Mol Cell Endocrinol. 2002; 186:189-98.

Blockeel C, De Vos M, Verpoest W, Stoop D, Haentjens P, Devroey P. Can 200 IU of hCG replace recombinant FSH in the late follicular phase in a GnRH-antagonist cycle? A pilot study. Hum Reprod. 2009; 24: 2910-6.

Boime I, Keene J, Galway AB, Fares FM, LaPolt P, Hsueh AJW. Expression of Recombinant Human FSH, LH, and CG in Mammalian Cells: A Structure-Function Model for Therapeutic Drug Design. Seminars in Repro. Endocrinol. 1992; 10: 45-50.

Burgon PG, Stanton PG, Robertson DM. In vivo bioactivities and clearance patterns of highly purified human luteinizing hormone isoforms. Endocrinology. 1996; 137: 4827-36.

Buvat J, Buvat-Herbaut M, Marcolin G, Dehaene JL, Verbecq P, Renouard O. Purified follicle-stimulating hormone in polycystic ovary syndrome: slow administration is safer and more effective. Fertil Steril. 1989; 52: 553-9.

Campbell BK, Dobson H, Baird DT, Scaramuzzi RJ. Examination of the relative role of FSH and LH in the mechanism of ovulatory follicle selection in sheep. J Reprod Fertil. 1999; 117: 355-67.

Casarini L, La Marca A, Lispi M, Longobardi S, Pignatti E, Simoni M. Non-equivalence of LH and hCG: an in vitro study. Abstracts of the 27th Annual Meeting of ESHRE, Stockholm, Sweden, Jul. 3-Jul. 6, 2011, Abstract No. P-312.

Couzinet B, Lestrat N, Brailly S, Forest M, Schaison G. Stimulation of ovarian follicular maturation with pure follicle-stimulating hormone in women with gonadotropin deficiency. J Clin Endocrinol Metab. 1988; 66: 552-6.

Devroey P, van Steirteghem A, Mannaerts B, Bennink HC. Successful in-vitro fertilisation and embryo transfer after treatment with recombinant human FSH. Lancet. 1992; 339:1170.

Dickinson RE, Stewart AJ, Myers M, Millar RP, Duncan WC. Differential expression and functional characterization of luteinizing hormone receptor splice variants in human luteal cells: implications for luteolysis. Endocrinology. 2009;150:2873-81.

Filicori M, Cognigni GE, Taraborrelli S, Spettoli D, Ciampaglia W, Tabarelli C, de Fatis CT, and P. Pocognoli, C. Luteinizing Hormone Activity Supplementation Enhances Follicle-Stimulating Hormone Efficacy and Improves Ovulation Induction Outcome J. Clin. Endocrinol. & Metabol. 1999; 84: 2659-2663.

Filicori M, Cognigni GE, Taraborrelli S, Spettoli D, Ciampaglia W, de Fatis CT. Low-dose human chorionic gonadotropin therapy can improve sensitivity to exogenous follicle-stimulating hormone in patients with secondary amenorrhea. Fertil Steril. 1999; 72: 1118-20.

Filicori M, Cognigni GE, Pocognoli P, Tabarelli C, Spettoli D, Taraborrelli S, Ciampaglia W. Modulation of folliculogenesis and steroidogenesis in women by graded menotrophin administration. Hum Reprod. 2002; 17: 2009-15.

Filicori M. Use of luteinizing hormone in the treatment of infertility: time for reassessment? Fertil Steril. 2003; 79: 253-5.

Germond M, Dessole S, Senn A, Loumaye E, Howles C, Beltrami V. Successful in-vitro fertilization and embryo transfer after treatment with recombinant human FSH. Lancet. 1992; 339: 1170.

Giudice E, Crisci C, Altarocca V, O'Brien M. Characterization of a partially purified human menopausal gonadotropin preparation. J. Clin. Res. 2001; 4: 27-34.

Hamilton-Fairley D, Kiddy D, Watson H, Sagle M, Franks S. Low-dose gonadotrophin therapy for induction of ovulation in 100 women with polycystic ovary syndrome. Hum Reprod. 1991; 6: 1095-9.

Hillier SG, Whitelaw PF, Smyth CD. Follicular oestrogen synthesis: the 'two-cell, two-gonadotrophin' model revisited. Mol Cell Endocrinol. 1994; 100: 51-4.

Hillier SG. Current concepts of the roles of follicle stimulating hormone and luteinizing hormone in folliculogenesis. Hum Reprod. 1994; 9: 188-91.

Hull M, Corrigan E, Piazzi A, Loumaye E. Recombinant human lutelnising hormone: aneffective new gonadotropin preparation. Lancet. 1994; 344: 334-335.

Humaidan P, Kol S, Papanikolaou EG; Copenhagen GnRH Agonist Triggering Workshop Group. GnRH agonist for triggering of final oocyte maturation: time for a change of practice? Hum Reprod Update. 2011;17:510-24.

Keene JL, Matzuk MM, Otani T, Fauser BC, Galway AB, Hsueh AJ, Boime I. Expression of biologically active human follitropin in Chinese hamster ovary cells. J Biol Chem. 1989; 264: 4769-75.

Levene MI, Wild J, Steer P. Higher multiple births and the modern management of infertility in Britain. The British Association of Perinatal Medicine. Br J Obstet Gynaecol. 1992;99:607-13.

Mannaerts B, de Leeuw R, Geelen J, Van Ravestein A, Van Wezenbeek P, Schuurs A, Kloosterboer H. Comparative in vitro and in vivo studies on the biological characteristics of recombinant human follicle-stimulating hormone. Endocrinology. 1991; 129: 2623-30.

Martin L, Marek D, Doody K, Nackley A, Doody K, ART: Ovarian Stimulation Fertil. Steril. 2002; 76: 0-49.

Matsuzawa S, Kimura H and Suzuki S. Quantitation of Human Chorionic Gonadotrophin by the Planimetry of Latex Agglutination-inhibition Results on Microtiter Plates, J Immunoassay. 1988; 9:1-18.

Meldrum DR. Low dose follicle-stimulating hormone Therapy for polycystic ovarian disease. Fertil Steril. 1991; 55: 1039-1040.

Papanikolaou EG, Verpoest W, Fatemi H, Tarlatzis B, Devroey P, Tournaye H. A novel method of luteal supplementation with recombinant luteinizing hormone when a gonadotropin-releasing hormone agonist is used instead of human chorionic gonadotropin for ovulation triggering: a randomized prospective proof of concept study. Fertil Steril. 2011; 95: 1174-7.

Sagle MA, Hamilton-Fairley D, Kiddy DS, Franks S. A comparative, randomized study of low-dose human menopausal gonadotropin and follicle-stimulating hormone in women with polycystic ovarian syndrome. Fertil Steril. 1991; 55: 56-60.

Seibel MM, Kamrava MM, McArdle C, Taymor ML. Treatment of polycystic ovary disease with chronic low-dose follicle stimulating hormone: biochemical changes and ultrasound correlation. Int J Fertil. 1984; 29: 39-43.

Shoham Z, Patel A, Jacobs HS. Polycystic ovarian syndrome: safety and effectiveness of stepwise and low-dose administration of purified follicle-stimulating hormone. Fertil Steril. 1991; 55: 1051-6.

Shoham Z. The clinical therapeutic window for luteinizing hormone in controlled ovarian stimulation. Fertil Steril. 2002; 77: 1170-7.

Stanton PG, Burgon PG, Hearn MT, Robertson DM. Structural and functional characterisation of hFSH and hLH isoforms. Mol Cell Endocrinol. 1996; 125: 133-41.

Stokman PG, de Leeuw R, van den Wijngaard HA, Kloosterboer HJ, Vemer HM, Sanders AL. Human chorionic gonadotropin in commercial human menopausal gonadotropin preparations. Fertil Steril. 1993; 60: 175-8.

Sullivan MW, Stewart-Akers A, Krasnow JS, Berga SL, Zeleznik AJ. Ovarian responses in women to recombinant follicle-stimulating hormone and luteinizing hormone (LH): a role for LH in the final stages of follicular maturation. J Clin Endocrinol Metab. 1999; 84: 228-32.

Van de Weijer BH, Mulders JW, Bos ES, Verhaert PD, van den Hooven HW. Compositional analyses of a human menopausal gonadotrophin preparation extracted from urine (menotropin). Identification of some of its major impurities. Reprod Biomed Online. 2003; 7: 547-57.

Van Wezenbeek Draaijer J, Van Meel, F and Olijve, W. in From clone to Clinic (eds Crommelin D. J.A. and Schellekens H.). 1990; 245-251).

Westergaard LW, Bossuyt PMM, Van der Veen F, van Wely M. Human menopausal gonadotropin versus recombinant follicle stimulation hormone for ovarian stimulation in assisted reproductive cycles. Cochrane Database Syst Rev. 2003; (1): CD003973.

Yding Andersen C, Ezcurra D. What is the Clinical Relevance of Follicle-Stimulating Hormone Isoforms in Fertility Treatment? Reproductive Biology Insights 2011;4:1-10.

\* cited by examiner

```
GLHA_MOUSE  : LPDGDFIIQGCPECKLKENKYFSKLGAPIYQCMGCCFSRAYPTPARSKKT : 50
GLHA_RAT    : LPDGDLIIQGCPECKLKENKYFSKLGAPIYQCMGCCFSRAYPTPARSKKT : 50
GLHA_HUMAN  : APD----VQDCPECTLQENPFFSQPGAPILQCMGCCFSRAYPTPLRSKKT : 46
              lPDgd iiQgCPECkLkENkyFSklGAPIyQCMGCCFSRAYPTPaRSKKT

60         *         80         *
GLHA_MOUSE  : MLVPKNITSEATCCVAKAFTKATVMGNARVENHTECHCSTCYYHKS : 96
GLHA_RAT    : MLVPKNITSEATCCVAKSFTKATVMGNARVENHTDCHCSTCYYHKS : 96
GLHA_HUMAN  : MLVQKNVTSESTCCVAKSYNRVTVMGGFKVENHTACHCSTCYYHKS : 92
              MLVpKNiTSEaTCCVAKsftkaTVMGnarVENHT CHCSTCYYHKS
```

Fig 5

```
                   *         20         *         40         *
LSHB_HUMAN  : SREPLRPWCHPINAILAVEKEGCPVCITVNTTICAGYCPTMMRVLQAVLP : 50
LSHB_PANTR  : SREPLRPWCHPINATLAVEKEGCPVCITVNTTICAGYCPTMMRVLQAVLP : 50
LSHB_GORGO  : SREPLRPRCRPINATLAVEKEGCPVCITVNTTICAGYCPTMMRVLQGVLP : 50
LSHB_MOUSE  : SRGPLRPLCRPVNATLAAENEFCPVCITFTTSICAGYCPSMVRVLPAALP : 50
LSHB_RAT    : SRGPLRPLCRPVNATLAAENEFCPVCITFTTSICAGYCPSMVRVLPAALP : 50
              SR PLRP C P NAtLA E E CPVCIT T ICAGYCP M RVL a LP

60         *         80         *       100
LSHB_HUMAN  : PLPQVVCTYRDVRFESIRLPGCPRGVDPVVSFPVALSCRCGPCRRSTSDC : 100
LSHB_PANTR  : PLPQVVCTYRDVRFESIRLPGCPRGVDPVVSFPVALSCRCGPCRRSTSDC : 100
LSHB_GORGO  : PLPQVVCTYRDVRFESIXLPGCPRGVDPMVSFPVALSCRCGPCHRSTSDC : 100
LSHB_MOUSE  : PVPQPVCTYRELAFASVRLPGCPPGVDPIVSFPVALSCRCGPCLSSSDC  : 100
LSHB_RAT    : PVPQPVCTYRELFFASVRLPGCPPGVDPIVSFPVALSCRCGPCLSSSDC  : 100
              P PQ VCTYR  rF S rLPGCP GVDP VSFPVALSCRCGPCr S SDC

*        120
LSHB_HUMAN  : GGPKDHPLTCDHPQLSGLLFL : 121
LSHB_PANTR  : GGPKDHPLTCDHPQLSGLLFL : 121
LSHB_GORGO  : GGPNDHPLTCDHPQLSGLLFL : 121
LSHB_MOUSE  : GGPRTQPMACDLPHLPGLLLL : 121
LSHB_RAT    : GGPRTQPMICDLPHLPGLLLF : 121
              GGP    P tCD P L GLL l
```

Fig 6

```
                            *         20         *         40         *
FSNB_MOUSE  : -SCELTNITISVEKEECRFCISINTTWCAGYCYTRDLVYKDPARPNTQKV :  49
FSHB_RAT_P  : -SCELTNITISVEKEECRFCISINTTWCEGYCYTRDLVYKDPARPNTQKV :  49
FSHB_GORGO  : --CELTNITIAIEKEECRFCISINTTWCAGYCYTRDLVYKDPARPHIQKT :  48
FSHB_PANTR  : --CELTNITIAIEKEECRFCISINTTWCAGHCYTRDLVYKDPARPNIQKT :  48
FSHB_HUMAN  : NSCELTNITIAIEKEECRFCISINTTWCAGYCYTRDLVYKDPARPKIQKT :  50
                CELTNITI  EKEECRFCISINTTWCaGyCYTRDLVYKDPARPn QK

60         *         80         *         100
FSNB_MOUSE  : CTFKELVYETVRLPGCARHSDSLYTYPVATECHCGKCDSDSTDCTVRGLG :  99
FSHB_RAT_P  : CTFKELVYETIRLPGCARHSDSLYTYPVATECHCGKCDSDSTDCTVRGLG :  99
FSHB_GORGO  : CTFKELVYETVRVPGCAHHADSLYTYPVATQCHCGKCDSDSTDCTVRGLG :  98
FSHB_PANTR  : CTFKELVYETVRVPGCAHHADSLYTYPVATQCHCGKCDSDSTDCTVRGLG :  98
FSHB_HUMAN  : CTFKELVYETVRVPGCAHHADSLYTYPVATQCHCGKCDSDSTDCTVRGLG : 100
              CTFKELVYETvR PGCA H DSLYTYPVAT CHCGKCDSDSTDCTVRGLG

*
FSNB_MOUSE  : PSYCSFSEMKE : 110
FSHB_RAT_P  : PSYCSFGEMKE : 110
FSHB_GORGO  : PSYCSFGEMKE : 109
FSHB_PANTR  : PSYCSFGEMKE : 109
FSHB_HUMAN  : PSYCSFGEMKE : 111
              PSYCSFgEMKE
```

Fig. 7

SDS PAGE (non-reducing) of Conjugate1
Track 1. rHA
Track 2. hCG
Track 3. hCG:rHA Conjugate1

SDS PAGE (reducing) of Conjugate1
Track 1.        Molecular weight markers
Track 2.        0.5mg/ml rHA
Track 3.        Conjugate1
Track 4.        0.05mg/ml hCG
Track 5.        0.1mg/ml hCG
Track 6.        0.2mg/ml hCG
Track 7.        0.3mg/ml hCG
Track 8.        0.4mg/ml hCG
Track 9.        Molecular weight markers Figure 8c. SEC- HPLC Analysis of purified Conjugate1
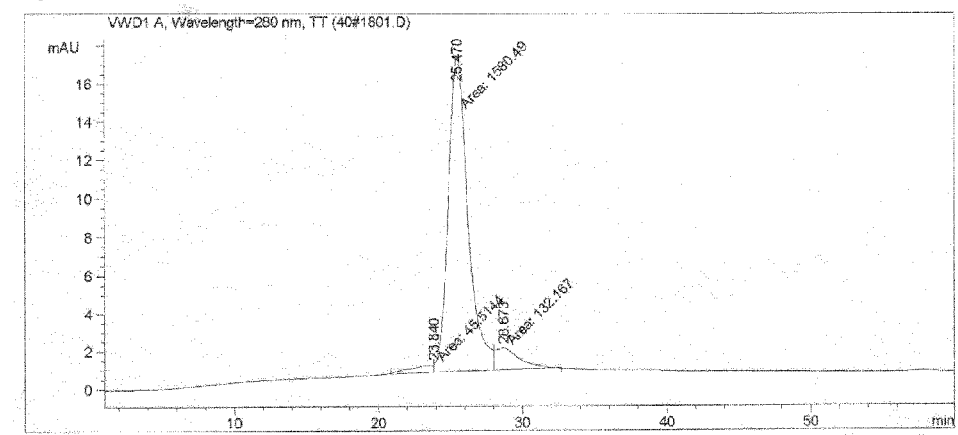

Figure 9a. SDS PAGE (non-reducing) of Conjugate3
Track 1. rHA
Track 2. hCG
Track 3. hCG:rHA Conjugate3
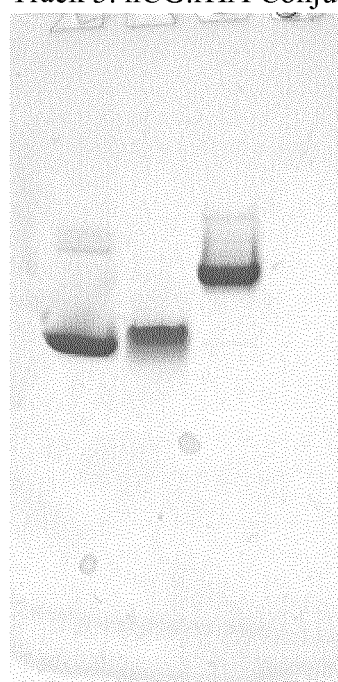

Figure 9b. SDS PAGE (reducing) of Conjugate3
Track 1.            Molecular weight markers
Track 2.            Conjugate3
Track 3.            0.10mg/ml hCG
Track 4.            0.125mg/ml hCG
Track 5.            0.15mg/ml hCG
Track 6.            0.175mg/ml hCG
Track 7.            0.20mg/ml hCG
Track 8.            Conjugate3
Track 9.            5mg/ml rHA
Track 10.           Molecular weight markers
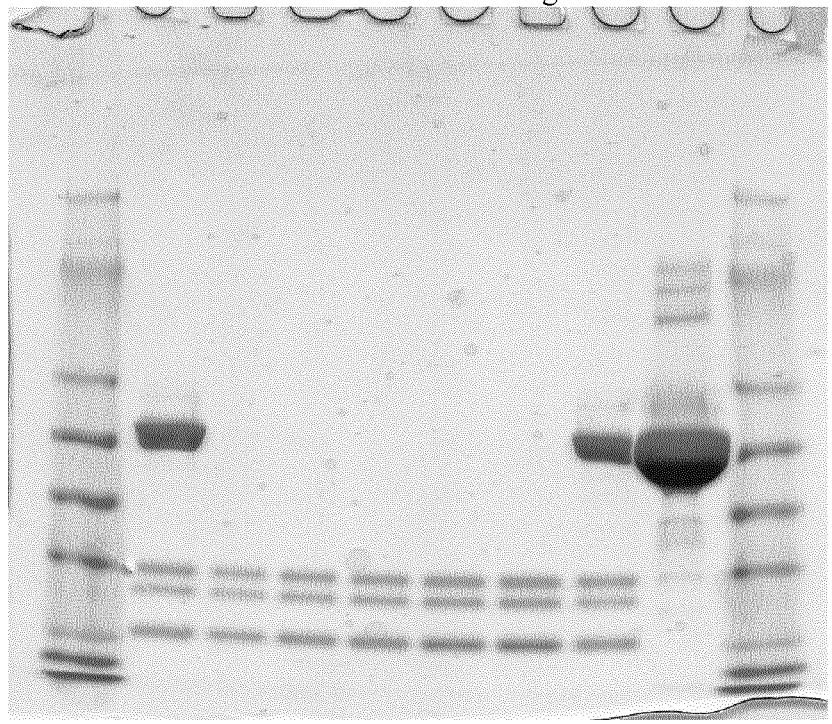

Figure 9c. SEC- HPLC Analysis of purified Conjugate3
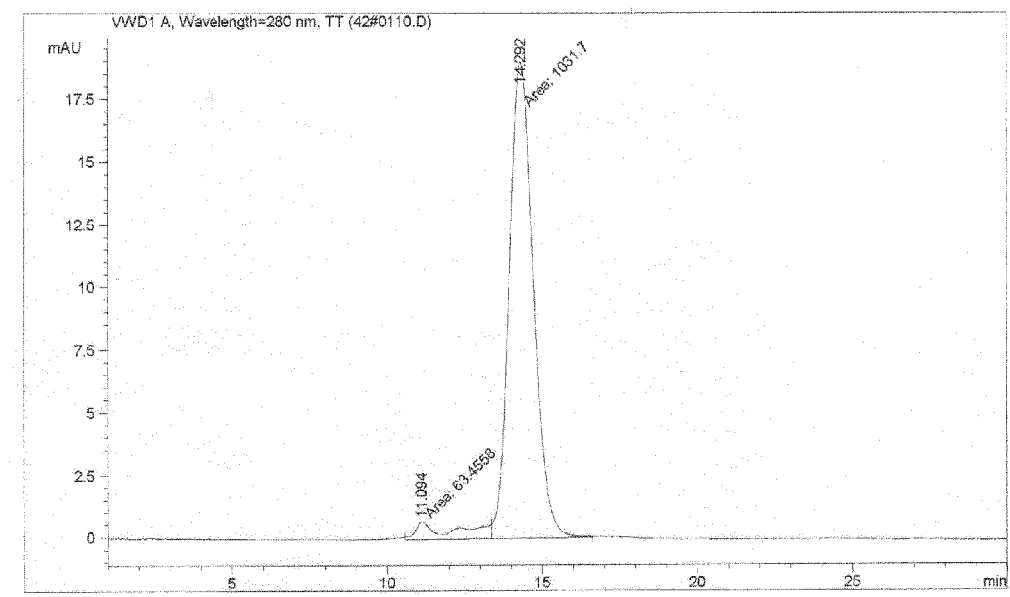

Figure 10a. SDS PAGE (non-reducing) of Conjugate4
Track 1 rHA
Track 2 hCG
Track 3 hCG:rHA Conjugate4
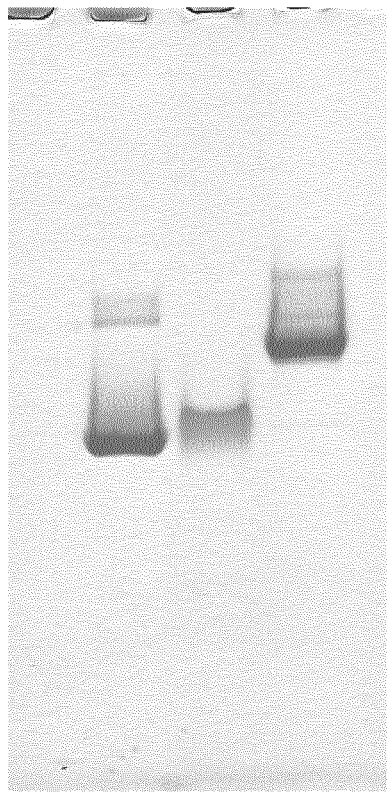

Figure 10b. SDS PAGE (reducing) of Conjugate4
Track 1.            Molecular weight markers
Track 2.            rHA 0.5mg/ml
Track 3.            Conjugate4
Track 4.            0.10mg/ml hCG
Track 5.            0.125mg/ml hCG
Track 6.            0.15mg/ml hCG
Track 7.            0.175mg/ml hCG
Track 8.            0.20mg/ml hCG
Track 9.            0.25mg/ml hCG
Track 10.           Molecular weight markers
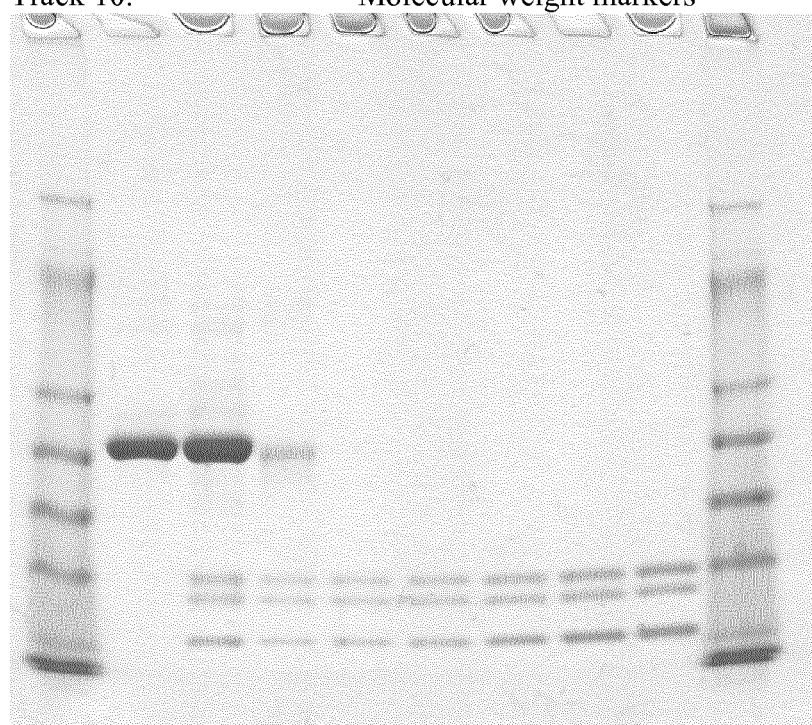

Figure 10c. SEC- HPLC Analysis of purified Conjugate4
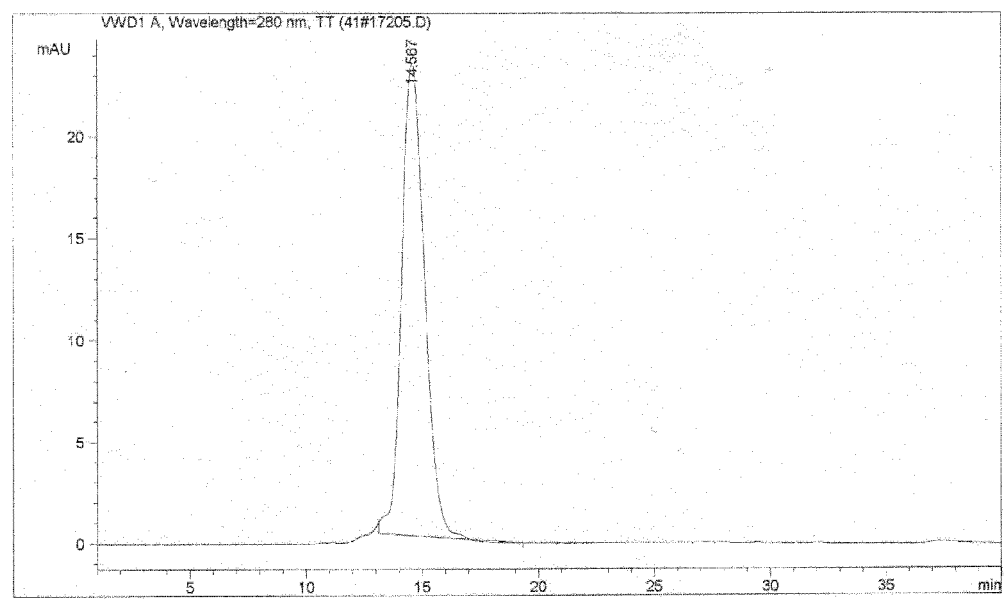

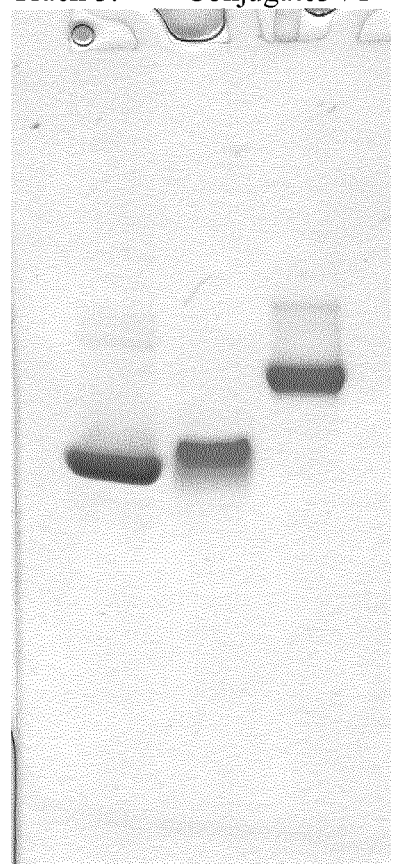
Figure 11a. SDS PAGE (non-reducing) of Conjugate3V1
Track 1.   K573P-rHA
Track 2.   hCG
Track 3.   Conjugate3V1

Figure 11b. SDS PAGE (reducing) of Conjugate3V1
Track 1.            Molecular weight markers
Track 2.            K573P-rHA
Track 3.            Conjugate3V1
Track 4.            0.15mg/ml hCG
Track 5.            0.175mg/ml hCG
Track 6.            0.20mg/ml hCG
Track 7.            0.225mg/ml hCG
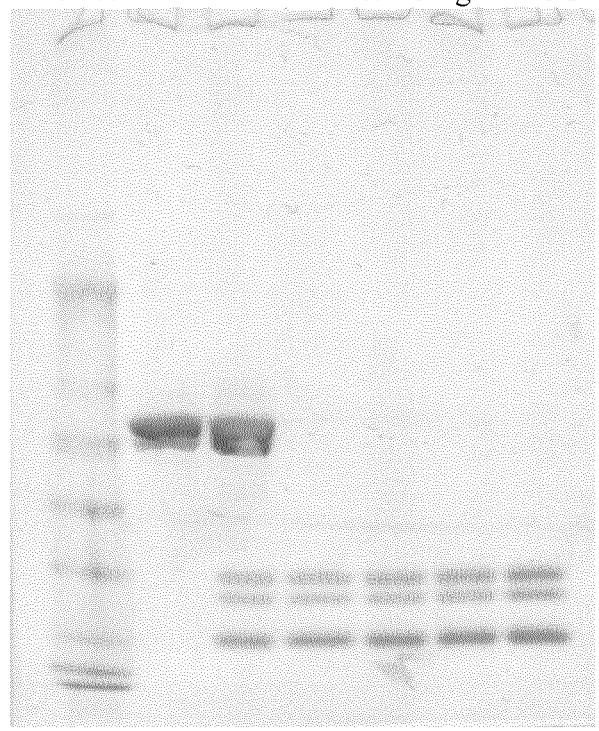

Figure 11c. SEC- HPLC Analysis of purified Conjugate3V1
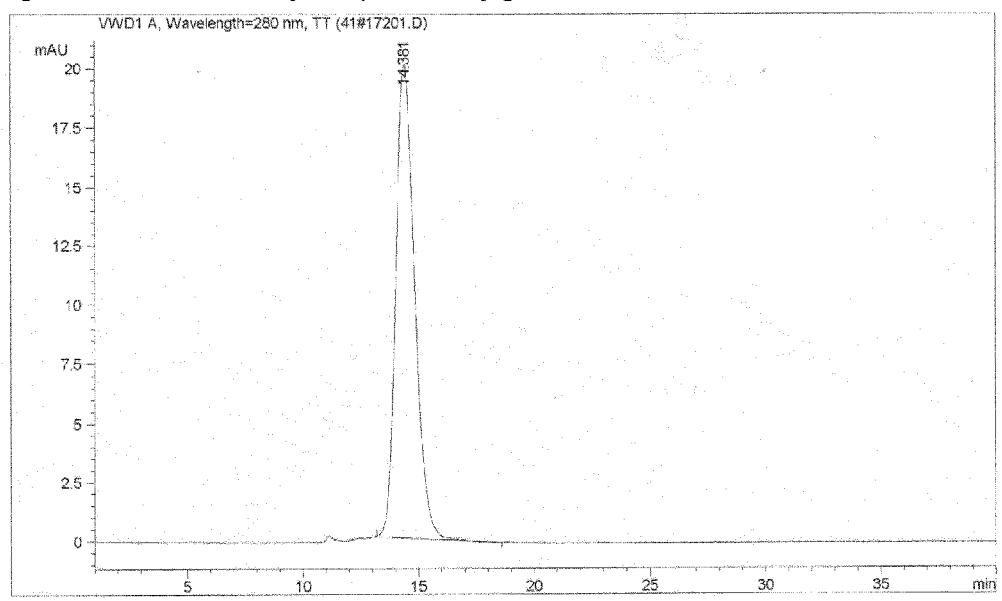

Figure 12a. SDS PAGE (non-reducing) of Conjugate4V1
Track 1.                K573P-rHA
Track 2.                hCG
Track 3.                Conjugate4V1
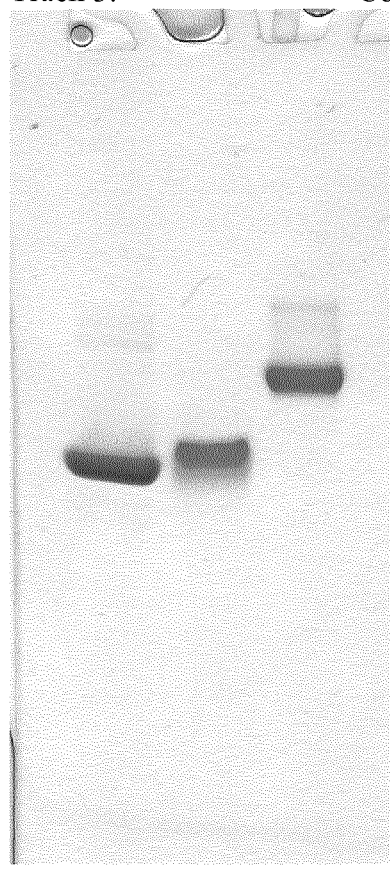

Figure 12b. SDS PAGE (reducing) of Conjugate4V1
Track 1.   Molecular weight markers
Track 2.   K573P-rHA
Track 3.   Conjugate4V1
Track 4.   0.20mg/ml hCG
Track 5.   0.225mg/ml hCG
Track 6.   0.25mg/ml hCG
Track 7.   0.275mg/ml hCG
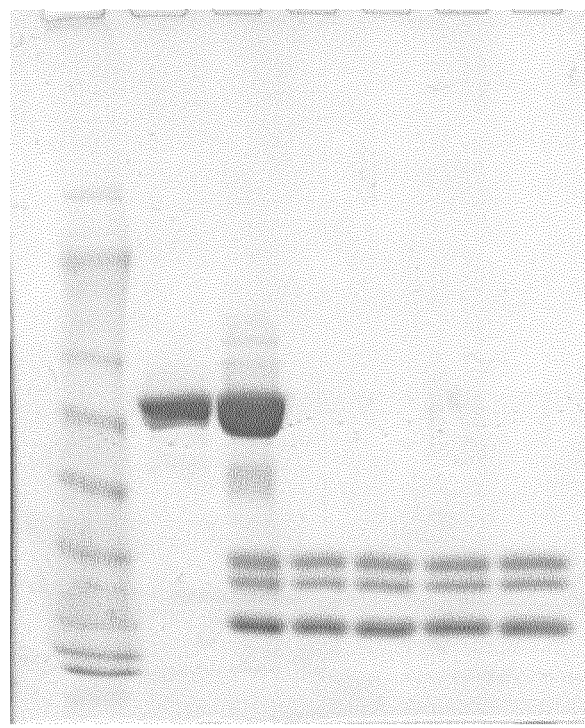

Figure 12c. SEC- HPLC Analysis of purified Conjugate4V1
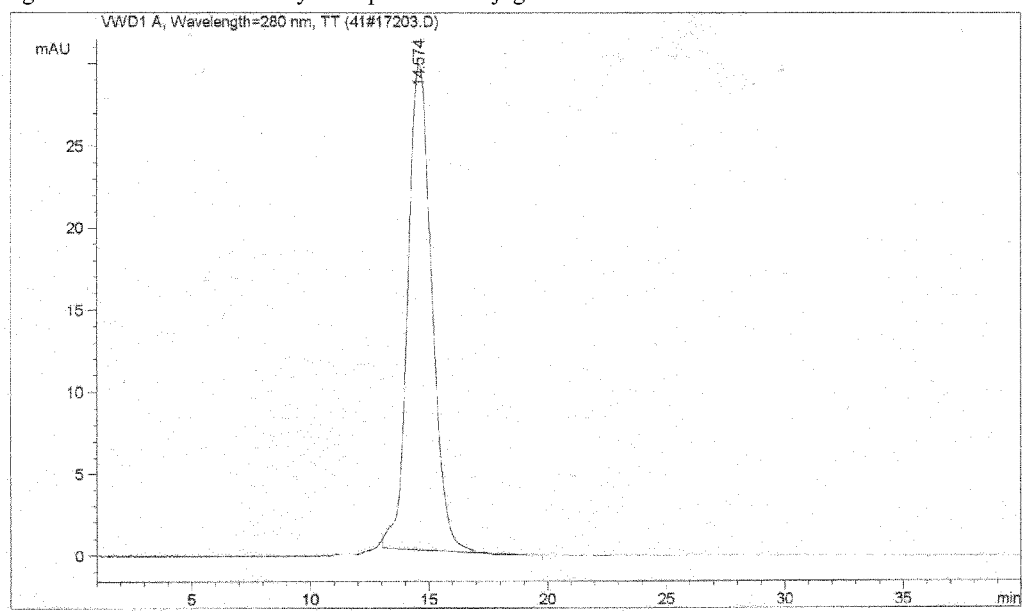

Figure 13. Confirmation of amplified single gene vectors prior to transfection
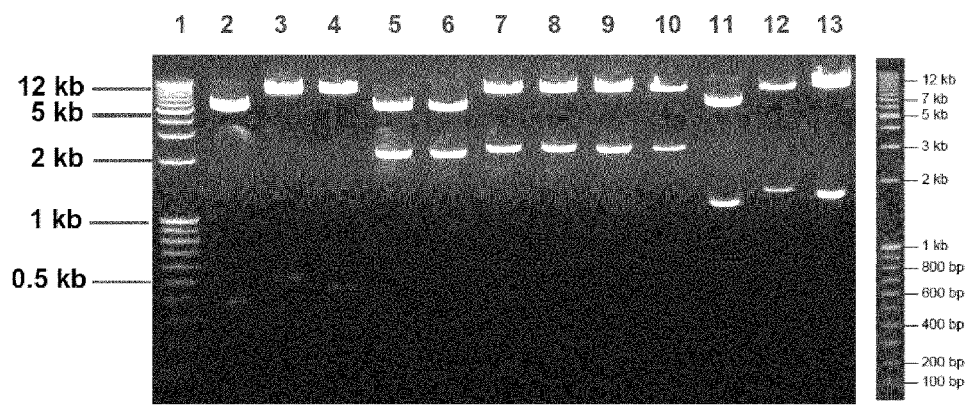

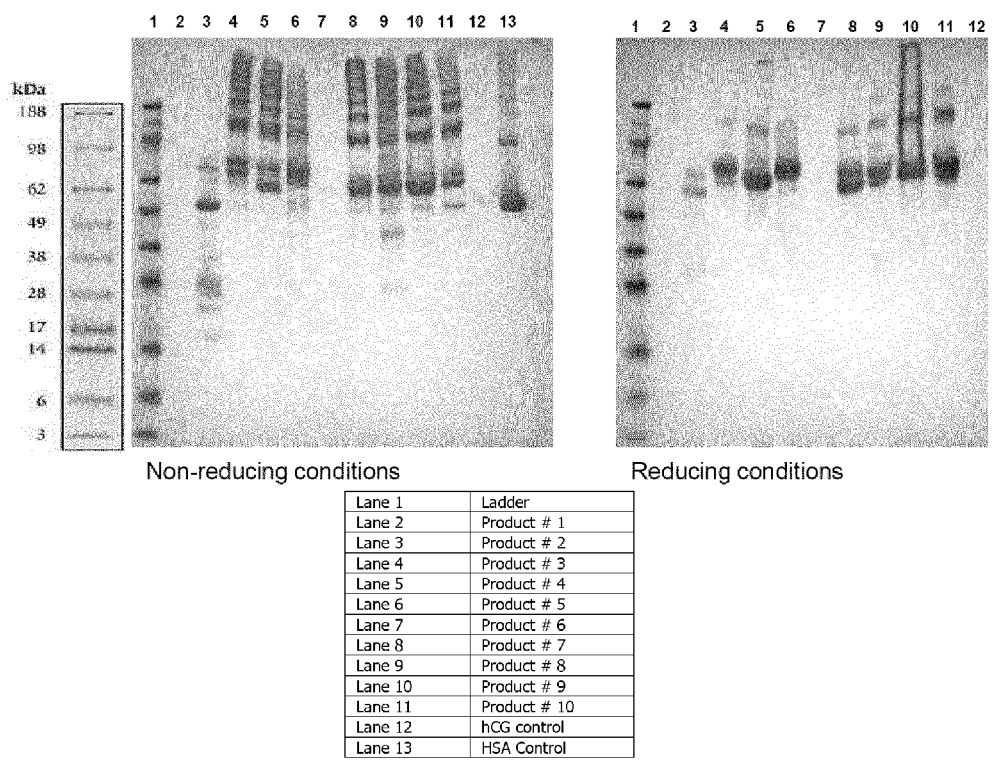
Figure 14. Western Blot using anti-HAS (human serum albumin)

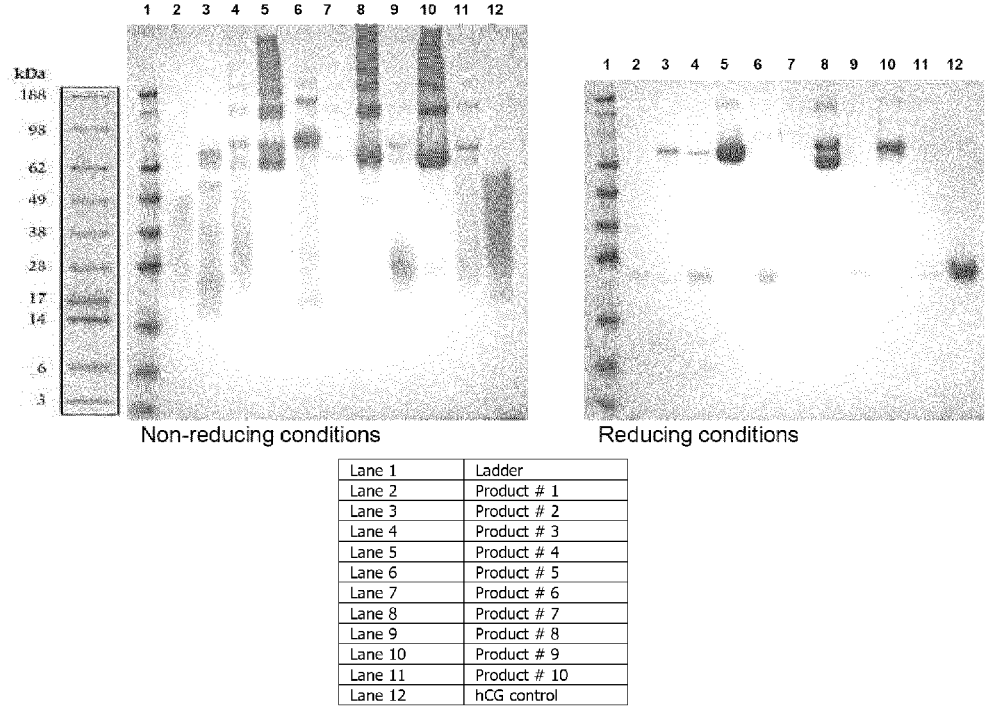
Figure 15. Western Blot using anti-gonadotropin common α-subunit

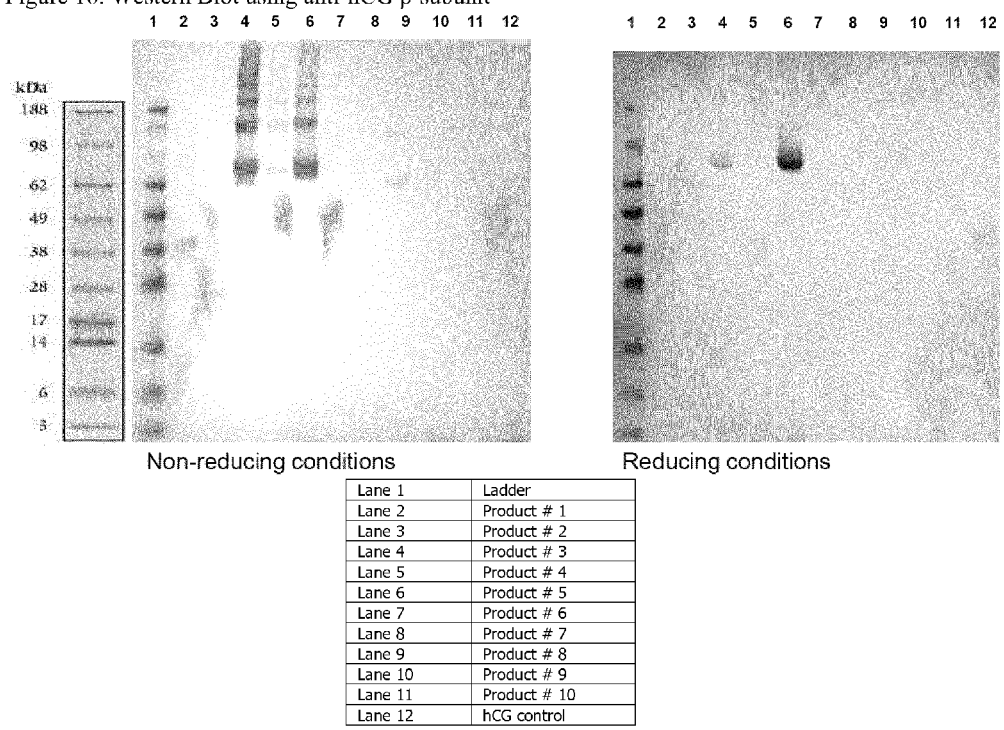
Figure 16. Western Blot using anti-hCG β-subunit

Figure 17. SDS PAGE analysis of products 1-10
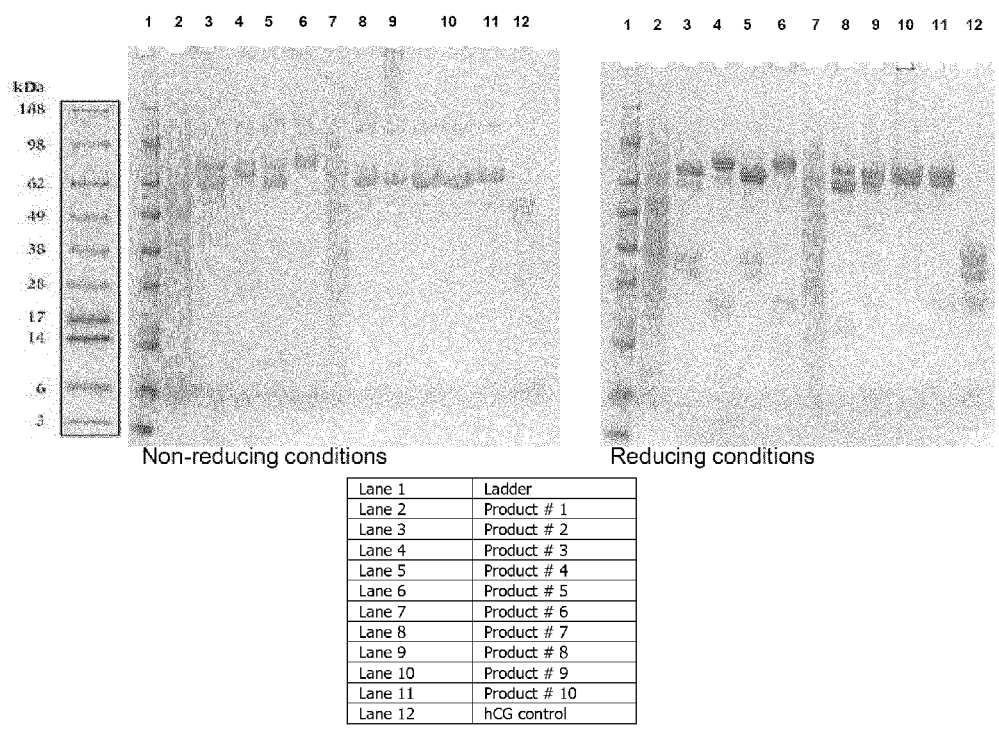

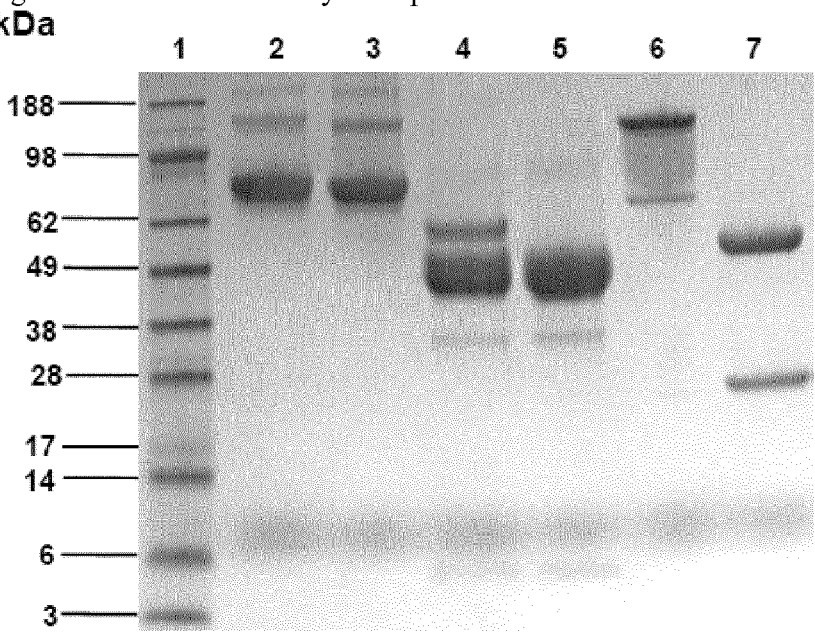
Figure 18. SDS PAGE analysis of products 11-12

Figure 19a. Measurement of *in vitro* activity of hCG and LH variants
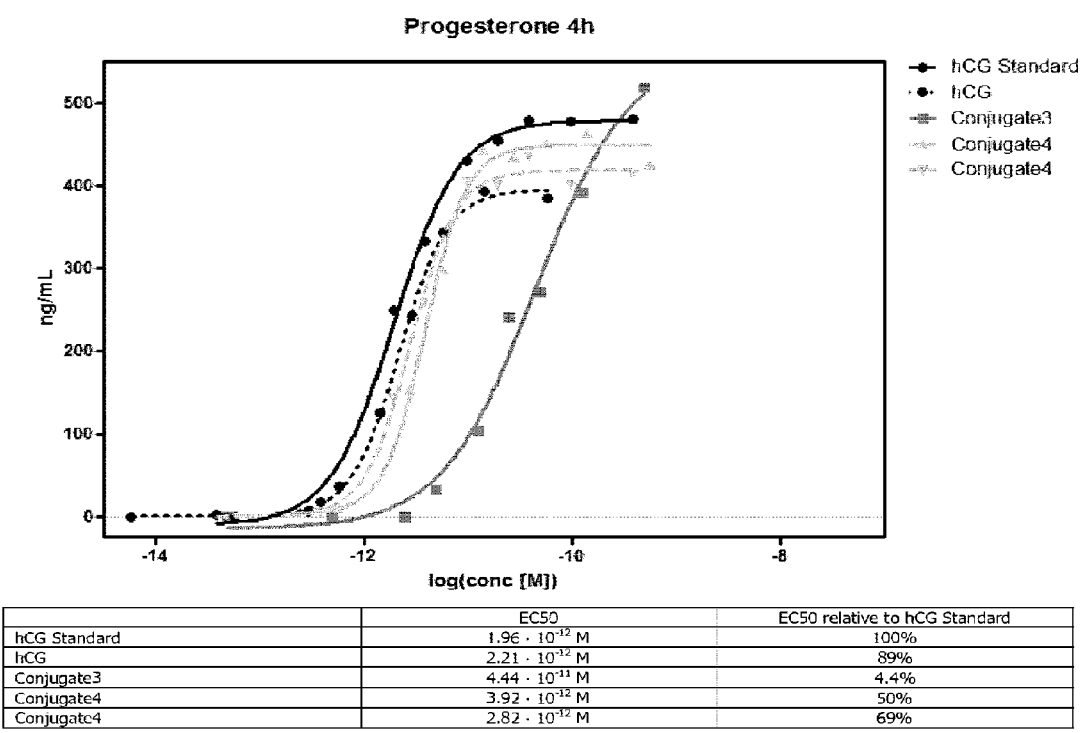
| | EC50 | EC50 relative to hCG Standard |
|---|---|---|
| hCG Standard | $1.96 \cdot 10^{-12}$ M | 100% |
| hCG | $2.21 \cdot 10^{-12}$ M | 89% |
| Conjugate3 | $4.44 \cdot 10^{-11}$ M | 4.4% |
| Conjugate4 | $3.92 \cdot 10^{-12}$ M | 50% |
| Conjugate4 | $2.82 \cdot 10^{-12}$ M | 69% |

Figure 19b. Measurement of *in vitro* activity of hCG and LH variants
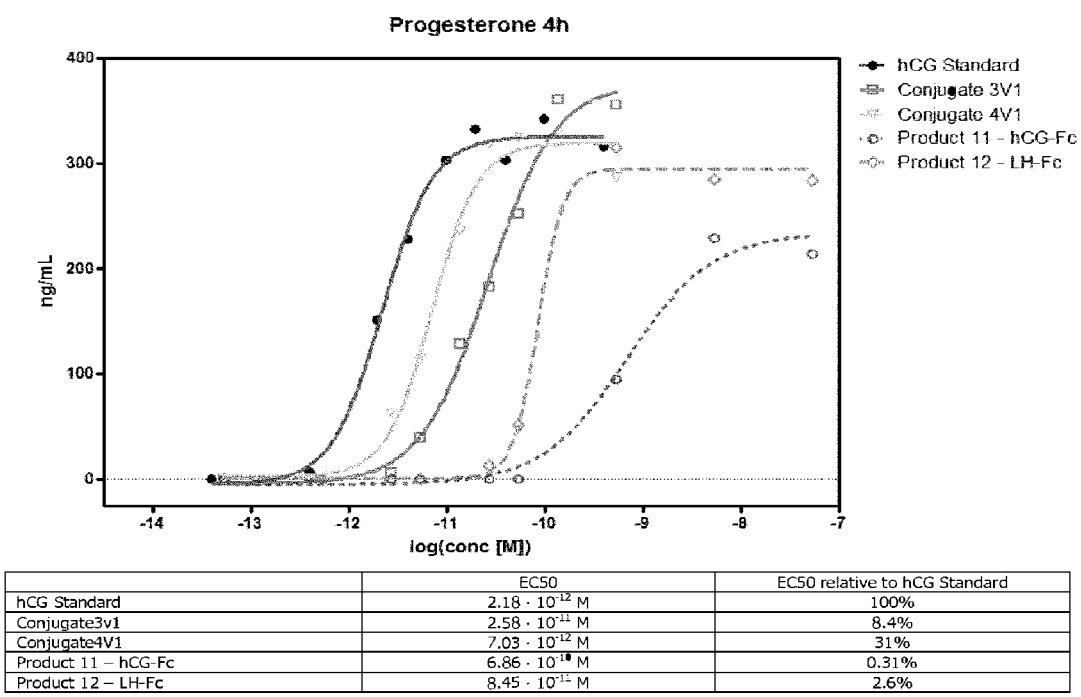
| | EC50 | EC50 relative to hCG Standard |
|---|---|---|
| hCG Standard | $2.18 \cdot 10^{-12}$ M | 100% |
| Conjugate3v1 | $2.58 \cdot 10^{-11}$ M | 8.4% |
| Conjugate4V1 | $7.03 \cdot 10^{-12}$ M | 31% |
| Product 11 – hCG-Fc | $6.86 \cdot 10^{-10}$ M | 0.31% |
| Product 12 – LH-Fc | $8.45 \cdot 10^{-11}$ M | 2.6% |

Figure 19c. Measurement of *in vitro* activity of hCG and LH variants
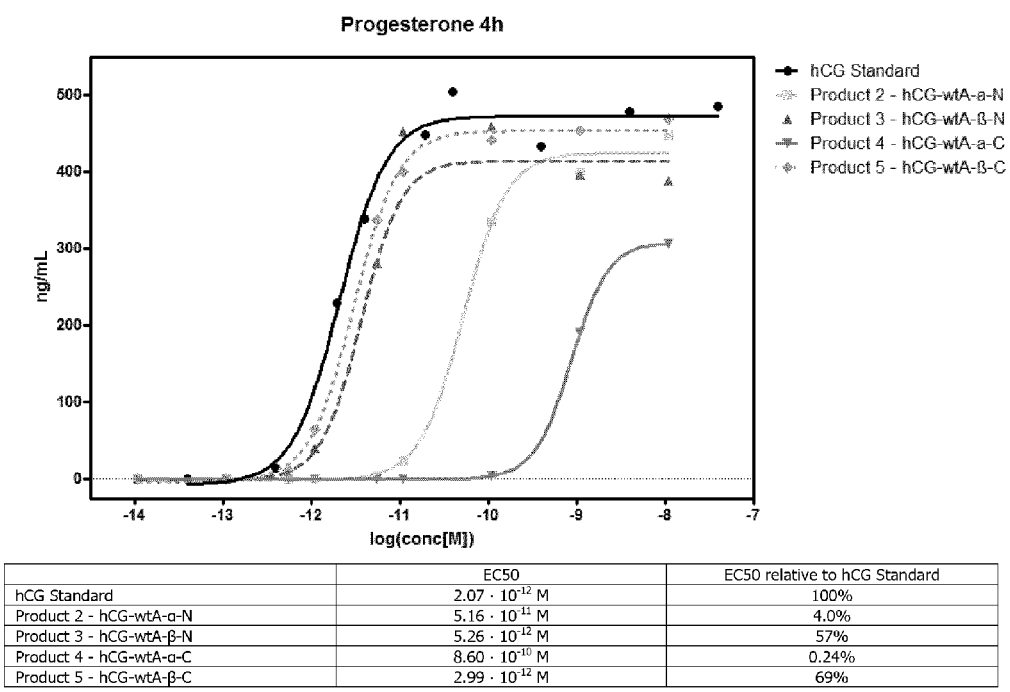
| | EC50 | EC50 relative to hCG Standard |
|---|---|---|
| hCG Standard | $2.07 \cdot 10^{-12}$ M | 100% |
| Product 2 - hCG-wtA-α-N | $5.16 \cdot 10^{-11}$ M | 4.0% |
| Product 3 - hCG-wtA-β-N | $5.26 \cdot 10^{-12}$ M | 57% |
| Product 4 - hCG-wtA-α-C | $8.60 \cdot 10^{-10}$ M | 0.24% |
| Product 5 - hCG-wtA-β-C | $2.99 \cdot 10^{-12}$ M | 69% |

Figure 19d. Measurement of *in vitro* activity of hCG and LH variants
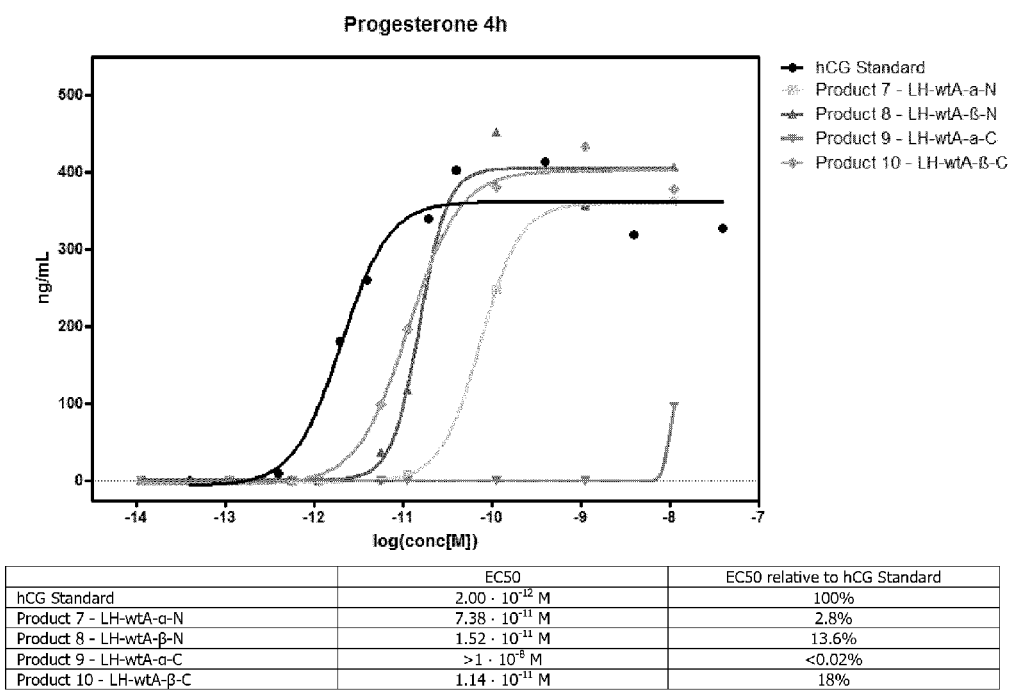
| | EC50 | EC50 relative to hCG Standard |
|---|---|---|
| hCG Standard | $2.00 \cdot 10^{-12}$ M | 100% |
| Product 7 - LH-wtA-α-N | $7.38 \cdot 10^{-11}$ M | 2.8% |
| Product 8 - LH-wtA-β-N | $1.52 \cdot 10^{-11}$ M | 13.6% |
| Product 9 - LH-wtA-α-C | $>1 \cdot 10^{-8}$ M | <0.02% |
| Product 10 - LH-wtA-β-C | $1.14 \cdot 10^{-11}$ M | 18% |

Figure 20A. Measurement of in vivo activity of hCG and LH variants
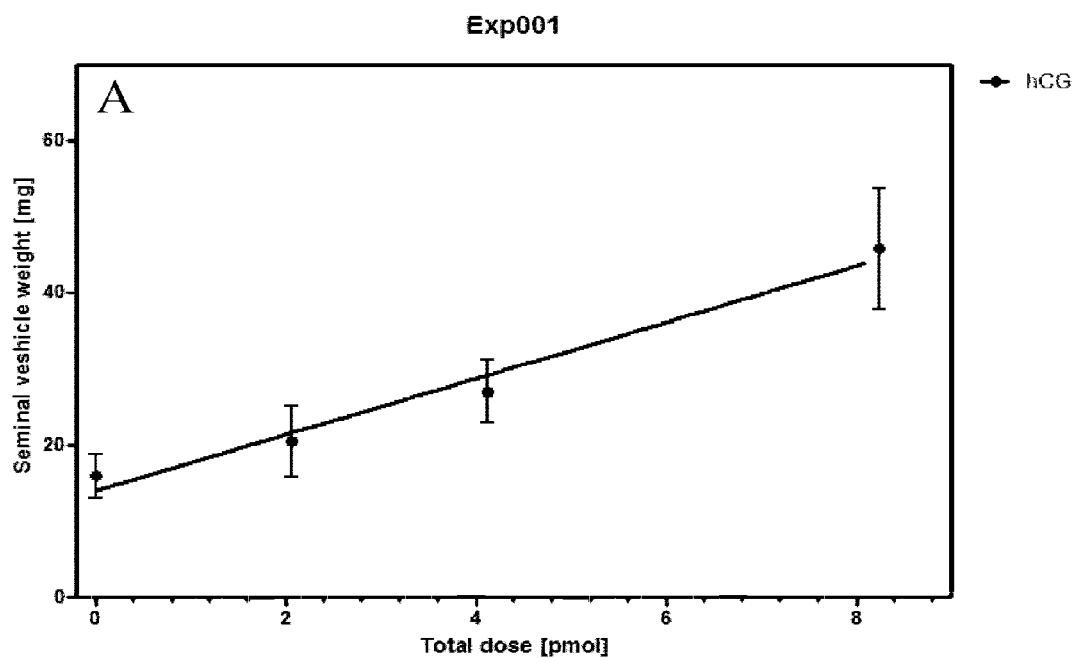

Figure 20B. Measurement of in vivo activity of hCG and LH variants
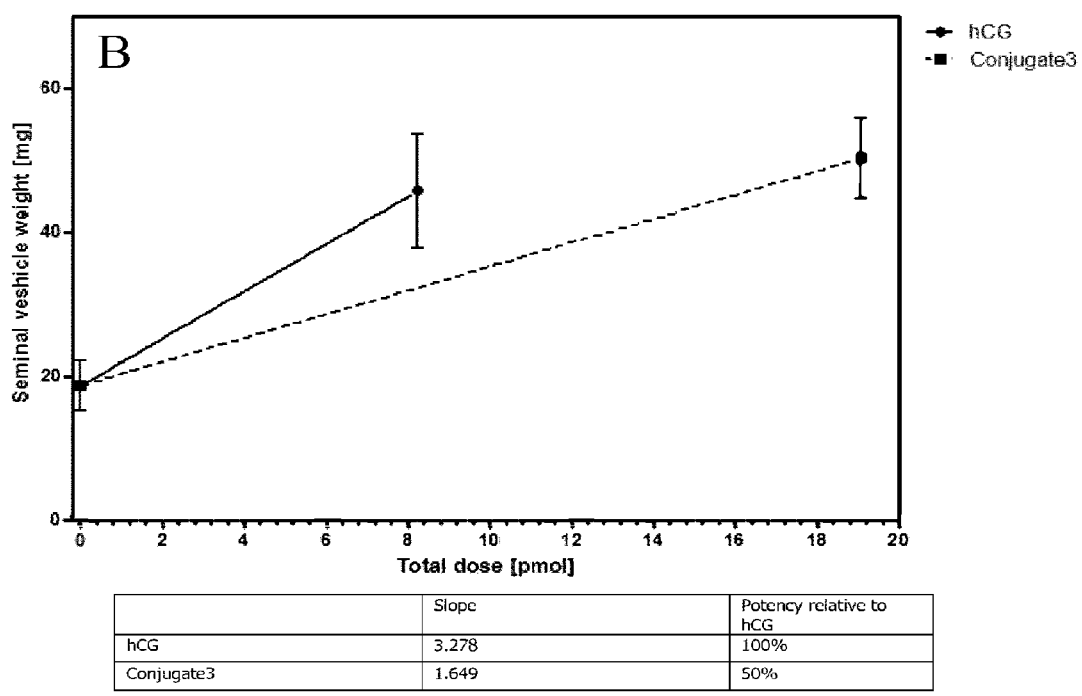
|  | Slope | Potency relative to hCG |
|---|---|---|
| hCG | 3.278 | 100% |
| Conjugate3 | 1.649 | 50% |

Figure 20C. Measurement of in vivo activity of hCG and LH variants
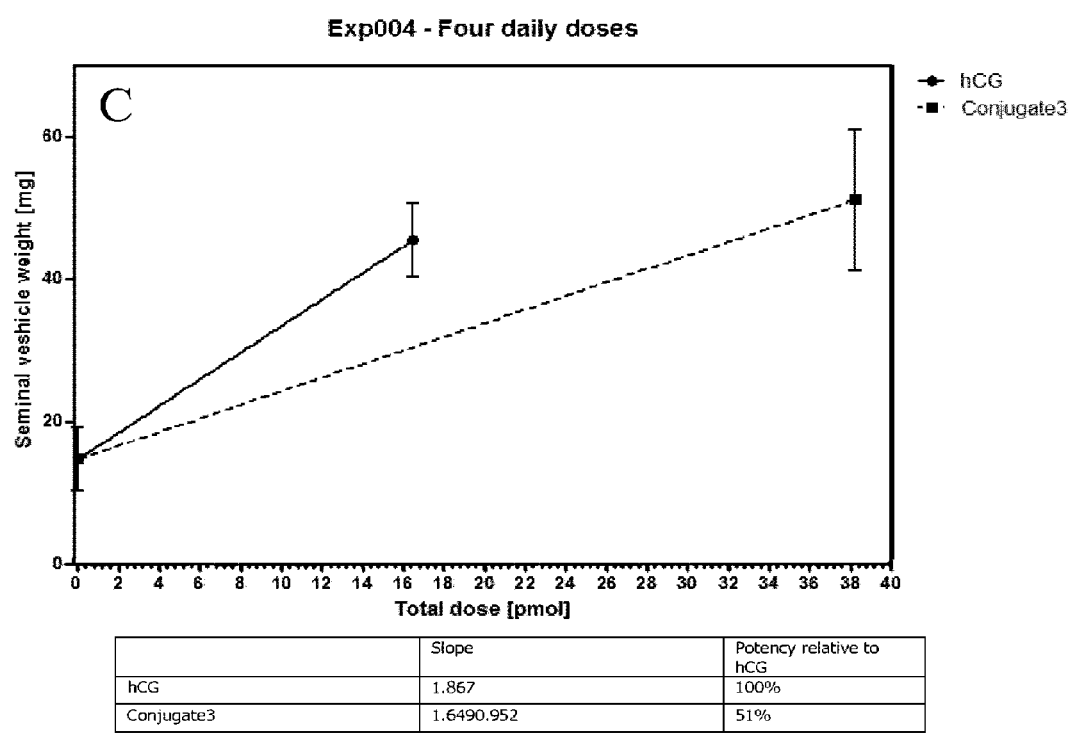
| | Slope | Potency relative to hCG |
|---|---|---|
| hCG | 1.867 | 100% |
| Conjugate3 | 1.6490.952 | 51% |

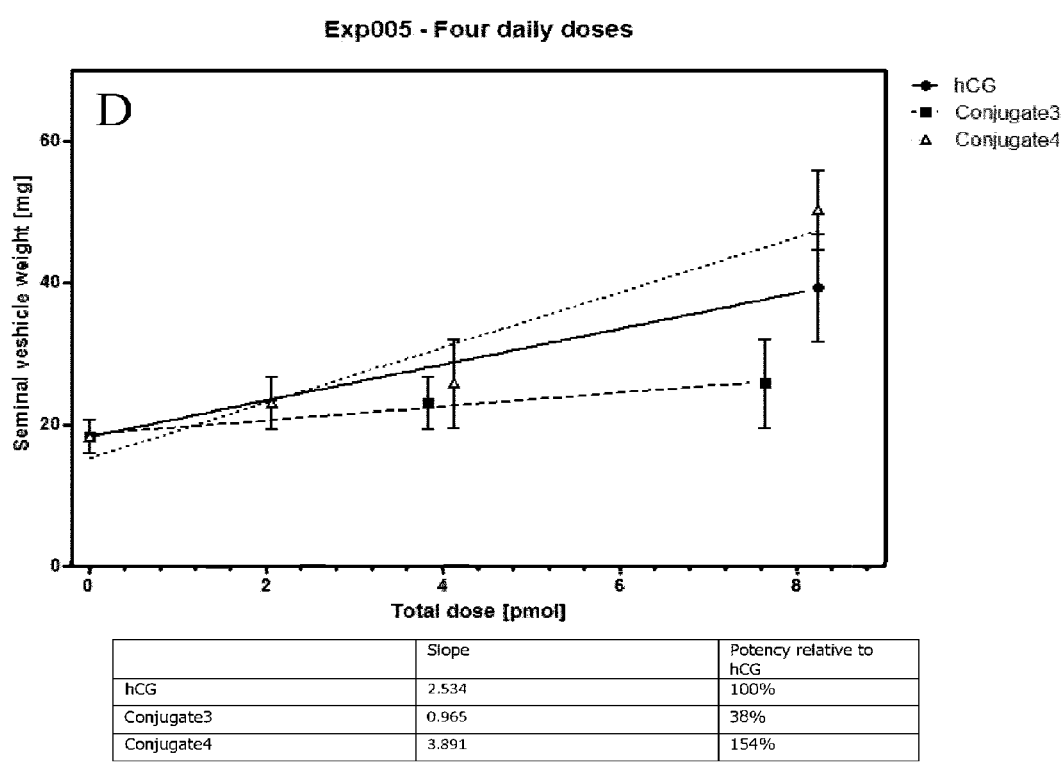
Figure 20D. Measurement of in vivo activity of hCG and LH variants

Figure 20E. Measurement of in vivo activity of hCG and LH variants
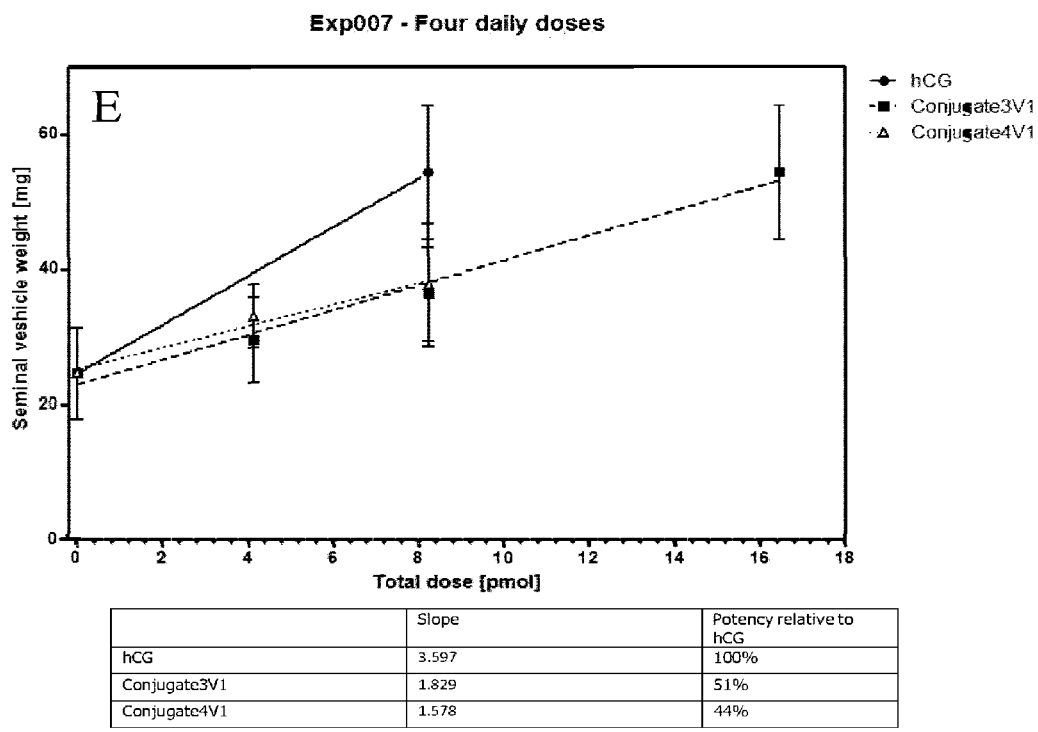

Figure 20F. Measurement of in vivo activity of hCG and LH variants
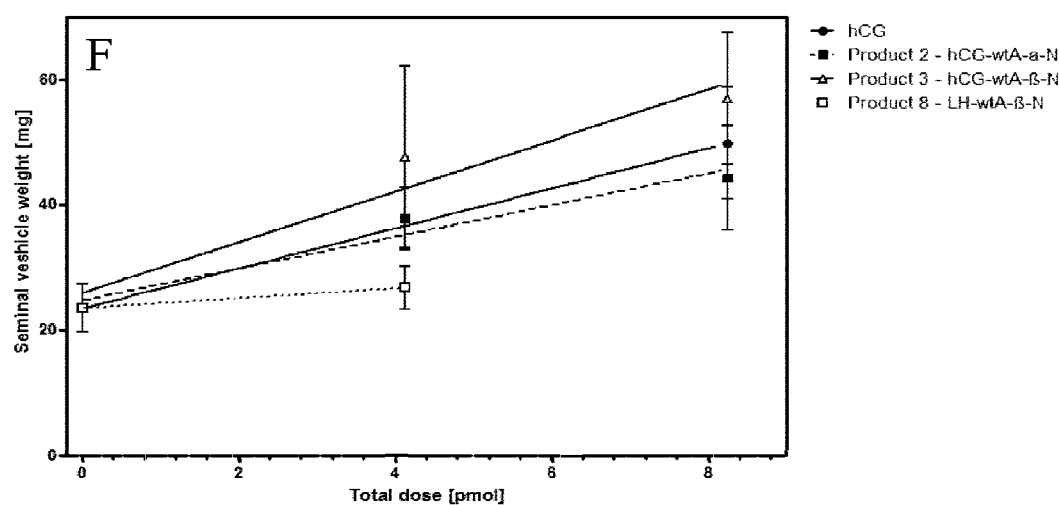
|  | Slope | Potency relative to hCG |
|---|---|---|
| hCG | 3.202 | 100% |
| Product 2 - hCG-wtA-a-N | 2.534 | 79% |
| Product 3 - hCG-wtA-ß-N | 4.067 | 127% |
| Product 8 - LH-wtA-ß-N | 0.789 | 25% |

Figure 20G. Measurement of in vivo activity of hCG and LH variants
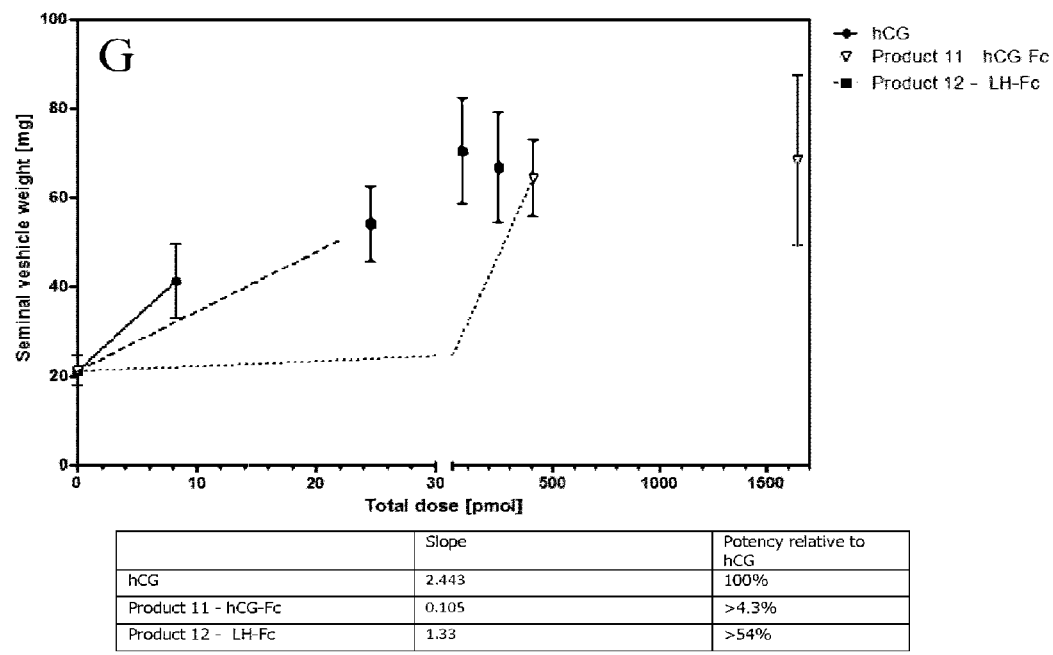
| | Slope | Potency relative to hCG |
|---|---|---|
| hCG | 2.443 | 100% |
| Product 11 - hCG-Fc | 0.105 | >4.3% |
| Product 12 - LH-Fc | 1.33 | >54% |

Figure 20H. Measurement of in vivo activity of hCG and LH variants
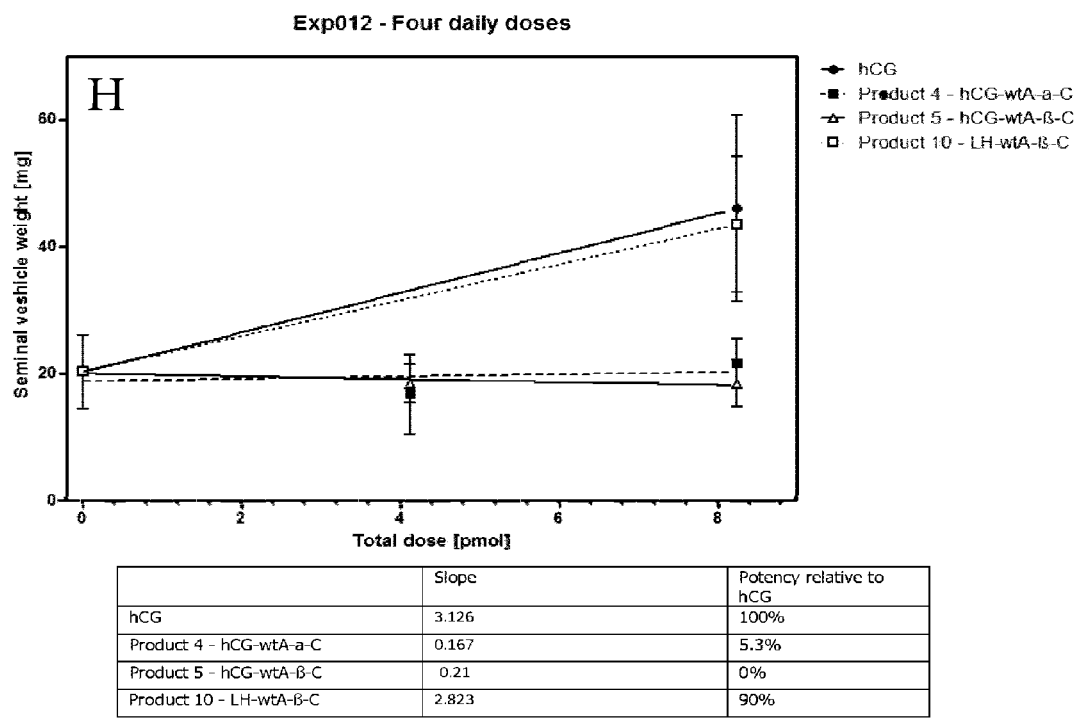
|  | Slope | Potency relative to hCG |
|---|---|---|
| hCG | 3.126 | 100% |
| Product 4 - hCG-wtA-a-C | 0.167 | 5.3% |
| Product 5 - hCG-wtA-ß-C | 0.21 | 0% |
| Product 10 - LH-wtA-ß-C | 2.823 | 90% |

Figure 20I. Measurement of in vivo activity of hCG and LH variants
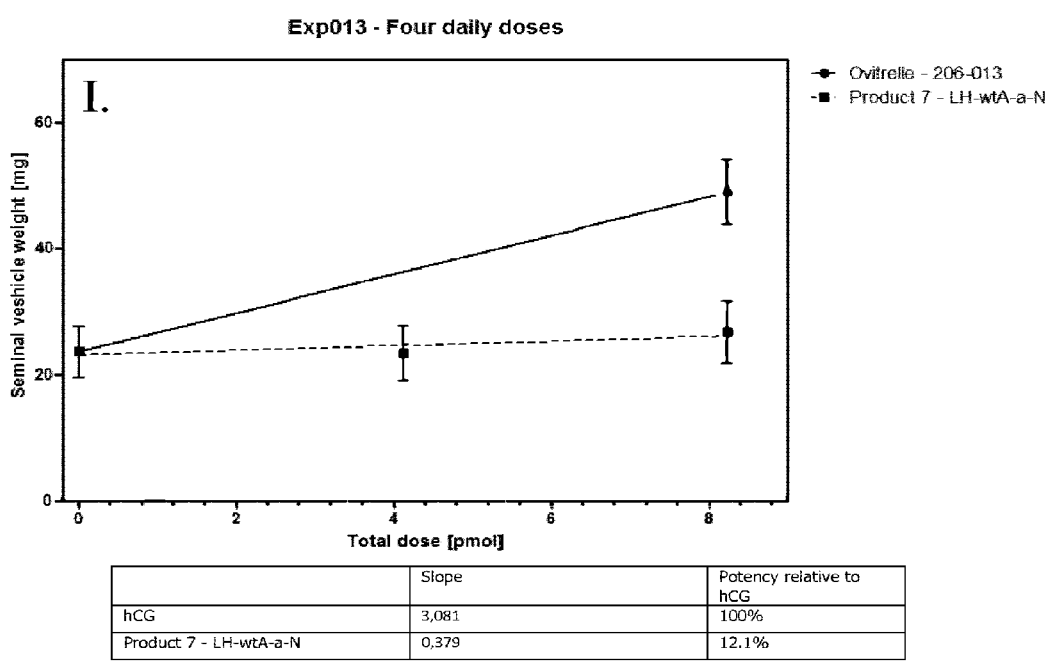

Figure 20J. Measurement of in vivo activity of hCG and LH variants
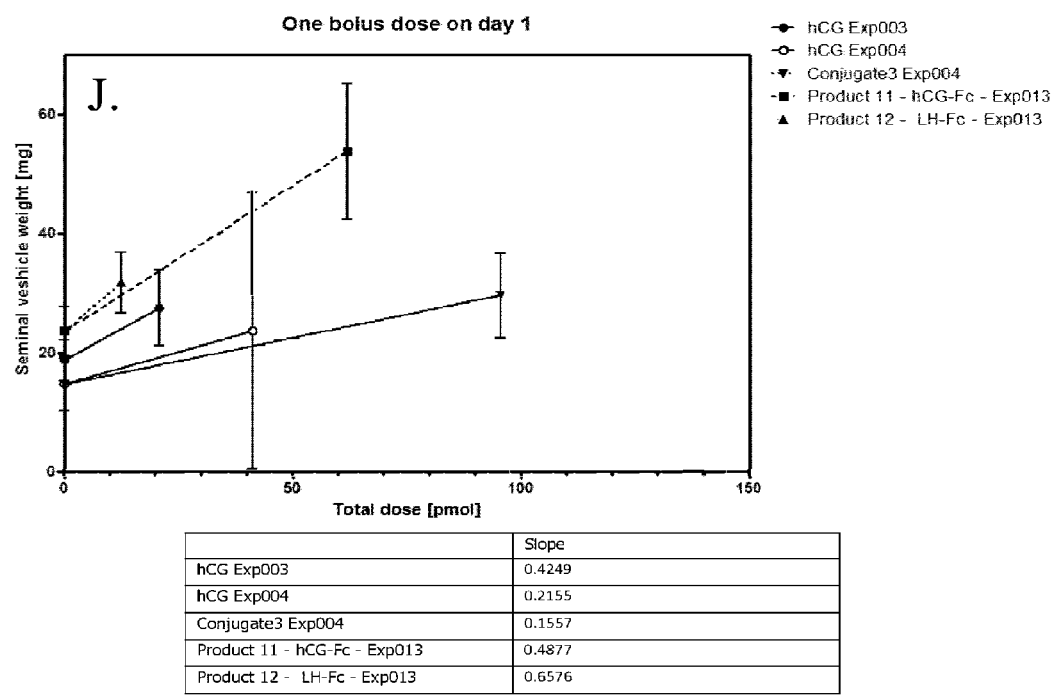

Figure 21A. PK data of hCG, Conjugate3 and Conjugate3V1 in hypophysectomized male rats.
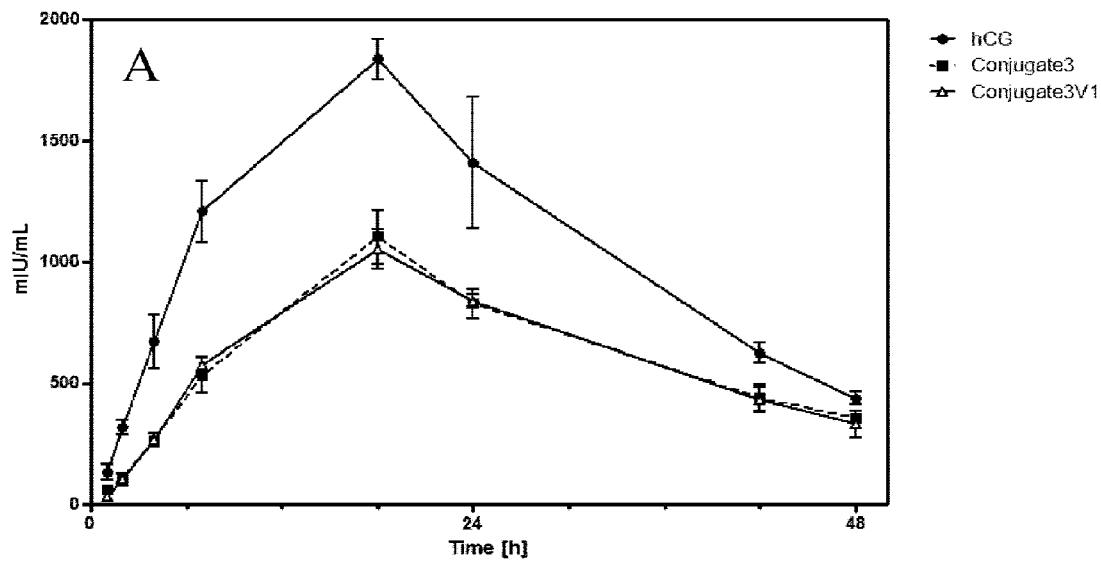
Figure 21B. PK data of hCG, Conjugate3 and Conjugate3V1 in hypophysectomized male rats.
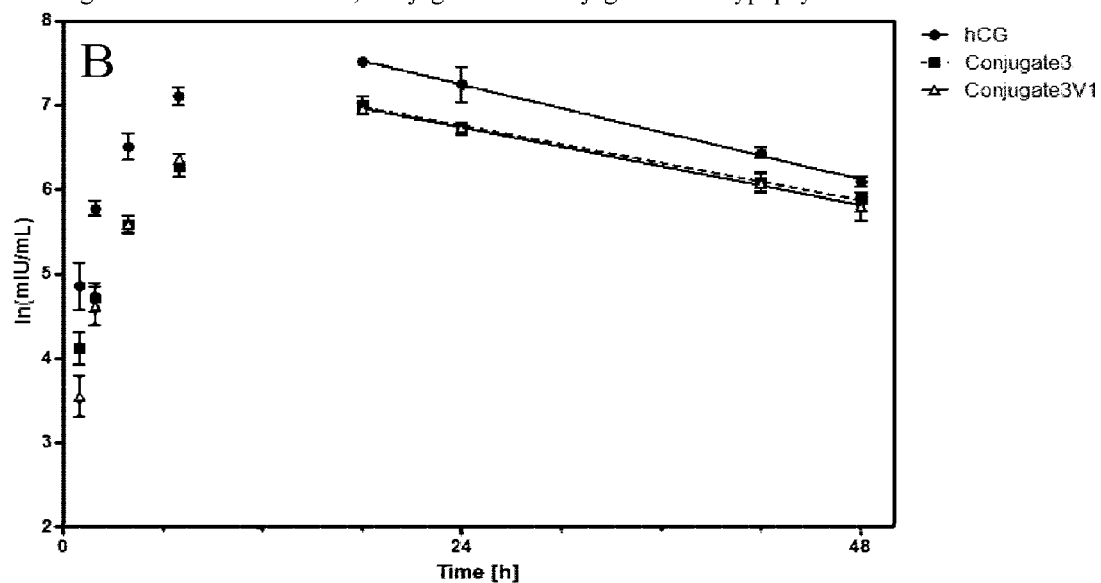

Figure 21C: Standard curves of hCG, Conjugate3 and Conjugate3V1.
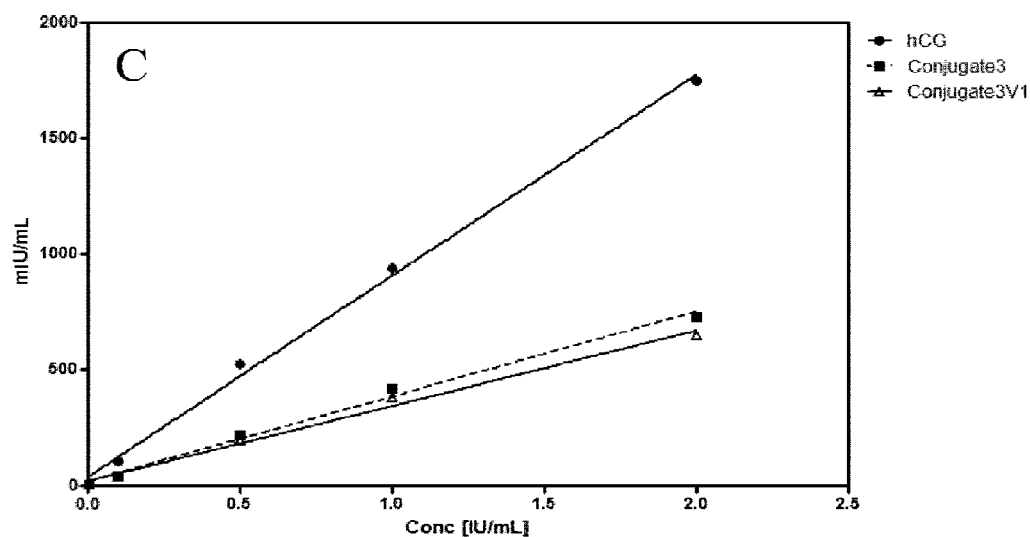
Figure 21D: Calculation of terminal half-life for hCG, Conjugate3 and Conjugate3V1 in hypophysectomized male rats
|  | Terminal half-life [h] | STD curve slope [mIU measured/IU] |
|---|---|---|
| hCG | 14.8h ± 0.8h | 869 |
| Conjugate3 | 18.8h ± 1.0h | 366 |
| Conjugate3V1 | 18.1h ± 1.1h | 324 |

Figure 22A. PK data of hCG, Conjugate4V1, Product 11 and Product 12 in hypophysectomized male rats.
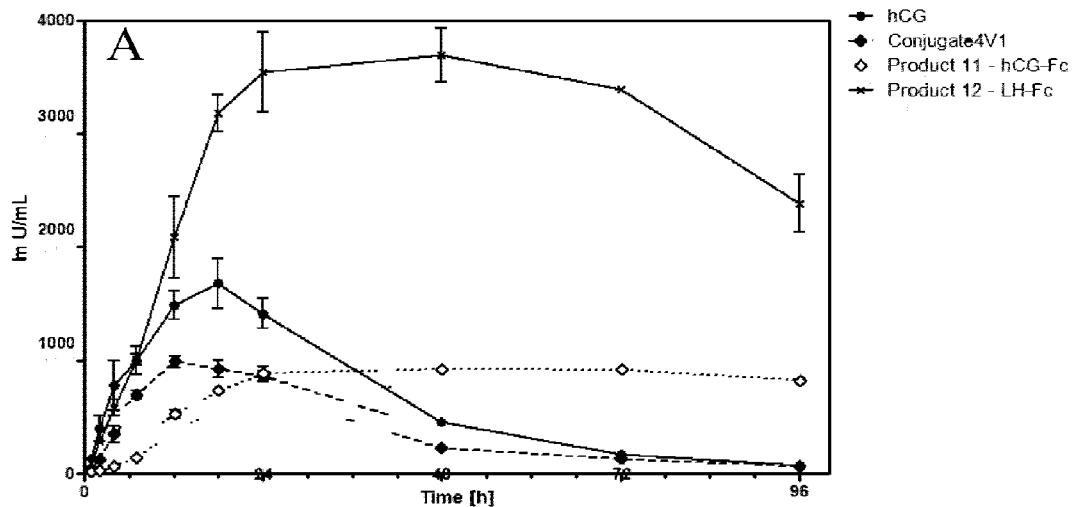
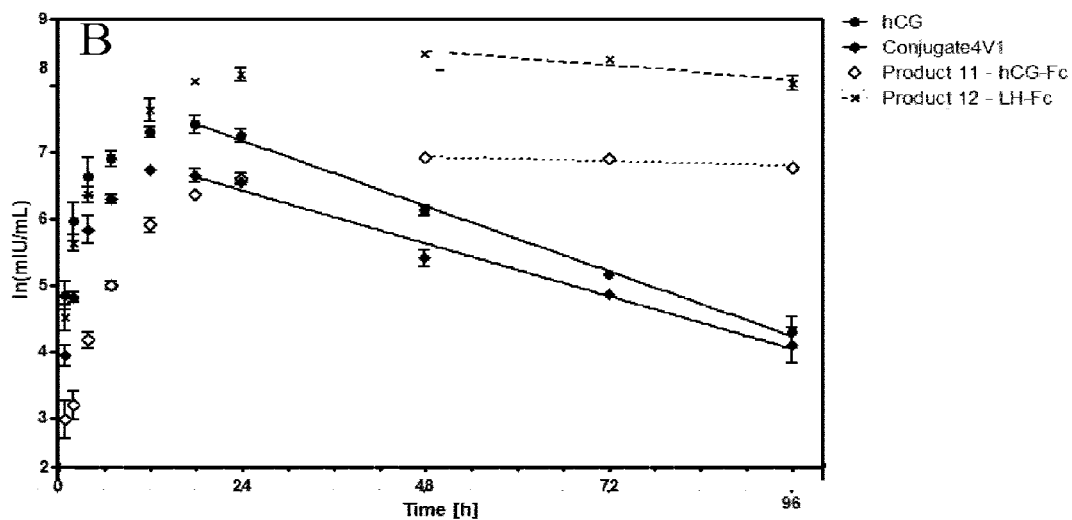
Figure 22B: Pharmacokinetic data of hCG, Conjugate4V1, Product 11 and Product 12 in hypophysectomized male rats Figure 22C: Standard curves of hCG, Conjugate4V1, Product 11 and Product 12.

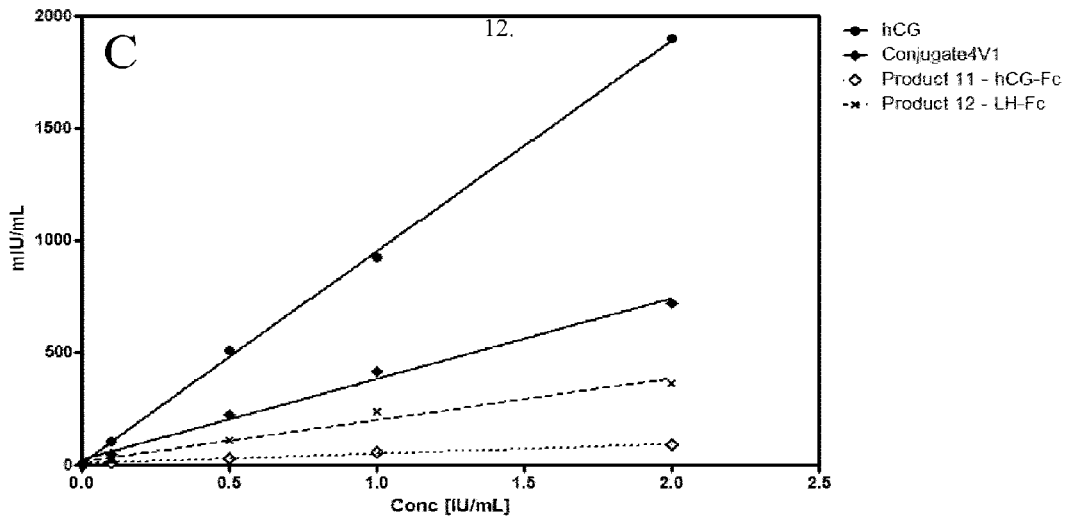

Figure 22D. Calculation of terminal half-life for hCG, Conjugate4V1, Product 11 and Product 12 in hypophysectomized male rats

|  | Terminal half-life [h] | STD curve slope [mIU measured/IU] |
| --- | --- | --- |
| hCG | 17.0h ± 0.5h | 941 |
| Conjugate4V1 | 20.9h ± 1.0h | 358 |
| Product 11 – hCG-Fc | 239h ± 61h | 43.8 |
| Product 12 – LH-Fc | 76h ± 14h | 185 |

Figure 22E: PK data of Product 7 and Product 10 in hypophysectomized male rats

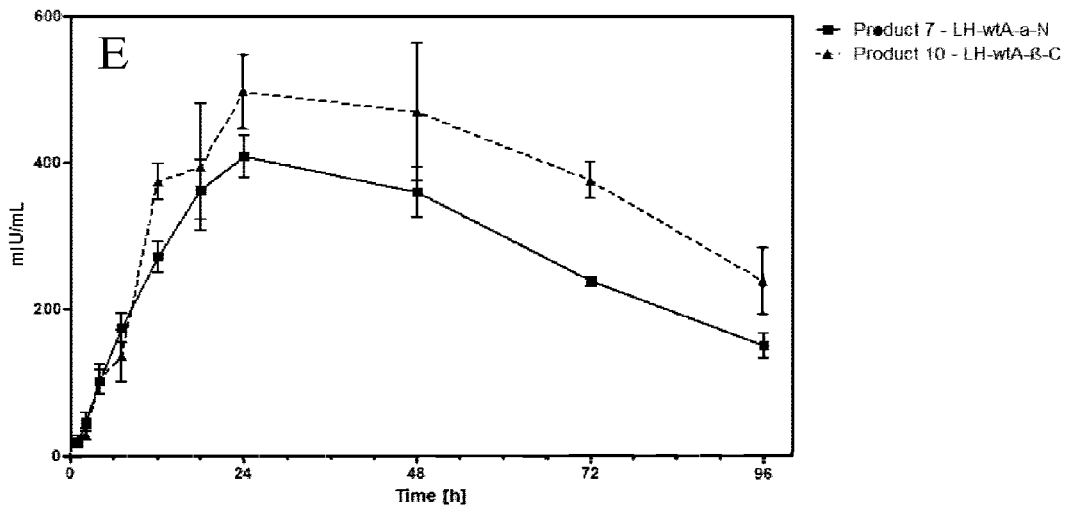

Figure 22F. PK data of Product 7 and Product 10 in hypophysectomized male rats
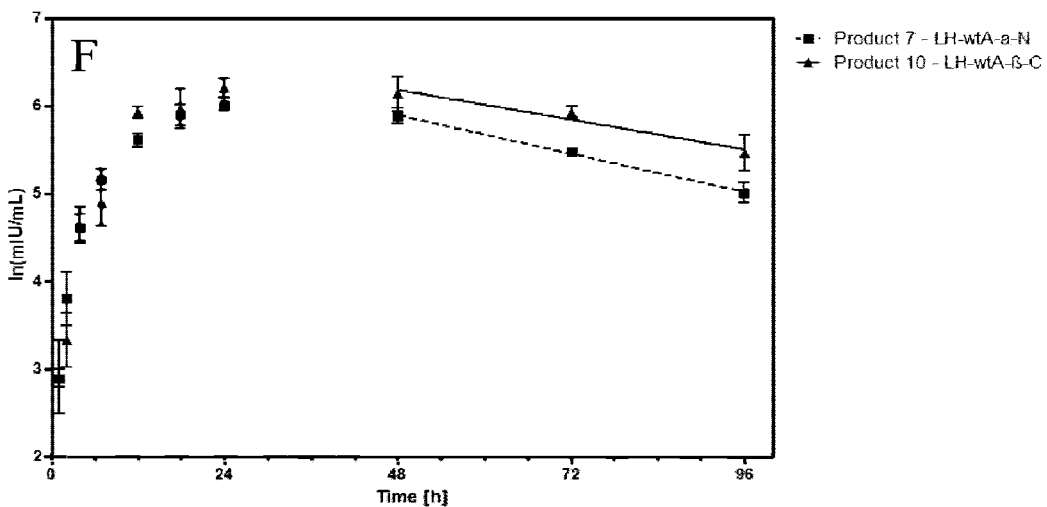
Figure 22G: Standard curves of Product 7 and Product 10
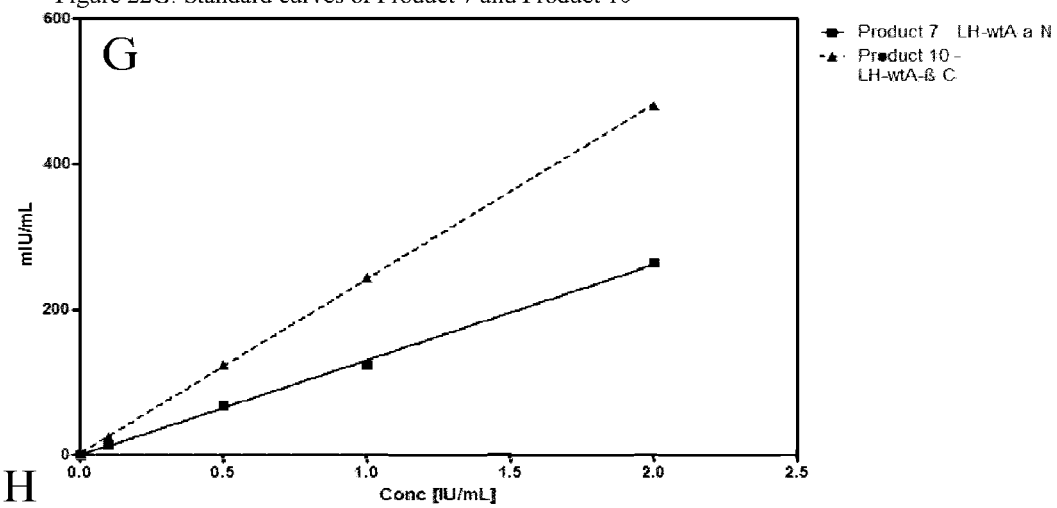
|  | Terminal half-life [h] | STD curve slope [mIU measured/IU] |
|---|---|---|
| Product 7 - LH-wtA-a-N | 37h ± 3h | 131 |
| Product 10 - LH-wtA-ß-C | 49h ± 10h | 240 |
Figure 22H: Calculation of terminal half-life for Product 7 and Product 10 in hypophysectomized male rats

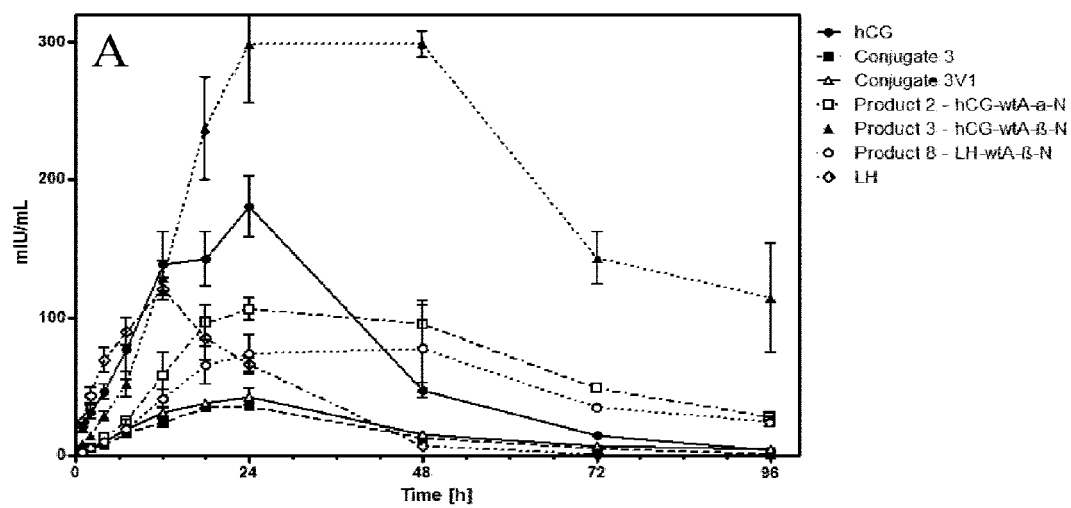
Figure 23A. PK data of hCG, Conjugate3, Conjugate3V1, Product 2, Product 3 and Product 7 in normal adult male rats.

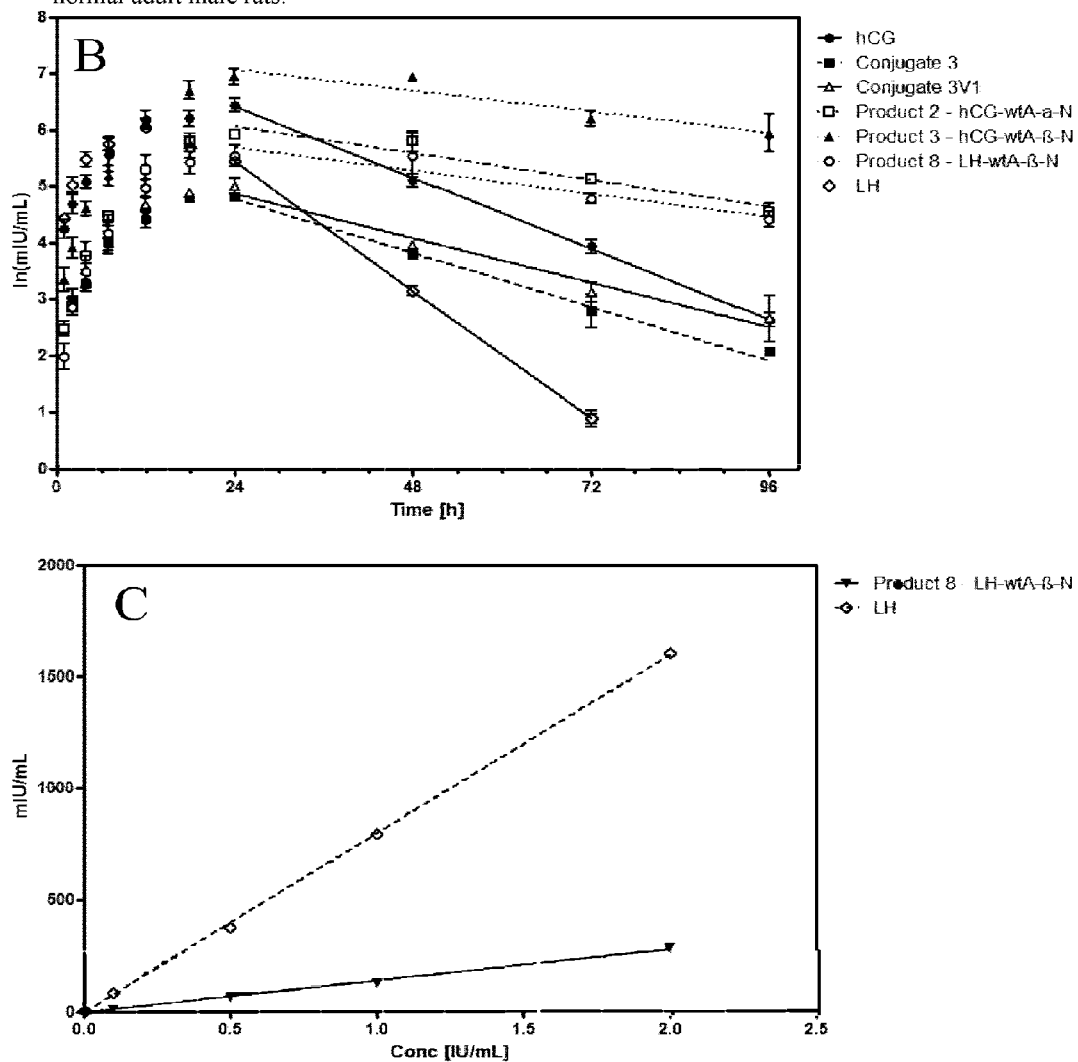
Figure 23B. PK data of hCG, Conjugate3, Conjugate3V1, Product 2, Product 3 and Product 7 in normal adult male rats.
Figure 23C: Standard curves of LH and Product 7

D

| | Terminal half-life [h] | STD curve slope [mIU measured/IU] |
|---|---|---|
| hCG | 13.2h ± 0.3h | Not determined |
| LH | 7.6h ± 0.3h | 785 |
| Conjugate3 | 17.4h ± 1.0h | Not determined |
| Conjugate3V1 | 21.1h ± 1.8h | Not determined |
| Product 2 - hCG-wtA-a-N | 35h ± 4h | Not determined |
| Product 3 - hCG-wtA-ß-N | 45h ± 7h | Not determined |
| Product 8 - LH-wtA-ß-N | 40h ± 7h | 139 |

Figure 23D: Calculation of terminal half-life for hCG, LH, Conjugate3, Conjugate3V1, Product 2, Product 3 and Product 7 in normal adult male rats

SEQUENCE LISTING

```
<160> NUMBER OF SEQ ID NOS: 71

<210> SEQ ID NO 1
<211> LENGTH: 92
<212> TYPE: PRT
<213> ORGANISM: Homo sapiens

<400> SEQUENCE: 1

Ala Pro Asp Val Gln Asp Cys Pro Glu Cys Thr Leu Gln Glu Asn Pro
1               5                   10                  15

Phe Phe Ser Gln Pro Gly Ala Pro Ile Leu Gln Cys Met Gly Cys Cys
            20                  25                  30

Phe Ser Arg Ala Tyr Pro Thr Pro Leu Arg Ser Lys Lys Thr Met Leu
        35                  40                  45

Val Gln Lys Asn Val Thr Ser Glu Ser Thr Cys Cys Val Ala Lys Ser
    50                  55                  60

Tyr Asn Arg Val Thr Val Met Gly Gly Phe Lys Val Glu Asn His Thr
65                  70                  75                  80

Ala Cys His Cys Ser Thr Cys Tyr Tyr His Lys Ser
                85                  90

<210> SEQ ID NO 2
<211> LENGTH: 96
<212> TYPE: PRT
<213> ORGANISM: Mus musculus

<400> SEQUENCE: 2
```

```
Leu Pro Asp Gly Asp Phe Ile Ile Gln Gly Cys Pro Glu Cys Lys Leu
1               5                   10                  15

Lys Glu Asn Lys Tyr Phe Ser Lys Leu Gly Ala Pro Ile Tyr Gln Cys
            20                  25                  30

Met Gly Cys Cys Phe Ser Arg Ala Tyr Pro Thr Pro Ala Arg Ser Lys
            35                  40                  45

Lys Thr Met Leu Val Pro Lys Asn Ile Thr Ser Glu Ala Thr Cys Cys
50                  55                  60

Val Ala Lys Ala Phe Thr Lys Ala Thr Val Met Gly Asn Ala Arg Val
65                  70                  75                  80

Glu Asn His Thr Glu Cys His Cys Ser Thr Cys Tyr Tyr His Lys Ser
            85                  90                  95
```

<210> SEQ ID NO 3
<211> LENGTH: 96
<212> TYPE: PRT
<213> ORGANISM: Rattus norvegicus

<400> SEQUENCE: 3

```
Leu Pro Asp Gly Asp Leu Ile Ile Gln Gly Cys Pro Glu Cys Lys Leu
1               5                   10                  15

Lys Glu Asn Lys Tyr Phe Ser Lys Leu Gly Ala Pro Ile Tyr Gln Cys
            20                  25                  30

Met Gly Cys Cys Phe Ser Arg Ala Tyr Pro Thr Pro Ala Arg Ser Lys
            35                  40                  45

Lys Thr Met Leu Val Pro Lys Asn Ile Thr Ser Glu Ala Thr Cys Cys
50                  55                  60

Val Ala Lys Ser Phe Thr Lys Ala Thr Val Met Gly Asn Ala Arg Val
65                  70                  75                  80

Glu Asn His Thr Asp Cys His Cys Ser Thr Cys Tyr Tyr His Lys Ser
            85                  90                  95
```

<210> SEQ ID NO 4
<211> LENGTH: 121
<212> TYPE: PRT
<213> ORGANISM: Homo sapiens

<400> SEQUENCE: 4

```
Ser Arg Glu Pro Leu Arg Pro Trp Cys His Pro Ile Asn Ala Ile Leu
1               5                   10                  15

Ala Val Glu Lys Glu Gly Cys Pro Val Cys Ile Thr Val Asn Thr Thr
            20                  25                  30

Ile Cys Ala Gly Tyr Cys Pro Thr Met Met Arg Val Leu Gln Ala Val
            35                  40                  45

Leu Pro Pro Leu Pro Gln Val Val Cys Thr Tyr Arg Asp Val Arg Phe
50                  55                  60

Glu Ser Ile Arg Leu Pro Gly Cys Pro Arg Gly Val Asp Pro Val Val
65                  70                  75                  80

Ser Phe Pro Val Ala Leu Ser Cys Arg Cys Gly Pro Cys Arg Arg Ser
            85                  90                  95

Thr Ser Asp Cys Gly Gly Pro Lys Asp His Pro Leu Thr Cys Asp His
            100                 105                 110

Pro Gln Leu Ser Gly Leu Leu Phe Leu
            115                 120
```

<210> SEQ ID NO 5

```
<211> LENGTH: 121
<212> TYPE: PRT
<213> ORGANISM: Mus musculus

<400> SEQUENCE: 5

Ser Arg Gly Pro Leu Arg Pro Leu Cys Arg Pro Val Asn Ala Thr Leu
1               5                   10                  15

Ala Ala Glu Asn Glu Phe Cys Pro Val Cys Ile Thr Phe Thr Thr Ser
            20                  25                  30

Ile Cys Ala Gly Tyr Cys Pro Ser Met Val Arg Val Leu Pro Ala Ala
        35                  40                  45

Leu Pro Pro Val Pro Gln Pro Val Cys Thr Tyr Arg Glu Leu Ala Phe
50                  55                  60

Ala Ser Val Arg Leu Pro Gly Cys Pro Pro Gly Val Asp Pro Ile Val
65                  70                  75                  80

Ser Phe Pro Val Ala Leu Ser Cys Arg Cys Gly Pro Cys Arg Leu Ser
                85                  90                  95

Ser Ser Asp Cys Gly Gly Pro Arg Thr Gln Pro Met Ala Cys Asp Leu
            100                 105                 110

Pro His Leu Pro Gly Leu Leu Leu Leu
            115                 120

<210> SEQ ID NO 6
<211> LENGTH: 121
<212> TYPE: PRT
<213> ORGANISM: Rattus norvegicus

<400> SEQUENCE: 6

Ser Arg Gly Pro Leu Arg Pro Leu Cys Arg Pro Val Asn Ala Thr Leu
1               5                   10                  15

Ala Ala Glu Asn Glu Phe Cys Pro Val Cys Ile Thr Phe Thr Thr Ser
            20                  25                  30

Ile Cys Ala Gly Tyr Cys Pro Ser Met Val Arg Val Leu Pro Ala Ala
        35                  40                  45

Leu Pro Pro Val Pro Gln Pro Val Cys Thr Tyr Arg Glu Leu Arg Phe
50                  55                  60

Ala Ser Val Arg Leu Pro Gly Cys Pro Pro Gly Val Asp Pro Ile Val
65                  70                  75                  80

Ser Phe Pro Val Ala Leu Ser Cys Arg Cys Gly Pro Cys Arg Leu Ser
                85                  90                  95

Ser Ser Asp Cys Gly Gly Pro Arg Thr Gln Pro Met Thr Cys Asp Leu
            100                 105                 110

Pro His Leu Pro Gly Leu Leu Leu Phe
            115                 120

<210> SEQ ID NO 7
<211> LENGTH: 121
<212> TYPE: PRT
<213> ORGANISM: Gorilla gorilla
<220> FEATURE:
<221> NAME/KEY: MOD_RES
<222> LOCATION: (68)..(68)
<223> OTHER INFORMATION: Any amino acid

<400> SEQUENCE: 7

Ser Arg Glu Pro Leu Arg Pro Arg Cys Arg Pro Ile Asn Ala Thr Leu
1               5                   10                  15

Ala Val Glu Lys Glu Gly Cys Pro Val Cys Ile Thr Val Asn Thr Thr
            20                  25                  30
```

Ile Cys Ala Gly Tyr Cys Pro Thr Met Met Arg Val Leu Gln Gly Val
            35                  40                  45

Leu Pro Pro Leu Pro Gln Val Val Cys Thr Tyr Arg Asp Val Arg Phe
 50                  55                  60

Glu Ser Ile Xaa Leu Pro Gly Cys Pro Arg Gly Val Asp Pro Met Val
65                  70                  75                  80

Ser Phe Pro Val Ala Leu Ser Cys Arg Cys Gly Pro Cys His Arg Ser
                85                  90                  95

Thr Ser Asp Cys Gly Gly Pro Asn Asp His Pro Leu Thr Cys Asp His
            100                 105                 110

Pro Gln Leu Ser Gly Leu Leu Phe Leu
        115                 120

<210> SEQ ID NO 8
<211> LENGTH: 121
<212> TYPE: PRT
<213> ORGANISM: Pan paniscus

<400> SEQUENCE: 8

Ser Arg Glu Pro Leu Arg Pro Trp Cys His Pro Ile Asn Ala Thr Leu
1               5                   10                  15

Ala Val Glu Lys Glu Gly Cys Pro Val Cys Ile Thr Val Asn Thr Thr
            20                  25                  30

Ile Cys Ala Gly Tyr Cys Pro Thr Met Met Arg Val Leu Gln Ala Val
            35                  40                  45

Leu Pro Pro Leu Pro Gln Val Val Cys Thr Tyr Arg Asp Val Arg Phe
 50                  55                  60

Glu Ser Ile Arg Leu Pro Gly Cys Pro Arg Gly Val Asp Pro Val Val
65                  70                  75                  80

Ser Phe Pro Val Ala Leu Ser Cys Arg Cys Gly Pro Cys Arg Arg Ser
                85                  90                  95

Thr Ser Asp Cys Gly Gly Pro Lys Asp His Pro Leu Thr Cys Asp His
            100                 105                 110

Pro Gln Leu Ser Gly Leu Leu Phe Leu
        115                 120

<210> SEQ ID NO 9
<211> LENGTH: 145
<212> TYPE: PRT
<213> ORGANISM: Homo sapiens

<400> SEQUENCE: 9

Ser Lys Glu Pro Leu Arg Pro Arg Cys Arg Pro Ile Asn Ala Thr Leu
1               5                   10                  15

Ala Val Glu Lys Glu Gly Cys Pro Val Cys Ile Thr Val Asn Thr Thr
            20                  25                  30

Ile Cys Ala Gly Tyr Cys Pro Thr Met Thr Arg Val Leu Gln Gly Val
            35                  40                  45

Leu Pro Ala Leu Pro Gln Val Val Cys Asn Tyr Arg Asp Val Arg Phe
 50                  55                  60

Glu Ser Ile Arg Leu Pro Gly Cys Pro Arg Gly Val Asn Pro Val Val
65                  70                  75                  80

Ser Tyr Ala Val Ala Leu Ser Cys Gln Cys Ala Leu Cys Arg Arg Ser
                85                  90                  95

Thr Thr Asp Cys Gly Gly Pro Lys Asp His Pro Leu Thr Cys Asp Asp
            100                 105                 110

```
Pro Arg Phe Gln Asp Ser Ser Ser Lys Ala Pro Pro Ser Leu
        115                 120                 125
Pro Ser Pro Ser Arg Leu Pro Gly Pro Ser Asp Thr Pro Ile Leu Pro
    130                 135                 140
Gln
145

<210> SEQ ID NO 10
<211> LENGTH: 111
<212> TYPE: PRT
<213> ORGANISM: Homo sapiens

<400> SEQUENCE: 10

Asn Ser Cys Glu Leu Thr Asn Ile Thr Ile Ala Ile Glu Lys Glu Glu
1               5                   10                  15
Cys Arg Phe Cys Ile Ser Ile Asn Thr Thr Trp Cys Ala Gly Tyr Cys
                20                  25                  30
Tyr Thr Arg Asp Leu Val Tyr Lys Asp Pro Ala Arg Pro Lys Ile Gln
            35                  40                  45
Lys Thr Cys Thr Phe Lys Glu Leu Val Tyr Glu Thr Val Arg Val Pro
        50                  55                  60
Gly Cys Ala His His Ala Asp Ser Leu Tyr Thr Tyr Pro Val Ala Thr
65                  70                  75                  80
Gln Cys His Cys Gly Lys Cys Asp Ser Asp Ser Thr Asp Cys Thr Val
                85                  90                  95
Arg Gly Leu Gly Pro Ser Tyr Cys Ser Phe Gly Glu Met Lys Glu
            100                 105                 110

<210> SEQ ID NO 11
<211> LENGTH: 110
<212> TYPE: PRT
<213> ORGANISM: Mus musculus

<400> SEQUENCE: 11

Ser Cys Glu Leu Thr Asn Ile Thr Ile Ser Val Glu Lys Glu Glu Cys
1               5                   10                  15
Arg Phe Cys Ile Ser Ile Asn Thr Thr Trp Cys Ala Gly Tyr Cys Tyr
                20                  25                  30
Thr Arg Asp Leu Val Tyr Lys Asp Pro Ala Arg Pro Asn Thr Gln Lys
            35                  40                  45
Val Cys Thr Phe Lys Glu Leu Val Tyr Glu Thr Val Arg Leu Pro Gly
        50                  55                  60
Cys Ala Arg His Ser Asp Ser Leu Tyr Thr Tyr Pro Val Ala Thr Glu
65                  70                  75                  80
Cys His Cys Gly Lys Cys Asp Ser Asp Ser Thr Asp Cys Thr Val Arg
                85                  90                  95
Gly Leu Gly Pro Ser Tyr Cys Ser Phe Ser Glu Met Lys Glu
            100                 105                 110

<210> SEQ ID NO 12
<211> LENGTH: 110
<212> TYPE: PRT
<213> ORGANISM: Rattus norvegicus

<400> SEQUENCE: 12

Ser Cys Glu Leu Thr Asn Ile Thr Ile Ser Val Glu Lys Glu Glu Cys
1               5                   10                  15
```

Arg Phe Cys Ile Ser Ile Asn Thr Thr Trp Cys Glu Gly Tyr Cys Tyr
            20                  25                  30

Thr Arg Asp Leu Val Tyr Lys Asp Pro Ala Arg Pro Asn Thr Gln Lys
        35                  40                  45

Val Cys Thr Phe Lys Glu Leu Val Tyr Glu Thr Ile Arg Leu Pro Gly
 50                  55                  60

Cys Ala Arg His Ser Asp Ser Leu Tyr Thr Tyr Pro Val Ala Thr Glu
65              70                  75                  80

Cys His Cys Gly Lys Cys Asp Ser Asp Ser Thr Asp Cys Thr Val Arg
            85                  90                  95

Gly Leu Gly Pro Ser Tyr Cys Ser Phe Gly Glu Met Lys Glu
            100                 105                 110

<210> SEQ ID NO 13
<211> LENGTH: 109
<212> TYPE: PRT
<213> ORGANISM: Gorilla gorilla

<400> SEQUENCE: 13

Cys Glu Leu Thr Asn Ile Thr Ile Ala Ile Glu Lys Glu Glu Cys Arg
1               5                   10                  15

Phe Cys Ile Ser Ile Asn Thr Thr Trp Cys Ala Gly Tyr Cys Tyr Thr
            20                  25                  30

Arg Asp Leu Val Tyr Lys Asp Pro Ala Arg Pro Asn Ile Gln Lys Thr
        35                  40                  45

Cys Thr Phe Lys Glu Leu Val Tyr Glu Thr Val Arg Val Pro Gly Cys
 50                  55                  60

Ala His His Ala Asp Ser Leu Tyr Thr Tyr Pro Val Ala Thr Gln Cys
65              70                  75                  80

His Cys Gly Lys Cys Asp Ser Asp Ser Thr Asp Cys Thr Val Arg Gly
            85                  90                  95

Leu Gly Pro Ser Tyr Cys Ser Phe Gly Glu Met Lys Glu
            100                 105

<210> SEQ ID NO 14
<211> LENGTH: 109
<212> TYPE: PRT
<213> ORGANISM: Pan paniscus

<400> SEQUENCE: 14

Cys Glu Leu Thr Asn Ile Thr Ile Ala Ile Glu Lys Glu Glu Cys Arg
1               5                   10                  15

Phe Cys Ile Ser Ile Asn Thr Thr Trp Cys Ala Gly His Cys Tyr Thr
            20                  25                  30

Arg Asp Leu Val Tyr Lys Asp Pro Ala Arg Pro Asn Ile Gln Lys Thr
        35                  40                  45

Cys Thr Phe Lys Glu Leu Val Tyr Glu Thr Val Arg Val Pro Gly Cys
 50                  55                  60

Ala His His Ala Asp Ser Leu Tyr Thr Tyr Pro Val Ala Thr Gln Cys
65              70                  75                  80

His Cys Gly Lys Cys Asp Ser Asp Ser Thr Asp Cys Thr Val Arg Gly
            85                  90                  95

Leu Gly Pro Ser Tyr Cys Ser Phe Gly Glu Met Lys Glu
            100                 105

<210> SEQ ID NO 15
<211> LENGTH: 139

```
<212> TYPE: PRT
<213> ORGANISM: Artificial Sequence
<220> FEATURE:
<223> OTHER INFORMATION: Description of Artificial Sequence: Synthetic
      Fusion between human FSHB and the C-terminal 28 amino acids
      of hCG sequence

<400> SEQUENCE: 15
```

Asn Ser Cys Glu Leu Thr Asn Ile Thr Ile Ala Ile Glu Lys Glu Glu
1               5                   10                  15

Cys Arg Phe Cys Ile Ser Ile Asn Thr Thr Trp Cys Ala Gly Tyr Cys
            20                  25                  30

Tyr Thr Arg Asp Leu Val Tyr Lys Asp Pro Ala Arg Pro Lys Ile Gln
        35                  40                  45

Lys Thr Cys Thr Phe Lys Glu Leu Val Tyr Glu Thr Val Arg Val Pro
    50                  55                  60

Gly Cys Ala His His Ala Asp Ser Leu Tyr Thr Tyr Pro Val Ala Thr
65                  70                  75                  80

Gln Cys His Cys Gly Lys Cys Asp Ser Asp Ser Thr Asp Cys Thr Val
                85                  90                  95

Arg Gly Leu Gly Pro Ser Tyr Cys Ser Phe Gly Glu Met Lys Glu Ser
            100                 105                 110

Ser Ser Ser Lys Ala Pro Pro Pro Ser Leu Pro Ser Pro Ser Arg Leu
        115                 120                 125

Pro Gly Pro Ser Asp Thr Pro Ile Leu Pro Gln
    130                 135

```
<210> SEQ ID NO 16
<211> LENGTH: 116
<212> TYPE: PRT
<213> ORGANISM: Homo sapiens

<400> SEQUENCE: 16
```

Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Gln Asp Cys Pro
            20                  25                  30

Glu Cys Thr Leu Gln Glu Asn Pro Phe Phe Ser Gln Pro Gly Ala Pro
        35                  40                  45

Ile Leu Gln Cys Met Gly Cys Cys Phe Ser Arg Ala Tyr Pro Thr Pro
    50                  55                  60

Leu Arg Ser Lys Lys Thr Met Leu Val Gln Lys Asn Val Thr Ser Glu
65                  70                  75                  80

Ser Thr Cys Cys Val Ala Lys Ser Tyr Asn Arg Val Thr Val Met Gly
                85                  90                  95

Gly Phe Lys Val Glu Asn His Thr Ala Cys His Cys Ser Thr Cys Tyr
            100                 105                 110

Tyr His Lys Ser
        115

```
<210> SEQ ID NO 17
<211> LENGTH: 165
<212> TYPE: PRT
<213> ORGANISM: Homo sapiens

<400> SEQUENCE: 17
```

Met Glu Met Phe Gln Gly Leu Leu Leu Leu Leu Leu Leu Ser Met Gly
1               5                   10                  15

```
Gly Thr Trp Ala Ser Lys Glu Pro Leu Arg Pro Arg Cys Arg Pro Ile
                20                  25                  30

Asn Ala Thr Leu Ala Val Glu Lys Glu Gly Cys Pro Val Cys Ile Thr
            35                  40                  45

Val Asn Thr Thr Ile Cys Ala Gly Tyr Cys Pro Thr Met Thr Arg Val
 50                  55                  60

Leu Gln Gly Val Leu Pro Ala Leu Pro Gln Val Val Cys Asn Tyr Arg
 65                  70                  75                  80

Asp Val Arg Phe Glu Ser Ile Arg Leu Pro Gly Cys Pro Arg Gly Val
                85                  90                  95

Asn Pro Val Val Ser Tyr Ala Val Ala Leu Ser Cys Gln Cys Ala Leu
            100                 105                 110

Cys Arg Arg Ser Thr Thr Asp Cys Gly Gly Pro Lys Asp His Pro Leu
        115                 120                 125

Thr Cys Asp Asp Pro Arg Phe Gln Asp Ser Ser Ser Lys Ala Pro
130                 135                 140

Pro Pro Ser Leu Pro Ser Pro Ser Arg Leu Pro Gly Pro Ser Asp Thr
145                 150                 155                 160

Pro Ile Leu Pro Gln
                165

<210> SEQ ID NO 18
<211> LENGTH: 141
<212> TYPE: PRT
<213> ORGANISM: Homo sapiens

<400> SEQUENCE: 18

Met Glu Met Leu Gln Gly Leu Leu Leu Leu Leu Leu Ser Met Gly
 1                5                  10                  15

Gly Ala Trp Ala Ser Arg Glu Pro Leu Arg Pro Trp Cys His Pro Ile
                20                  25                  30

Asn Ala Ile Leu Ala Val Glu Lys Glu Gly Cys Pro Val Cys Ile Thr
            35                  40                  45

Val Asn Thr Thr Ile Cys Ala Gly Tyr Cys Pro Thr Met Met Arg Val
 50                  55                  60

Leu Gln Ala Val Leu Pro Pro Leu Pro Gln Val Val Cys Thr Tyr Arg
 65                  70                  75                  80

Asp Val Arg Phe Glu Ser Ile Arg Leu Pro Gly Cys Pro Arg Gly Val
                85                  90                  95

Asp Pro Val Val Ser Phe Pro Val Ala Leu Ser Cys Arg Cys Gly Pro
            100                 105                 110

Cys Arg Arg Ser Thr Ser Asp Cys Gly Gly Pro Lys Asp His Pro Leu
        115                 120                 125

Thr Cys Asp His Pro Gln Leu Ser Gly Leu Leu Phe Leu
130                 135                 140

<210> SEQ ID NO 19
<211> LENGTH: 609
<212> TYPE: PRT
<213> ORGANISM: Homo sapiens

<400> SEQUENCE: 19

Met Lys Trp Val Thr Phe Ile Ser Leu Leu Phe Leu Phe Ser Ser Ala
 1                5                  10                  15

Tyr Ser Arg Gly Val Phe Arg Arg Asp Ala His Lys Ser Glu Val Ala
                20                  25                  30
```

His Arg Phe Lys Asp Leu Gly Glu Glu Asn Phe Lys Ala Leu Val Leu
         35                  40                  45

Ile Ala Phe Ala Gln Tyr Leu Gln Gln Cys Pro Phe Glu Asp His Val
         50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                 85                  90                  95

Lys Leu Cys Thr Val Ala Thr Leu Arg Glu Thr Tyr Gly Glu Met Ala
             100                 105                 110

Asp Cys Cys Ala Lys Gln Glu Pro Glu Arg Asn Glu Cys Phe Leu Gln
         115                 120                 125

His Lys Asp Asp Asn Pro Asn Leu Pro Arg Leu Val Arg Pro Glu Val
     130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                 165                 170                 175

Glu Leu Leu Phe Phe Ala Lys Arg Tyr Lys Ala Ala Phe Thr Glu Cys
             180                 185                 190

Cys Gln Ala Ala Asp Lys Ala Ala Cys Leu Leu Pro Lys Leu Asp Glu
         195                 200                 205

Leu Arg Asp Glu Gly Lys Ala Ser Ser Ala Lys Gln Arg Leu Lys Cys
     210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                 245                 250                 255

Lys Leu Val Thr Asp Leu Thr Lys Val His Thr Glu Cys Cys His Gly
             260                 265                 270

Asp Leu Leu Glu Cys Ala Asp Asp Arg Ala Asp Leu Ala Lys Tyr Ile
         275                 280                 285

Cys Glu Asn Gln Asp Ser Ile Ser Ser Lys Leu Lys Glu Cys Cys Glu
     290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                 325                 330                 335

Lys Asp Val Cys Lys Asn Tyr Ala Glu Ala Lys Asp Val Phe Leu Gly
             340                 345                 350

Met Phe Leu Tyr Glu Tyr Ala Arg Arg His Pro Asp Tyr Ser Val Val
         355                 360                 365

Leu Leu Leu Arg Leu Ala Lys Thr Tyr Glu Thr Thr Leu Glu Lys Cys
     370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                 405                 410                 415

Glu Leu Phe Glu Gln Leu Gly Glu Tyr Lys Phe Gln Asn Ala Leu Leu
             420                 425                 430

Val Arg Tyr Thr Lys Lys Val Pro Gln Val Ser Thr Pro Thr Leu Val
         435                 440                 445

Glu Val Ser Arg Asn Leu Gly Lys Val Gly Ser Lys Cys Cys Lys His

```
               450                 455                 460
Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
                500                 505                 510

Ser Ala Leu Glu Val Asp Glu Thr Tyr Val Pro Lys Glu Phe Asn Ala
                515                 520                 525

Glu Thr Phe Thr Phe His Ala Asp Ile Cys Thr Leu Ser Glu Lys Glu
                530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
                580                 585                 590

Ala Glu Glu Gly Lys Lys Leu Val Ala Ala Ser Gln Ala Ala Leu Gly
                595                 600                 605

Leu

<210> SEQ ID NO 20
<211> LENGTH: 585
<212> TYPE: PRT
<213> ORGANISM: Homo sapiens

<400> SEQUENCE: 20

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
                35                  40                  45

Phe Ala Lys Thr Cys Val Ala Asp Glu Ser Ala Glu Asn Cys Asp Lys
                50                  55                  60

Ser Leu His Thr Leu Phe Gly Asp Lys Leu Cys Thr Val Ala Thr Leu
65              70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
                100                 105                 110

Pro Arg Leu Val Arg Pro Glu Val Asp Val Met Cys Thr Ala Phe His
                115                 120                 125

Asp Asn Glu Glu Thr Phe Leu Lys Lys Tyr Leu Tyr Glu Ile Ala Arg
                130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
                180                 185                 190

Ser Ala Lys Gln Arg Leu Lys Cys Ala Ser Leu Gln Lys Phe Gly Glu
                195                 200                 205

Arg Ala Phe Lys Ala Trp Ala Val Ala Arg Leu Ser Gln Arg Phe Pro
```

```
                    210                 215                 220
Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                    245                 250                 255

Arg Ala Asp Leu Ala Lys Tyr Ile Cys Glu Asn Gln Asp Ser Ile Ser
                260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
                340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
    530                 535                 540

Lys Ala Val Met Asp Asp Phe Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
                580                 585

<210> SEQ ID NO 21
<211> LENGTH: 585
<212> TYPE: PRT
<213> ORGANISM: Artificial Sequence
<220> FEATURE:
<223> OTHER INFORMATION: Description of Artificial Sequence: Synthetic
      Human serum albumin K573P variant sequence
```

<400> SEQUENCE: 21

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
```

```
                        405                 410                 415
Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Pro Lys Leu Val
                565                 570                 575

Ala Ala Ser Gln Ala Ala Leu Gly Leu
            580                 585

<210> SEQ ID NO 22
<211> LENGTH: 227
<212> TYPE: PRT
<213> ORGANISM: Homo sapiens

<400> SEQUENCE: 22

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190
```

```
Asp Lys Ser Arg Trp Gln Gln Gly Asn Val Phe Ser Cys Ser Val Met
        195                 200                 205
His Glu Ala Leu His Asn His Tyr Thr Gln Lys Ser Leu Ser Leu Ser
    210                 215                 220
Pro Gly Lys
225

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      linker sequence

<400> SEQUENCE: 23

Gly Gly Gly Gly Ser Gly Gly Gly Gly Ser Gly Gly Gly Gly Ser
1               5                   10                  15

<210> SEQ ID NO 24
<211> LENGTH: 242
<212> TYPE: PRT
<213> ORGANISM: Artificial Sequence
<220> FEATURE:
<223> OTHER INFORMATION: Description of Artificial Sequence: Synthetic
      linker + human Fc sequence

<400> SEQUENCE: 24

Gly Gly Gly Gly Ser Gly Gly Gly Gly Ser Gly Gly Gly Gly Ser Asp
1               5                   10                  15
Lys Thr His Thr Cys Pro Pro Cys Pro Ala Pro Glu Leu Leu Gly Gly
            20                  25                  30
Pro Ser Val Phe Leu Phe Pro Pro Lys Pro Lys Asp Thr Leu Met Ile
        35                  40                  45
Ser Arg Thr Pro Glu Val Thr Cys Val Val Val Asp Val Ser His Glu
    50                  55                  60
Asp Pro Glu Val Lys Phe Asn Trp Tyr Val Asp Gly Val Glu Val His
65                  70                  75                  80
Asn Ala Lys Thr Lys Pro Arg Glu Glu Gln Tyr Asn Ser Thr Tyr Arg
                85                  90                  95
Val Val Ser Val Leu Thr Val Leu His Gln Asp Trp Leu Asn Gly Lys
            100                 105                 110
Glu Tyr Lys Cys Lys Val Ser Asn Lys Ala Leu Pro Ala Pro Ile Glu
        115                 120                 125
Lys Thr Ile Ser Lys Ala Lys Gly Gln Pro Arg Glu Pro Gln Val Tyr
    130                 135                 140
Thr Leu Pro Pro Ser Arg Asp Glu Leu Thr Lys Asn Gln Val Ser Leu
145                 150                 155                 160
Thr Cys Leu Val Lys Gly Phe Tyr Pro Ser Asp Ile Ala Val Glu Trp
                165                 170                 175
Glu Ser Asn Gly Gln Pro Glu Asn Asn Tyr Lys Thr Thr Pro Pro Val
            180                 185                 190
Leu Asp Ser Asp Gly Ser Phe Phe Leu Tyr Ser Lys Leu Thr Val Asp
        195                 200                 205
Lys Ser Arg Trp Gln Gln Gly Asn Val Phe Ser Cys Ser Val Met His
    210                 215                 220
Glu Ala Leu His Asn His Tyr Thr Gln Lys Ser Leu Ser Leu Ser Pro
225                 230                 235                 240
```

Gly Lys

<210> SEQ ID NO 25
<211> LENGTH: 248
<212> TYPE: PRT
<213> ORGANISM: Artificial Sequence
<220> FEATURE:
<223> OTHER INFORMATION: Description of Artificial Sequence: Synthetic
      Linker + Fc + His-tag sequence

<400> SEQUENCE: 25

Gly Gly Gly Gly Ser Gly Gly Gly Ser Gly Gly Gly Gly Ser Asp
1               5                   10                  15

Lys Thr His Thr Cys Pro Pro Cys Pro Ala Pro Glu Leu Leu Gly Gly
                20                  25                  30

Pro Ser Val Phe Leu Phe Pro Pro Lys Pro Lys Asp Thr Leu Met Ile
            35                  40                  45

Ser Arg Thr Pro Glu Val Thr Cys Val Val Val Asp Val Ser His Glu
        50                  55                  60

Asp Pro Glu Val Lys Phe Asn Trp Tyr Val Asp Gly Val Glu Val His
65                  70                  75                  80

Asn Ala Lys Thr Lys Pro Arg Glu Glu Gln Tyr Asn Ser Thr Tyr Arg
                85                  90                  95

Val Val Ser Val Leu Thr Val Leu His Gln Asp Trp Leu Asn Gly Lys
            100                 105                 110

Glu Tyr Lys Cys Lys Val Ser Asn Lys Ala Leu Pro Ala Pro Ile Glu
        115                 120                 125

Lys Thr Ile Ser Lys Ala Lys Gly Gln Pro Arg Glu Pro Gln Val Tyr
130                 135                 140

Thr Leu Pro Pro Ser Arg Asp Glu Leu Thr Lys Asn Gln Val Ser Leu
145                 150                 155                 160

Thr Cys Leu Val Lys Gly Phe Tyr Pro Ser Asp Ile Ala Val Glu Trp
                165                 170                 175

Glu Ser Asn Gly Gln Pro Glu Asn Asn Tyr Lys Thr Thr Pro Pro Val
            180                 185                 190

Leu Asp Ser Asp Gly Ser Phe Phe Leu Tyr Ser Lys Leu Thr Val Asp
        195                 200                 205

Lys Ser Arg Trp Gln Gln Gly Asn Val Phe Ser Cys Ser Val Met His
    210                 215                 220

Glu Ala Leu His Asn His Tyr Thr Gln Lys Ser Leu Ser Leu Ser Pro
225                 230                 235                 240

Gly Lys His His His His His His
                245

<210> SEQ ID NO 26
<211> LENGTH: 677
<212> TYPE: PRT
<213> ORGANISM: Artificial Sequence
<220> FEATURE:
<223> OTHER INFORMATION: Description of Artificial Sequence: Synthetic
      Mature wt Albumin + alpha-chain sequence

<400> SEQUENCE: 26

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu

```
                 35                  40                  45
Phe Ala Lys Thr Cys Val Ala Asp Glu Ser Ala Glu Asn Cys Asp Lys
         50                  55                  60

Ser Leu His Thr Leu Phe Gly Asp Lys Leu Cys Thr Val Ala Thr Leu
 65                  70                  75                  80

Arg Glu Thr Tyr Gly Glu Met Ala Asp Cys Cys Ala Lys Gln Glu Pro
                 85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
        130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
                180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
450                 455                 460
```

```
Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
            485                 490                 495

Tyr Val Pro Lys Glu Phe Asn Ala Glu Thr Phe Thr Phe His Ala Asp
        500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
            565                 570                 575

Ala Ala Ser Gln Ala Ala Leu Gly Leu Ala Pro Asp Val Gln Asp Cys
        580                 585                 590

Pro Glu Cys Thr Leu Gln Glu Asn Pro Phe Phe Ser Gln Pro Gly Ala
        595                 600                 605

Pro Ile Leu Gln Cys Met Gly Cys Cys Phe Ser Arg Ala Tyr Pro Thr
        610                 615                 620

Pro Leu Arg Ser Lys Lys Thr Met Leu Val Gln Lys Asn Val Thr Ser
625                 630                 635                 640

Glu Ser Thr Cys Cys Val Ala Lys Ser Tyr Asn Arg Val Thr Val Met
            645                 650                 655

Gly Gly Phe Lys Val Glu Asn His Thr Ala Cys His Cys Ser Thr Cys
        660                 665                 670

Tyr Tyr His Lys Ser
        675

<210> SEQ ID NO 27
<211> LENGTH: 677
<212> TYPE: PRT
<213> ORGANISM: Artificial Sequence
<220> FEATURE:
<223> OTHER INFORMATION: Description of Artificial Sequence: Synthetic
      Mature alpha-chain + wt Albumin sequence

<400> SEQUENCE: 27

Ala Pro Asp Val Gln Asp Cys Pro Glu Cys Thr Leu Gln Glu Asn Pro
1               5                   10                  15

Phe Phe Ser Gln Pro Gly Ala Pro Ile Leu Gln Cys Met Gly Cys Cys
            20                  25                  30

Phe Ser Arg Ala Tyr Pro Thr Pro Leu Arg Ser Lys Lys Thr Met Leu
        35                  40                  45

Val Gln Lys Asn Val Thr Ser Glu Ser Thr Cys Cys Val Ala Lys Ser
    50                  55                  60

Tyr Asn Arg Val Thr Val Met Gly Gly Phe Lys Val Glu Asn His Thr
65                  70                  75                  80

Ala Cys His Cys Ser Thr Cys Tyr Tyr His Lys Ser Asp Ala His Lys
            85                  90                  95

Ser Glu Val Ala His Arg Phe Lys Asp Leu Gly Glu Glu Asn Phe Lys
        100                 105                 110

Ala Leu Val Leu Ile Ala Phe Ala Gln Tyr Leu Gln Gln Cys Pro Phe
        115                 120                 125

Glu Asp His Val Lys Leu Val Asn Glu Val Thr Glu Phe Ala Lys Thr
```

```
               130                 135                 140
Cys Val Ala Asp Glu Ser Ala Glu Asn Cys Asp Lys Ser Leu His Thr
145                 150                 155                 160

Leu Phe Gly Asp Lys Leu Cys Thr Val Ala Thr Leu Arg Glu Thr Tyr
                165                 170                 175

Gly Glu Met Ala Asp Cys Cys Ala Lys Gln Glu Pro Glu Arg Asn Glu
                180                 185                 190

Cys Phe Leu Gln His Lys Asp Asp Asn Pro Asn Leu Pro Arg Leu Val
                195                 200                 205

Arg Pro Glu Val Asp Val Met Cys Thr Ala Phe His Asp Asn Glu Glu
210                 215                 220

Thr Phe Leu Lys Lys Tyr Leu Tyr Glu Ile Ala Arg Arg His Pro Tyr
225                 230                 235                 240

Phe Tyr Ala Pro Glu Leu Leu Phe Phe Ala Lys Arg Tyr Lys Ala Ala
                245                 250                 255

Phe Thr Glu Cys Cys Gln Ala Ala Asp Lys Ala Ala Cys Leu Leu Pro
                260                 265                 270

Lys Leu Asp Glu Leu Arg Asp Glu Gly Lys Ala Ser Ser Ala Lys Gln
                275                 280                 285

Arg Leu Lys Cys Ala Ser Leu Gln Lys Phe Gly Glu Arg Ala Phe Lys
                290                 295                 300

Ala Trp Ala Val Ala Arg Leu Ser Gln Arg Phe Pro Lys Ala Glu Phe
305                 310                 315                 320

Ala Glu Val Ser Lys Leu Val Thr Asp Leu Thr Lys Val His Thr Glu
                325                 330                 335

Cys Cys His Gly Asp Leu Leu Glu Cys Ala Asp Asp Arg Ala Asp Leu
                340                 345                 350

Ala Lys Tyr Ile Cys Glu Asn Gln Asp Ser Ile Ser Ser Lys Leu Lys
                355                 360                 365

Glu Cys Cys Glu Lys Pro Leu Leu Glu Lys Ser His Cys Ile Ala Glu
                370                 375                 380

Val Glu Asn Asp Glu Met Pro Ala Asp Leu Pro Ser Leu Ala Ala Asp
385                 390                 395                 400

Phe Val Glu Ser Lys Asp Val Cys Lys Asn Tyr Ala Glu Ala Lys Asp
                405                 410                 415

Val Phe Leu Gly Met Phe Leu Tyr Glu Tyr Ala Arg Arg His Pro Asp
                420                 425                 430

Tyr Ser Val Val Leu Leu Leu Arg Leu Ala Lys Thr Tyr Glu Thr Thr
                435                 440                 445

Leu Glu Lys Cys Cys Ala Ala Ala Asp Pro His Glu Cys Tyr Ala Lys
450                 455                 460

Val Phe Asp Glu Phe Lys Pro Leu Val Glu Glu Pro Gln Asn Leu Ile
465                 470                 475                 480

Lys Gln Asn Cys Glu Leu Phe Glu Gln Leu Gly Glu Tyr Lys Phe Gln
                485                 490                 495

Asn Ala Leu Leu Val Arg Tyr Thr Lys Lys Val Pro Gln Val Ser Thr
                500                 505                 510

Pro Thr Leu Val Glu Val Ser Arg Asn Leu Gly Lys Val Gly Ser Lys
                515                 520                 525

Cys Cys Lys His Pro Glu Ala Lys Arg Met Pro Cys Ala Glu Asp Tyr
                530                 535                 540

Leu Ser Val Val Leu Asn Gln Leu Cys Val Leu His Glu Lys Thr Pro
545                 550                 555                 560
```

```
Val Ser Asp Arg Val Thr Lys Cys Cys Thr Glu Ser Leu Val Asn Arg
                565                 570                 575

Arg Pro Cys Phe Ser Ala Leu Glu Val Asp Glu Thr Tyr Val Pro Lys
                580                 585                 590

Glu Phe Asn Ala Glu Thr Phe Thr Phe His Ala Asp Ile Cys Thr Leu
                595                 600                 605

Ser Glu Lys Glu Arg Gln Ile Lys Lys Gln Thr Ala Leu Val Glu Leu
            610                 615                 620

Val Lys His Lys Pro Lys Ala Thr Lys Glu Gln Leu Lys Ala Val Met
625                 630                 635                 640

Asp Asp Phe Ala Ala Phe Val Glu Lys Cys Cys Lys Ala Asp Asp Lys
                645                 650                 655

Glu Thr Cys Phe Ala Glu Glu Gly Lys Lys Leu Val Ala Ala Ser Gln
                660                 665                 670

Ala Ala Leu Gly Leu
            675

<210> SEQ ID NO 28
<211> LENGTH: 730
<212> TYPE: PRT
<213> ORGANISM: Artificial Sequence
<220> FEATURE:
<223> OTHER INFORMATION: Description of Artificial Sequence: Synthetic
      Mature human Albumin + hCG beta-chain sequence

<400> SEQUENCE: 28

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
```

-continued

```
                225                 230                 235                 240
            Val His Thr Glu Cys Cys His Gly Asp Leu Leu Glu Cys Ala Asp Asp
                            245                 250                 255
            Arg Ala Asp Leu Ala Lys Tyr Ile Cys Glu Asn Gln Asp Ser Ile Ser
                            260                 265                 270
            Ser Lys Leu Lys Glu Cys Cys Glu Lys Pro Leu Leu Glu Lys Ser His
                            275                 280                 285
            Cys Ile Ala Glu Val Glu Asn Asp Glu Met Pro Ala Asp Leu Pro Ser
                            290                 295                 300
            Leu Ala Ala Asp Phe Val Glu Ser Lys Asp Val Cys Lys Asn Tyr Ala
            305                 310                 315                 320
            Glu Ala Lys Asp Val Phe Leu Gly Met Phe Leu Tyr Glu Tyr Ala Arg
                            325                 330                 335
            Arg His Pro Asp Tyr Ser Val Val Leu Leu Leu Arg Leu Ala Lys Thr
                            340                 345                 350
            Tyr Glu Thr Thr Leu Glu Lys Cys Cys Ala Ala Ala Asp Pro His Glu
                            355                 360                 365
            Cys Tyr Ala Lys Val Phe Asp Glu Phe Lys Pro Leu Val Glu Glu Pro
                            370                 375                 380
            Gln Asn Leu Ile Lys Gln Asn Cys Glu Leu Phe Glu Gln Leu Gly Glu
            385                 390                 395                 400
            Tyr Lys Phe Gln Asn Ala Leu Leu Val Arg Tyr Thr Lys Lys Val Pro
                            405                 410                 415
            Gln Val Ser Thr Pro Thr Leu Val Glu Val Ser Arg Asn Leu Gly Lys
                            420                 425                 430
            Val Gly Ser Lys Cys Cys Lys His Pro Glu Ala Lys Arg Met Pro Cys
                            435                 440                 445
            Ala Glu Asp Tyr Leu Ser Val Val Leu Asn Gln Leu Cys Val Leu His
                            450                 455                 460
            Glu Lys Thr Pro Val Ser Asp Arg Val Thr Lys Cys Cys Thr Glu Ser
            465                 470                 475                 480
            Leu Val Asn Arg Arg Pro Cys Phe Ser Ala Leu Glu Val Asp Glu Thr
                            485                 490                 495
            Tyr Val Pro Lys Glu Phe Asn Ala Glu Thr Phe Thr Phe His Ala Asp
                            500                 505                 510
            Ile Cys Thr Leu Ser Glu Lys Glu Arg Gln Ile Lys Lys Gln Thr Ala
                            515                 520                 525
            Leu Val Glu Leu Val Lys His Lys Pro Lys Ala Thr Lys Glu Gln Leu
            530                 535                 540
            Lys Ala Val Met Asp Asp Phe Ala Ala Phe Val Glu Lys Cys Cys Lys
            545                 550                 555                 560
            Ala Asp Asp Lys Glu Thr Cys Phe Ala Glu Gly Lys Lys Leu Val
                            565                 570                 575
            Ala Ala Ser Gln Ala Ala Leu Gly Leu Ser Lys Glu Pro Leu Arg Pro
                            580                 585                 590
            Arg Cys Arg Pro Ile Asn Ala Thr Leu Ala Val Glu Lys Glu Gly Cys
                            595                 600                 605
            Pro Val Cys Ile Thr Val Asn Thr Thr Ile Cys Ala Gly Tyr Cys Pro
                            610                 615                 620
            Thr Met Thr Arg Val Leu Gln Gly Val Leu Pro Ala Leu Pro Gln Val
            625                 630                 635                 640
            Val Cys Asn Tyr Arg Asp Val Arg Phe Glu Ser Ile Arg Leu Pro Gly
                            645                 650                 655
```

Cys Pro Arg Gly Val Asn Pro Val Val Ser Tyr Ala Val Ala Leu Ser
            660                 665                 670

Cys Gln Cys Ala Leu Cys Arg Arg Ser Thr Thr Asp Cys Gly Gly Pro
            675                 680                 685

Lys Asp His Pro Leu Thr Cys Asp Asp Pro Arg Phe Gln Asp Ser Ser
            690                 695                 700

Ser Ser Lys Ala Pro Pro Ser Leu Pro Ser Pro Ser Arg Leu Pro
705                 710                 715                 720

Gly Pro Ser Asp Thr Pro Ile Leu Pro Gln
            725                 730

<210> SEQ ID NO 29
<211> LENGTH: 730
<212> TYPE: PRT
<213> ORGANISM: Artificial Sequence
<220> FEATURE:
<223> OTHER INFORMATION: Description of Artificial Sequence: Synthetic
      Mature human hCG beta-chain + wt human Albumin sequence

<400> SEQUENCE: 29

Ser Lys Glu Pro Leu Arg Pro Arg Cys Arg Pro Ile Asn Ala Thr Leu
1               5                   10                  15

Ala Val Glu Lys Glu Gly Cys Pro Val Cys Ile Thr Val Asn Thr Thr
            20                  25                  30

Ile Cys Ala Gly Tyr Cys Pro Thr Met Thr Arg Val Leu Gln Gly Val
        35                  40                  45

Leu Pro Ala Leu Pro Gln Val Val Cys Asn Tyr Arg Asp Val Arg Phe
    50                  55                  60

Glu Ser Ile Arg Leu Pro Gly Cys Pro Arg Gly Val Asn Pro Val Val
65                  70                  75                  80

Ser Tyr Ala Val Ala Leu Ser Cys Gln Cys Ala Leu Cys Arg Arg Ser
                85                  90                  95

Thr Thr Asp Cys Gly Gly Pro Lys Asp His Pro Leu Thr Cys Asp Asp
            100                 105                 110

Pro Arg Phe Gln Asp Ser Ser Ser Lys Ala Pro Pro Pro Ser Leu
        115                 120                 125

Pro Ser Pro Ser Arg Leu Pro Gly Pro Ser Asp Thr Pro Ile Leu Pro
    130                 135                 140

Gln Asp Ala His Lys Ser Glu Val Ala His Arg Phe Lys Asp Leu Gly
145                 150                 155                 160

Glu Glu Asn Phe Lys Ala Leu Val Leu Ile Ala Phe Ala Gln Tyr Leu
                165                 170                 175

Gln Gln Cys Pro Phe Glu Asp His Val Lys Leu Val Asn Glu Val Thr
            180                 185                 190

Glu Phe Ala Lys Thr Cys Val Ala Asp Glu Ser Ala Glu Asn Cys Asp
        195                 200                 205

Lys Ser Leu His Thr Leu Phe Gly Asp Lys Leu Cys Thr Val Ala Thr
    210                 215                 220

Leu Arg Glu Thr Tyr Gly Glu Met Ala Asp Cys Cys Ala Lys Gln Glu
225                 230                 235                 240

Pro Glu Arg Asn Glu Cys Phe Leu Gln His Lys Asp Asp Asn Pro Asn
                245                 250                 255

Leu Pro Arg Leu Val Arg Pro Glu Val Asp Val Met Cys Thr Ala Phe
            260                 265                 270

His Asp Asn Glu Glu Thr Phe Leu Lys Lys Tyr Leu Tyr Glu Ile Ala

-continued

```
               275                 280                 285
Arg Arg His Pro Tyr Phe Tyr Ala Pro Glu Leu Leu Phe Phe Ala Lys
            290                 295                 300
Arg Tyr Lys Ala Ala Phe Thr Glu Cys Cys Gln Ala Ala Asp Lys Ala
305                 310                 315                 320
Ala Cys Leu Leu Pro Lys Leu Asp Glu Leu Arg Asp Glu Gly Lys Ala
                325                 330                 335
Ser Ser Ala Lys Gln Arg Leu Lys Cys Ala Ser Leu Gln Lys Phe Gly
            340                 345                 350
Glu Arg Ala Phe Lys Ala Trp Ala Val Ala Arg Leu Ser Gln Arg Phe
                355                 360                 365
Pro Lys Ala Glu Phe Ala Glu Val Ser Lys Leu Val Thr Asp Leu Thr
            370                 375                 380
Lys Val His Thr Glu Cys Cys His Gly Asp Leu Leu Glu Cys Ala Asp
385                 390                 395                 400
Asp Arg Ala Asp Leu Ala Lys Tyr Ile Cys Glu Asn Gln Asp Ser Ile
                405                 410                 415
Ser Ser Lys Leu Lys Glu Cys Cys Glu Lys Pro Leu Leu Glu Lys Ser
            420                 425                 430
His Cys Ile Ala Glu Val Glu Asn Asp Glu Met Pro Ala Asp Leu Pro
                435                 440                 445
Ser Leu Ala Ala Asp Phe Val Glu Ser Lys Asp Val Cys Lys Asn Tyr
            450                 455                 460
Ala Glu Ala Lys Asp Val Phe Leu Gly Met Phe Leu Tyr Glu Tyr Ala
465                 470                 475                 480
Arg Arg His Pro Asp Tyr Ser Val Val Leu Leu Leu Arg Leu Ala Lys
                485                 490                 495
Thr Tyr Glu Thr Thr Leu Glu Lys Cys Cys Ala Ala Ala Asp Pro His
            500                 505                 510
Glu Cys Tyr Ala Lys Val Phe Asp Glu Phe Lys Pro Leu Val Glu Glu
            515                 520                 525
Pro Gln Asn Leu Ile Lys Gln Asn Cys Glu Leu Phe Glu Gln Leu Gly
            530                 535                 540
Glu Tyr Lys Phe Gln Asn Ala Leu Leu Val Arg Tyr Thr Lys Lys Val
545                 550                 555                 560
Pro Gln Val Ser Thr Pro Thr Leu Val Glu Val Ser Arg Asn Leu Gly
                565                 570                 575
Lys Val Gly Ser Lys Cys Cys Lys His Pro Glu Ala Lys Arg Met Pro
            580                 585                 590
Cys Ala Glu Asp Tyr Leu Ser Val Val Leu Asn Gln Leu Cys Val Leu
                595                 600                 605
His Glu Lys Thr Pro Val Ser Asp Arg Val Thr Lys Cys Cys Thr Glu
            610                 615                 620
Ser Leu Val Asn Arg Arg Pro Cys Phe Ser Ala Leu Glu Val Asp Glu
625                 630                 635                 640
Thr Tyr Val Pro Lys Glu Phe Asn Ala Glu Thr Phe Thr Phe His Ala
                645                 650                 655
Asp Ile Cys Thr Leu Ser Glu Lys Glu Arg Gln Ile Lys Lys Gln Thr
            660                 665                 670
Ala Leu Val Glu Leu Val Lys His Lys Pro Lys Ala Thr Lys Glu Gln
            675                 680                 685
Leu Lys Ala Val Met Asp Asp Phe Ala Ala Phe Val Glu Lys Cys Cys
            690                 695                 700
```

```
Lys Ala Asp Asp Lys Glu Thr Cys Phe Ala Glu Gly Lys Lys Leu
705                 710                 715                 720

Val Ala Ala Ser Gln Ala Ala Leu Gly Leu
            725                 730
```

<210> SEQ ID NO 30
<211> LENGTH: 706
<212> TYPE: PRT
<213> ORGANISM: Artificial Sequence
<220> FEATURE:
<223> OTHER INFORMATION: Description of Artificial Sequence: Synthetic
      Mature human wt Albumin + human LH beta-chain sequence

<400> SEQUENCE: 30

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
        290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
```

```
                    325                 330                 335
Arg His Pro Asp Tyr Ser Val Val Leu Leu Arg Leu Ala Lys Thr
            340                 345                 350
Tyr Glu Thr Thr Leu Glu Lys Cys Cys Ala Ala Asp Pro His Glu
        355                 360                 365
Cys Tyr Ala Lys Val Phe Asp Glu Phe Lys Pro Leu Val Glu Pro
    370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
            405                 410                 415
Gln Val Ser Thr Pro Thr Leu Val Glu Val Ser Arg Asn Leu Gly Lys
        420                 425                 430
Val Gly Ser Lys Cys Cys Lys His Pro Glu Ala Lys Arg Met Pro Cys
    435                 440                 445
Ala Glu Asp Tyr Leu Ser Val Val Leu Asn Gln Leu Cys Val Leu His
450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                485                 490                 495
Tyr Val Pro Lys Glu Phe Asn Ala Glu Thr Phe Thr Phe His Ala Asp
            500                 505                 510
Ile Cys Thr Leu Ser Glu Lys Glu Arg Gln Ile Lys Lys Gln Thr Ala
        515                 520                 525
Leu Val Glu Leu Val Lys His Lys Pro Lys Ala Thr Lys Glu Gln Leu
    530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Glu Gly Lys Lys Leu Val
                565                 570                 575
Ala Ala Ser Gln Ala Ala Leu Gly Leu Ser Arg Glu Pro Leu Arg Pro
            580                 585                 590
Trp Cys His Pro Ile Asn Ala Ile Leu Ala Val Glu Lys Glu Gly Cys
        595                 600                 605
Pro Val Cys Ile Thr Val Asn Thr Thr Ile Cys Ala Gly Tyr Cys Pro
    610                 615                 620
Thr Met Met Arg Val Leu Gln Ala Val Leu Pro Pro Leu Pro Gln Val
625                 630                 635                 640
Val Cys Thr Tyr Arg Asp Val Arg Phe Glu Ser Ile Arg Leu Pro Gly
                645                 650                 655
Cys Pro Arg Gly Val Asp Pro Val Val Ser Phe Pro Val Ala Leu Ser
            660                 665                 670
Cys Arg Cys Gly Pro Cys Arg Arg Ser Thr Ser Asp Cys Gly Gly Pro
        675                 680                 685
Lys Asp His Pro Leu Thr Cys Asp His Pro Gln Leu Ser Gly Leu Leu
    690                 695                 700
Phe Leu
705

<210> SEQ ID NO 31
<211> LENGTH: 706
<212> TYPE: PRT
<213> ORGANISM: Artificial Sequence
```

<220> FEATURE:
<223> OTHER INFORMATION: Description of Artificial Sequence: Synthetic
      Mature human LH beta-chain + human wt Albumin sequence

<400> SEQUENCE: 31

```
Ser Arg Glu Pro Leu Arg Pro Trp Cys His Pro Ile Asn Ala Ile Leu
1               5                   10                  15

Ala Val Glu Lys Glu Gly Cys Pro Val Cys Ile Thr Val Asn Thr Thr
            20                  25                  30

Ile Cys Ala Gly Tyr Cys Pro Thr Met Met Arg Val Leu Gln Ala Val
        35                  40                  45

Leu Pro Pro Leu Pro Gln Val Val Cys Thr Tyr Arg Asp Val Arg Phe
    50                  55                  60

Glu Ser Ile Arg Leu Pro Gly Cys Pro Arg Gly Val Asp Pro Val Val
65                  70                  75                  80

Ser Phe Pro Val Ala Leu Ser Cys Arg Cys Gly Pro Cys Arg Arg Ser
                85                  90                  95

Thr Ser Asp Cys Gly Gly Pro Lys Asp His Pro Leu Thr Cys Asp His
            100                 105                 110

Pro Gln Leu Ser Gly Leu Leu Phe Leu Asp Ala His Lys Ser Glu Val
        115                 120                 125

Ala His Arg Phe Lys Asp Leu Gly Glu Glu Asn Phe Lys Ala Leu Val
    130                 135                 140

Leu Ile Ala Phe Ala Gln Tyr Leu Gln Gln Cys Pro Phe Glu Asp His
145                 150                 155                 160

Val Lys Leu Val Asn Glu Val Thr Glu Phe Ala Lys Thr Cys Val Ala
                165                 170                 175

Asp Glu Ser Ala Glu Asn Cys Asp Lys Ser Leu His Thr Leu Phe Gly
            180                 185                 190

Asp Lys Leu Cys Thr Val Ala Thr Leu Arg Glu Thr Tyr Gly Glu Met
        195                 200                 205

Ala Asp Cys Cys Ala Lys Gln Glu Pro Glu Arg Asn Glu Cys Phe Leu
    210                 215                 220

Gln His Lys Asp Asp Asn Pro Asn Leu Pro Arg Leu Val Arg Pro Glu
225                 230                 235                 240

Val Asp Val Met Cys Thr Ala Phe His Asp Asn Glu Glu Thr Phe Leu
                245                 250                 255

Lys Lys Tyr Leu Tyr Glu Ile Ala Arg Arg His Pro Tyr Phe Tyr Ala
            260                 265                 270

Pro Glu Leu Leu Phe Phe Ala Lys Arg Tyr Lys Ala Ala Phe Thr Glu
        275                 280                 285

Cys Cys Gln Ala Ala Asp Lys Ala Ala Cys Leu Leu Pro Lys Leu Asp
    290                 295                 300

Glu Leu Arg Asp Glu Gly Lys Ala Ser Ser Ala Lys Gln Arg Leu Lys
305                 310                 315                 320

Cys Ala Ser Leu Gln Lys Phe Gly Glu Arg Ala Phe Lys Ala Trp Ala
                325                 330                 335

Val Ala Arg Leu Ser Gln Arg Phe Pro Lys Ala Glu Phe Ala Glu Val
            340                 345                 350

Ser Lys Leu Val Thr Asp Leu Thr Lys Val His Thr Glu Cys Cys His
        355                 360                 365

Gly Asp Leu Leu Glu Cys Ala Asp Asp Arg Ala Asp Leu Ala Lys Tyr
    370                 375                 380

Ile Cys Glu Asn Gln Asp Ser Ile Ser Ser Lys Leu Lys Glu Cys Cys
```

```
             385                 390                 395                 400
        Glu Lys Pro Leu Leu Glu Lys Ser His Cys Ile Ala Glu Val Glu Asn
                        405                 410                 415

Asp Glu Met Pro Ala Asp Leu Pro Ser Leu Ala Ala Asp Phe Val Glu
                        420                 425                 430

Ser Lys Asp Val Cys Lys Asn Tyr Ala Glu Ala Lys Asp Val Phe Leu
                        435                 440                 445

Gly Met Phe Leu Tyr Glu Tyr Ala Arg Arg His Pro Asp Tyr Ser Val
                        450                 455                 460

Val Leu Leu Leu Arg Leu Ala Lys Thr Tyr Glu Thr Thr Leu Glu Lys
        465                 470                 475                 480

Cys Cys Ala Ala Ala Asp Pro His Glu Cys Tyr Ala Lys Val Phe Asp
                        485                 490                 495

Glu Phe Lys Pro Leu Val Glu Glu Pro Gln Asn Leu Ile Lys Gln Asn
                        500                 505                 510

Cys Glu Leu Phe Glu Gln Leu Gly Glu Tyr Lys Phe Gln Asn Ala Leu
                        515                 520                 525

Leu Val Arg Tyr Thr Lys Lys Val Pro Gln Val Ser Thr Pro Thr Leu
                        530                 535                 540

Val Glu Val Ser Arg Asn Leu Gly Lys Val Gly Ser Lys Cys Cys Lys
        545                 550                 555                 560

His Pro Glu Ala Lys Arg Met Pro Cys Ala Glu Asp Tyr Leu Ser Val
                        565                 570                 575

Val Leu Asn Gln Leu Cys Val Leu His Glu Lys Thr Pro Val Ser Asp
                        580                 585                 590

Arg Val Thr Lys Cys Cys Thr Glu Ser Leu Val Asn Arg Arg Pro Cys
                        595                 600                 605

Phe Ser Ala Leu Glu Val Asp Glu Thr Tyr Val Pro Lys Glu Phe Asn
                        610                 615                 620

Ala Glu Thr Phe Thr Phe His Ala Asp Ile Cys Thr Leu Ser Glu Lys
        625                 630                 635                 640

Glu Arg Gln Ile Lys Lys Gln Thr Ala Leu Val Glu Leu Val Lys His
                        645                 650                 655

Lys Pro Lys Ala Thr Lys Glu Gln Leu Lys Ala Val Met Asp Asp Phe
                        660                 665                 670

Ala Ala Phe Val Glu Lys Cys Cys Lys Ala Asp Asp Lys Glu Thr Cys
                        675                 680                 685

Phe Ala Glu Glu Gly Lys Lys Leu Val Ala Ala Ser Gln Ala Ala Leu
                        690                 695                 700

Gly Leu
        705

<210> SEQ ID NO 32
<211> LENGTH: 334
<212> TYPE: PRT
<213> ORGANISM: Artificial Sequence
<220> FEATURE:
<223> OTHER INFORMATION: Description of Artificial Sequence: Synthetic
      Mature human alpha-chain + linker + human Fc sequence

<400> SEQUENCE: 32

Ala Pro Asp Val Gln Asp Cys Pro Glu Cys Thr Leu Gln Glu Asn Pro
1               5                   10                  15

Phe Phe Ser Gln Pro Gly Ala Pro Ile Leu Gln Cys Met Gly Cys Cys
                20                  25                  30
```

```
Phe Ser Arg Ala Tyr Pro Thr Pro Leu Arg Ser Lys Lys Thr Met Leu
            35                  40                  45

Val Gln Lys Asn Val Thr Ser Glu Ser Thr Cys Cys Val Ala Lys Ser
 50                  55                  60

Tyr Asn Arg Val Thr Val Met Gly Gly Phe Lys Val Glu Asn His Thr
65                  70                  75                  80

Ala Cys His Cys Ser Thr Cys Tyr Tyr His Lys Ser Gly Gly Gly
                85                  90                  95

Ser Gly Gly Gly Gly Ser Gly Gly Gly Ser Asp Lys Thr His Thr
                100                 105                 110

Cys Pro Pro Cys Pro Ala Pro Glu Leu Leu Gly Gly Pro Ser Val Phe
            115                 120                 125

Leu Phe Pro Pro Lys Pro Lys Asp Thr Leu Met Ile Ser Arg Thr Pro
130                 135                 140

Glu Val Thr Cys Val Val Val Asp Val Ser His Glu Asp Pro Glu Val
145                 150                 155                 160

Lys Phe Asn Trp Tyr Val Asp Gly Val Glu Val His Asn Ala Lys Thr
                165                 170                 175

Lys Pro Arg Glu Glu Gln Tyr Asn Ser Thr Tyr Arg Val Val Ser Val
            180                 185                 190

Leu Thr Val Leu His Gln Asp Trp Leu Asn Gly Lys Glu Tyr Lys Cys
        195                 200                 205

Lys Val Ser Asn Lys Ala Leu Pro Ala Pro Ile Glu Lys Thr Ile Ser
    210                 215                 220

Lys Ala Lys Gly Gln Pro Arg Glu Pro Gln Val Tyr Thr Leu Pro Pro
225                 230                 235                 240

Ser Arg Asp Glu Leu Thr Lys Asn Gln Val Ser Leu Thr Cys Leu Val
                245                 250                 255

Lys Gly Phe Tyr Pro Ser Asp Ile Ala Val Glu Trp Glu Ser Asn Gly
            260                 265                 270

Gln Pro Glu Asn Asn Tyr Lys Thr Thr Pro Pro Val Leu Asp Ser Asp
        275                 280                 285

Gly Ser Phe Phe Leu Tyr Ser Lys Leu Thr Val Asp Lys Ser Arg Trp
290                 295                 300

Gln Gln Gly Asn Val Phe Ser Cys Ser Val Met His Glu Ala Leu His
305                 310                 315                 320

Asn His Tyr Thr Gln Lys Ser Leu Ser Leu Ser Pro Gly Lys
                325                 330

<210> SEQ ID NO 33
<211> LENGTH: 393
<212> TYPE: PRT
<213> ORGANISM: Artificial Sequence
<220> FEATURE:
<223> OTHER INFORMATION: Description of Artificial Sequence: Synthetic
      Mature human hCG beta-chain + linker + human Fc + Histag
      sequence

<400> SEQUENCE: 33

Ser Lys Glu Pro Leu Arg Pro Arg Cys Arg Pro Ile Asn Ala Thr Leu
1               5                   10                  15

Ala Val Glu Lys Glu Gly Cys Pro Val Cys Ile Thr Val Asn Thr Thr
                20                  25                  30

Ile Cys Ala Gly Tyr Cys Pro Thr Met Thr Arg Val Leu Gln Gly Val
            35                  40                  45

Leu Pro Ala Leu Pro Gln Val Val Cys Asn Tyr Arg Asp Val Arg Phe
```

Glu Ser Ile Arg Leu Pro Gly Cys Pro Arg Gly Val Asn Pro Val Val
65                  70                  75                  80

Ser Tyr Ala Val Ala Leu Ser Cys Gln Cys Ala Leu Cys Arg Arg Ser
                85                  90                  95

Thr Thr Asp Cys Gly Gly Pro Lys Asp His Pro Leu Thr Cys Asp Asp
            100                 105                 110

Pro Arg Phe Gln Asp Ser Ser Ser Lys Ala Pro Pro Pro Ser Leu
        115                 120                 125

Pro Ser Pro Ser Arg Leu Pro Gly Pro Ser Asp Thr Pro Ile Leu Pro
130                 135                 140

Gln Gly Gly Gly Ser Gly Gly Gly Ser Gly Gly Gly Ser
145                 150                 155                 160

Asp Lys Thr His Thr Cys Pro Pro Cys Pro Ala Pro Glu Leu Leu Gly
                165                 170                 175

Gly Pro Ser Val Phe Leu Phe Pro Pro Lys Pro Lys Asp Thr Leu Met
            180                 185                 190

Ile Ser Arg Thr Pro Glu Val Thr Cys Val Val Val Asp Val Ser His
        195                 200                 205

Glu Asp Pro Glu Val Lys Phe Asn Trp Tyr Val Asp Gly Val Glu Val
210                 215                 220

His Asn Ala Lys Thr Lys Pro Arg Glu Glu Gln Tyr Asn Ser Thr Tyr
225                 230                 235                 240

Arg Val Val Ser Val Leu Thr Val Leu His Gln Asp Trp Leu Asn Gly
                245                 250                 255

Lys Glu Tyr Lys Cys Lys Val Ser Asn Lys Ala Leu Pro Ala Pro Ile
            260                 265                 270

Glu Lys Thr Ile Ser Lys Ala Lys Gly Gln Pro Arg Glu Pro Gln Val
        275                 280                 285

Tyr Thr Leu Pro Pro Ser Arg Asp Glu Leu Thr Lys Asn Gln Val Ser
290                 295                 300

Leu Thr Cys Leu Val Lys Gly Phe Tyr Pro Ser Asp Ile Ala Val Glu
305                 310                 315                 320

Trp Glu Ser Asn Gly Gln Pro Glu Asn Asn Tyr Lys Thr Thr Pro Pro
                325                 330                 335

Val Leu Asp Ser Asp Gly Ser Phe Phe Leu Tyr Ser Lys Leu Thr Val
            340                 345                 350

Asp Lys Ser Arg Trp Gln Gln Gly Asn Val Phe Ser Cys Ser Val Met
        355                 360                 365

His Glu Ala Leu His Asn His Tyr Thr Gln Lys Ser Leu Ser Leu Ser
370                 375                 380

Pro Gly Lys His His His His His
385                 390

<210> SEQ ID NO 34
<211> LENGTH: 369
<212> TYPE: PRT
<213> ORGANISM: Artificial Sequence
<220> FEATURE:
<223> OTHER INFORMATION: Description of Artificial Sequence: Synthetic
      Mature human LH beta-chain + linker + human Fc + Histag
      sequence

<400> SEQUENCE: 34

Ser Arg Glu Pro Leu Arg Pro Trp Cys His Pro Ile Asn Ala Ile Leu
1               5                   10                  15

```
Ala Val Glu Lys Glu Gly Cys Pro Val Cys Ile Thr Val Asn Thr Thr
                20                  25                  30

Ile Cys Ala Gly Tyr Cys Pro Thr Met Met Arg Val Leu Gln Ala Val
            35                  40                  45

Leu Pro Pro Leu Pro Gln Val Val Cys Thr Tyr Arg Asp Val Arg Phe
 50                  55                  60

Glu Ser Ile Arg Leu Pro Gly Cys Pro Arg Gly Val Asp Pro Val Val
 65                  70                  75                  80

Ser Phe Pro Val Ala Leu Ser Cys Arg Cys Gly Pro Cys Arg Arg Ser
                 85                  90                  95

Thr Ser Asp Cys Gly Gly Pro Lys Asp His Pro Leu Thr Cys Asp His
            100                 105                 110

Pro Gln Leu Ser Gly Leu Leu Phe Leu Gly Gly Gly Ser Gly Gly Gly
                115                 120                 125

Gly Gly Ser Gly Gly Gly Gly Ser Asp Lys Thr His Thr Cys Pro Pro
130                 135                 140

Cys Pro Ala Pro Glu Leu Leu Gly Gly Pro Ser Val Phe Leu Phe Pro
145                 150                 155                 160

Pro Lys Pro Lys Asp Thr Leu Met Ile Ser Arg Thr Pro Glu Val Thr
                165                 170                 175

Cys Val Val Val Asp Val Ser His Glu Asp Pro Glu Val Lys Phe Asn
            180                 185                 190

Trp Tyr Val Asp Gly Val Glu Val His Asn Ala Lys Thr Lys Pro Arg
        195                 200                 205

Glu Glu Gln Tyr Asn Ser Thr Tyr Arg Val Val Ser Val Leu Thr Val
    210                 215                 220

Leu His Gln Asp Trp Leu Asn Gly Lys Glu Tyr Lys Cys Lys Val Ser
225                 230                 235                 240

Asn Lys Ala Leu Pro Ala Pro Ile Glu Lys Thr Ile Ser Lys Ala Lys
                245                 250                 255

Gly Gln Pro Arg Glu Pro Gln Val Tyr Thr Leu Pro Pro Ser Arg Asp
            260                 265                 270

Glu Leu Thr Lys Asn Gln Val Ser Leu Thr Cys Leu Val Lys Gly Phe
        275                 280                 285

Tyr Pro Ser Asp Ile Ala Val Glu Trp Glu Ser Asn Gly Gln Pro Glu
    290                 295                 300

Asn Asn Tyr Lys Thr Thr Pro Pro Val Leu Asp Ser Asp Gly Ser Phe
305                 310                 315                 320

Phe Leu Tyr Ser Lys Leu Thr Val Asp Lys Ser Arg Trp Gln Gln Gly
                325                 330                 335

Asn Val Phe Ser Cys Ser Val Met His Glu Ala Leu His Asn His Tyr
            340                 345                 350

Thr Gln Lys Ser Leu Ser Leu Ser Pro Gly Lys His His His His His
        355                 360                 365

His
```

<210> SEQ ID NO 35
<211> LENGTH: 701
<212> TYPE: PRT
<213> ORGANISM: Artificial Sequence
<220> FEATURE:
<223> OTHER INFORMATION: Description of Artificial Sequence: Synthetic
      wt human Albumin with signal peptide and propeptide +
      human alpha-chain sequence

```
<400> SEQUENCE: 35

Met Lys Trp Val Thr Phe Ile Ser Leu Leu Phe Leu Phe Ser Ser Ala
1               5                  10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
        290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415
```

```
Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
            435                 440                 445

Glu Val Ser Arg Asn Leu Gly Lys Val Gly Ser Lys Cys Cys Lys His
450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
            515                 520                 525

Glu Thr Phe Thr Phe His Ala Asp Ile Cys Thr Leu Ser Glu Lys Glu
            530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
            595                 600                 605

Leu Ala Pro Asp Val Gln Asp Cys Pro Glu Cys Thr Leu Gln Glu Asn
            610                 615                 620

Pro Phe Phe Ser Gln Pro Gly Ala Pro Ile Leu Gln Cys Met Gly Cys
625                 630                 635                 640

Cys Phe Ser Arg Ala Tyr Pro Thr Pro Leu Arg Ser Lys Lys Thr Met
                645                 650                 655

Leu Val Gln Lys Asn Val Thr Ser Glu Ser Thr Cys Cys Val Ala Lys
            660                 665                 670

Ser Tyr Asn Arg Val Thr Val Met Gly Gly Phe Lys Val Glu Asn His
            675                 680                 685

Thr Ala Cys His Cys Ser Thr Cys Tyr Tyr His Lys Ser
            690                 695                 700

<210> SEQ ID NO 36
<211> LENGTH: 701
<212> TYPE: PRT
<213> ORGANISM: Artificial Sequence
<220> FEATURE:
<223> OTHER INFORMATION: Description of Artificial Sequence: Synthetic
      Human alpha-chain with signal peptide + wt human Albumin
      sequence

<400> SEQUENCE: 36

Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Gln Asp Cys Pro
            20                  25                  30

Glu Cys Thr Leu Gln Glu Asn Pro Phe Phe Ser Gln Pro Gly Ala Pro
            35                  40                  45

Ile Leu Gln Cys Met Gly Cys Cys Phe Ser Arg Ala Tyr Pro Thr Pro
    50                  55                  60
```

```
Leu Arg Ser Lys Lys Thr Met Leu Val Gln Lys Asn Val Thr Ser Glu
 65                  70                  75                  80

Ser Thr Cys Cys Val Ala Lys Ser Tyr Asn Arg Val Thr Val Met Gly
             85                   90                  95

Gly Phe Lys Val Glu Asn His Thr Ala Cys His Cys Ser Thr Cys Tyr
            100                 105                 110

Tyr His Lys Ser Asp Ala His Lys Ser Glu Val Ala His Arg Phe Lys
            115                 120                 125

Asp Leu Gly Glu Glu Asn Phe Lys Ala Leu Val Leu Ile Ala Phe Ala
            130                 135                 140

Gln Tyr Leu Gln Gln Cys Pro Phe Glu Asp His Val Lys Leu Val Asn
145                 150                 155                 160

Glu Val Thr Glu Phe Ala Lys Thr Cys Val Ala Asp Glu Ser Ala Glu
                165                 170                 175

Asn Cys Asp Lys Ser Leu His Thr Leu Phe Gly Asp Lys Leu Cys Thr
            180                 185                 190

Val Ala Thr Leu Arg Glu Thr Tyr Gly Glu Met Ala Asp Cys Cys Ala
            195                 200                 205

Lys Gln Glu Pro Glu Arg Asn Glu Cys Phe Leu Gln His Lys Asp Asp
210                 215                 220

Asn Pro Asn Leu Pro Arg Leu Val Arg Pro Glu Val Asp Val Met Cys
225                 230                 235                 240

Thr Ala Phe His Asp Asn Glu Glu Thr Phe Leu Lys Lys Tyr Leu Tyr
                245                 250                 255

Glu Ile Ala Arg Arg His Pro Tyr Phe Tyr Ala Pro Glu Leu Leu Phe
            260                 265                 270

Phe Ala Lys Arg Tyr Lys Ala Ala Phe Thr Glu Cys Cys Gln Ala Ala
            275                 280                 285

Asp Lys Ala Ala Cys Leu Leu Pro Lys Leu Asp Glu Leu Arg Asp Glu
            290                 295                 300

Gly Lys Ala Ser Ser Ala Lys Gln Arg Leu Lys Cys Ala Ser Leu Gln
305                 310                 315                 320

Lys Phe Gly Glu Arg Ala Phe Lys Ala Trp Ala Val Ala Arg Leu Ser
                325                 330                 335

Gln Arg Phe Pro Lys Ala Glu Phe Ala Glu Val Ser Lys Leu Val Thr
            340                 345                 350

Asp Leu Thr Lys Val His Thr Glu Cys Cys His Gly Asp Leu Leu Glu
            355                 360                 365

Cys Ala Asp Asp Arg Ala Asp Leu Ala Lys Tyr Ile Cys Glu Asn Gln
370                 375                 380

Asp Ser Ile Ser Ser Lys Leu Lys Glu Cys Cys Glu Lys Pro Leu Leu
385                 390                 395                 400

Glu Lys Ser His Cys Ile Ala Glu Val Glu Asn Asp Glu Met Pro Ala
                405                 410                 415

Asp Leu Pro Ser Leu Ala Ala Asp Phe Val Glu Ser Lys Asp Val Cys
            420                 425                 430

Lys Asn Tyr Ala Glu Ala Lys Asp Val Phe Leu Gly Met Phe Leu Tyr
            435                 440                 445

Glu Tyr Ala Arg Arg His Pro Asp Tyr Ser Val Val Leu Leu Leu Arg
            450                 455                 460

Leu Ala Lys Thr Tyr Glu Thr Thr Leu Glu Lys Cys Cys Ala Ala Ala
465                 470                 475                 480

Asp Pro His Glu Cys Tyr Ala Lys Val Phe Asp Glu Phe Lys Pro Leu
```

```
                485                 490                 495
Val Glu Glu Pro Gln Asn Leu Ile Lys Gln Asn Cys Glu Leu Phe Glu
            500                 505                 510

Gln Leu Gly Glu Tyr Lys Phe Gln Asn Ala Leu Leu Val Arg Tyr Thr
        515                 520                 525

Lys Lys Val Pro Gln Val Ser Thr Pro Thr Leu Val Glu Val Ser Arg
    530                 535                 540

Asn Leu Gly Lys Val Gly Ser Lys Cys Cys Lys His Pro Glu Ala Lys
545                 550                 555                 560

Arg Met Pro Cys Ala Glu Asp Tyr Leu Ser Val Val Leu Asn Gln Leu
                565                 570                 575

Cys Val Leu His Glu Lys Thr Pro Val Ser Asp Arg Val Thr Lys Cys
            580                 585                 590

Cys Thr Glu Ser Leu Val Asn Arg Arg Pro Cys Phe Ser Ala Leu Glu
        595                 600                 605

Val Asp Glu Thr Tyr Val Pro Lys Glu Phe Asn Ala Glu Thr Phe Thr
    610                 615                 620

Phe His Ala Asp Ile Cys Thr Leu Ser Glu Lys Glu Arg Gln Ile Lys
625                 630                 635                 640

Lys Gln Thr Ala Leu Val Glu Leu Val Lys His Lys Pro Lys Ala Thr
                645                 650                 655

Lys Glu Gln Leu Lys Ala Val Met Asp Asp Phe Ala Ala Phe Val Glu
            660                 665                 670

Lys Cys Cys Lys Ala Asp Asp Lys Glu Thr Cys Phe Ala Glu Glu Gly
        675                 680                 685

Lys Lys Leu Val Ala Ala Ser Gln Ala Ala Leu Gly Leu
    690                 695                 700

<210> SEQ ID NO 37
<211> LENGTH: 754
<212> TYPE: PRT
<213> ORGANISM: Artificial Sequence
<220> FEATURE:
<223> OTHER INFORMATION: Description of Artificial Sequence: Synthetic
      Human wt Albumin with signal peptide and propeptide +
      human hCG beta-chain sequence

<400> SEQUENCE: 37

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140
```

```
Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
            165                 170                 175

Glu Leu Leu Phe Phe Ala Lys Arg Tyr Lys Ala Ala Phe Thr Glu Cys
        180                 185                 190

Cys Gln Ala Ala Asp Lys Ala Ala Cys Leu Leu Pro Lys Leu Asp Glu
            195                 200                 205

Leu Arg Asp Glu Gly Lys Ala Ser Ser Ala Lys Gln Arg Leu Lys Cys
        210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
            245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
        290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
            325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
        370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
            405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
        450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
            485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
        530                 535                 540

Arg Gln Ile Lys Lys Gln Thr Ala Leu Val Glu Leu Val Lys His Lys
545                 550                 555                 560
```

```
Pro Lys Ala Thr Lys Glu Gln Leu Lys Ala Val Met Asp Asp Phe Ala
            565                 570                 575
Ala Phe Val Glu Lys Cys Cys Lys Ala Asp Asp Lys Glu Thr Cys Phe
            580                 585                 590
Ala Glu Glu Gly Lys Lys Leu Val Ala Ala Ser Gln Ala Ala Leu Gly
            595                 600                 605
Leu Ser Lys Glu Pro Leu Arg Pro Arg Cys Arg Pro Ile Asn Ala Thr
            610                 615                 620
Leu Ala Val Glu Lys Glu Gly Cys Pro Val Cys Ile Thr Val Asn Thr
625                 630                 635                 640
Thr Ile Cys Ala Gly Tyr Cys Pro Thr Met Thr Arg Val Leu Gln Gly
            645                 650                 655
Val Leu Pro Ala Leu Pro Gln Val Val Cys Asn Tyr Arg Asp Val Arg
            660                 665                 670
Phe Glu Ser Ile Arg Leu Pro Gly Cys Pro Arg Gly Val Asn Pro Val
            675                 680                 685
Val Ser Tyr Ala Val Ala Leu Ser Cys Gln Cys Ala Leu Cys Arg Arg
            690                 695                 700
Ser Thr Thr Asp Cys Gly Gly Pro Lys Asp His Pro Leu Thr Cys Asp
705                 710                 715                 720
Asp Pro Arg Phe Gln Asp Ser Ser Ser Lys Ala Pro Pro Pro Ser
            725                 730                 735
Leu Pro Ser Pro Ser Arg Leu Pro Gly Pro Ser Asp Thr Pro Ile Leu
            740                 745                 750

Pro Gln

<210> SEQ ID NO 38
<211> LENGTH: 750
<212> TYPE: PRT
<213> ORGANISM: Artificial Sequence
<220> FEATURE:
<223> OTHER INFORMATION: Description of Artificial Sequence: Synthetic
      Human hCG beta-chain with signal peptide + human wt Albumin
      sequence

<400> SEQUENCE: 38

Met Glu Met Phe Gln Gly Leu Leu Leu Leu Leu Leu Ser Met Gly
1               5                   10                  15
Gly Thr Trp Ala Ser Lys Glu Pro Leu Arg Pro Arg Cys Arg Pro Ile
            20                  25                  30
Asn Ala Thr Leu Ala Val Glu Lys Glu Gly Cys Pro Val Cys Ile Thr
            35                  40                  45
Val Asn Thr Thr Ile Cys Ala Gly Tyr Cys Pro Thr Met Thr Arg Val
50                  55                  60
Leu Gln Gly Val Leu Pro Ala Leu Pro Gln Val Val Cys Asn Tyr Arg
65                  70                  75                  80
Asp Val Arg Phe Glu Ser Ile Arg Leu Pro Gly Cys Pro Arg Gly Val
            85                  90                  95
Asn Pro Val Val Ser Tyr Ala Val Ala Leu Ser Cys Gln Cys Ala Leu
            100                 105                 110
Cys Arg Arg Ser Thr Thr Asp Cys Gly Gly Pro Lys Asp His Pro Leu
            115                 120                 125
Thr Cys Asp Asp Pro Arg Phe Gln Asp Ser Ser Ser Ser Lys Ala Pro
            130                 135                 140
Pro Pro Ser Leu Pro Ser Pro Ser Arg Leu Pro Gly Pro Ser Asp Thr
145                 150                 155                 160
```

```
Pro Ile Leu Pro Gln Asp Ala His Lys Ser Glu Val Ala His Arg Phe
            165                 170                 175

Lys Asp Leu Gly Glu Glu Asn Phe Lys Ala Leu Val Leu Ile Ala Phe
            180                 185                 190

Ala Gln Tyr Leu Gln Gln Cys Pro Phe Glu Asp His Val Lys Leu Val
            195                 200                 205

Asn Glu Val Thr Glu Phe Ala Lys Thr Cys Val Ala Asp Glu Ser Ala
            210                 215                 220

Glu Asn Cys Asp Lys Ser Leu His Thr Leu Phe Gly Asp Lys Leu Cys
225                 230                 235                 240

Thr Val Ala Thr Leu Arg Glu Tyr Gly Glu Met Ala Asp Cys Cys
            245                 250                 255

Ala Lys Gln Glu Pro Glu Arg Asn Glu Cys Phe Leu Gln His Lys Asp
            260                 265                 270

Asp Asn Pro Asn Leu Pro Arg Leu Val Arg Pro Glu Val Asp Val Met
            275                 280                 285

Cys Thr Ala Phe His Asp Asn Glu Glu Thr Phe Leu Lys Lys Tyr Leu
            290                 295                 300

Tyr Glu Ile Ala Arg Arg His Pro Tyr Phe Tyr Ala Pro Glu Leu Leu
305                 310                 315                 320

Phe Phe Ala Lys Arg Tyr Lys Ala Ala Phe Thr Glu Cys Cys Gln Ala
            325                 330                 335

Ala Asp Lys Ala Ala Cys Leu Leu Pro Lys Leu Asp Glu Leu Arg Asp
            340                 345                 350

Glu Gly Lys Ala Ser Ser Ala Lys Gln Arg Leu Lys Cys Ala Ser Leu
            355                 360                 365

Gln Lys Phe Gly Glu Arg Ala Phe Lys Ala Trp Ala Val Ala Arg Leu
            370                 375                 380

Ser Gln Arg Phe Pro Lys Ala Glu Phe Ala Glu Val Ser Lys Leu Val
385                 390                 395                 400

Thr Asp Leu Thr Lys Val His Thr Glu Cys Cys His Gly Asp Leu Leu
            405                 410                 415

Glu Cys Ala Asp Asp Arg Ala Asp Leu Ala Lys Tyr Ile Cys Glu Asn
            420                 425                 430

Gln Asp Ser Ile Ser Ser Lys Leu Lys Glu Cys Cys Glu Lys Pro Leu
            435                 440                 445

Leu Glu Lys Ser His Cys Ile Ala Glu Val Glu Asn Asp Glu Met Pro
450                 455                 460

Ala Asp Leu Pro Ser Leu Ala Ala Asp Phe Val Glu Ser Lys Asp Val
465                 470                 475                 480

Cys Lys Asn Tyr Ala Glu Ala Lys Asp Val Phe Leu Gly Met Phe Leu
            485                 490                 495

Tyr Glu Tyr Ala Arg Arg His Pro Asp Tyr Ser Val Val Leu Leu Leu
            500                 505                 510

Arg Leu Ala Lys Thr Tyr Glu Thr Thr Leu Glu Lys Cys Cys Ala Ala
            515                 520                 525

Ala Asp Pro His Glu Cys Tyr Ala Lys Val Phe Asp Glu Phe Lys Pro
            530                 535                 540

Leu Val Glu Glu Pro Gln Asn Leu Ile Lys Gln Asn Cys Glu Leu Phe
545                 550                 555                 560

Glu Gln Leu Gly Glu Tyr Lys Phe Gln Asn Ala Leu Leu Val Arg Tyr
            565                 570                 575
```

Thr Lys Lys Val Pro Gln Val Ser Thr Pro Thr Leu Val Glu Val Ser
                580                 585                 590

Arg Asn Leu Gly Lys Val Gly Ser Lys Cys Cys Lys His Pro Glu Ala
            595                 600                 605

Lys Arg Met Pro Cys Ala Glu Asp Tyr Leu Ser Val Val Leu Asn Gln
        610                 615                 620

Leu Cys Val Leu His Glu Lys Thr Pro Val Ser Asp Arg Val Thr Lys
625                 630                 635                 640

Cys Cys Thr Glu Ser Leu Val Asn Arg Arg Pro Cys Phe Ser Ala Leu
                645                 650                 655

Glu Val Asp Glu Thr Tyr Val Pro Lys Glu Phe Asn Ala Glu Thr Phe
            660                 665                 670

Thr Phe His Ala Asp Ile Cys Thr Leu Ser Glu Lys Glu Arg Gln Ile
        675                 680                 685

Lys Lys Gln Thr Ala Leu Val Glu Leu Val Lys His Lys Pro Lys Ala
    690                 695                 700

Thr Lys Glu Gln Leu Lys Ala Val Met Asp Asp Phe Ala Ala Phe Val
705                 710                 715                 720

Glu Lys Cys Cys Lys Ala Asp Asp Lys Glu Thr Cys Phe Ala Glu Glu
                725                 730                 735

Gly Lys Lys Leu Val Ala Ala Ser Gln Ala Ala Leu Gly Leu
            740                 745                 750

<210> SEQ ID NO 39
<211> LENGTH: 730
<212> TYPE: PRT
<213> ORGANISM: Artificial Sequence
<220> FEATURE:
<223> OTHER INFORMATION: Description of Artificial Sequence: Synthetic
      Human wt Albumin with signal peptide and propeptide +
      human LH beta-chain sequence

<400> SEQUENCE: 39

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys

```
                180                 185                 190
Cys Gln Ala Ala Asp Lys Ala Ala Cys Leu Leu Pro Lys Leu Asp Glu
            195                 200                 205

Leu Arg Asp Glu Gly Lys Ala Ser Ser Ala Lys Gln Arg Leu Lys Cys
210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
            245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
            275                 280                 285

Cys Glu Asn Gln Asp Ser Ile Ser Ser Lys Leu Lys Glu Cys Cys Glu
            290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
            325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
            355                 360                 365

Leu Leu Leu Arg Leu Ala Lys Thr Tyr Glu Thr Thr Leu Glu Lys Cys
370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
            405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
            435                 440                 445

Glu Val Ser Arg Asn Leu Gly Lys Val Gly Ser Lys Cys Cys Lys His
450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
            485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
            515                 520                 525

Glu Thr Phe Thr Phe His Ala Asp Ile Cys Thr Leu Ser Glu Lys Glu
            530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
            565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
            595                 600                 605
```

```
Leu Ser Arg Glu Pro Leu Arg Pro Trp Cys His Pro Ile Asn Ala Ile
    610                 615                 620

Leu Ala Val Glu Lys Glu Gly Cys Pro Val Cys Ile Thr Val Asn Thr
625                 630                 635                 640

Thr Ile Cys Ala Gly Tyr Cys Pro Thr Met Met Arg Val Leu Gln Ala
            645                 650                 655

Val Leu Pro Pro Leu Pro Gln Val Val Cys Thr Tyr Arg Asp Val Arg
            660                 665                 670

Phe Glu Ser Ile Arg Leu Pro Gly Cys Pro Arg Gly Val Asp Pro Val
        675                 680                 685

Val Ser Phe Pro Val Ala Leu Ser Cys Arg Cys Gly Pro Cys Arg Arg
    690                 695                 700

Ser Thr Ser Asp Cys Gly Gly Pro Lys Asp His Pro Leu Thr Cys Asp
705                 710                 715                 720

His Pro Gln Leu Ser Gly Leu Leu Phe Leu
            725                 730

<210> SEQ ID NO 40
<211> LENGTH: 726
<212> TYPE: PRT
<213> ORGANISM: Artificial Sequence
<220> FEATURE:
<223> OTHER INFORMATION: Description of Artificial Sequence: Synthetic
      Human LH beta-chain with signal peptide + human wt Albumin
      sequence

<400> SEQUENCE: 40

Met Glu Met Leu Gln Gly Leu Leu Leu Leu Leu Leu Ser Met Gly
1               5                   10                  15

Gly Ala Trp Ala Ser Arg Glu Pro Leu Arg Pro Trp Cys His Pro Ile
            20                  25                  30

Asn Ala Ile Leu Ala Val Glu Lys Glu Gly Cys Pro Val Cys Ile Thr
            35                  40                  45

Val Asn Thr Thr Ile Cys Ala Gly Tyr Cys Pro Thr Met Met Arg Val
50                  55                  60

Leu Gln Ala Val Leu Pro Pro Leu Pro Gln Val Val Cys Thr Tyr Arg
65                  70                  75                  80

Asp Val Arg Phe Glu Ser Ile Arg Leu Pro Gly Cys Pro Arg Gly Val
            85                  90                  95

Asp Pro Val Val Ser Phe Pro Val Ala Leu Ser Cys Arg Cys Gly Pro
            100                 105                 110

Cys Arg Arg Ser Thr Ser Asp Cys Gly Gly Pro Lys Asp His Pro Leu
        115                 120                 125

Thr Cys Asp His Pro Gln Leu Ser Gly Leu Leu Phe Leu Asp Ala His
    130                 135                 140

Lys Ser Glu Val Ala His Arg Phe Lys Asp Leu Gly Glu Glu Asn Phe
145                 150                 155                 160

Lys Ala Leu Val Leu Ile Ala Phe Ala Gln Tyr Leu Gln Gln Cys Pro
            165                 170                 175

Phe Glu Asp His Val Lys Leu Val Asn Glu Val Thr Glu Phe Ala Lys
            180                 185                 190

Thr Cys Val Ala Asp Glu Ser Ala Glu Asn Cys Asp Lys Ser Leu His
        195                 200                 205

Thr Leu Phe Gly Asp Lys Leu Cys Thr Val Ala Thr Leu Arg Glu Thr
    210                 215                 220
```

-continued

```
Tyr Gly Glu Met Ala Asp Cys Cys Ala Lys Gln Pro Glu Arg Asn
225                 230                 235                 240

Glu Cys Phe Leu Gln His Lys Asp Asp Asn Pro Asn Leu Pro Arg Leu
            245                 250                 255

Val Arg Pro Glu Val Asp Val Met Cys Thr Ala Phe His Asp Asn Glu
        260                 265                 270

Glu Thr Phe Leu Lys Lys Tyr Leu Tyr Glu Ile Ala Arg Arg His Pro
    275                 280                 285

Tyr Phe Tyr Ala Pro Glu Leu Leu Phe Phe Ala Lys Arg Tyr Lys Ala
290                 295                 300

Ala Phe Thr Glu Cys Cys Gln Ala Ala Asp Lys Ala Ala Cys Leu Leu
305                 310                 315                 320

Pro Lys Leu Asp Glu Leu Arg Asp Glu Gly Lys Ala Ser Ser Ala Lys
            325                 330                 335

Gln Arg Leu Lys Cys Ala Ser Leu Gln Lys Phe Gly Glu Arg Ala Phe
        340                 345                 350

Lys Ala Trp Ala Val Ala Arg Leu Ser Gln Arg Phe Pro Lys Ala Glu
    355                 360                 365

Phe Ala Glu Val Ser Lys Leu Val Thr Asp Leu Thr Lys Val His Thr
370                 375                 380

Glu Cys Cys His Gly Asp Leu Leu Glu Cys Ala Asp Asp Arg Ala Asp
385                 390                 395                 400

Leu Ala Lys Tyr Ile Cys Glu Asn Gln Asp Ser Ile Ser Ser Lys Leu
            405                 410                 415

Lys Glu Cys Cys Glu Lys Pro Leu Leu Glu Lys Ser His Cys Ile Ala
        420                 425                 430

Glu Val Glu Asn Asp Glu Met Pro Ala Asp Leu Pro Ser Leu Ala Ala
    435                 440                 445

Asp Phe Val Glu Ser Lys Asp Val Cys Lys Asn Tyr Ala Glu Ala Lys
450                 455                 460

Asp Val Phe Leu Gly Met Phe Leu Tyr Glu Tyr Ala Arg Arg His Pro
465                 470                 475                 480

Asp Tyr Ser Val Val Leu Leu Leu Arg Leu Ala Lys Thr Tyr Glu Thr
            485                 490                 495

Thr Leu Glu Lys Cys Cys Ala Ala Ala Asp Pro His Glu Cys Tyr Ala
        500                 505                 510

Lys Val Phe Asp Glu Phe Lys Pro Leu Val Glu Glu Pro Gln Asn Leu
    515                 520                 525

Ile Lys Gln Asn Cys Glu Leu Phe Glu Gln Leu Gly Glu Tyr Lys Phe
530                 535                 540

Gln Asn Ala Leu Leu Val Arg Tyr Thr Lys Lys Val Pro Gln Val Ser
545                 550                 555                 560

Thr Pro Thr Leu Val Glu Val Ser Arg Asn Leu Gly Lys Val Gly Ser
            565                 570                 575

Lys Cys Cys Lys His Pro Glu Ala Lys Arg Met Pro Cys Ala Glu Asp
        580                 585                 590

Tyr Leu Ser Val Val Leu Asn Gln Leu Cys Val Leu His Glu Lys Thr
    595                 600                 605

Pro Val Ser Asp Arg Val Thr Lys Cys Cys Thr Glu Ser Leu Val Asn
610                 615                 620

Arg Arg Pro Cys Phe Ser Ala Leu Glu Val Asp Glu Thr Tyr Val Pro
625                 630                 635                 640

Lys Glu Phe Asn Ala Glu Thr Phe Thr Phe His Ala Asp Ile Cys Thr
```

```
                    645                 650                 655
Leu Ser Glu Lys Glu Arg Gln Ile Lys Lys Gln Thr Ala Leu Val Glu
                660                 665                 670

Leu Val Lys His Lys Pro Lys Ala Thr Lys Glu Gln Leu Lys Ala Val
            675                 680                 685

Met Asp Asp Phe Ala Ala Phe Val Glu Lys Cys Cys Lys Ala Asp Asp
690                 695                 700

Lys Glu Thr Cys Phe Ala Glu Glu Gly Lys Lys Leu Val Ala Ala Ser
705                 710                 715                 720

Gln Ala Ala Leu Gly Leu
                725

<210> SEQ ID NO 41
<211> LENGTH: 358
<212> TYPE: PRT
<213> ORGANISM: Artificial Sequence
<220> FEATURE:
<223> OTHER INFORMATION: Description of Artificial Sequence: Synthetic
      Human alpha-chain with signal peptide + linker + human Fc
      sequence

<400> SEQUENCE: 41

Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Gln Asp Cys Pro
            20                  25                  30

Glu Cys Thr Leu Gln Glu Asn Pro Phe Phe Ser Gln Pro Gly Ala Pro
        35                  40                  45

Ile Leu Gln Cys Met Gly Cys Cys Phe Ser Arg Ala Tyr Pro Thr Pro
50                  55                  60

Leu Arg Ser Lys Lys Thr Met Leu Val Gln Lys Asn Val Thr Ser Glu
65                  70                  75                  80

Ser Thr Cys Cys Val Ala Lys Ser Tyr Asn Arg Val Thr Val Met Gly
                85                  90                  95

Gly Phe Lys Val Glu Asn His Thr Ala Cys His Cys Ser Thr Cys Tyr
            100                 105                 110

Tyr His Lys Ser Gly Gly Gly Ser Gly Gly Gly Ser Gly Gly
        115                 120                 125

Gly Gly Ser Asp Lys Thr His Thr Cys Pro Pro Cys Pro Ala Pro Glu
130                 135                 140

Leu Leu Gly Gly Pro Ser Val Phe Leu Phe Pro Pro Lys Pro Lys Asp
145                 150                 155                 160

Thr Leu Met Ile Ser Arg Thr Pro Glu Val Thr Cys Val Val Val Asp
                165                 170                 175

Val Ser His Glu Asp Pro Glu Val Lys Phe Asn Trp Tyr Val Asp Gly
            180                 185                 190

Val Glu Val His Asn Ala Lys Thr Lys Pro Arg Glu Glu Gln Tyr Asn
        195                 200                 205

Ser Thr Tyr Arg Val Val Ser Val Leu Thr Val Leu His Gln Asp Trp
210                 215                 220

Leu Asn Gly Lys Glu Tyr Lys Cys Lys Val Ser Asn Lys Ala Leu Pro
225                 230                 235                 240

Ala Pro Ile Glu Lys Thr Ile Ser Lys Ala Lys Gly Gln Pro Arg Glu
                245                 250                 255

Pro Gln Val Tyr Thr Leu Pro Pro Ser Arg Asp Glu Leu Thr Lys Asn
            260                 265                 270
```

```
Gln Val Ser Leu Thr Cys Leu Val Lys Gly Phe Tyr Pro Ser Asp Ile
            275                 280                 285

Ala Val Glu Trp Glu Ser Asn Gly Gln Pro Glu Asn Asn Tyr Lys Thr
    290                 295                 300

Thr Pro Pro Val Leu Asp Ser Asp Gly Ser Phe Phe Leu Tyr Ser Lys
305                 310                 315                 320

Leu Thr Val Asp Lys Ser Arg Trp Gln Gln Gly Asn Val Phe Ser Cys
                325                 330                 335

Ser Val Met His Glu Ala Leu His Asn His Tyr Thr Gln Lys Ser Leu
            340                 345                 350

Ser Leu Ser Pro Gly Lys
        355

<210> SEQ ID NO 42
<211> LENGTH: 413
<212> TYPE: PRT
<213> ORGANISM: Artificial Sequence
<220> FEATURE:
<223> OTHER INFORMATION: Description of Artificial Sequence: Synthetic
      Human hCG beta-chain with signal peptide + linker +
      human Fc + Histag sequence

<400> SEQUENCE: 42

Met Glu Met Phe Gln Gly Leu Leu Leu Leu Leu Leu Leu Ser Met Gly
1               5                   10                  15

Gly Thr Trp Ala Ser Lys Glu Pro Leu Arg Pro Arg Cys Arg Pro Ile
            20                  25                  30

Asn Ala Thr Leu Ala Val Glu Lys Glu Gly Cys Pro Val Cys Ile Thr
        35                  40                  45

Val Asn Thr Thr Ile Cys Ala Gly Tyr Cys Pro Thr Met Thr Arg Val
    50                  55                  60

Leu Gln Gly Val Leu Pro Ala Leu Pro Gln Val Val Cys Asn Tyr Arg
65                  70                  75                  80

Asp Val Arg Phe Glu Ser Ile Arg Leu Pro Gly Cys Pro Arg Gly Val
                85                  90                  95

Asn Pro Val Val Ser Tyr Ala Val Ala Leu Ser Cys Gln Cys Ala Leu
            100                 105                 110

Cys Arg Arg Ser Thr Thr Asp Cys Gly Gly Pro Lys Asp His Pro Leu
        115                 120                 125

Thr Cys Asp Asp Pro Arg Phe Gln Asp Ser Ser Ser Ser Lys Ala Pro
    130                 135                 140

Pro Pro Ser Leu Pro Ser Pro Ser Arg Leu Pro Gly Pro Ser Asp Thr
145                 150                 155                 160

Pro Ile Leu Pro Gln Gly Gly Gly Ser Gly Gly Gly Gly Ser Gly
                165                 170                 175

Gly Gly Gly Ser Asp Lys Thr His Thr Cys Pro Pro Cys Pro Ala Pro
            180                 185                 190

Glu Leu Leu Gly Gly Pro Ser Val Phe Leu Phe Pro Pro Lys Pro Lys
        195                 200                 205

Asp Thr Leu Met Ile Ser Arg Thr Pro Glu Val Thr Cys Val Val Val
    210                 215                 220

Asp Val Ser His Glu Asp Pro Glu Val Lys Phe Asn Trp Tyr Val Asp
225                 230                 235                 240

Gly Val Glu Val His Asn Ala Lys Thr Lys Pro Arg Glu Glu Gln Tyr
                245                 250                 255
```

Asn Ser Thr Tyr Arg Val Ser Val Leu Thr Val Leu His Gln Asp
            260             265             270

Trp Leu Asn Gly Lys Glu Tyr Lys Cys Lys Val Ser Asn Lys Ala Leu
        275             280             285

Pro Ala Pro Ile Glu Lys Thr Ile Ser Lys Ala Lys Gly Gln Pro Arg
    290             295             300

Glu Pro Gln Val Tyr Thr Leu Pro Pro Ser Arg Asp Glu Leu Thr Lys
305             310             315             320

Asn Gln Val Ser Leu Thr Cys Leu Val Lys Gly Phe Tyr Pro Ser Asp
            325             330             335

Ile Ala Val Glu Trp Glu Ser Asn Gly Gln Pro Glu Asn Asn Tyr Lys
        340             345             350

Thr Thr Pro Pro Val Leu Asp Ser Asp Gly Ser Phe Phe Leu Tyr Ser
    355             360             365

Lys Leu Thr Val Asp Lys Ser Arg Trp Gln Gln Gly Asn Val Phe Ser
370             375             380

Cys Ser Val Met His Glu Ala Leu His Asn His Tyr Thr Gln Lys Ser
385             390             395             400

Leu Ser Leu Ser Pro Gly Lys His His His His His His
            405             410

<210> SEQ ID NO 43
<211> LENGTH: 389
<212> TYPE: PRT
<213> ORGANISM: Artificial Sequence
<220> FEATURE:
<223> OTHER INFORMATION: Description of Artificial Sequence: Synthetic
      Human LH beta-chain with signal peptide + linker + human
      Fc + Histag sequence

<400> SEQUENCE: 43

Met Glu Met Leu Gln Gly Leu Leu Leu Leu Leu Leu Ser Met Gly
1               5                   10                  15

Gly Ala Trp Ala Ser Arg Glu Pro Leu Arg Pro Trp Cys His Pro Ile
            20                  25                  30

Asn Ala Ile Leu Ala Val Glu Lys Glu Gly Cys Pro Val Cys Ile Thr
        35                  40                  45

Val Asn Thr Thr Ile Cys Ala Gly Tyr Cys Pro Thr Met Met Arg Val
    50                  55                  60

Leu Gln Ala Val Leu Pro Pro Leu Pro Gln Val Val Cys Thr Tyr Arg
65                  70                  75                  80

Asp Val Arg Phe Glu Ser Ile Arg Leu Pro Gly Cys Pro Arg Gly Val
                85                  90                  95

Asp Pro Val Val Ser Phe Pro Val Ala Leu Ser Cys Arg Cys Gly Pro
            100                 105                 110

Cys Arg Arg Ser Thr Ser Asp Cys Gly Gly Pro Lys Asp His Pro Leu
        115                 120                 125

Thr Cys Asp His Pro Gln Leu Ser Gly Leu Leu Phe Leu Gly Gly Gly
    130                 135                 140

Gly Ser Gly Gly Gly Ser Gly Gly Gly Ser Asp Lys Thr His
145                 150                 155                 160

Thr Cys Pro Pro Cys Pro Ala Pro Glu Leu Gly Gly Pro Ser Val
                165                 170                 175

Phe Leu Phe Pro Pro Lys Pro Lys Asp Thr Leu Met Ile Ser Arg Thr
            180                 185                 190

Pro Glu Val Thr Cys Val Val Val Asp Val Ser His Glu Asp Pro Glu

```
            195                 200                 205
Val Lys Phe Asn Trp Tyr Val Asp Gly Val Glu Val His Asn Ala Lys
    210                 215                 220
Thr Lys Pro Arg Glu Glu Gln Tyr Asn Ser Thr Tyr Arg Val Val Ser
225                 230                 235                 240
Val Leu Thr Val Leu His Gln Asp Trp Leu Asn Gly Lys Glu Tyr Lys
                245                 250                 255
Cys Lys Val Ser Asn Lys Ala Leu Pro Ala Pro Ile Glu Lys Thr Ile
            260                 265                 270
Ser Lys Ala Lys Gly Gln Pro Arg Glu Pro Gln Val Tyr Thr Leu Pro
        275                 280                 285
Pro Ser Arg Asp Glu Leu Thr Lys Asn Gln Val Ser Leu Thr Cys Leu
290                 295                 300
Val Lys Gly Phe Tyr Pro Ser Asp Ile Ala Val Glu Trp Glu Ser Asn
305                 310                 315                 320
Gly Gln Pro Glu Asn Asn Tyr Lys Thr Thr Pro Pro Val Leu Asp Ser
                325                 330                 335
Asp Gly Ser Phe Phe Leu Tyr Ser Lys Leu Thr Val Asp Lys Ser Arg
            340                 345                 350
Trp Gln Gln Gly Asn Val Phe Ser Cys Ser Val Met His Glu Ala Leu
        355                 360                 365
His Asn His Tyr Thr Gln Lys Ser Leu Ser Leu Ser Pro Gly Lys His
    370                 375                 380
His His His His His
385

<210> SEQ ID NO 44
<211> LENGTH: 348
<212> TYPE: DNA
<213> ORGANISM: Artificial Sequence
<220> FEATURE:
<223> OTHER INFORMATION: Description of Artificial Sequence: Synthetic
      Human alpha-chain with signal peptide optimized (348 bases)
      sequence

<400> SEQUENCE: 44
atggactact accggaagta cgccgccatc ttcctcgtga ccctgtccgt gttcctgcac    60
gtgctgcact ctgcccccga tgtgcaggac tgccctgagt gcaccctgca ggaaaaccca   120
ttcttcagcc agcctggcgc ccctatcctg cagtgcatgg gctgctgctt ctcccgggct   180
taccccaccc tctgcggtc caagaaaacc atgctggtgc agaaaaacgt gacctccgag   240
tctacctgct gcgtggccaa gtcctacaac agagtgaccg tgatgggcgg cttcaaggtg   300
gaaaaccaca ccgcctgcca ctgctccacc tgttactacc acaagtcc              348

<210> SEQ ID NO 45
<211> LENGTH: 495
<212> TYPE: DNA
<213> ORGANISM: Artificial Sequence
<220> FEATURE:
<223> OTHER INFORMATION: Description of Artificial Sequence: Synthetic
      Human hCG beta-chain with signal peptide, opdimized (495 bases)
      sequence

<400> SEQUENCE: 45
atggaaatgt tccagggcct ccttctcctg ctgctgctgt ctatgggcgg cacctgggcc    60
tccaaagagc tctgaggcc ccggtgcaga cccatcaatg ctaccctggc cgtgaaaaaa   120
gagggctgcc ccgtgtgcat caccgtgaac accaccatct cgccggcta ctgccctacc   180
```

```
atgaccagag tgctgcaggg cgtgctgcct gctctgcctc aggtcgtgtg caactaccgg    240
gacgtgcgct tcgagtccat cagactgcct ggctgcccca gaggcgtgaa ccctgtggtg    300
tcttacgccg tggccctgtc ttgccagtgc gccctgtgca aagatccac accgattgt     360 ggcggcccta aggaccaccc tctgacctgc gacgaccctc ggttccagga ctcctccagc    420
tctaaggccc ctccaccttc cctgcctagc ccttctagac tgccaggccc ttccgacacc    480
cccatcctgc ctcag                                                     495
```

<210> SEQ ID NO 46
<211> LENGTH: 423
<212> TYPE: DNA
<213> ORGANISM: Artificial Sequence
<220> FEATURE:
<223> OTHER INFORMATION: Description of Artificial Sequence: Synthetic
      Human LH beta-chain with signal peptide, optimized (423 bases)
      sequence

<400> SEQUENCE: 46

```
atggaaatgc tgcagggcct ccttctcctg ctgctgctgt ctatgggcgg agcctgggcc    60
tctagagagc cactgaggcc ttggtgccac cccatcaatg ccatcctggc cgtgaaaaa    120 gagggctgcc ccgtgtgcat caccgtgaac accaccatct cgccggcta ctgccccacc    180 atgatgagag tgctgcaggc cgtgctgccc cctctgcctc aggtcgtgtg cacctacaga    240
gatgtgcgct tcgagtccat ccggctgcct ggctgtccta gaggcgtgga ccctgtggtg    300
tctttccctg tggccctgtc ctgcagatgc ggcccttgca aagatccac ctccgactgt    360 ggcggcccta aggaccaccc tctgacctgc gatcaccctc agctgtccgg cctgctgttc    420
ctg                                                                  423
```

<210> SEQ ID NO 47
<211> LENGTH: 2103
<212> TYPE: DNA
<213> ORGANISM: Artificial Sequence
<220> FEATURE:
<223> OTHER INFORMATION: Description of Artificial Sequence: Synthetic
      Human wt Albumin with signal peptide and propeptide +
      human alpha-chain (2103 bases) sequence

<400> SEQUENCE: 47

```
atgaaatggg tcacctttat ctccctgctg ttcctgttct cctccgccta ctctcggggc    60
gtgttcagaa gggacgccca caagtctgag gtggcccacc ggttcaagga cctgggcgag    120
gaaaacttca aggccctggt gctgatcgcc ttcgcccagt acctgcagca gtgccccttc    180
gaggaccacg tgaagctcgt gaacgaagtg accgagttcg ccaagacctg cgtggccgat    240
gagtccgccg agaactgcga caagtccctg cacaccctgt tcggcgacaa gctgtgtacc    300
gtggccaccc tgagagaaac ctacggcgag atggccgact gctgcgccaa gcaggaacct    360
gagcggaacg agtgcttcct gcagcacaag gacgacaacc caacctgcc cagactcgtg    420 cggcctgagg tggacgtgat gtgcaccgcc ttccacgaca cgaggaaac cttcctgaag    480 aagtacctgt acgagatcgc cagacggcac ccctacttct acgcccccga gctgctgttc    540
ttcgccaagc ggtacaaggc cgccttcacc gagtgttgcc aggccgccga taaggccgct    600
tgcctgctgc ctaagctgga cgagctgagg gatgagggca aggcctcctc tgccaagcag    660
agactgaagt gcgcctccct gcagaagttc ggcgagcggg cctttaaggc ctgggccgtg    720
gctagactgt cccagagatt ccccaaggcc gagtttgccg aggtgtccaa gctcgtgacc    780
```

| | |
|---|---|
| gacctgacca aggtgcacac cgagtgctgt cacggcgacc tgctggaatg cgccgacgac | 840 |
| agagccgatc tggccaagta catctgcgag aaccaggact ccatctcctc caagctgaaa | 900 |
| gagtgctgcg agaagcctct gctggaaaag tcccactgta tcgccgaggt ggaaaacgac | 960 |
| gagatgcccg ccgacctgcc ttctctggcc gccgacttcg tggaatccaa ggacgtgtgc | 1020 |
| aagaactacg ccgaggccaa ggatgtgttc ctgggcatgt ttctgtacga gtacgctcgg | 1080 |
| cggcaccccg actactctgt ggtgctgctg ctgagactgg ctaagaccta cgagacaacc | 1140 |
| ctggaaaaat gctgcgccgc tgccgacccc cacgagtgtt acgccaaggt gttcgacgag | 1200 |
| ttcaagccac tggtggaaga accccagaac ctgatcaagc agaattgcga gctgttcgag | 1260 |
| cagctgggcg agtacaagtt ccagaacgcc ctgctcgtgc ggtacaccaa gaaagtgccc | 1320 |
| caggtgtcca ccccccaccct ggtggaagtg tcccggaacc tgggcaaagt gggctccaag | 1380 |
| tgctgcaagc accctgaggc caagcggatg ccttgcgccg aggactacct gtccgtggtg | 1440 |
| ctgaaccagc tgtgcgtgct gcacgaaaag accccgtgt ccgacagagt gaccaagtgt | 1500 |
| tgcaccgagt ccctcgtgaa cagacggccc tgcttctccg ccctggaagt ggacgagaca | 1560 |
| tacgtgccca agagttcaa cgccgagaca ttccccttcc acgccgacat ctgcaccctg | 1620 |
| tccgagaaag agcggcagat caagaaacag accgctctgg tggaactcgt gaagcacaag | 1680 |
| cccaaggcca ccaaagaaca gctgaaggcc gtgatggacg acttcgccgc ctttgtggaa | 1740 |
| aagtgctgta agccgatga caaagagaca tgcttcgccg aagagggcaa gaaactggtg | 1800 |
| gccgcctctc aggctgcact gggactggct ccagacgtgc aggactgccc tgagtgcacc | 1860 |
| ctgcaggaaa acccattctt cagccagcct ggcgcccta tcctgcagtg catgggctgc | 1920 |
| tgcttcagcc gggcttaccc caccctctg cggtccaaga aaccatgct ggtgcagaaa | 1980 |
| aacgtgacct ccgagtctac ctgctgtgtg gccaagtcct acaatagagt gaccgtgatg | 2040 |
| ggcggcttca agtggaaaaa ccacaccgcc tgccactgct ccacctgtta ctaccacaag | 2100 |
| tcc | 2103 |

<210> SEQ ID NO 48
<211> LENGTH: 2103
<212> TYPE: DNA
<213> ORGANISM: Artificial Sequence
<220> FEATURE:
<223> OTHER INFORMATION: Description of Artificial Sequence: Synthetic
      Human alpha-chain with signal peptide + human wt Albumin
      (2103 bases) sequence

<400> SEQUENCE: 48

| | |
|---|---|
| atggactact accggaagta cgccgccatc ttcctcgtga ccctgtccgt gttcctgcac | 60 |
| gtgctgcact ctgcccccga tgtgcaggac tgccctgagt gcaccctgca ggaaaaccca | 120 |
| ttcttcagcc agcctggcgc ccctatcctg cagtgcatgg gctgctgctt ctcccgggct | 180 |
| taccccaccc tctgcgggtc caagaaaacc atgctggtgc agaaaaacgt gacctccgag | 240 |
| tctacctgct gcgtggccaa gtcctacaac agagtgaccg tgatgggcgg cttcaaggtg | 300 |
| gaaaaccaca ccgcctgcca ctgctccacc tgttactacc acaagtccga cgcccacaag | 360 |
| agcgaggtgg cccacagatt caaggacctg ggcgaggaaa acttcaaggc cctggtgctg | 420 |
| atcgccttcg cccagtacct gcagcagtgc cccttcgagg accacgtgaa gctcgtgaac | 480 |
| gaagtgaccg agttcgccaa gacctgtgtg gccgacgagt ccgccgagaa ctgcgacaag | 540 |
| tctctgcaca cccctgttcgg cgacaagctg tgcaccgtgg ccaccctgag agaaacctac | 600 |
| ggcgagatgg ccgactgctg cgccaagcag gaacctgagc ggaacgagtg cttcctgcag | 660 |

```
cacaaggacg acaaccccaa cctgcccaga ctcgtgcggc ctgaggtgga cgtgatgtgc      720
accgccttcc acgacaacga ggaaaccttc ctgaagaagt acctgtacga gatcgccaga      780
cggcacccct acttctacgc ccccgagctg ctgttcttcg ccaagcggta caaggccgcc      840
ttcaccgagt gttgccaggc cgccgataag gccgcttgcc tgctgcctaa gctggacgag      900
ctgagggatg agggcaaggc ctcctctgcc aagcagagac tgaagtgcgc ctccctgcag      960
aagttcggcg agcgggcctt taaggcctgg gccgtggcta actgtcccca gagattcccc     1020
aaggccgagt ttgccgaggt gtccaagctc gtgaccgacc tgaccaaggt gcacaccgag     1080
tgctgtcacg gcgacctgct ggaatgcgcc gacgacagac cgatctggc caagtacatc     1140 tgcgagaacc aggactccat ctcctccaag ctgaagagt gctgcgagaa gcctctgctg     1200
gaaaagtccc actgtatcgc cgaagtggaa acgacgaga tgcccgccga cctgccttct     1260
ctggccgccg acttcgtgga atccaaggac gtgtgcaaga actacgccga ggccaaggat     1320
gtgttcctgg gcatgtttct gtacgagtac gctcggcggc accccgacta ctctgtggtg     1380
ctgctgctga gactggctaa gacctacgag acaaccctgg aaaaatgctg cgccgctgcc     1440 gaccccacg agtgttacgc caaggtgttc gacgagttca gccactggt ggaagaaccc     1500 cagaacctga tcaagcagaa ttgcgagctg ttcgagcagc tgggcgagta caagttccag     1560
aacgccctgc tcgtgcggta caccaagaaa gtgccccagg tgtccacccc caccctggtg     1620
gaagtgtccc ggaacctggg caaagtgggc tccaagtgct gcaagcaccc tgaggccaag     1680
cggatgcctt gcgccgagga ctacctgagc gtggtgctga accagctgtg tgtgctgcac     1740
gaaaagaccc ccgtgtccga tagagtgacc aagtgttgca ccgagtccct cgtgaacaga     1800
cggccttgct ctccgccct ggaagtggac gagacatacg tgcccaaaga gttcaacgcc     1860
gagacattca ccttccacgc cgacatctgc accctgtctg agaaagagcg gcagatcaag     1920
aaacagaccg ctctggtgga actcgtgaag cacaagccca aggccaccaa gaaacagctg     1980
aaggccgtga tggacgactt cgccgccttt gtggaaaagt gctgtaaagc cgatgacaaa     2040
gagacatgct tcgccgaaga gggcaagaaa ctggtggccg cctctcaggc tgctctggga     2100
ctg                                                                    2103
```

<210> SEQ ID NO 49
<211> LENGTH: 2262
<212> TYPE: DNA
<213> ORGANISM: Artificial Sequence
<220> FEATURE:
<223> OTHER INFORMATION: Description of Artificial Sequence: Synthetic
      Human wt Albumin with signal peptide and propeptide +
      human hCG beta-chain, optimized (2262 bases) sequence

<400> SEQUENCE: 49

```
atgaaatggg tcacctttat ctccctgctg ttcctgttct cctccgccta ctctcggggc       60
gtgttcagaa gggacgccca aagtctgag gtggcccacc ggttcaagga cctgggcgag      120
gaaaacttca aggccctggt gctgatcgcc ttcgcccagt acctgcagca gtgccccttc      180
gaggaccacg tgaagctcgt gaacgaagtg accgagttcg ccaagacctg cgtggccgat      240
gagtccgccg agaactgcga caagtccctg cacaccctgt tcggcgacaa gctgtgtacc      300
gtggccaccc tgagagaaac ctacggcgag atggccgact gctgcgccaa gcaggaacct      360
gagcggaacg agtgcttcct gcagcacaag gacgacaacc ccaacctgcc cagactcgtg      420
cggcctgagg tggacgtgat gtgcaccgcc ttccacgaca acgaggaaac cttcctgaag      480
```

```
aagtacctgt acgagatcgc cagacggcac ccctacttct acgccccga gctgctgttc    540
ttcgccaagc ggtacaaggc cgccttcacc gagtgttgcc aggccgccga taaggccgct    600
tgcctgctgc ctaagctgga cgagctgagg gatgagggca aggcctcctc tgccaagcag    660
agactgaagt gcgcctccct gcagaagttc ggcgagcggg cctttaaggc ctgggccgtg    720
gctagactgt cccagagatt ccccaaggcc gagtttgccg aggtgtccaa gctcgtgacc    780
gacctgacca aggtgcacac cgagtgctgt cacggcgacc tgctggaatg cgccgacgac    840
agagccgatc tggccaagta catctgcgag aaccaggact ccatctcctc caagctgaaa    900
gagtgctgcg agaagcctct gctggaaaag tcccactgta cgccgaggt ggaaaacgac     960
gagatgcccg ccgacctgcc ttctctggcc gccgacttcg tggaatccaa ggacgtgtgc    1020
aagaactacg ccgaggccaa ggatgtgttc ctgggcatgt ttctgtacga gtacgctcgg    1080
cggcaccccg actactctgt ggtgctgctg ctgagactgg ctaagaccta cgagacaacc    1140
ctggaaaaat gctgcgccgc tgccgacccc cacgagtgtt acgccaaggt gttcgacgag    1200
ttcaagccac tggtggaaga ccccagaac ctgatcaagc agaattgcga gctgttcgag     1260
cagctgggcg agtacaagtt ccagaacgcc ctgctcgtgc ggtacaccaa gaaagtgccc    1320
caggtgtcca cccccaccct ggtggaagtg tcccggaacc tgggcaaagt gggctccaag    1380
tgctgcaagc accctgaggc caagcggatg ccttgcgccg aggactacct gtccgtggtg    1440
ctgaaccagc tgtgcgtgct gcacgaaaag accccgtgt ccgacagagt gaccaagtgt     1500
tgcaccgagt ccctcgtgaa cagacggccc tgcttctccg ccctggaagt ggacgagaca    1560
tacgtgccca agagttcaa cgccgagaca ttccttcc acgccgacat ctgcacccg       1620
tccgagaaag agcggcagat caagaaacag accgctctgg tggaactcgt gaagcacaag    1680
cccaaggcca ccaaagaaca gctgaaggcc gtgatgacg acttcgccgc ctttgtggaa     1740
aagtgctgta agccgatga caaagagaca tgcttcgccg aagagggcaa gaaactggtg    1800
gccgcctctc aggctgctct gggcctgtct aaagagcctc tgcggcctcg gtgccggcct    1860
atcaatgcta ccctggccgt ggaaaaagag ggctgccccg tgtgcatcac cgtgaacacc    1920
accatctgcg ccggctactg ccctaccatg acaagggtgc tgcagggcgt gctgcctgct    1980
ctgcctcagg tcgtgtgcaa ctaccgggac gtgcgcttcg agtccatcag actgcctggc    2040
tgccccagag gcgtgaaccc tgtggtgtct tacgccgtgg ccctgtcttg ccagtgcgcc    2100
ctgtgcagaa gatccaccac cgattgtggc ggccctaagg accaccctct gacctgcgac    2160
gaccctcggt tccaggacag ctccagctct aaggcccctc cacttccct gcctagccct     2220
tctagactgc aggcccttc cgacacccct atcctgcctc ag                       2262
```

<210> SEQ ID NO 50
<211> LENGTH: 2250
<212> TYPE: DNA
<213> ORGANISM: Artificial Sequence
<220> FEATURE:
<223> OTHER INFORMATION: Description of Artificial Sequence: Synthetic
      Human hCG beta-chain with signal peptide + human wt
      Albumin, optimized (2250 bases) sequence

<400> SEQUENCE: 50

```
atggaaatgt tccagggcct ccttctcctg ctgctgctgt ctatgggcgg cacctgggcc     60
tccaaagagc ctctgaggcc ccggtgcaga cccatcaatg ctaccctggc cgtggaaaaa    120
gagggctgcc ccgtgtgcat caccgtgaac accaccatct cgccggcta ctgccctacc    180 atgaccagag tgctgcaggg cgtgctgcct gctctgcctc aggtcgtgtg caactaccgg    240
```

```
gacgtgcgct tcgagtccat cagactgcct ggctgcccca gaggcgtgaa ccctgtggtg      300
tcttacgccg tggccctgtc ttgccagtgc gccctgtgca aagatccac caccgattgt       360
ggcggcccta aggaccaccc tctgacctgc gacgaccctc ggttccagga ctcctccagc      420
tctaaggccc ctccaccttc cctgcctagc ccttctagac tgccaggccc ttcgacacc       480
cccatcctgc acaggatgc ccacaagtct gaggtggccc accggttcaa ggacctgggc       540
gaggaaaact tcaaggccct ggtgctgatc gccttcgccc agtacctgca gcagtgcccc      600
ttcgaggacc acgtgaagct cgtgaacgaa gtgaccgagt cgccaagac tgcgtggcc       660
gatgagtccg ccgagaactg cgacaagtcc ctgcacaccc tgttcggcga caagctgtgt     720
accgtggcca ccctgagaga aacctacggc gagatggccg actgctgcgc caagcaggaa     780
cctgagcgga cgagtgcttt ctgcagcac aaggacgaca ccctaaccct gcctcggctc      840
gtgcggcctg aggtggacgt gatgtgtacc gccttccacg acaacgagga aaccttcctg     900
aagaagtacc tgtacgagat cgccagacgg caccccctact ctacgcccc cgagctgctg     960
ttcttcgcca gcggtacaa ggccgccttc accgagtgtt gccaggccgc cgataaggcc     1020
gcttgcctgc tgcctaagct ggacgagctg agggatgagg gcaaggcctc ctctgccaag     1080
cagagactga agtgcgcctc cctgcagaag ttcggcgagc gggccttcaa ggcctgggcc     1140
gtggctagac tgtcccagag attccccaag gccgagtttg ccgaggtgtc caagctcgtg    1200
accgacctga ccaaggtgca caccgagtgc tgtcacggcg acctgctgga atgcgccgac    1260
gacagagccg atctgccaa gtacatctgc gagaaccagg acagcatctc ctccaagctg     1320
aaagagtgtt gcgagaagcc tctgctggaa aagtcccact gtatcgccga ggtggaaaac    1380
gacgagatgc ccgccgacct gccttctctg gccgccgact cgtggaatc aaggacgtg      1440
tgcaagaact acgccgaggc caaggatgtg ttcctgggca tgtttctgta cgagtacgct    1500
cggcggcacc ccgactactc tgtggtgctg ctgctgagac tggccaagac ctacgagaca    1560
accctggaaa agtgctgcgc cgctgccgac cctcacgagt gttacgccaa ggtgttcgac    1620
gagttcaagc cactggtgga agaacccag aacctgatca gcagaattg cgagctgttc      1680
gagcagctgg gcgagtacaa gttccagaac gccctgctcg tgcgctacac caagaaagtg    1740
ccccaggtgt ccaccccac cctggtggaa gtgtcccgga acctgggcaa agtgggctcc     1800
aagtgctgca gcaccctga ggccaagcgg atgccttgcg ccgaggacta cctgtccgtg     1860
gtgctgaacc agctgtgcgt gctgcacgaa aagaccccg tgtccgacag agtgaccaag     1920
tgttgcaccg agtccctcgt gaacagacgg ccctgcttct ccgccctgga gtggacgag     1980
acatacgtgc caaagagtt caacgccgag acattcacct tccacgccga catctgcacc    2040
ctgtccgaga aagagcggca gatcaagaaa cagaccgctc tggtggaact cgtgaagcac    2100
aagcccaagg ccaccaaaga acagctgaag gccgtgatgg acgacttcgc cgcctttgtg    2160
gaaaaatgtt gcaaggccga tgacaaagag acatgcttcg ccgaagaggg caagaaactg    2220
gtggccgcct ctcaggctgc tctgggactg                                      2250
```

<210> SEQ ID NO 51
<211> LENGTH: 2190
<212> TYPE: DNA
<213> ORGANISM: Artificial Sequence
<220> FEATURE:
<223> OTHER INFORMATION: Description of Artificial Sequence: Synthetic
      Human wt Albumin with signal peptide and propeptide +
      human LH beta-chain, optimized (2190 bases) sequence

<400> SEQUENCE: 51

```
atgaaatggg tcacctttat ctccctgctg ttcctgttct cctccgccta ctctcggggc      60
gtgttcagaa gggacgccca caagtctgag gtggcccacc ggttcaagga cctgggcgag     120
gaaaacttca aggccctggt gctgatcgcc ttcgcccagt acctgcagca gtgcccttc      180
gaggaccacg tgaagctcgt gaacgaagtg accgagttcg ccaagacctg cgtggccgat     240
gagtccgccg agaactgcga caagtccctg cacaccctgt tcggcgacaa gctgtgtacc     300
gtggccaccc tgagagaaac ctacggcgag atggccgact gctgcgccaa gcaggaacct     360
gagcggaacg agtgcttcct gcagcacaag gacgacaacc caacctgcc cagactcgtg      420
cggcctgagg tggacgtgat gtgcaccgcc ttccacgaca cgaggaaac cttcctgaag       480
aagtacctgt acgagatcgc cagacggcac ccctacttct acgccccga gctgctgttc      540
ttcgccaagc ggtacaaggc cgccttcacc gagtgttgcc aggccgccga taaggccgct     600
tgcctgctgc ctaagctgga cgagctgagg gatgagggca aggcctcctc tgccaagcag     660
agactgaagt gcgcctccct gcagaagttc ggcgagcggg cctttaaggc ctgggccgtg     720
gctagactgt cccagagatt ccccaaggcc gagtttgccg aggtgtccaa gctcgtgacc     780
gacctgacca aggtgcacac cgagtgctgt cacgcgacc tgctggaatg cgccgacgac      840
agagccgatc tggccaagta catctgcgag aaccaggact ccatctcctc caagctgaaa     900
gagtgctgcg agaagcctct gctggaaaag tcccactgta tcgccgaggt ggaaaacgac     960
gagatgcccg ccgacctgcc ttctctggcc gccgacttcg tggaatccaa ggacgtgtgc    1020
aagaactacg ccgaggccaa ggatgtgttc ctgggcatgt ttctgtacga gtacgctcgg    1080
cggcacccg actactctgt ggtgctgctg ctgagactgg ctaagaccta cgagacaacc     1140
ctggaaaaat gctgcgccgc tgccgacccc acgagtgtt acgccaaggt gttcgacgag    1200
ttcaagccac tggtggaaga accccagaac ctgatcaagc agaattgcga gctgttcgag    1260
cagctgggcg agtacaagtt ccagaacgcc ctgctcgtgc ggtacaccaa gaaagtgccc    1320
caggtgtcca cccccacct ggtggaagtg tcccggaacc tgggcaaagt gggctccaag    1380
tgctgcaagc accctgaggc caagcggatg ccttgcgccg aggactacct gtccgtggtg    1440
ctgaaccagc tgtgcgtgct gcacgaaaag accccgtgt ccgacagagt gaccaagtgt    1500
tgcaccgagt ccctcgtgaa cagacggccc tgcttctccg ccctggaagt ggacgagaca    1560
tacgtgccca aagagttcaa cgccgagaca ttcaccttcc acgccgacat ctgcaccctg    1620
tccgagaaag agcggcagat caagaaacag accgctctgg tggaactcgt gaagcacaag    1680
cccaaggcca ccaaagaaca gctgaaggcc gtgatggacg acttcgccgc ctttgtggaa    1740
aagtgctgta aagccgatga caaagagaca tgcttcgccg aagagggcaa gaaactggtg    1800
gccgcctctc aggctgctct gggcctgtct agagagcctc tgaggccttg gtgccacccc    1860
atcaatgcca tcctggccgt ggaaaaagag ggctgccccg tgtgcatcac cgtgaacacc    1920
accatctgcg ccggctactg ccccaccatg atgagggtgc tgcaggccgt gctgcctcca    1980
ctgcctcagg tcgtgtgtac ctaccgggac gtgcgcttcg agtccatcag actgcctggc    2040
tgccctagag gcgtggaccc tgtggtgtct ttccctgtgg ccctgtcctg cagatgcggc    2100
ccttgcagaa gatccaccc cgactgtggc ggccctaagg accaccctct gacctgcgat    2160
caccccagc tgtccggcct gctgtttctg                                       2190
```

<210> SEQ ID NO 52
<211> LENGTH: 2178

<212> TYPE: DNA
<213> ORGANISM: Artificial Sequence
<220> FEATURE:
<223> OTHER INFORMATION: Description of Artificial Sequence: Synthetic
Human LH beta-chain with signal peptide + human wt
Albumin (2178 bases) sequence

<400> SEQUENCE: 52

```
atggaaatgc tgcagggcct ccttctcctg ctgctgctgt ctatgggcgg agcctgggcc      60
tctagagagc cactgaggcc ttggtgccac cccatcaatg ccatcctggc cgtggaaaaa     120
gagggctgcc ccgtgtgcat caccgtgaac accaccatct gcgccggcta ctgccccacc     180
atgatgagag tgctgcaggc cgtgctgccc cctctgcctc aggtcgtgtg cacctacaga     240
gatgtgcgct tcgagtccat ccggctgcct ggctgtccta gaggcgtgga ccctgtggtg     300
tctttccctg tggccctgtc ctgcagatgc ggcccttgca aagatccac ctccgactgt     360
ggcggcccta aggaccaccc tctgacctgc gatcaccctc agctgtccgg cctgctgttc     420
ctggacgccc acaagtctga ggtggcccac cggttcaagg acctgggcga ggaaaacttc     480
aaggccctgg tgctgatcgc cttcgcccag tacctgcagc agtgcccctt cgaggaccac     540
gtgaagctcg tgaacgaagt gaccgagttc gccaagacct gcgtggccga tgagtccgcc     600
gagaactgcg acaagtccct gcacaccctg ttcggcgaca agctgtgtac cgtggccacc     660
ctgagagaaa cctacggcga gatggccgac tgctgcgcca gcaggaacc tgagcggaac     720
gagtgctttc tgcagcacaa ggacgacaac cccaacctgc cagactcgt gcggcctgag     780
gtggacgtga tgtgcaccgc cttccacgac aacgaggaaa ccttcctgaa gaagtacctg     840
tacgagatcg ccagacggca cccctacttc tacgccccg agctgctgtt cttcgccaag     900
cggtacaagg ccgccttcac cgagtgttgc caggccgccg ataaggccgc ttgcctgctg     960
cctaagctgg acgagctgcg ggatgagggc aaggcctctt ctgccaagca gcggctgaag    1020
tgcgcctccc tgcagaagtt tggcgagcgg gcctttaagg cctgggccgt ggctagactg    1080
tcccagagat cccccaaggc cgagtttgcc gaggtgtcca agctcgtgac cgacctgacc    1140
aaagtgcaca ccgagtgctg tcacggcgac ctgctggaat gcgccgacga cagagccgac    1200
ctggccaagt acatctgcga gaaccaggac tccatctcct ccaagctgaa agagtgttgc    1260
gagaagcctc tgctgaaaaa gtcccactgt atcgccgagg tggaaaacga cgagatgccc    1320
gccgacctgc cttctctggc cgccgacttc gtggaatcca aggacgtgtg caagaactac    1380
gccgaggcca aggatgtgtt cctgggcatg tttctgtacg agtacgctcg gcggcacccc    1440
gactactctg tggtgctgct gctgagactg gccaagacct acgagacaac cctggaaaag    1500
tgctgcgccg ctgccgaccc tcacgagtgt tacgccaagg tgttcgacga gttcaagcca    1560
ctggtggaag aacccagaa cctgatcaag cagaattgcg agctgttcga gcagctgggc    1620
gagtacaagt ccagaacgc cctgctcgtg cggtacacca gaaagtgcc ccaggtgtcc    1680
acccccaccc tggtggaagt gtcccggaac ctgggcaaag tgggctccaa gtgctgcaag    1740
cacccctgagg ccaagcggat gccttgcgcc gaggactacc tgtccgtggt gctgaaccag    1800
ctgtgcgtgc tgcacgaaaa gacccccgtg tccgacagag tgaccaagtg ttgcaccgag    1860
tccctcgtga cagacggcc ctgcttctcc gccctggaag tggacgagac atacgtgccc    1920
aaagagttca acgccgagac attcaccttc cacgccgaca tctgcaccct gtccgagaaa    1980
gagcggcaga tcaagaaaca gaccgctctg gtggaactcg tgaagcacaa gcccaaggcc    2040
accaaagaac agctgaaggc cgtgatggac gacttcgccg cctttgtgga aaaatgttgc    2100
```

```
aaggccgatg acaaagagac atgcttcgcc gaagagggca agaaactggt ggccgcctct    2160
caggctgctc tgggactg                                                  2178
```

<210> SEQ ID NO 53
<211> LENGTH: 1074
<212> TYPE: DNA
<213> ORGANISM: Artificial Sequence
<220> FEATURE:
<223> OTHER INFORMATION: Description of Artificial Sequence: Synthetic
      Human alpha-chain with signal peptide + linker + human Fc,
      optimized (1074 bases) sequence

<400> SEQUENCE: 53

```
atggactact accggaagta cgccgccatc ttcctcgtga ccctgtccgt gttcctgcac      60
gtgctgcact ctgcccccga tgtgcaggac tgccctgagt gcaccctgca ggaaaaccca     120
ttcttcagcc agcctggcgc ccctatcctg cagtgcatgg gctgctgctt ctcccgggct     180
taccccaccc ctctgcggtc caagaaaacc atgctggtgc agaaaaacgt gacctccgag     240
tctacctgct gcgtggccaa gtcctacaac agagtgaccg tgatgggcgg cttcaaggtg     300
gaaaaccaca ccgcctgcca ctgctccacc tgttactacc acaagtccgg cggaggcgga     360
tctggcggcg gaggttctgg tggtggtggc tccgataaga cccacacctg tccccttgt     420 cccgcccctg aactgctggg aggcccttct gtgttcctgt tccccccaaa gcccaaggac     480
accctgatga tctcccggac ccccgaagtg acctgcgtgg tggtggatgt gtcccacgag     540
gaccctgaag tgaagttcaa ttggtacgtg gacggcgtgg aagtgcacaa cgccaagacc     600
aagcccagag aggaacagta caactccacc taccgggtgg tgtccgtgct gaccgtgctg     660
catcaggatt ggctgaacgg caaagagtac aagtgcaagg tgtccaacaa ggccctgcct     720
gcccccatcg aaaagaccat ctccaaggcc aagggccagc ccgggaacc ccaggtgtac      780 acactgcccc ctagcaggga cgagctgacc aagaaccagg tgtccctgac ctgtctcgtg     840
aagggcttct acccctccga tatcgccgtg gaatgggagt ccaacggcca gcctgagaac     900
aactacaaga ccacccccc tgtgctggac tccgacggct cattcttcct gtactccaag     960
ctgacagtgg acaagtcccg gtggcagcag ggcaacgtgt tctcctgctc cgtgatgcac    1020
gaggccctgc acaaccacta cacccagaag tccctgtccc tgagccccgg caaa          1074
```

<210> SEQ ID NO 54
<211> LENGTH: 1239
<212> TYPE: DNA
<213> ORGANISM: Artificial Sequence
<220> FEATURE:
<223> OTHER INFORMATION: Description of Artificial Sequence: Synthetic
      Human hCG beta-chain + linker + human Fc + Histag,
      optimized (1239 bases) sequence

<400> SEQUENCE: 54

```
atggaaatgt ccagggcct ccttctcctg ctgctgctgt ctatgggcgg cacctgggcc      60
tccaaagagc tctgaggcc ccggtgcaga cccatcaatg ctaccctggc cgtggaaaaa     120
gagggctgcc ccgtgtgcat caccgtgaac accaccatct cgccggcta ctgccctacc    180 atgaccagag tgctgcaggg cgtgctgcct gctctgcctc aggtcgtgtg caactaccgg     240
gacgtgcgct tcgagtccat cagactgcct ggctgcccca gaggcgtgaa ccctgtggtg     300
tcttacgccg tggccctgtc ttgccagtgc gccctgtgca gaagatccac caccgattgt     360
ggcggcccta aggaccaccc tctgacctgc gacgacctc ggttccagga ctcctccagc     420
tctaaggccc ctccaccttc cctgcctagc ccttctagac tgccaggccc ttccgacacc     480
```

```
cccatcctgc cacagggtgg cggaggatct ggcggaggcg gttctggcgg cggtggctct    540
gataagaccc acacctgtcc cccttgccct gcccctgaac tgctgggagg ccctagcgtg    600
ttcctgttcc ccccaaagcc caaggacacc ctgatgatct cccggacccc cgaagtgacc    660
tgcgtggtgg tggacgtgtc ccacgaggac cctgaagtga agttcaattg gtacgtggac    720
ggcgtggaag tgcacaacgc caagaccaag cccagagagg aacagtacaa ctccacctac    780
cgggtggtgt ccgtgctgac cgtgctgcac caggattggc tgaacggcaa agagtacaag    840
tgcaaggtgt ccaacaaggc cctgcctgcc ccatcgaaa gaccatctc caaggccaag    900 ggccagcccc gggaacccca ggtgtacaca ctgcccccta gcagggacga gctgaccaag    960
aaccaggtgt ccctgacctg tctcgtgaag ggcttctacc cctccgatat cgccgtggaa   1020
tgggagtcca acggccagcc tgagaacaac tacaagacca ccccccctgt gctggactcc   1080
gacggctcat tcttcctgta ctccaagctg acagtggaca agtcccggtg gcagcagggc   1140
aacgtgttct cctgcagcgt gatgcacgag gccctgcaca accactacac ccagaagtcc   1200
ctgtccctga gccccggcaa gcaccatcac caccaccat                          1239

<210> SEQ ID NO 55
<211> LENGTH: 1167
<212> TYPE: DNA
<213> ORGANISM: Artificial Sequence
<220> FEATURE:
<223> OTHER INFORMATION: Description of Artificial Sequence: Synthetic
      Human LH beta-chain with signal peptide + linker + human
      Fc + Histag, optimized (1167 bases) sequence

<400> SEQUENCE: 55
atggaaatgc tgcagggcct ccttctcctg ctgctgctgt ctatgggcgg agcctgggcc     60
tctagagagc cactgaggcc ttggtgccac cccatcaatg ccatcctggc cgtggaaaaa    120
gagggctgcc ccgtgtgcat caccgtgaac accaccatct cgccggcta ctgccccacc    180 atgatgagag tgctgcaggc cgtgctgccc cctctgcctc aggtcgtgtg cacctacaga    240
gatgtgcgct tcgagtccat ccggctgcct ggctgtccta gaggcgtgga ccctgtggtg    300
tctttccctg tggccctgtc ctgcagatgc ggccttgca aagatccac ctccgactgt    360 ggcggcccta aggaccaccc tctgacctgc gatcaccctc agctgtccgg cctgctgttt    420
ctgggaggcg aggatctgg cggaggcggt tctggtggtg gcggctctga taagacccac    480
acctgtcccc cttgccctgc cctgaactg ctgggaggcc cttccgtgtt cctgttcccc    540
ccaaagccca aggacaccct gatgatctcc cggacccccg aagtgacctg cgtggtggtg    600
gatgtgtccc acgaggaccc tgaagtgaag ttcaattggt acgtggacgg cgtggaagtg    660
cacaacgcca agaccaagcc cagagaggaa cagtacaact ccacctaccg ggtggtgtcc    720
gtgctgaccg tgctgcacca ggattggctg aacggcaaag agtacaagtg caaggtgtcc    780
aacaaggccc tgcctgcccc catcgaaaag accatctcca aggccaaggg ccagcccgg   840 gaaccccagg tgtacacact gccccctagc agggacgagc tgaccaagaa ccaggtgtcc    900
ctgacctgtc tcgtgaaggg cttctacccc tccgatatcg ccgtggaatg ggagtccaac    960
ggccagcctg agaacaacta caagaccacc cccctgtgc tggactccga cggctcattc   1020
ttcctgtact ccaagctgac agtggacaag tcccggtggc agcagggcaa cgtgttctcc   1080
tgcagcgtga tgcacgaggc cctgcacaac cactacaccc agaagtccct gtccctgagc   1140
cccggcaagc accatcacca ccaccat                                       1167
```

```
<210> SEQ ID NO 56
<211> LENGTH: 8
<212> TYPE: PRT
<213> ORGANISM: Artificial Sequence
<220> FEATURE:
<223> OTHER INFORMATION: Description of Artificial Sequence: Synthetic
      linker sequence

<400> SEQUENCE: 56

Glu Phe Ala Gly Ala Ala Ala Val
1               5

<210> SEQ ID NO 57
<211> LENGTH: 15
<212> TYPE: PRT
<213> ORGANISM: Artificial Sequence
<220> FEATURE:
<223> OTHER INFORMATION: Description of Artificial Sequence: Synthetic
      linker sequence

<400> SEQUENCE: 57

Gly Gly Gly Gly Ser Gly Gly Gly Gly Ser Gly Gly Gly Gly Ser
1               5                   10                  15

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      linker sequence

<400> SEQUENCE: 58

Ser Gly Gly Ser Gly Gly Ser
1               5

<210> SEQ ID NO 59
<211> LENGTH: 15
<212> TYPE: PRT
<213> ORGANISM: Artificial Sequence
<220> FEATURE:
<223> OTHER INFORMATION: Description of Artificial Sequence: Synthetic
      linker sequence

<400> SEQUENCE: 59

Gly Gly Ser Gly Gly Ser Gly Gly Ser Gly Gly Ser Gly Gly Gly
1               5                   10                  15

<210> SEQ ID NO 60
<211> LENGTH: 18
<212> TYPE: PRT
<213> ORGANISM: Artificial Sequence
<220> FEATURE:
<223> OTHER INFORMATION: Description of Artificial Sequence: Synthetic
      linker sequence

<400> SEQUENCE: 60

Gly Gly Ser Gly Gly Ser Gly Gly Ser Gly Gly Ser Gly Gly Ser Gly
1               5                   10                  15

Gly Ser

<210> SEQ ID NO 61
<211> LENGTH: 387
<212> TYPE: PRT
<213> ORGANISM: Artificial Sequence
<220> FEATURE:
<223> OTHER INFORMATION: Description of Artificial Sequence: Synthetic
``` hCG beta chain + linker + Fc sequence

<400> SEQUENCE: 61

Ser Lys Glu Pro Leu Arg Pro Arg Cys Arg Pro Ile Asn Ala Thr Leu
1               5                   10                  15

Ala Val Glu Lys Glu Gly Cys Pro Val Cys Ile Thr Val Asn Thr Thr
            20                  25                  30

Ile Cys Ala Gly Tyr Cys Pro Thr Met Thr Arg Val Leu Gln Gly Val
        35                  40                  45

Leu Pro Ala Leu Pro Gln Val Val Cys Asn Tyr Arg Asp Val Arg Phe
    50                  55                  60

Glu Ser Ile Arg Leu Pro Gly Cys Pro Arg Gly Val Asn Pro Val Val
65                  70                  75                  80

Ser Tyr Ala Val Ala Leu Ser Cys Gln Cys Ala Leu Cys Arg Arg Ser
                85                  90                  95

Thr Thr Asp Cys Gly Gly Pro Lys Asp His Pro Leu Thr Cys Asp Asp
            100                 105                 110

Pro Arg Phe Gln Asp Ser Ser Ser Lys Ala Pro Pro Pro Ser Leu
            115                 120                 125

Pro Ser Pro Ser Arg Leu Pro Gly Pro Ser Asp Thr Pro Ile Leu Pro
    130                 135                 140

Gln Gly Gly Gly Ser Gly Gly Gly Ser Gly Gly Gly Ser
145                 150                 155                 160

Asp Lys Thr His Thr Cys Pro Pro Cys Pro Ala Pro Glu Leu Leu Gly
                165                 170                 175

Gly Pro Ser Val Phe Leu Phe Pro Pro Lys Pro Lys Asp Thr Leu Met
                180                 185                 190

Ile Ser Arg Thr Pro Glu Val Thr Cys Val Val Val Asp Val Ser His
            195                 200                 205

Glu Asp Pro Glu Val Lys Phe Asn Trp Tyr Val Asp Gly Val Glu Val
            210                 215                 220

His Asn Ala Lys Thr Lys Pro Arg Glu Glu Gln Tyr Asn Ser Thr Tyr
225                 230                 235                 240

Arg Val Val Ser Val Leu Thr Val Leu His Gln Asp Trp Leu Asn Gly
                245                 250                 255

Lys Glu Tyr Lys Cys Lys Val Ser Asn Lys Ala Leu Pro Ala Pro Ile
            260                 265                 270

Glu Lys Thr Ile Ser Lys Ala Lys Gly Gln Pro Arg Glu Pro Gln Val
            275                 280                 285

Tyr Thr Leu Pro Pro Ser Arg Asp Glu Leu Thr Lys Asn Gln Val Ser
    290                 295                 300

Leu Thr Cys Leu Val Lys Gly Phe Tyr Pro Ser Asp Ile Ala Val Glu
305                 310                 315                 320

Trp Glu Ser Asn Gly Gln Pro Glu Asn Asn Tyr Lys Thr Thr Pro Pro
                325                 330                 335

Val Leu Asp Ser Asp Gly Ser Phe Phe Leu Tyr Ser Lys Leu Thr Val
            340                 345                 350

Asp Lys Ser Arg Trp Gln Gln Gly Asn Val Phe Ser Cys Ser Val Met
            355                 360                 365

His Glu Ala Leu His Asn His Tyr Thr Gln Lys Ser Leu Ser Leu Ser
        370                 375                 380

Pro Gly Lys
385

<210> SEQ ID NO 62
<211> LENGTH: 363
<212> TYPE: PRT
<213> ORGANISM: Artificial Sequence
<220> FEATURE:
<223> OTHER INFORMATION: Description of Artificial Sequence: Synthetic
      LH Beta chain + linker + Fc sequence

<400> SEQUENCE: 62

Ser Arg Glu Pro Leu Arg Pro Trp Cys His Pro Ile Asn Ala Ile Leu
1               5                   10                  15

Ala Val Glu Lys Glu Gly Cys Pro Val Cys Ile Thr Val Asn Thr Thr
            20                  25                  30

Ile Cys Ala Gly Tyr Cys Pro Thr Met Met Arg Val Leu Gln Ala Val
        35                  40                  45

Leu Pro Pro Leu Pro Gln Val Val Cys Thr Tyr Arg Asp Val Arg Phe
    50                  55                  60

Glu Ser Ile Arg Leu Pro Gly Cys Pro Arg Gly Val Asp Pro Val Val
65                  70                  75                  80

Ser Phe Pro Val Ala Leu Ser Cys Arg Cys Gly Pro Cys Arg Arg Ser
                85                  90                  95

Thr Ser Asp Cys Gly Gly Pro Lys Asp His Pro Leu Thr Cys Asp His
            100                 105                 110

Pro Gln Leu Ser Gly Leu Leu Phe Leu Gly Gly Gly Ser Gly Gly
        115                 120                 125

Gly Gly Ser Gly Gly Gly Ser Asp Lys Thr His Thr Cys Pro Pro
    130                 135                 140

Cys Pro Ala Pro Glu Leu Leu Gly Gly Pro Ser Val Phe Leu Phe Pro
145                 150                 155                 160

Pro Lys Pro Lys Asp Thr Leu Met Ile Ser Arg Thr Pro Glu Val Thr
                165                 170                 175

Cys Val Val Val Asp Val Ser His Glu Asp Pro Glu Val Lys Phe Asn
            180                 185                 190

Trp Tyr Val Asp Gly Val Glu Val His Asn Ala Lys Thr Lys Pro Arg
        195                 200                 205

Glu Glu Gln Tyr Asn Ser Thr Tyr Arg Val Val Ser Val Leu Thr Val
    210                 215                 220

Leu His Gln Asp Trp Leu Asn Gly Lys Glu Tyr Lys Cys Lys Val Ser
225                 230                 235                 240

Asn Lys Ala Leu Pro Ala Pro Ile Glu Lys Thr Ile Ser Lys Ala Lys
                245                 250                 255

Gly Gln Pro Arg Glu Pro Gln Val Tyr Thr Leu Pro Pro Ser Arg Asp
            260                 265                 270

Glu Leu Thr Lys Asn Gln Val Ser Leu Thr Cys Leu Val Lys Gly Phe
        275                 280                 285

Tyr Pro Ser Asp Ile Ala Val Glu Trp Glu Ser Asn Gly Gln Pro Glu
    290                 295                 300

Asn Asn Tyr Lys Thr Thr Pro Pro Val Leu Asp Ser Asp Gly Ser Phe
305                 310                 315                 320

Phe Leu Tyr Ser Lys Leu Thr Val Asp Lys Ser Arg Trp Gln Gln Gly
                325                 330                 335

Asn Val Phe Ser Cys Ser Val Met His Glu Ala Leu His Asn His Tyr
            340                 345                 350

Thr Gln Lys Ser Leu Ser Leu Ser Pro Gly Lys
        355                 360

```
<210> SEQ ID NO 63
<211> LENGTH: 4
<212> TYPE: PRT
<213> ORGANISM: Homo sapiens

<400> SEQUENCE: 63

Glu Leu Leu Gly
1

<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence: Synthetic
      linker sequence
<220> FEATURE:
<221> NAME/KEY: MISC_FEATURE
<222> LOCATION: (1)..(10)
<223> OTHER INFORMATION: This sequence may encompass 1-10 repeating
      "Gly" residues

<400> SEQUENCE: 64

Gly Gly Gly Gly Gly Gly Gly Gly Gly Gly
1               5                   10

<210> SEQ ID NO 65
<211> LENGTH: 30
<212> TYPE: PRT
<213> ORGANISM: Artificial Sequence
<220> FEATURE:
<223> OTHER INFORMATION: Description of Artificial Sequence: Synthetic
      linker sequence
<220> FEATURE:
<221> NAME/KEY: MISC_FEATURE
<222> LOCATION: (1)..(30)
<223> OTHER INFORMATION: This sequence may encompass 1-10 repeating
      "Gly Gly Ser" units

<400> SEQUENCE: 65

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Gly Ser
            20                  25                  30

<210> SEQ ID NO 66
<211> LENGTH: 50
<212> TYPE: PRT
<213> ORGANISM: Artificial Sequence
<220> FEATURE:
<223> OTHER INFORMATION: Description of Artificial Sequence: Synthetic
      linker sequence
<220> FEATURE:
<221> NAME/KEY: MISC_FEATURE
<222> LOCATION: (1)..(50)
<223> OTHER INFORMATION: This sequence may encompass 1-10 repeating
      "Gly Gly Gly Gly Ser" units

<400> SEQUENCE: 66

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser
```

50

<210> SEQ ID NO 67
<211> LENGTH: 50
<212> TYPE: PRT
<213> ORGANISM: Artificial Sequence
<220> FEATURE:
<223> OTHER INFORMATION: Description of Artificial Sequence: Synthetic
      linker sequence
<220> FEATURE:
<221> NAME/KEY: MISC_FEATURE
<222> LOCATION: (1)..(50)
<223> OTHER INFORMATION: This sequence may encompass 1-50 repeating
      "Gly" residues

<400> SEQUENCE: 67

Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly Gly
            20                  25                  30

Gly Gly Gly Gly Gly Gly Gly Gly Gly Gly Gly Gly Gly Gly Gly
        35                  40                  45

Gly Gly
    50

<210> SEQ ID NO 68
<211> LENGTH: 150
<212> TYPE: PRT
<213> ORGANISM: Artificial Sequence
<220> FEATURE:
<223> OTHER INFORMATION: Description of Artificial Sequence: Synthetic
      linker sequence
<220> FEATURE:
<221> NAME/KEY: MISC_FEATURE
<222> LOCATION: (1)..(150)
<223> OTHER INFORMATION: This sequence may encompass 1-50 repeating
      "Gly Gly Ser" units

<400> SEQUENCE: 68

Gly Gly Ser Gly Gly Ser Gly Gly Ser Gly Gly Ser Gly Gly Ser
1               5                   10                  15

Gly Ser Gly Gly Ser Gly Gly Ser Gly Gly Ser Gly Gly Ser Gly
            20                  25                  30

Ser Gly Gly Ser Gly Gly Ser Gly Gly Ser Gly Gly Ser Gly Gly Ser
        35                  40                  45

Gly Gly Ser Gly Gly Ser Gly Gly Ser Gly Gly Ser Gly Gly Ser Gly
    50                  55                  60

Gly Ser Gly Gly Ser Gly Gly Ser Gly Gly Ser Gly Gly Ser Gly Gly
65                  70                  75                  80

Ser Gly Gly Ser Gly Gly Ser Gly Gly Ser Gly Gly Ser Gly Gly Ser
                85                  90                  95

Gly Gly Ser Gly Gly Ser Gly Gly Ser Gly Gly Ser Gly Gly Ser
            100                 105                 110

Gly Ser Gly Gly Ser Gly Gly Ser Gly Gly Ser Gly Gly Ser Gly Gly
    115                 120                 125

Ser Gly Gly Ser Gly Gly Ser Gly Gly Ser Gly Gly Ser Gly Gly Ser
    130                 135                 140

Gly Gly Ser Gly Gly Ser
145                 150

<210> SEQ ID NO 69
<211> LENGTH: 250

<212> TYPE: PRT
<213> ORGANISM: Artificial Sequence
<220> FEATURE:
<223> OTHER INFORMATION: Description of Artificial Sequence: Synthetic
      linker sequence
<220> FEATURE:
<221> NAME/KEY: MISC_FEATURE
<222> LOCATION: (1)..(250)
<223> OTHER INFORMATION: This sequence may encompass 1-50 repeating
      "Gly Gly Gly Gly Ser" units

<400> SEQUENCE: 69

Gly Gly Gly Gly Ser Gly Gly Gly Gly Ser Gly Gly Gly Gly Ser Gly
1               5                   10                  15
Gly Gly Gly Ser Gly Gly Gly Gly Ser Gly Gly Gly Gly Ser Gly Gly
            20                  25                  30
Gly Gly Ser Gly Gly Gly Gly Ser Gly Gly Gly Gly Ser Gly Gly Gly
        35                  40                  45
Gly Ser Gly Gly Gly Gly Ser Gly Gly Gly Gly Ser Gly Gly Gly Gly
    50                  55                  60
Ser Gly Gly Gly Gly Ser Gly Gly Gly Gly Ser Gly Gly Gly Gly Ser
65                  70                  75                  80
Gly Gly Gly Gly Ser Gly Gly Gly Gly Ser Gly Gly Gly Gly Ser Gly
                85                  90                  95
Gly Gly Gly Ser Gly Gly Gly Gly Ser Gly Gly Gly Gly Ser Gly Gly
            100                 105                 110
Gly Gly Ser Gly Gly Gly Gly Ser Gly Gly Gly Gly Ser Gly Gly Gly
        115                 120                 125
Gly Ser Gly Gly Gly Gly Ser Gly Gly Gly Gly Ser Gly Gly Gly Gly
    130                 135                 140
Ser Gly Gly Gly Gly Ser Gly Gly Gly Gly Ser Gly Gly Gly Gly Ser
145                 150                 155                 160
Gly Gly Gly Gly Ser Gly Gly Gly Gly Ser Gly Gly Gly Gly Ser Gly
                165                 170                 175
Gly Gly Gly Ser Gly Gly Gly Gly Ser Gly Gly Gly Gly Ser Gly Gly
            180                 185                 190
Gly Gly Ser Gly Gly Gly Gly Ser Gly Gly Gly Gly Ser Gly Gly Gly
        195                 200                 205
Gly Ser Gly Gly Gly Gly Ser Gly Gly Gly Gly Ser Gly Gly Gly Gly
    210                 215                 220
Ser Gly Gly Gly Gly Ser Gly Gly Gly Gly Ser Gly Gly Gly Gly Ser
225                 230                 235                 240
Gly Gly Gly Gly Ser Gly Gly Gly Gly Ser
                245                 250

<210> SEQ ID NO 70
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
gctgacagac taacagactg ttcc                                        24

<210> SEQ ID NO 71
<211> LENGTH: 18
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 71
caaatgtggt atggctga                                                    18
```

LONG ACTING BIOLOGICALLY ACTIVE LUTEINIZING HORMONE (LH) COMPOUND

SEQUENCE LISTING

The instant application contains a Sequence Listing which has been submitted electronically in ASCII format and is hereby incorporated by reference in its entirety. Said ASCII copy, created on Oct. 12, 2015, is named LBK-56009-US_S-L.txt and is 179,986 bytes in size.

FIELD OF THE INVENTION

The present invention relates to a long acting biologically active luteinizing hormone (LH) compound comprising an LH agonist linked to a pharmaceutically acceptable molecule, and to methods of preparing and using such LH compounds. These LH compounds have a protracted profile of action and are useful in assisted reproduction technology procedures, such as for promotion of fertility or treatment of infertility and for use in hypogonadotropic hypogonadal males and in boys with cryptorchidism. The modified LH have a protracted profile of action and are useful in combination with follicle stimulating hormone (FSH) for inducing follicular development in anovulatory women or for inducing controlled ovarian stimulation in the follicular phase of the menstrual cycle of a mammalian female subject. Furthermore, the present invention relates to methods for controlled ovarian stimulation, which can be used in conjunction with assisted reproduction technologies such as in vitro fertilisation (IVF), intra cytoplasmatic sperm injection (ICSI), intra uterine insemination (IUD, in vitro maturation (IVM), and induction of oculation. In other aspects the invention relates to methods for inducing folliculogenesis and methods for providing luteal and gestational support for corpora lutea.

BACKGROUND OF THE INVENTION

Assisted reproduction technology (ART) procedures typically require treatment with exogenous gonadotropins to stimulate growth and maturation of the ovarian follicles. When gonadotropins are used to treat anovulatory females, the goal is to replicate the normal menstrual cycle, when a single, dominant follicle matures prior to induction of ovulation. In contrast, for women undergoing in vitro fertilization (IVF), controlled ovarian stimulation (COS) is employed to stimulate the growth and maturation of several ovarian follicles, yielding multiple oocytes, which then are retrieved for use in the IVF procedure.

In connection with ART, COS, that secures development of multiple follicles it is essential to achieve the best possible chance for the patient to become pregnant. To obtain multiple follicle growth circulating levels of FSH need to surpass the physiological threshold level that triggers growth of responsive follicles for a longer period than the natural three to four day period. This is achieved by administration of exogenous FSH or by manipulating the pituitary gland to secrete enhanced amounts of FSH, and COS performed in the right way may easily result in the harvest of excess mature oocytes for in vitro fertilization (IVF).

In addition to stimulating follicular growth, an important function of FSH is to stimulate the development of LH-receptors on granulosa cells. LH-receptors are constitutively expressed on theca cells immediately surrounding the follicle and secure the production of—among other substances— androgens (i.e. androstenedione and testosterone) for conversion into oestrogens in the granulosa cell layer, but LH-receptors also have important functions in the granulosa cell layer of the follicle. Currently it is not known precisely when in follicular development LH-receptors become expressed on granulosa cells.

In the normal menstrual cycle, the LH-receptor is only activated by LH activity released from the pituitary, but hCG, which essentially is a pregnancy associated protein, may also bind and stimulate the LH-receptor. hCG has a longer half-life than LH and the accumulated in vivo activity of hCG (from equal doses of LH and hCG in an ampule) is usually considered to be 6 to 8 times higher than LH (Stockman P G W et al. Fertil Steril 1993; 60:175, Giudice E et al. J Clin Res 2001; 4:27).

Some preparations for COS only contain FSH while others contain a combination of FSH and LH-like activity (i.e. either LH or hCG alone or a mixture of LH and hCG). For instance, Menopur contains urine derived FSH and LH-like activity. In these preparations about 95 percent of the in vivo receptor mediated LH-like bioactivity derives from hCG due to its longer half-life (Van den Hooven H et al. RBM Online 2003; 7: 547). Recombinant LH is also available in a pure form as add on for COS (i.e. Luveris, Merck-Serono, Darmstadt, Germany). However, hCG for COS is only available in the presence of a product containing FSH and is not marketed in small doses to be used in connection with COS.

The clinical benefit of using LH-activity in connection with COS has been heavily debated during the past decade. Although a number of meta-analyses have suggested that the addition of LH-like activity, which in essence is provided via hCG, show an augmented baby-take-home rate as compared to pure FSH alone, this issue has not been clarified (Al-Inany H G et al., Reprod Biomed Online. 2008; 16: 81-88, Westergaard LW, Cochrane Database Syst Rev 2003; 1:CD003973., Al-Inany H G et al., Gynecol Endocrinol. 2009; 25:372-8). Adding to the complexity are differences between the FSH isoform profile of the most frequently used FSH containing hCG (i.e. Menopur (highly purified hMG containing urine derived FSH, LH and hCG)) and the pure FSH (i.e. recombinant FSH, Puregon or Gonal F). However, there is no doubt that LH levels can be reduced below a threshold limit at which adding LH-like activity will be helpful and there is also an upper threshold limit above which negative effects on treatment outcome become apparent. Thus LH-like activity should ideally remain in a therapeutically narrow window.

LH and CG are very homologous. In comparison to LH, CG has a C-terminal glycosylated extension that has been shown to be important for the longer half-life of CG. Human LH and hCG are more than 80% identical in sequence. Although both LH and hCG binds to and activate the LH-receptor, both hormones exist as a family of iso hormones that differ in their oligosaccharide composition. Each of the different isoforms affects the receptor in a specific way and may elicit variable cellular responses (Burgon P G et al., Endocrinology, 1996; 137:4827; Stanton P G et al., Mol Cell Endocrinol. 1996; 125:133-141.), as have also been shown for the different FSH isoforms (Barrios-de-Tomasi J, et al. Mol Cell Endocrinol. 2002; 186:189-98, Yding Andersen C & Ezcurra D, Reproductive Biology Insights 2011:4, 1-10). Thus the more subtle and fine-tuned effects of LH and hCG may actually differ. Recent studies presented at the ESHRE conference in Stockholm (July 2011) showed that LH acted much faster than hCG, but less efficient overall at the receptor level (L. Casarini et al., ESHRE Stockholm 2011-P312, Universita degli Studi di Modena, Italy). hCG is a pregnancy associated protein which is secreted following the implantation of the embryo starting around 8 days after ovulation. hCG is capable of stimulating the corpus luteum to remain active and continue its secretion of progesterone and other substances necessary for the pregnancy to become established. Despite the fact that levels of LH at that moment of the menstrual cycle are present in appreciable amounts, this level is insufficient to stimulate the corpus luteum further and unless the woman becomes pregnant the corpus luteum will regress, a menstrual bleeding will occur and a new menstrual cycle start. Although this difference between LH and hCG has puzzled science for some time, it has now been demonstrated that the LH-receptor (LH-R) changes during the luteal phase. The functional full-length receptor maintains its expression when hCG is present, whereas LH is unable to accomplish that (Dickinson R E et al., Endocrinology 150: 2873-2881, 2009). This demonstrates differences in the effect of LH and hCG during the luteal phase and this could suggest that LH and hCG also in the follicular phase of the menstrual cycle exert different effects at the receptor level.

It is now well recognised that LH-R expression on human granulosa cells is sufficient to drive follicular development from a diameter of around 10-12 millimeter and until ovulation with the presence of FSH in only small permissive amounts in connection with COS (Blockheel et al., 2009; Filicori et al., 1999). Thereby this stimulation resembles conditions of the natural menstrual cycle, in which levels of FSH is attenuated during the second half of the follicular phase, while levels of LH remain fairly constant and it has been shown that LH has a very strong stimulating effect on oestradiol production in granulosa cells from preovulatory follicles prior to the mid-cycle surge of gonadotropins. The ability to provide a more natural environment for the final maturation of the follicles is likely to provide oocytes that has an even better capacity to sustain fertilization, embryogenesis and implantation and subsequently result in a better reproductive outcome.

One of the most severe side-effects of COS is the occurrence of ovarian hyper stimulation syndrome (OHSS), which is a potential life threatening condition. Recent studies have shown that it is now possible to almost completely eliminate OHSS by the use of an agonist trigger for final follicular maturation (Humaidan P, Kol S, Papanikolaou E; Copenhagen GnRH Agonist Triggering Workshop Group. GnRH agonist for triggering of final oocyte maturation: time for a change of practice? Hum Reprod Update. 2011; 17:510-24. PMID:21450755) without compromising the reproductive outcome. In combination with a GnRH antagonist down regulated pituitary function, a bolus of a GnRH agonist is capable of displacing the antagonist and cause a flare-up of gonadotropin release, which is then used as a signal for ovulation induction. However, subsequent to the flare up the agonist causes pituitary down regulation, which removes the stimulatory signals to the ovary. Removal of these stimuli also reduces the risk of OHSS. However, this down regulation also has a profound negative impact on the function of the corpus luteum and the reproductive outcome is unacceptably low. So in order to maintain a certain function of the corpus luteum it has successfully been attempted to add a bolus of hCG (1500 IU) at the time of oocyte retrieval and later on in the luteal phase. Alternatively daily injections of LH can rescue the luteal phase and provide a good reproductive outcome (A novel method of luteal supplementation with recombinant luteinizing hormone when a gonadotropin-releasing hormone agonist is used instead of human chorionic gonadotropin for ovulation triggering: a randomized prospective proof of concept study. Papanikolaou E G, Verpoest W, Fatemi H, Tarlatzis B, Devroey P, Tournaye H. Fertil Steril. 2011 Mar. 1; 95(3):1174-7. Epub 2010 Oct. 27. PMID: 20979997).

Despite recent advances in ART, ovarian stimulation through exogenous gonadotropins is not uniformly successful due, in part, to varying individual responses to treatment with gonadotropins. This variability complicates patient management and can result in multiple births and potentially life-threatening complications.

The gonadotropins form a family of structurally related glycoprotein hormones. Typical members include chorionic gonadotropin (CG), follicle stimulating hormone (FSH; follitropin), luteinizing hormone (LH; lutropin) and thyroid stimulating hormone (TSH; thyrotropin). FSH, LH and TSH are present in most vertebrate species and are synthesized and secreted by the pituitary. CG has so far been found only in primates, including humans, and in horses and is synthesized by placental tissue. FSH and LH are the pituitary hormones essential for follicular maturation and luteinization in the female and for testis maturation and spermatogenesis in the male. Gonadotropins are secreted by the pituitary gland under the control of hypothalamic gonadotropin-releasing hormone (GnRH). Follicle stimulating hormone (FSH) and luteinizing hormone (LH) are the pituitary hormones essential for follicular maturation (follicular development) and luteinization. FSH is required for follicular recruitment (i.e., the early growth of ovarian follicles) at the beginning of the spontaneous menstrual cycle, and it also supports mid- and late-stage follicular development.

In recent years very pure preparations, of the gonadotropins have become available through the use of recombinant DNA technology (see for instance Boime et al., Seminars in Reproductive Endocrinology 10, 45-50, 1992: "Expression of recombinant human FSH, LH and CG in mammalian cells"). The recombinant gonadotropins are of constant quality i.e. have reproducible biochemical and biological properties. Genomic and cDNA clones have been prepared for all subunits and their primary structure has been resolved. Moreover, Chinese Hamster Ovary (CHO) cells have been transfected with human gonadotropin subunit genes and these cells are shown to be capable of secreting intact dimers (e.g. Keene et al (1989), J. Biol. Chem., 264, 4769-4775; Van Wezenbeek et al (1990), in From clone to Clinic (eds Crommelin D. J. A. and Schellekens H.), 245-251). It has been demonstrated that the biochemical and biological characteristics of e.g. recombinant FSH are almost identical to those of natural FSH (Mannaerts et al (1991), Endocrinology, 129, 2623-2630). Moreover, pregnancies were achieved after controlled ovarian superovulation using recombinant FSH (Germond et al (1992), Lancet, 339, 1170; Devroey et al (1992), Lancet, 339, 1170-1171).

The gonadotropin may also be isolated from natural sources, e.g. from human urine, or the gonadotropin may be prepared in a (bio)synthetic way, c.f. by recombinant DNA techniques.

Gonadotrophins are widely used in clinical practice to treat women with WHO group II and WHO group I anovulation (World Health Organisation Technical Report 514, (1973)). Conventionally, follicular development is induced by administering hMG (human menopausal gonadotrophin) or u-hFSH (urinary human follicle stimulating hormone) at a dose of 75-150 IU/day. This dose is increased after a few days (usually five) by steps of 75 IU. It is rare to exceed 450 IU/day. When there is at least one follicle having a mean diameter of at least 18 mm and no more than two follicles having a mean diameter of at least 16 mm, a high dose (of 5000 IU for example) of hCG (human chorionic gonadotrophin) is administered to induce ovulation. This "conventional protocol" has been used successfully for more than 20 years. It carries some risks however, mainly in patients with polycystic ovaries or polysystic ovarian syndrome (PCOS).

These risks include the occurrence of OHSS, and a relatively high incidence of multiple pregnancies (Schenker et al, Fertil. Steril. 35: 105-123 (1981)). Although the majority of multiple pregnancies are twins, induction of ovulation contributes to one third of the high rank multiple births in the UK (Levene et al, Br. J. Obstet. Gynacol. 99: 607-613 (1992)).

Careful monitoring during treatment by ultrasound (US) and assessment of serum oestradiol (E2) have reduced these risks but have not been able to prevent them in all patients. These problems are directly related to the difficulty of obtaining the growth of a single dominant follicle leading to non-physiological multifollicular development.

FSH is administered therapeutically to induce follicular development in anovulatory women and women undergoing COS. In traditional ovulatory stimulation methods, FSH is administered throughout treatment until shortly before the oocytes are retrieved. This continued stimulation by FSH usually causes multiple follicular development and can in combination with an exogenous bolus of hCG to induce ovulation lead to a potentially fatal condition, OHSS. It has now been estimated that COS is fatal to otherwise healthy patients in around 3 per 100,000 stimulation cycles. Decreasing the dosage of FSH can reduce the risk of OHSS, but low FSH dosages yield inadequate number of follicles and thus lower the chances of success in assisted reproduction.

LH functions during all stages of a normal menstrual cycle. LH stimulates the theca cells of the follicle to produce the androgen substrate which is converted into estrogen by the aromatase system in the granulosa cells. During the late stages of follicle maturation, approximately 5 to 7 days before ovulation, large ovarian follicles begin to express LH receptors in granulosa cells, which render those follicles responsive to LH for continued maturation and development. Hillier et al., Mol. Cell. Endocrinol. 100:51 (1994), Campbell et al. J. Reprod. Fertil. 117:244 (1999). Next, a mid-cycle surge of LH triggers the final stage of follicular maturation and ovulation in a normal menstrual cycle. Ovulation follows the mid-cycle LH surge within 24 to 48 hours. Finally, in the second part of the menstrual cycle, the luteal phase, LH stimulates production of estrogen and progesterone in the corpus luteum of the ovary as it prepares the uterus for implantation and pregnancy.

In ovarian stimulation protocols, hCG can serve as a source of LH activity because hCG and LH act through the same receptor. Filicori et al. Human Reprod. 17:2009 (2002a); Martin et al., Fertil. Steril. 76: 0-49 (2002). Relative to LH, hCG has a longer half-life and, hence, is more potent in vivo than LH, although the literature tends to treat hCG and LH as fungible. Indeed, the scientific literature generally does not mention determining the source of LH activity in naturally-derived gonadotropin preparations.

The literature discloses using LH activity or low doses of hCG in combination with FSH throughout ovulatory stimulation, but guidance regarding effective amounts and timing of LH activity supplementation is lacking. For example, the abstract of Martin et al, Fertil. Steril. 76: 0-49 (2002), discloses administering 2.5 µg recombinant hCG daily (maintaining serum hCG levels from 1-3 mIU/mL) during ovulatory stimulation. Gordon et al. disclose administering 75 IU FSH with 0, 1, 25, and 75 IU LH activity. Human Reprod. 12 (Suppl. 1): 52 (1997a); ibid.: 53 (1997b).

Published studies disclose administering LH activity, throughout stimulation, at FSH to LH ratios of 150:0, 150: 37.5, 150:75, and 150:150. Filicori et al. (2002a). Further, the literature documents supplementing FSH stimulation with 50 IU hCG/day (Filicori et al., J. Clin. Endocrinol. & Metabol. 84: 2659 (1999)), and protocols in which 150 IU FSH is administered for 7 days, followed by treatment with FSH-to-hCG ratios of 150:0, 50:50, 25:100, and 0:200 (ibid. 87:1156 (2002c) and US20080108571).

During the last 10 years, a new protocol has been designed (the "chronic low dose protocol") and tested in order to reduce further the incidence of the complications of gonadotrophin therapy (Seibel et al, Int. J. Fertil., 29: 338-339 (1984); Buvat et al, Fertil. Steril., 52: 553-559 (1989); Hamilton-Fairley et al, Human Reprod. 6: 1095-1099 (1991); Sagle et al, Fertil Steril., 55: 56-60 (1991); Shoham et al, Fertil. Steril., 55: 1051-1056 (1991); Meldrum, Fertil Steril., 55: 1039-1040 (1991)). This protocol starts with a low dose of FSH or hMG (75 IU/day) and no dose adjustment before seven or preferably 14 days of treatment. If a dose adjustment is required, this is made by incremental steps of only 37.5 IU. In addition, each subsequent increase may only be effected after seven days of treatment at a given dose. The concept of this chronic low dose protocol is to find the threshold amount of FSH necessary to promote unifolliculogenesis. Encouraging results have been published so far, showing that this approach reduces the mean number of preovulatory follicles, the average preovulatory E2 level and the size of the ovary at mid-luteal phase.

However, despite the use of the chronic low dose protocol, some treatment cycles still have to be cancelled due to an over-response (e.g. where there are more than 3 follicles with a mean diameter of 16 mm or more). In addition, the multiple pregnancy rate, although clearly improved when compared to the conventional protocol, is still higher than in spontaneous conception cycles i.e. 5-10% in induced ovulation as opposed to 1.5% in spontaneous cycles. This is due to the fact that development of a single pre-ovulatory follicle is obtained in only about two thirds to three quarters of the induced cycles and follicles having a mean diameter of 15 mm or less are usually not considered when assessing the number of pre-ovulatory follicles on the day of hCG administration (Buvat et al, FertiL Steril., 52: 553-559 (1989); Hamilton-Fairley et al, Human Reprod. 6: 1095-1099 (1991)). It is, however, not clear whether follicles with a mean diameter of 14 to 15 mm, or even less, on the day of hCG administration, will ovulate and lead to the release of a healthy fertilisable oocyte. Thus, it would be desirable to have improvements in FSH-induced follicular development treatment in which the rates of multiple pregnancy and cycle cancellation are reduced.

Antral follicle growth is induced by FSH. Continuously throughout life and up to the menopause, some follicles enter a growth phase which is interrupted by regression and atresia before reaching the full maturity stage of preovulatory status (Hillier, Hum. Reprod., 9: 181-191 (1994)). During the growth phase, most follicles could be rescued from atresia, provided that it is exposed to a sufficient concentration of FSH. The level of FSH required to prevent atresia and promote further growth of a follicle is called the "FSH threshold" level (Brown, Aus. NZJ Obstet. Gynecol., 18: 47-55 (1987). The FSH threshold level varies with time and, at a given time-point, the follicles which are currently in a growth phase have different FSH threshold levels. This is the rationale on which the "chronic low dose" protocol is based. A progressive and cautious increase in the dose of FSH is used for finding the threshold level of a minimal number of follicles, and hopefully achieving mono-ovulation.

It is known that LH also contributes to the phenomenon of follicle dominance and mono-ovulation. Indeed, although some LH is essential for E2 synthesis during follicular development, there is evidence that excessive exposure to LH will trigger follicular atresia and suppress granulosa cell proliferation. Developing follicles appear thus to have finite requirements for stimulation by LH, beyond which normal follicular development ceases. This is the "LH ceiling" concept (Hillier, Hum. Reprod., 9: 181-191 (1994)). It is believed that, at a given time-point, the follicles which are currently in a growth phase have different LH ceiling levels. It is suggested that the more mature follicles are more resistant to the atretic action of LH than less mature follicles.

Two cases of WHO group I anovulation treated by either FSH alone or hMG using a step-up protocol have been reported (Glasier et al, Journal of Æ ndocrinology, 119 A-159 (1988)). The "FSH alone" cycle had a much larger number of mature follicles than the hMG cycle, possibly supporting a role of LH in the atresia of secondary follicles. Afterwards two comparative studies were published. In a first cross-over study in 10 hypogonadotrophic hypogonadal women, a striking difference was recorded in terms of preovulatory E2 levels, but follicular count was not reported (Couzinet et al, J. Clin. Endocrinol. Metab. 66: 552-556 (1988)). A second cross-over study in 9 hypogonadotrophic hypogonadal women reported a mean number of follicles having a mean diameter of more than 16 mm on the day of hCG administration of 2.0 (0.7 in hMG-treated cycles and of 1.2 in FSH-treated cycles (Shoham et al, FertiL Steril., 55: 1051-1056 (1991)). No information is available on the number of smaller follicles.

More recently, the results of administering 150 IU hFSH (human FSH) and 75 IU r-hLH (recombinant human LH) to a single patient with unmeasurably low serum FSH, LH and E2 concentrations have been published (Hall et al, The Lancet, 344 (8918): 334-335 (1994)). Administration of r-hLH and r-hFSH caused E2 levels to be raised, and the total number of follicles of 10 mm or more in diameter to be reduced, as compared to administration of hFSH alone. However, the number of large follicles remained sufficiently high to suggest an unacceptably high multiple pregnancy rate.

A further study compared the effect of administering r-hLH (at a dose of either 300 IU/day or 750 IU/day) and r-hFSH to normal ovulatory women after treatment with FSH for stimulating multiple follicular development prior to intrauterine implantation (Sullivan et al, Journal of Clinical Endocrinology and Metabolism, 84,228-232, 1999)). The results indicate that serum E2 levels were raised in those women who received LH, although no measurements of the number and size of follicles were made and a multiple pregnancy occurred in the group receiving 750 IU/day of LH.

The literature documents other compositions that contain both FSH and LH activity, as well as use of FSH in combination with LH activity. For example, PCT application WO 00/67778, published Nov. 16, 2000, is directed to using LH or an equivalent amount of hCG in combination with FSH to induce follicular development in anovulatory women. More particularly, the '778 application discloses administering LH or "a biologically-active analogue thereof" in doses of 100 to 1500 IU per day (page 4, lines 26-29) and in FSH:LH ratios that range from 1:1.5 to 1:20 (id., lines 16-18).

U.S. Pat. No. 5,929,028 is directed to liquid formulations that contain one or more natural or recombinant gonadotropins, including FSH, LH, and hCG. The '028 patent discusses naturally derived compositions of human menopausal gonadotropin (hMG), which have FSH and LH activities in a ratio of approximately 1:1, but mentions no ratio of FSH to LH activity other than the 1:1 ratio of commercial hMG preparations.

Additionally, there are commercial formulations that contain both FSH and LH. Human-derived preparations are available containing 75 IU FSH with 75 IU LH activity (Pergonal, Humegon, Menogon, Repronex, and Menopur) and 75 IU FSH with 25 or 35 IU LH activity (Normegon and Pergogreen).

It is conventional wisdom, however, that "excessive" LH levels, albeit ill-defined, result in follicular atresia, suppression of granulosa cell proliferation, and premature luteinization. See, generally, Filicori, Fertil. Steril. 79: 253 (2003). Although recent work suggests otherwise, a notion persists in the field that LH activity levels must be within a certain range, and that levels below or above an "LH ceiling" impair normal follicle development. Shoham, Fertil. Steril. 70: 1170 (2002).

In summary, there is published evidence that supplementing FSH with LH activity during ovulation induction reduces the duration of treatment and the amount of gonadotropin used to achieve proper follicle development. Filicori et al. (1999), (2002b). On the other hand, the belief persists that "high" LH activity levels negatively impacts follicle development.

Despite the numerous advances in COS protocols there is a need for further improvement and to remove the occurrence of OHSS, to improve the subsequent implantation rates and to improve the convenience for the females undergoing assisted reproductive therapy as well as safety.

That belief has guided the conventional ovarian-stimulation paradigm, which involves administration of FSH throughout controlled ovarian stimulation. Exogenous LH activity is deemed unnecessary and even detrimental during the early to middle stages of follicular development. Accordingly, the traditional means of ovarian stimulation entail treatment with FSH alone, typically at 75-300 IU/day. In this traditional protocol, LH activity is administered to induce ovulation only after the follicle reaches a certain stage of development. Only recently has LH activity been administered throughout treatment, and the optimal amount and timing of LH activity that is effective in this context remains controversial.

In order for boys to develop normal fertility, both testicles need to be located outside of the body at a lower temperature in the scrotum. If one or both testicles remain at body temperature for prolonged periods of time, fertility may be compromised and the ability to produce functional sperm cells in adult life may be hampered. In order to reduce the negative impact on fertility by an undescended testicle, it is usually physically moved to the scrotum through an operation or by hormone treatment with hCG that cause the testicle(s) to move to the scrotum. hCG stimulates production of testicular steroid hormones by stimulating the Leydig cells to produce androgens. The exact mechanism of action of the increased levels of androgens in causing the testicule(s) to move to the scrotum is not known precisely.

The frequency of at least one undecended testicles among boys is about 3% of full-term and 30% of premature infant boys. However, during the first year of life the majority of testicles within the body arrive in the scrotum themselves (the majority within three months), making the true incidence of cryptorchidism around 1% overall. The effect of hCG is well documented but due to differences in patient age, treatment schedules, and possible inclusion of retractile testes, very divergent results have been reported and the true efficacy is not known. A number of different dosage schedules have been reported, ranging from 3-15 doses given twice a week (10 injections over 5 weeks is common). One of the most common schedules prescribes 250 IU/dose in young infants, 500 IU/dose in children 6 years or younger, and 1000 IU/dose in individuals older than 6 years.

Men with hypogonadotropic hypogonadism have an inability to carry out pituitary release of the gonadotropins LH and FSH. Various genetic defects may cause a defect in the hypothalamus resulting in a deficiency in the release of gonadotropin releasing hormone (GnRH), which in turn causes the pituitary to reduce release in FSH and LH. One such condition is the so-called Kallmann syndrome that affects approximately 1:10.000 males and 1:50.000 females. Apart from affecting the fertility, the main health problem to both men and women is oesteoporosis.

When levels of LH are low the androgen production in men is reduced and they are often infertile and show reduced male characteristics. Treatment is focused on restoring the deficient hormones. Males are administered hCG or testosterone. A number of different testosterone preparations are available; the more widely used ones only requires administering with monthly intervals. However, to induce sperm production and fertility in these men, it is required to with administration of hCG, because exogenously administered testosterone reaching the testicles via circulation seldom reaches intratesticular levels sufficient to cause sperm production. It appears more effective using hCG to stimulate the testicular androgen production sufficiently to provoke sperm production often in combination with FSH administration. Since sperm production from the spermatogonial stage to the fully mature spermatozoa takes 60 to 70 days it is often a lengthy process with multiple injections of hCG for initiation of sperm production.

SUMMARY OF THE INVENTION

The present inventors have realized that a modified mammalian CG or LH, e.g. human CG or human LH, that agonize and activate the LH receptor in a mammal and provides a biological body composition or concentration of the mammalian CG or LH, e.g. human CG or human LH,
a) sufficient to drive an antral follicle from about 5-6 mm, such as from 10 mm in diameter up to about 30 mm in diameter in which a maturing oocyte can finalize the maturation to be ready for resumption of the meiosis,
b) sufficient to drive androgen production in the early adolescent, about 1 year after birth of a male offspring or in puberty for both female and male subjects,
c) sufficient to support steroid production in hypogonadotrhophic hypogonadal for both female and male subjects,
d) sufficient to sustain progesterone in the perk, in the ovulatoric- and the post ovulatoric-phase of a mammalian subject with the object regulating the endometrium and womb for allowing implantation of a mammalian blastocyst,
e) sufficient to sustain a progesterone in the perk, in the ovulatoric- and the post ovulatoric-phase of a mammalian subject with the object of preparing the endometrium and womb for implantation,
f) sufficient to drive androgen production in hypogonadotropic hypogonadism men with the object of provoking sperm production and augment androgen production.
g) sufficient to drive androgen production in boys with cryptorchidism with the object of provoking testis relocation to the scrotum.
h) sufficient to drive progesterone production in women with recurrent pregnancy with the object of reducing the risk of losing the pregnancy. is important for improving the present platform of the ARTs (except for b).

Accordingly, in a broad aspect the present invention relates to a long acting biologically active luteinizing hormone (LH) compound comprising an LH agonist linked to a pharmaceutically acceptable molecule providing an in vivo plasma half-life of the LH agonist or LH compound which is increased substantially compared to the in vivo plasma half-life of the LH agonist administered in the same manner as the LH compound.

In another aspect the present invention relates to a long acting biologically active luteinizing hormone (LH) compound comprising an LH agonist linked to a pharmaceutically acceptable molecule providing an in vivo plasma half-life of the LH agonist or LH compound which is increased substantially compared to in vivo plasma half-life of endogenous chorionic gonadotropin (CG).

In a further aspect the present invention relates to a long acting biologically active luteinizing hormone (LH) compound comprising a mammal CG or analog thereof or a mammal LH or analog thereof linked to a pharmaceutically acceptable molecule selected from a molecule having binding to a mammal neonatal Fc receptor, transferrin and a $CH_3(CH_2)_nCO-$, wherein n is 8 to 22 and a polymer.

The LH agonist may be of mammalian origin, and may be selected from a mammal CG, such as human CG, and equine CG, such as horse CG; or a mammal LH, such as human LH, cow LH, pig LH, horse LH, sheep LH, dog LH, cat LH, and goat LH. The LH agonist may also be an analog of a mammalian LH agonist, and typically the analog has at least 80% identity to the corresponding mammalian sequence of the LH agonist, such as chorionic gonadotropin or luteinizing hormone, such as at least 85% identity, 90% identity, 95% identity, 98% identity, or at least 99% identity.

The LH agonist may also be of non-mammalian origin, and may be selected from small organic molecules, peptides, polypeptides and proteins.

The LH agonist is linked to another molecule, preferably a pharmaceutically acceptable molecule, and it is this modified compound that herein is referred to as an LH compound. The LH agonist may be linked to the pharmaceutically acceptable molecule in various ways as described in the prior art literature, such as without limitation chemical coupling through a bifunctional linker, gene technologically by coupling the N-terminal or C-terminal of the LH agonist, such as hCG or hLH, to the pharmaceutically acceptable molecule, such as albumin. In particular, the N-terminal of albumin, e.g. human albumin, can be coupled to the C-terminal of the alfa-chain of hCG or hLH, or the C-terminal of the beta-chain of hCG or hLH or the C-terminal of albumin, e.g. human albumin, can be coupled to the N-terminal of the alfa-chain of hCG or hLH, or the N-terminal of the beta-chain of hCG or hLH. A linker sequence can be inserted between the albumin and the hCG or LH chain. The two chains in hCG and/or hLH, i.e. alfa and beta chains, can be coupled together through a linker peptide, thus producing one polypeptide sequence, which in turn can be linked, such as through chemical linking or genetically linking, to the pharmaceutically acceptable molecule.

The LH agonist may be linked to the pharmaceutically acceptable molecule through a stable linker or a more labile linker. Several linkers are known in the art, including bifunctional PEG molecules (e.g. see Paige et. al Pharmaceutical Research, vol. 12, no. 12, 1995), hydrolysable linkers (Shechter et al Bioconjugate Chem. 2005, 16, 913-920 and International Journal of Peptide Research and Therapeutics, Vol. 13, Nos. 1-2, June 2007 and WO2009095479), PDPH and EMCH see e.g. in WO2010092135. In the special case where chemical conjugation (linking of two or more molecules) of the LH agonist, such as hCG, to the pharmaceutically acceptable molecule, strongly reduce the functional LH activity it may be preferable to use a more labile linker that can release the functional LH agonist.

The LH agonist may be glycosylated in which case linking to the pharmaceutically acceptable molecule may be through such sugar moiety, or the sugar moiety may be inserted and used to create a link between the LH agonist and the pharmaceutically acceptable molecule.

The LH agonist may be linked to one or more pharmaceutically acceptable molecule(s) or one pharmaceutically acceptable molecule may be linked to one or more LH agonist(s), typically the LH agonist is linked to one or two pharmaceutically acceptable molecule(s), preferably one pharmaceutically acceptable molecule. For instance, one hCG is linked to one albumin, e.g. human albumin or modified albumin.

A further advantage of the LH compound of the present invention is that the pharmaceutically acceptable molecule provides a serum concentration of the LH agonist or LH compound sufficient to support the formation and maintenance of Corpus Luteum/corpora lutea (CL). Such advantage is obtained when an injection of the LH compound is given during the follicular phase of the menstrual cycle in connection with follicle stimulating hormone (FSH) treatment, preferably 5-10 days after initiation of FSH treatment.

A still further advantage of the LH compound of the present invention is that the pharmaceutically acceptable molecule provides a concentration of the LH agonist or LH compound to stimulate sufficient progesterone release from CL. Such advantage is obtained after an injection of the LH compound during the follicular phase of the menstrual cycle in connection with FSH treatment, preferably 5-10 days after initiation of FSH treatment or in connection with ovulation induction or in connection with embryo transfer or sometime in the luteal or gestational phases.

A further aspect of the present invention concerns a pharmaceutical composition comprising the LH compound, and optionally a pharmaceutically acceptable carrier or excipient. Such composition may comprise one or more LH compounds.

A still further aspect of the present invention relates to an LH compound of the present invention, for use in infertility treatment of a mammalian subject, such as assisted reproduction technologies treatment, e.g. IVF or ICSI treatment, or maldecensus of the testis or for the use of augmenting steroid production in hypoganadotropic hypogonadism. Typically, LH compound is for use in promoting fertility of a mammalian subject.

The present invention also concerns a method of infertility treatment of a mammalian subject comprising administering to a mammal in need thereof the LH compound of the present invention.

Moreover, the present invention concerns a method of promoting fertility of a mammalian subject comprising administering to a mammal in need thereof the LH compound of the present invention.

Furthermore, the present inventors have realized that a long-acting modified LH comprising a mammalian LH or analog thereof linked to a pharmaceutically acceptable molecule, e.g. human LH linked to e.g. fused to albumin, or fused to an Fc fragment of a mammalian antibody, or a variant of an Fc fragment of a mammalian antibody or conjugated to an acylation group or PEG, that agonize and activate the LH receptor in a mammal and provides an in vivo plasma half-life of the mammalian LH or analog thereof, or the modified LH which is from 2 to 48 hours, typically from 4 to 28 hours, such as 6-8 hours in a mammal. The modified LH either given in the follicular phase or as a luteal phase support is believed to improve safety, treatment outcome and patient convenience. This long-acting modified mammalian LH of the present invention with the specified in-vivo half-life is particularly useful in combination with FSH.

Accordingly, a further aspect of the present invention relates to a pharmaceutical composition comprising the modified LH of the present invention and an FSH or a molecule having FSH activity. The pharmaceutical composition may be one composition comprising both the modified LH and the FSH or the molecule having FSH activity, or may be a kit of parts comprising the modified LH and the FSH or the molecule having FSH activity in separate compositions, wherein such compositions may be administered simultaneously, sequentially, or separately.

The present invention also concerns a modified LH comprising a mammalian LH or analog thereof linked to a pharmaceutically acceptable molecule providing an in vivo plasma half-life of the mammalian LH or analog thereof, or the modified LH which is from 2 to 48 hours in a mammal, for use in combination with an FSH or a molecule having FSH activity for simultaneous, sequential or separate use to induce follicular development, such as paucifolliculogenesis or unifolliculogenesis, in anovulatory treatment of a mammalian female subject or induce COS in the follicular phase of the menstrual cycle of a mammalian female subject.

The present invention also concerns a method of inducing follicular development, such as paucifolliculogenesis or unifolliculogenesis, in anovulatory treatment of a mammalian female subject or induce COS in the follicular phase of the menstrual cycle of a mammalian female subject comprising administering to a mammal in need thereof an effective amount of the modified LH comprising a mammalian LH or analog thereof linked to a pharmaceutically acceptable molecule providing an in vivo plasma half-life of the mammalian LH or analog thereof, or the modified LH which is from 2 to 48 hours in a mammal, simultaneous, sequential or separate in combination with an FSH or a molecule having FSH activity.

In a further aspect the present invention relates to administering a LH compound during the first 12 weeks of gestation to women with recurrent pregnancy loss in order to enhance progesterone output by the CL and enhance the rate of deliveries of children.

Accordingly, in a further aspect the present invention relates to a modified LH comprising a mammalian LH or analog thereof linked to a pharmaceutically acceptable molecule providing an in vivo plasma half-life of the mammalian LH or analog thereof, or the modified LH which is from 2 to 48 hours in a mammal, typically from 4 to 28 hours, such as 6-8 hours. As stated above such modified LH is particularly useful in combination with FSH treatment.

The mammalian LH may be selected from a mammal LH, such as primate LH (e.g. abe or monkey LH), human LH, and horse LH. The LH may also be an analog of a mammalian LH, and typically the analog has at least 80% identity to the corresponding mammalian sequence of the LH, such as at least 85% identity, 90% identity, 95% identity, 98% identity, or at least 99% identity.

The mammalian LH is linked to another molecule, preferably a pharmaceutically acceptable molecule, and it is this modified LH that herein is referred to as a modified LH. The mammalian LH may be linked to the pharmaceutically acceptable molecule in various ways as described in the prior art literature, such as without limitation chemical coupling through a bifunctional linker, gene technologically by coupling the N-terminal or C-terminal of the LH, such as hLH, to the pharmaceutically acceptable molecule, such as albumin. In particular, the N-terminal of albumin, e.g. human albumin, can be coupled to the N-terminal of the alfa-chain of hLH, or the C-terminal of the beta-chain of hLH. The two chains in hLH, i.e. alfa and beta chains, can be coupled together through a linker peptide, thus producing one polypeptide sequence, which in turn can be linked, such as through chemical linking or genetically linking, to the pharmaceutically acceptable molecule.

The mammalian LH may be linked to the pharmaceutically acceptable molecule through a stable linker or a more labile linker. Several linkers are known in the art, including bifunctional PEG molecules (e.g. see Paige et. al Pharmaceutical Research, vol. 12, no. 12, 1995), hydrolysable linkers (Shechter et al Bioconjugate Chem. 2005, 16, 913-920 and International Journal of Peptide Research and Therapeutics, Vol. 13, Nos. 1-2, June 2007 and WO2009095479), PDPH and EMCH see e.g. in WO2010092135. In the special case where chemical conjugation (linking of two or more molecules) of the mammalian LH, such as hLH, to the pharmaceutically acceptable molecule, strongly reduce the functional LH activity it may be preferable to use a more labile linker that can release the mammalian LH.

The mammalian LH may be glycosylated in which case linking to the pharmaceutically acceptable molecule may be through such sugar moiety or the sugar moiety may be inserted and used to create a link between the LH agonist and the pharmaceutically acceptable molecule.

The mammalian LH may be linked to one or more pharmaceutically acceptable molecule(s) or one pharmaceutically acceptable molecule may be linked to one or more mammalian LH, typically the mammalian LH is linked to one to five, such as one or two pharmaceutically acceptable molecule(s). For instance, one hLH is linked to one albumin, e.g. human albumin or modified albumin.

A further aspect of the present invention concerns a pharmaceutical composition comprising the modified LH of the present invention, and optionally a pharmaceutically acceptable carrier or excipient. Such composition may comprise one or more modified LH.

A still further aspect of the present invention provides a method for assisted reproductive therapy in a female human, said method comprising
 a. starting stimulation by administering FSH on cycle day 1-3 of a menstrual cycle,
 b. administering a GnRH antagonist from day 4-7 of the stimulation until ovulation triggering,
 c. providing an LH agonist to said female by administering at least one dosage of an LH agonist in the period from day 1-9 of the stimulation, said dosage being sufficient to stimulate follicle development until ovulation triggering,
 d. discontinuing administration of FSH when at least one follicle has a diameter of 12-14 mm,
 e. inducing ovulation with at least one dosage of a GnRH agonist when at least one follicle has a diameter of at least 15 mm.

The stimulation protocols of the present invention seek to improve known methods by discontinuing FSH administration when a suitable number of follicles have been recruited and by switching at this point to hCG (or LH) administration in order to ensure maturation of the largest follicles, while the more immature follicles do not develop further. It is known in the art that a high number of immature follicles at ovulation increase the risk of OHSS.

The risk of OHSS is further reduced by inducing ovulation by use of a GnRH agonist trigger shot thus obviating the need for administrating a high dosage of hCG to provoke ovulation.

In preferred embodiments of the invention, the hCG administered during the follicular stimulation is a long-acting hCG or long-acting LH. The use of long-acting hCG or LH has several advantages. Obviously there is increased patient compliance as the number of injections is reduced. It is also expected that this could reduce the risk of OHSS even further, as there is no risk of accumulation of hCG or LH when the protein is administered only once or twice during the follicular phase.

It is also conceivable that the long-acting hCG or LH may be administered as a single dose during one of the very first days of the stimulation protocol. When making a bolus injection of a drug, such as a recombinant protein, there is almost always an initial surge in the serum level after which the serum level drops to a lower level which steadily decreases according to the serum half-life of the drug. During the initial days of the stimulation protocol the receptor for hCG or LH is not yet active on the granulosa cells, while they are constitutively expressed on the surrounding theca cells. The LH activity provided at this stage of follicular development is likely to enhance the androgen output by the theca cells. These androgens are likely to affect the granulosa cells to enhance their FSH receptor expression and thereby make them more sensitive to the exogenous administered FSH and thereby improve follicular health (Eilsø Nielsen M, Rasmussen I A, Kristensen S G, Christensen S T, Møllgård K, Wreford Andersen E, Byskov A G, Yding Andersen C: Expression of Androgen-receptor mRNA in granulosa cells from human small antral follicles and the corresponding follicular fluid concentrations of androgens are positively correlated to granulosa cell FSH receptor mRNA expression. Mol. Hum. Reprod. 2011; 17:63-70. PMID: 20843821). This means that the surge resulting from a bolus hCG injection can improve granulosa cell responsiveness and be terminated before the receptor becomes active on the granulosa cells. Hereafter, a more suitable and stable serum level of hCG can be obtained for maturing and developing the right follicles.

In some embodiments of the invention, the long-acting hCG or LH administered during the stimulation phase is sufficient only to support the follicle development until ovulation. In other embodiments, the dosage is also sufficient to provide support for the luteal phase according to the invention.

In an alternative protocol, ovulation induction is performed by administering a relatively low dosage of hCG, the dosage being 2000 IU or less, such as 1500 IU or less, for example 1000 IU or less, such as 750 IU, 500 IU, or 200 IU. Preferably the dosage is between 1000 and 2000 IU. Ovulation induction can also involve co-administration of a GnRH agonist. This alternative protocol also carries an inherently low risk of OHSS, because the dosage of hCG for ovulation induction is significantly lower than the dosage used for ovulation induction in the prior art.

In another aspect the invention relates to a method for providing luteal support to a female undergoing assisted reproductive therapy, said method comprising administering an LH agonist during the luteal phase at least until 2 weeks after ovulation.

According to this aspect, the LH agonist is administered from around the time of ovulation or oocyte pick up and continued during the luteal phase. Preferably, the LH agonist administration continues until at least 28 days after ovulation.

Preferably the LH agonist is administered during the luteal phase is LH or an LH analogue or LH variant as described herein.

LH and hCG as well as long-acting versions of these hormones may be administered in dosages and at intervals as described in the present application. The female may be one who has undergone assisted reproductive therapy according to the invention. The female may also be a female who has undergone controlled ovarian stimulation according to the prior art, including females who have received a bolus injection of hCG for triggering of ovulation. The latter females will have sufficient serum levels of hCG to provide luteal support for approximately one week after ovulation triggering.

In preferred embodiments the LH agonist is administered until at least 6 weeks after ovulation, such as 7 weeks, for example 8 weeks, such as 9 weeks, for example 10 weeks after fertilisation.

The long-acting hCG or long-acting LH may be administered every 2nd day, such as every 3rd day, for example every 4th day, such as every 5th day, for example every 6th day, such as every 7th day, for example every 8th day, such as every 9th day, for example every 10th day during the ovulation induction phase and/or the luteal phase and/or gestational phase.

The long-acting hCG or long-acting LH may be also administered every 14th day, such as every 21st, for example every month or even less frequently during the ovulation induction phase and/or the subsequent luteal phase and/or the subsequent gestational phase The controlled ovarian stimulation methods of the present invention generally result in improvement involving one or more of the following parameters: biochemical pregnancies, live births, improved implantation rates, improved retention rates, reduced miscarriage rates, reduced ectopic miscarriage rates, reduced occurrence of OHSS, and improved convenience due to reduced or no need for progesterone administration in the luteal phase.

The follicular stimulation protocols of the present invention may be used in conjunction with in vitro fertilization (IVF), through intra cytoplasmatic sperm injection (ICSI), intra uterine insemination (IUD, in vitro maturation (IVM), or other forms derived thereof such as ovarian ovulation alone.

The methods for providing luteal support may be used in conjunction with any of the stimulation protocols mentioned above or in conjunction with any attempted pregnancy or actual pregnancy in which there is a need for stimulating the progesterone level.

In a further aspect the invention relates to a method for inducing folliculogenesis and supporting subsequent embryo implantation comprising:
a. starting stimulation by administering FSH on cycle day 1-3 of a menstrual cycle,
b. administering a GnRH antagonist from day 4-7 of the stimulation until ovulation,
c. administering an LH agonist by administering at least one dosage of hCG in the period from day 1-9, said at least one dosage of hCG being sufficient to stimulate follicle development until ovulation,
d. discontinuing administration of FSH when at least one follicle has a mean diameter of 12-14 mm, and
e. providing luteal support by administering one or more dosages of an LH agonist sufficient to provide a serum progesterone concentration of at least 20 nmol/L 7-10 days after ovulation.
This method may result in monofolliculogenesis or paucifolliculogenesis. The method may also be used for stimulation of follicle development in anovulatory women. The method may also involve ovulation induction using hCG trigger short or GnRH trigger shot as part of a COS protocol.

A further aspect of the present invention is to provide a LH compound to such boys in order to provide a stable concentration of androgens and reduce the number of injection given to these young boys.

A still further aspect of the present invention is to provide a LH compound to such men with hypogonadotropic hypogonadism in order to provide a stable concentration of hCG that can provoke testicular androgen production sufficiently to cause sperm production and to maintain androgens at an acceptable level.

FIGURE LEGENDS

FIG. 1a. A schematic drawing of a typical short antagonist protocol with hCG/GnRHa triggering as known in the prior art. The drawing schematically shows daily administration of FSH from day 1 of the menstrual cycle and until ovulation triggering. A daily dose of GnRH antagonist is administered starting approximately on day 6 and until ovulation triggering. Ovulation is triggered by a bolus shot of hCG or GnRH agonist when follicles have reached a size of 16-18 mm diameter. 36 hrs later oocytes are harvested. Two days later, one or more fertilized embryos are transferred back to the uterus. In order to provide luteal support progesterone is administered e.g. vaginally or intramuscularly.

Figure 1B:
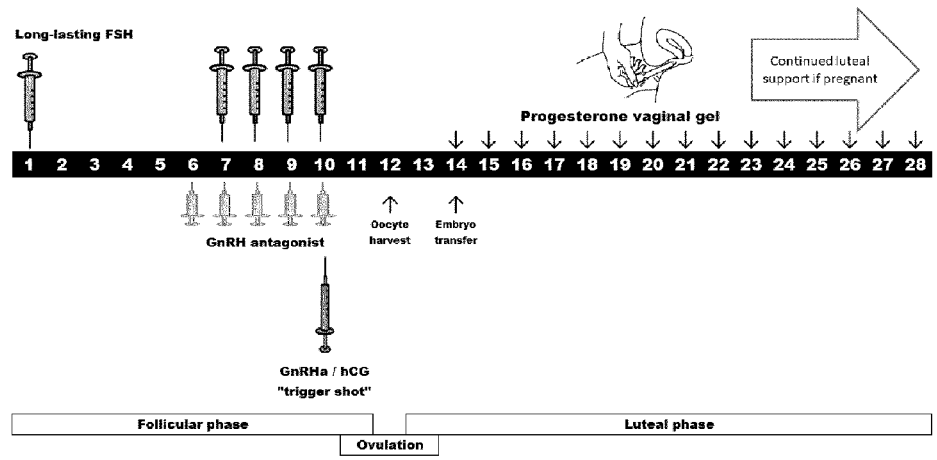

FIG. 1b. A schematic drawing of an alternative short antagonist protocol with hCG/GnRH agonist triggering. The protocol is based on administration of a long-acting FSH (Corifollitropin) on day one of the protocol. From day 6 or 7 and onwards daily dosages of recombinant or urinary FSH is administered to supplement the corifollitropin. GnRH antagonist, triggering and luteal support as for FIG. 1a.

Figure 2A:
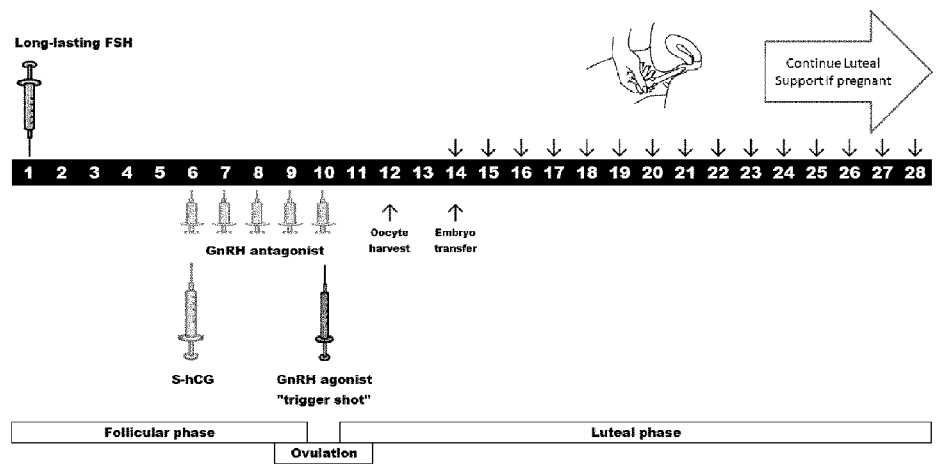
Figure 4A:
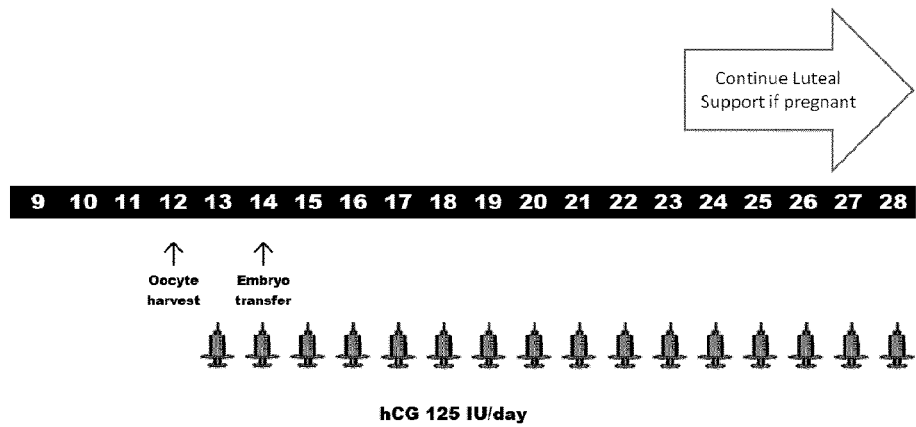
Figure 4B:
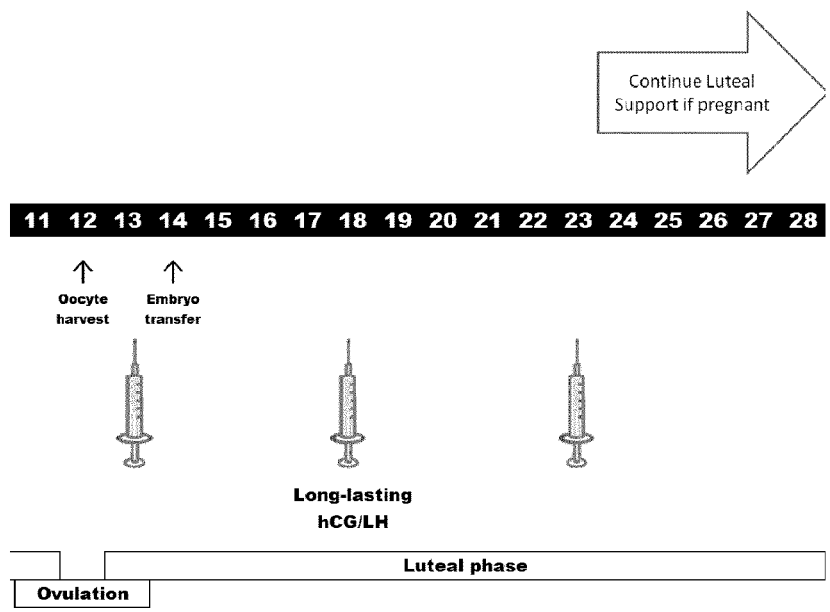

FIG. 2a. An exemplary COS protocol of the invention, wherein the daily dosages of FSH are replaced by one bolus injection of a long-lasting FSH, such as Corifollitropin. Follicle development is supported by administration of long-acting hCG (S-hCG), which is administered at approximately day 6 depending on follicle diameter. A GnRH antagonist is administered from around day 6 of the protocol, and ovulation is induced with a GnRH agonist. Luteal support can be provided by progesterone or by using luteal methods of the invention (FIG. 4a or 4b).

Figure 2B:
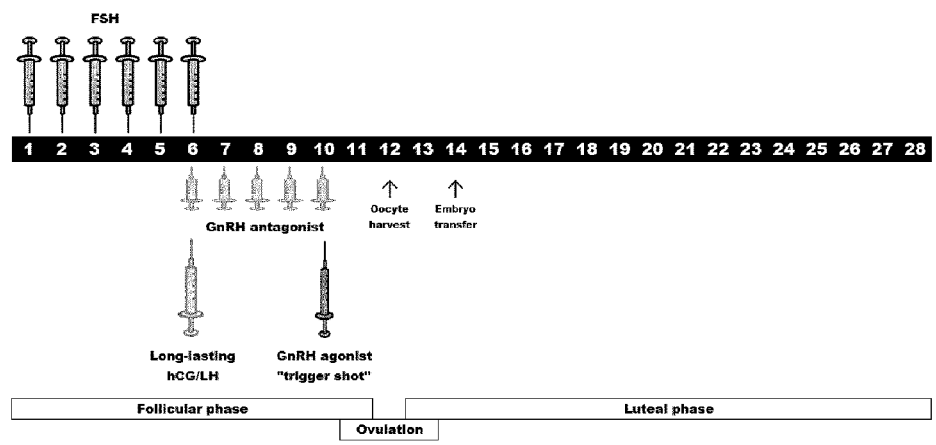

FIG. 2b. A schematic illustration of one exemplary controlled ovarian stimulation (COS) protocol according to the invention. FSH is administered as daily dosages of urinary or recombinant FSH. FSH administration is discontinued from around day 6, corresponding to a follicle size of approximately 12-14 mm. A GnRH antagonist is administered as daily dosages starting day 6 and until ovulation triggering. On day 6 a bolus shot of long-acting (long-lasting) hCG or long-acting LH is administered. Ovulation is triggered by administration of a GnRH agonist. Luteal support is not shown and may be achieved by administration of progesterone as in FIG. 1a, or through the administration of one or more subcutaneous injections of hCG or long-acting hCG or LH or long-acting LH during the luteal phase.

Figure 2C:
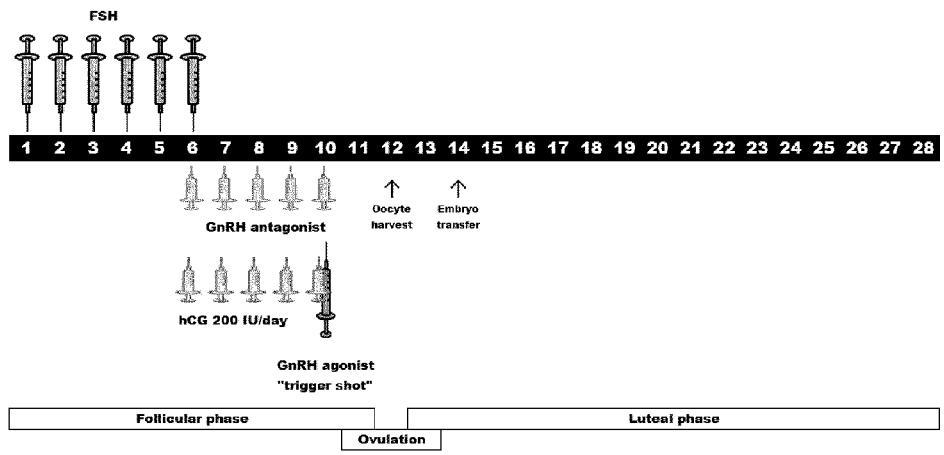

FIG. 2c. An exemplary COS protocol of the invention, wherein follicle recruitment is supported by daily dosages of recombinant or urinary FSH. Follicle development is supported by daily dosages of hCG or LH from about day 6, corresponding to a follicle size of approximately 12-14 mm. A GnRH antagonist is administered as daily dosages starting day 6 and until ovulation triggering. Ovulation is triggered by administration of a GnRH agonist. Luteal support is not shown and may be achieved by administration of progesterone as in FIG. 1a, or through the administration of one or more subcutaneous injections of hCG or long-acting hCG or LH or long-acting LH during the luteal phase. In case of pregnancy, the luteal support may be continued until gestational week 5-10.

Figure 3A:
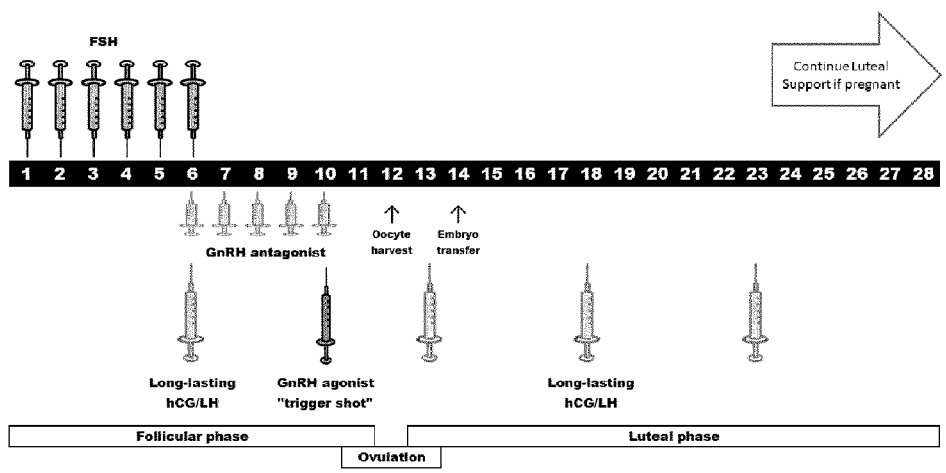

FIG. 3a. An exemplary COS protocol of the invention. Compared to the protocol in FIG. 2b, administration of long-acting (long lasting) hCG or LH is continued into the luteal phase to provide luteal support. In case of pregnancy, the luteal support may be continued until gestational week 5-10.

Figure 3B:
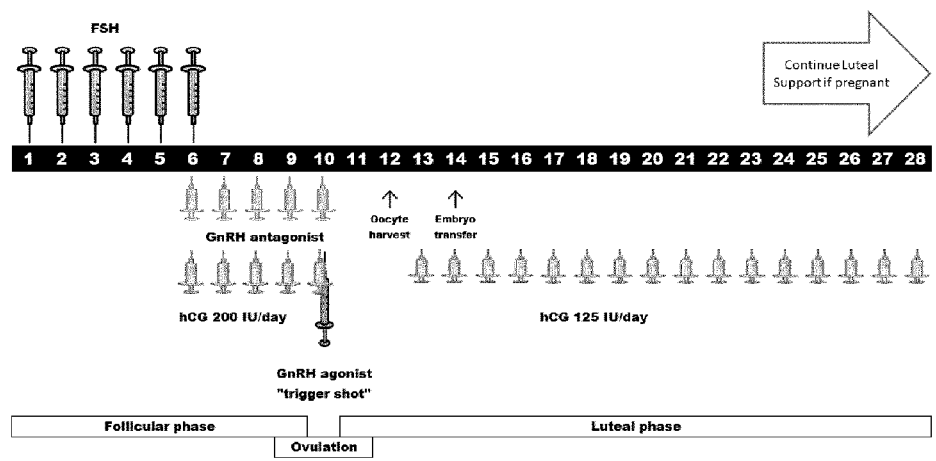

FIG. 3b. An exemplary COS protocol of the invention. Compared to the protocol in FIG. 3a, the hCG or LH is administered as daily injections of recombinant or urinary hCG or LH. The hCG may be replaced by equivalent LH dosages. In case of pregnancy, the luteal support may be continued until gestational week 5-10.

Figure 3C:
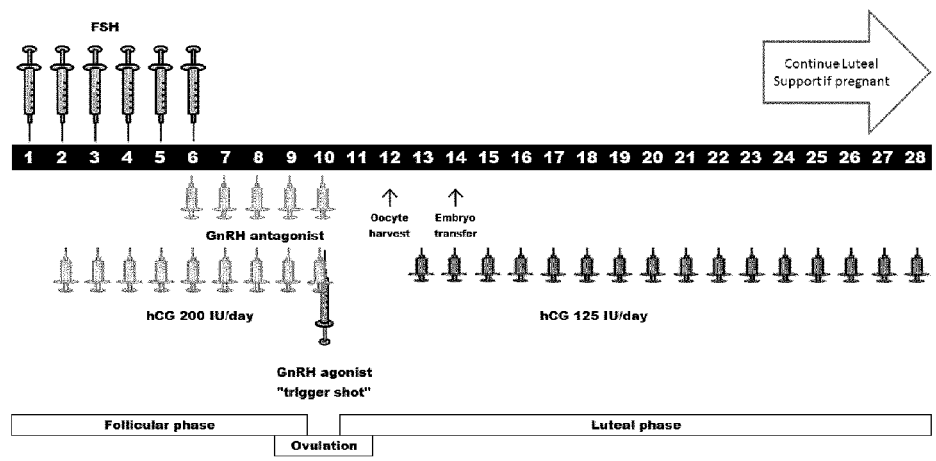

FIG. 3c. An exemplary COS protocol of the invention. Compared to the protocol in FIG. 3b, hCG/LH administration starts already from day 2 of the menstrual cycle as daily injections of hCG or LH. Alternatively the daily dosages may be replaced by equivalent dosages of one or more injections of long-acting hCG or long-acting LH. In case of pregnancy, the luteal support may be continued until gestational week 5-10.

FIG. 4a: An exemplary protocol of the invention illustrating luteal support. Irrespective of the stimulation protocol (not shown), daily dosages of urinary or recombinant LH or hCG provide luteal support during the luteal phase starting approximately day 2 after ovulation. The luteal support may be continued until gestational week 5 if the female is pregnant, for example until gestational week 10.

FIG. 4b. An exemplary protocol of the invention illustrating luteal support. Irrespective of the stimulation protocol (not shown), one or more doses of long-acting LH or long action hCG administered every 2 to 7 days provide luteal support during the luteal phase starting approximately day 2 after ovulation. The luteal support may continue until gestational week 5 if the female is pregnant, for example until gestational week 10.

FIG. 5: ClustalX2 alignment of gonadotropin alpha chains from different species. Sequences were retrieved from the Uniprot database. The Uniprot ID and accession number is given:

| Human | GLHA_HUMAN | P01215 |
| Mouse | GLHA_MOUSE | P01216 |
| Rat | GLHA_RAT | P11962 |

Fully conserved residues are marked with black background and the corresponding amino acid residue shown in capital below the alignment. Semi-conserved residues are shown with grey background and are marked with a lower case below the alignment.

Alignment performed with ClustalX2 (Larkin, M. A., Blackshields, G., Brown, N. P., Chenna, R., McGettigan, P. A., McWilliam, H., Valentin, F., Wallace, I. M., Wilm, A., Lopez, R., Thompson, J. D., Gibson, T. J., Higgins, D. G. (2007) Clustal W and Clustal X version 2.0. Bioinformatics, 23:2947-2948.)

FIG. 6: ClustalX2 alignment of Luteinizing hormone beta chains from various species: Sequences were retrieved from the Uniprot database. The Uniprot ID and accession number is given

| Human: | LSHB_HUMAN | P01229 |
| Mouse: | LSHB_MOUSE | O09108 |
| Rat: | LSHB_RAT | P01230 |
| Gorilla: | LSHB_GORGO | Q2Q1P1 |
| Chimpanzee: | LSHB_PANTR | Q2Q1P2 |

FIG. 7: ClustalX2 alignment of Follicle stimulating hormone beta chains from various species. Sequences were retrieved from the Uniprot database. The Uniprot ID and accession number is given:

| Follitropin subunit beta | | |
| Human: | FSHB_HUMAN | P01225 |
| Mouse: | FSNB_MOUSE | Q60687 |
| Rat: | FSHB_RAT | P18427 |
| Gorilla: | FSHB_GORGO | A1BN60 |
| Chimpanzee: | FSHB_PANTR | Q2PUH2 |

Figure 8A:
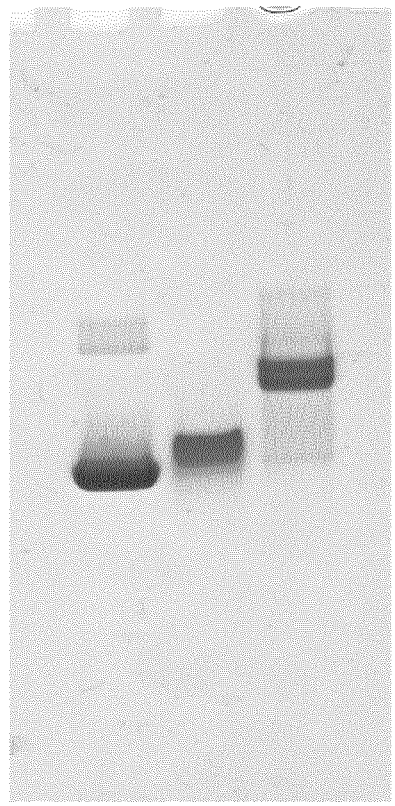

FIG. 8a: Non-reducing SDS PAGE of Conjugate) with rHA and hCG as controls.

Figure 8B:
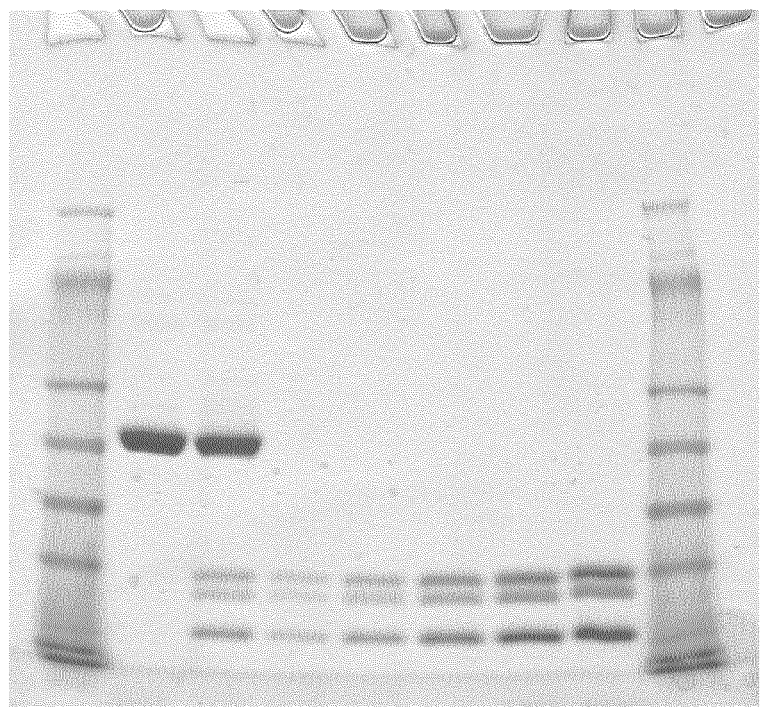

FIG. 8b: Reducing SDS PAGE of Conjugate) with rHA and different concentrations of hCG as controls.

FIG. 8c: SEC-HPLC Analysis of purified Conjugate).

FIG. 9a: Non-reducing SDS PAGE of Conjugate3 with rHA and hCG as controls.

FIG. 9b: Reducing SDS PAGE of Conjugate3 with rHA and different concentrations of hCG as controls.

FIG. 9c: SEC-HPLC Analysis of purified Conjugate3.

FIG. 10a: Non-reducing SDS PAGE of Conjugate4 with rHA and hCG as controls.

FIG. 10b: Reducing SDS PAGE of Conjugate4 with rHA and different concentrations of hCG as controls.

FIG. 10c: SEC-HPLC Analysis of purified Conjugate4.

FIG. 11a: Non-reducing SDS PAGE of Conjugate3V1 with K473P-rHA and hCG as controls.

FIG. 11b: Reducing SDS PAGE of Conjugate3V1 with K573P-rHA and different concentrations of hCG as controls.

FIG. 11c: SEC-HPLC Analysis of purified Conjugate3V1.

FIG. 12a: Non-reducing SDS PAGE of Conjugate4V1 with K573P-rHA and hCG as controls.

FIG. 12b. SDS PAGE (reducing) ofConjugate4Vl.

FIG. 12c: SEC-HPLC Analysis of purified Conjugate4V1.

FIG. 13: Confirmation of amplified single gene vectors prior to transfection.

FIG. 14: Western Blot of Product 1-10 using anti-HSA (human serum albumin).

FIG. 15: Western Blot of Product 1-10 using anti-gonadotropin common α-subunit.

FIG. 16: Western Blot of Product 1-10 using anti-hCG β-subunit.

FIG. 17: SDS PAGE (non-reducing and reducing) analysis of products 1-10.

FIG. 18: SDS PAGE (non-reducing and reducing) analysis of products 11-12.

FIG. 19a: Measurement of in vitro activity of hCG, Conjugate3 and Conjugate4.

FIG. 19b: Measurement of in vitro activity of hCG, Conjugate3v1, Conjugate4V1, Product 11 and Product 12.

FIG. 19c: Measurement of in vitro activity of hCG, Product 2, Product 3, Product 4 and Product 5.

FIG. 19d: Measurement of in vitro activity of hCG, Product 7, Product 8, Product 9 and Product 10.

FIG. 20a: Measurement of in vivo activity of hCG after four daily doses.

FIG. 20b: Measurement of in vivo activity of hCG and Conjugate3 after four daily doses.

FIG. 20c: Measurement of in vivo activity of hCG and Conjugate3 after four daily doses.

FIG. 20d: Measurement of in vivo activity of hCG, Conjugate3 and Conjugate4 after four daily doses.

FIG. 20e: Measurement of in vivo activity of hCG, Conjugate3V1 and Conjugate4V1 after four daily doses.

FIG. 20f: Measurement of in vivo activity of hCG, Product 2, Product 3 and Product 8 after four daily doses.

FIG. 20g: Measurement of in vivo activity of hCG, Product 11 and Product 12 after four daily doses.

FIG. 20h: Measurement of in vivo activity of hCG, Product 4, Product 5 and Product 10 after four daily doses.

FIG. 20i: Measurement of in vivo activity of hCG and Product 7 after four daily doses.

FIG. 20j: Measurement of in vivo activity of hCG, Conjugate3, Product 11 and Product 12 after a single bolus injection on day 1.

FIG. 21a: Pharmacokinetic data of hCG, Conjugate3 and Conjugate3V1 in hypophysectomized male rats (linear scale).

FIG. 21b: Pharmacokinetic data of hCG, Conjugate3 and Conjugate3V1 in hypophysectomized male rats (logarithmic scale).

FIG. 21c: Standard curves of hCG, Conjugate3 and Conjugate3V1.

FIG. 21d: Calculation of terminal half-life for hCG, Conjugate3 and Conjugate3V1 in hypophysectomized male rats.

FIG. 22a: Pharmacokinetic data of hCG, Conjugate4V1, Product 11 and Product 12 in hypophysectomized male rats (linear scale).

FIG. 22b: Pharmacokinetic data of hCG, Conjugate4V1, Product 11 and Product 12 in hypophysectomized male rats (logarithmic scale).

FIG. 22c: Standard curves of hCG, Conjugate4V1, Product 11 and Product 12.

FIG. 22d: Calculation of terminal half-life for hCG, Conjugate4V1, Product 11 and Product 12 in hypophysectomized male rats.

FIG. 22e: Pharmacokinetic data of Product 7 and Product 10 in hypophysectomized male rats (linear scale).

FIG. 22f: Pharmacokinetic data of Product 7 and Product 10 in hypophysectomized male rats (logarithmic scale).

FIG. 22g: Standard curves of Product 7 and Product 10.

FIG. 22h: Calculation of terminal half-life for Product 7 and Product 10 in hypophysectomized male rats.

FIG. 23a: Pharmacokinetic data of hCG, LH, Conjugate3, Conjugate3V1, Product 2, Product 3 and Product 7 in normal adult male rats (linear scale).

FIG. 23b: Pharmacokinetic data of hCG, LH, Conjugate3, Conjugate3V1, Product 2, Product 3 and Product 7 in normal adult male rats (logarithmic scale).

FIG. 23c: Standard curves of LH and Product 7.

FIG. 23d: Calculation of terminal half-life for hCG, LH, Conjugate3, Conjugate3V1, Product 2, Product 3 and Product 7 in normal adult male rats.

DEFINITIONS

In the present context, the term "LH agonist" as used herein means a molecule of mammalian or non-mammalian origin that binds to and activates a luteinizing hormone receptor of a mammal, such as a human. The LH agonist may be a small organic molecule, a peptide, a polypeptide, a protein, and may be produced by synthetic methods, by recombinant means or be obtained from tissue or body fluids. The term "LH agonist" as used herein also includes pharmaceutically acceptable salts thereof. The term "LH agonist" includes hLH, hLH analogues and variants, and long-acting hLH. The term also includes hCG, hCG analogues and variants, and long-acting hCG.

As used herein, an "IU ratio" is the ratio of the number of IU of one component to the number of IU of another component. It is noteworthy that gonadotrophins may now be expressed in (mass/g) instead of biological IU. In this case, a conversion factor has to be used to translate the new value into IU. As used herein the in vivo plasma concentration in a mammal is measured by ELISA or another immunological method known to the person skilled in the art and expressed in IU per liter used interchangeable with IU/L.

In the present context, the term "a long acting biologically active luteinizing hormone (LH) compound" or "LH compound" (these terms are used interchangeable throughout the specification) as used herein means an LH agonist linked to a pharmaceutically acceptable molecule, such as an hCG or hLH with the pharmaceutically acceptable molecule bonded to it in order to modify the properties of said hCG or hLH. The term "LH compound" as used herein also includes pharmaceutically acceptable salts thereof.

In the present context, the term "a modified luteinizing hormone" or "modified LH" (these terms are used interchangeable throughout the specification) as used herein means a mammal LH linked to a pharmaceutically acceptable molecule, such as a hLH with the pharmaceutically acceptable molecule bonded to it in order to modify the properties of said hLH. The term "modified LH" as used herein also includes pharmaceutically acceptable salts thereof.

In the present context, the term "a molecule having binding to a mammal neonatal Fc receptor" as used herein means any pharmaceutically acceptable molecule having affinity to a mammal neonatal Fc receptor (FcRn), such as strong affinity, weak affinity or medium affinity. FcRn is active in adult epithelial tissue and expressed in the lumen of the intestines, pulmonary airways, nasal surfaces, vaginal surfaces, colon and rectal surfaces (U.S. Pat. No. 6,485,726). Fusion proteins comprised of FcRn binding partners (e.g., IgG, Fc fragments) can be effectively shuttled across epithelial barriers by FcRn, thus providing a non-invasive means to systemically administer a desired therapeutic molecule. Additionally, fusion proteins comprising an FcRn binding partner are endocytosed and protected by cells expressing the FcRn. Instead of being marked for degradation, these fusion proteins are recycled out into circulation again, thus increasing the in vivo half-life of these proteins. One approach to improve the efficacy of a therapeutic protein is to increase its serum persistence, thereby allowing higher circulating levels, less frequent administration and reduced doses. The half-life of an albumin fusion or conjugate or of an Fc fusion or conjugate depends in one instance on its pH-dependent binding to the FcRn. FcRn, which is expressed on the surface of endothelial cells, binds the albumin and/or the Fc in a pH-dependent manner and protects it from degradation. Some albumin variants or variants of Fc fragments that selectively bind stronger than the respective wild type to the FcRn at pH 6.0, but not pH 7.4, exhibit a longer terminal half-life in a variety of animal models. For the Fc containing molecules several mutations located at the interface between the CH2 and CH3 domains, such as T250Q/M428L (Hinton P R. et al., 2004. Engineered human IgG antibodies with longer serum half-lives in primates. J Biol. Chem. 279(8):6213-6) and 252Y/S254T/T256E+H433K/N434F (Vaccaro C. et al., 2005. Engineering the Fc region of immunoglobulin G to modulate in vivo antibody levels. Nat. Biotechnol. 23(10):1283-8), have been shown to increase the binding affinity to FcRn and the half-life of the Fc-variant containing molecule in vivo. However, there is not always a direct relationship between increased FcRn binding and improved half-life (Datta-Mannan A. et al., 2007. Humanized IgG1 Variants with Differential Binding Properties to the Neonatal Fc Receptor: Relationship to Pharmacokinetics in Mice and Primates. Drug Metab. Dispos. 35: 86-94). Variants of human albumin have in a similar way shown to increase the binding affinity to FcRn and the half-life of the albumin-variant containing molecule in vivo (cf. WO 2010/092135 and WO2011/051489).

In the present context, the term "an Fc fragment of a mammalian antibody" as used herein means a constant region, i.e. Fc fragment of a mammalian antibody or a fragment thereof wherein such mammalian antibody may be selected from IgM, IgG, IgA, IgD and IgE from a mammal, such as a primate, e.g. human, abe, or monkey; an equine, e.g. horse. A typical Fc fragment of a mammalian antibody is a recombinant Fc fragment of a human antibody, such as a recombinant Fc fragment of a human IgG antibody. The creation of fusion proteins comprised of immunoglobulin constant regions linked to a protein of interest, or fragment thereof, has been described (see, e.g., U.S. Pat. Nos. 5,155,027, 5,428,130, 5,480,981, and 5,808,029). These molecules usually possess both the biological activity associated with the linked molecule of interest as well as the effector function, or some other desired characteristic, associated with the immunoglobulin constant region. Fusion proteins comprising an Fc portion of an immunoglobulin can bestow several desirable properties on a fusion protein including increased stability, increased serum half-life (see Capon et al. (1989) Nature 337:525) as well as binding to Fc receptors such as the neonatal Fc receptor (FcRn) (U.S. Pat. Nos. 6,086,875, 6,030,613, and 6,485, 726).

In the present context, the term "a variant of an Fc fragment of a mammalian antibody" or "Fc variant" (used interchangeably throughout the present description) as used herein means the Fc fragment of a mammalian antibody, wherein one or more amino acid residues, such as 1-10 amino acid residues, of the Fc fragment have been substituted by other amino acid residues and/or wherein one or more amino acid residues, such as 1-10 amino acid residues, have been deleted from the Fc fragment and/or wherein one or more amino acid residues, such as 1-10 amino acid residues, have been added to the Fc fragment and/or wherein one or more amino acid residues, such as 1-10 amino acid residues, in the Fc fragment have been modified. Such addition or deletion of amino acid residues can take e.g. place at the N-terminal of the Fc fragment and/or at the C-terminal of the Fc fragment. Fc variant refers to a molecule or sequence that is modified from a native Fc but still comprises a binding site for the salvage receptor, FcRn (WO 97/34631). Native refers to an Fc that has not been modified by a human. WO 96/32478 describes exemplary Fc variants, as well as interaction with the salvage receptor. Thus, the term "Fc variant" in one embodiment comprises a molecule or sequence that is humanized from a non-human native Fc. Furthermore, a native Fc comprises sites that may be removed because they provide structural features or biological activity that are not required for the fusion molecules of the present invention. Thus, Fc variant comprises a molecule or sequence that lacks one or more native Fc sites or residues that affect or are involved in (1) disulfide bond formation, (2) incompatibility with a selected host cell (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC). The Fc region of IgG can be modified according to well recognized procedures such as site directed mutagenesis and the like to yield modified IgG or Fc fragments or portions thereof that will be bound by FcRn. Such modifications include modifications remote from the FcRn contact sites as well as modifications within the contact sites that preserve or even enhance binding to the FcRn. For example the following single amino acid residues in human IgG1 Fc (Fcγ1) can be substituted without significant loss of Fc binding affinity for FcRn: P238A, S239A, K246A, K248A, D249A, M252A, T256A, E258A, T260A, D265A, S267A, H268A, E269A, D270A, E272A, L274A, N276A, Y278A, D280A, V282A, E283A, H285A, N286A, T289A, K290A, R292A, E293A, E294A, Q295A, Y296F, N297A, S298A, Y300F, R301A, V303A, V305A, T307A, L309A, Q311A, D312A, N315A, K317A, E318A, K320A, K322A, S324A, K326A, A327Q, P329A, A330Q, A330S, P331A, P331S, E333A, K334A, T335A, S337A, K338A, K340A, Q342A, R344A, E345A, Q347A, R355A, E356A, M358A, T359A, K360A, N361A, Q362A, Y373A, S375A D376A, A378Q, E380A, E382A, S383A, N384A, Q386A, E388A, N389A, N390A, Y391F, K392A, L398A, S400A, D401A, D413A, K414A, R416A, Q418A, Q419A, N421A, V422A, S424A, E430A, N434A, T437A, Q438A, K439A, S440A, S444A, and K447A, where for example P238A represents wildtype proline substituted by alanine at position number 238. In addition to alanine, other amino acids may be substituted for the wildtype amino acids at the positions specified above. Mutations may be introduced singly into Fc, giving rise to more than one hundred FcRn binding partners distinct from native Fc. Additionally, combinations of two, three, or more of these individual mutations may be introduced together, giving rise to hundreds more FcRn binding partners. Certain of the above mutations may confer new functionality upon the FcRn binding partner. For example, one embodiment incorporates N297 A, removing a highly conserved N-glycosylation site. The effect of this mutation is to reduce binding to immune effector cells and potentially decrease immunogenicity, thereby enhancing circulating half-life of the FcRn binding partner, and to render the FcRn binding partner incapable of binding to FcγRI, FcγRIIA, FcγRIIB, and FcγRIIIA, without compromising affinity for FcRn (Routledge et al. (1995) *Transplantation* 60:847; Friend et al. (1999) *Transplantation* 68:1632; Shields et al. (1995) *J. Biol. Chem.* 276:6591). Additionally, at least three human Fc gamma receptors appear to recognize a binding site on IgG within the lower hinge region, generally amino acids 234-237. Therefore, another example of new functionality and potential decreased immunogenicity may arise from mutations of this region, as for example by replacing amino acids 233-236 of human IgG1 "ELLG" SEQ ID NO: with the corresponding sequence from IgG2 "PVA" (with one amino acid deletion). It has been shown that FcγRI, FcγRII, and FcγRIII, which mediate various effector functions, will not bind to IgG1 when such mutations have been introduced (Ward and Ghetie (1995) *Therapeutic Immunology* 2:77 and Armour et al. (1999) *Eur. J. Immunol.* 29:2613). As a further example of new functionality arising from mutations described above, affinity for FcRn may be increased beyond that of wildtype in some instances. This increased affinity may reflect an increased "on" rate, a decreased "off" rate, or both an increased "on" rate and a decreased "off" rate. Mutations believed to impart an increased affinity for FcRn include T256A, T307A, E380A, and N434A (Shields et al. (2001) *J. Biol. Chem.* 276:6591). Furthermore, such variant(s) of the Fc fragment includes without limitation the "knob-into-hole" or "KnH" technology as described in for instance by Atwell et all J. Mol. Biol. (1997), 270, 26-35 and in Ridgway et al Protein Engineering, vol. 9, no. 7, pp 617-621, 1996. The term "knob-into-hole" or "KnH" technology as used herein refers to the technology directing the pairing of two polypeptides together in vitro or in vivo by introducing a protuberance (knob) into one polypeptide and a cavity (hole) into the other polypeptide at an interface in which they interact. For example, KnHs have been introduced in the Fc:Fc binding interfaces, CL:CH1 interfaces or VH:VL interfaces of antibodies (e.g., US2007/0178552, U.S. Ser. No. 12/811,207, US20100286374, WO96/027011, WO98/050431 and Zhu et al. (1997) Protein Science 6:781-788). This is especially useful in driving the pairing of two different heavy chains together during the manufacture of multispecific antibodies or heterodimeric Fc-fusion molecules. For example, multispecific antibodies having KnH in their Fc regions can further comprise single variable domains linked to each Fc region, or further comprise different heavy chain variable domains that pair with similar or different light chain variable domains. KnH technology can also be used to pair two different receptor extracellular domains together or any other polypeptide sequences that comprise different target recognition sequences (e.g., including affibodies, peptibodies and other Fc fusions). KnH technology can also be used to pair two different chains in e.g. gonadotropin molecules like FSH, LH, hCG or TSH in an Fc-fusion.

In the present context, the term "pharmaceutically acceptable salt" is intended to indicate salts which are not harmful to the mammalian subject to be treated. Such salts include pharmaceutically acceptable acid addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Further examples of pharmaceutically acceptable inorganic or organic acid addition salts include the pharmaceutically acceptable salts listed in *J. Pharm. Sci.* 66, 2, (1977) which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like.

In the present context, the term "chorionic gonadotropin" as used herein means chorionic gonadotropin of mammalian origin, e.g. primates such as human chorionic gonadotropin or equine chorionic gonadotropin such as horse chorionic gonadotropin, and recombinant chorionic gonadotropin, such as recombinant human chorionic gonadotropin, and analogues of such chorionic gonadotropins. As used herein "CG" and "chorionic gonadotropin" are interchangeable. When CG is an analogue of a chorionic gonadotropin of a mammal, such as hCG and recombinant hCG, said analogue is understood to be the compound obtained by substituting one or more amino acid residues in the CG, e.g. hCG, sequence with another natural or unnatural amino acid; and/or by adding one or more natural or unnatural amino acids to the CG, e.g. hCG, sequence; and/or by deleting one or more amino acid residue from the CG, e.g. hCG, sequence, wherein any of these steps may optionally be followed by further derivatization of one or more amino acid residues. In particular, such substitutions are conservative in the sense that one amino acid residue is substituted by another amino acid residue from the same group, i.e. by another amino acid residue with similar properties. Amino acids may conveniently be divided in the following groups based on their properties: Basic amino acids (such as arginine, lysine, histidine), acidic amino acids (such as glutamic acid and aspartic acid), polar amino acids (such as glutamine, cysteine and asparagine), hydrophobic amino acids (such as leucine, isoleucine, proline, methionine and valine), aromatic amino acids (such as phenylalanine, tryptophan, tyrosine) and small amino acids (such as glycine, alanine, serine and threonine). Typically, the CG has at least 80% identity with hCG, and typically, has at least 20% of the CG in vivo activity of hCG.

In the present context, the term "luteinizing hormone" or "mammalian luteinizing hormone" as used herein means luteinizing hormone of mammalian origin, such as primates, e.g. human, or horse luteinizing hormone, and recombinant luteinizing hormone, such as recombinant human, horse, abe, or monkey luteinizing hormone, and analogues of such luteinizing hormones. As used herein "LH" and "luteinizing hormone" are interchangeable. When LH is an analogue of a luteinizing hormone of a mammal, such as hLH and recombinant hLH, said analogue is understood to be the compound obtained by substituting one or more amino acid residues in the LH, e.g. hLH, sequence with another natural or unnatural amino acid; and/or by adding one or more natural or unnatural amino acids to the LH, e.g. hLH, sequence; and/or by deleting one or more amino acid residue from the LH, e.g. hLH, sequence, wherein any of these steps may optionally be followed by further derivatization of one or more amino acid residues. In particular, such substitutions are conservative in the sense that one amino acid residue is substituted by another amino acid residue from the same group, i.e. by another amino acid residue with similar properties. Amino acids may conveniently be divided in the following groups based on their properties: Basic amino acids (such as arginine, lysine, histidine), acidic amino acids (such as glutamic acid and aspartic acid), polar amino acids (such as glutamine, cysteine and asparagine), hydrophobic amino acids (such as leucine, isoleucine, proline, methionine and valine), aromatic amino acids (such as phenylalanine, tryptophan, tyrosine) and small amino acids (such as glycine, alanine, serine and threonine). Typically, the LH has at least 80% identity with hLH, and typically, has at least 20% of the LH in vivo activity of hLH. For purposes of the present invention, hLH, hLH analogues and variants, and long-acting hLH do not include hCG, hCG analogues and variants, and long-acting hCG.

In the present context, the term "follicular stimulating hormone" as used herein means follicular stimulating hormone of mammalian origin, such as human, equine, bovine, or porcine follicular stimulating hormone, and recombinant follicular stimulating hormone, such as recombinant human, equine, bovine, or porcine follicular stimulating hormone, and analogues of such follicular stimulating hormones. As used herein "FSH" and "follicular stimulating hormone" are interchangeable. For the stimulation of follicle growth the FSH may be derived exogenously or produced endogenously in the woman in amounts higher than normal, f.i. by providing clomiphene citrate that acts as an oestradiol antagonist on the pituitary.

When FSH is an analogue of a follicular stimulating hormone of a mammal, such as hFSH and recombinant hFSH, said analogue is understood to be the compound obtained by substituting one or more amino acid residues in the FSH, e.g. hFSH, sequence with another natural or unnatural amino acid; and/or by adding one or more natural or unnatural amino acids to the FSH, e.g. hFSH, sequence; and/or by deleting one or more amino acid residue from the FSH, e.g. hFSH, sequence, wherein any of these steps may optionally be followed by further derivatization of one or more amino acid residues. In particular, such substitutions are conservative in the sense that one amino acid residue is substituted by another amino acid residue from the same group, i.e. by another amino acid residue with similar properties. Amino acids may conveniently be divided in the following groups based on their properties: Basic amino acids (such as arginine, lysine, histidine), acidic amino acids (such as glutamic acid and aspartic acid), polar amino acids (such as glutamine, cysteine and asparagine), hydrophobic amino acids (such as leucine, isoleucine, proline, methionine and valine), aromatic amino acids (such as phenylalanine, tryptophan, tyrosine) and small amino acids (such as glycine, alanine, serine and threonine). Recombinantly produced FSH or analog of FSH is typically derived from mammalian cell lines, such as a human or hamster cell lines, e.g. cell lines selected from CHO, BHK, and HEK. Typically, the FSH has at least 80% identity with hFSH, and typically, has at least 20% of the FSH in vivo activity of hFSH.

The term "a molecule having FSH activity" as used herein means a molecule that binds to and activates an FSH receptor when administered to a mammal e.g. such molecule may without limitation be selected from any one of small organic molecules.

In the present context, the term "a linker" as used herein means a valence bond or multifunctional moiety, such as a bifunctional moiety that separates the LH agonist, e.g. the mammalian LH, and the pharmaceutically acceptable molecule. The multifunctional moiety, such as bi- or trifunctional, is covalently linked to one or more LH agonist(s), such as one or more mammalian LH, and covalently linked to one or more pharmaceutically acceptable molecule(s) so as to create the LH compound, such as the modified LH. The linker may be stabile which means that no significant chemical reactions, e.g. hydrolysis, occurs at physiological conditions (e.g. temperature of 37° Celcius and pH 7.4) over the time period of the treatment. This can be determined by stability studies known in the art. The linker may be labile which means that a chemical bond is broken, typically by hydrolysis, at physiologically relevant conditions (e.g. temperature of 37° Celcius and pH 7.4). This can be determined by stability studies known in the art. The linker may be a chemical linker meaning that it is generated by organic chemistry outside a living cell. The linker may be a sugar moiety, such as a glycosylation on a protein, or may be chemically prepared and used to link the LH agonist, e.g. the mammalian LH, and the pharmaceutically acceptable molecule. The linker may be a disulphide bridge, such as a —S—S— bond between two cysteine (Cys) amino acid residues in each of the LH agonist, e.g. the mammalian LH, and the pharmaceutically acceptable molecule. The linker may be a fused linker meaning that the LH compound, e.g. the modified LH, can be expressed in a living cell as one polypeptide or protein. The linker may be a hydrophilic linker that separates an LH agonist, e.g. the mammalian LH, and a pharmaceutically acceptable molecule with a chemical moiety, which comprises at least 5 non-hydrogen atoms where 30-50% of these are either N or O. The linker may be hydrolysable as described in U.S. Pat. No. 6,515,100, U.S. Pat. No. 7,122,189, U.S. Pat. No. 7,700,551, WO2004089280, WO2006138572 and WO2009095479. Typical compounds useful as linkers in the present invention include those selected from the group having dicarboxylic acids, malemido hydrazides, PDPH, SPDP, LC-SPDP, GMBS, carboxylic acid hydrazides, and small peptides. More specific examples of compounds useful as linkers, according to the present invention, include: (a) dicarboxylic acids such as succinic acid, glutaric acid, and adipic acid; (b) maleimido hydrazides such as N-[maleimidocaproic acid]hydrazide (EMCH), N-[maleimidopropionic acid]hydrazide (MPH or BMPH), 4-[N-maleimidomethyl]cyclohexan-1-carboxylyhydrazide, and N-[k-maleimidoundcanoic acid]hydrazide (KMUH), 4-(4-N-MaleimidoPhenyl)butyric acid Hydrazide (MPBH); (c) NHS-3-maleimidopropionate Succinimide ester (MPS-EDA); (d) PDPH linkers such as (3-[2-pyridyldithio]propionyl hydrazide) conjugated to sulfurhydryl reactive protein; (e)N-Succinimidyl 3-(2-pyridyldithio)-propionate (SPDP), (f) Succinimidyl 6-(3-[2-pyridyldithio]-propionamido)hexanoate (LC-SPDP), (g)N-(y-Maleimidobutyryloxy)succinimide ester (GMBS), and (h) carboxylic acid hydrazides selected from 2-5 carbon atoms. Other non-peptide linkers are also possible. For example, alkyl linkers such as —NH—(CH2)m-C(O)—, wherein m is an integer selected from 2-20, could be used. These alkyl linkers may further be substituted by any non-sterically hindering group such as lower alkyl (e.g., C1 to C6) lower acyl, halogen (e.g., Cl, Br, I, F), CN, $NH_2$, phenyl, etc. An exemplary non-peptide linker is a PEG linker. Additional linkers useful according to the present invention are described in U.S. Pat. No. 6,660,843. The LH compound of the present invention wherein the pharmaceutically acceptable molecule is fused to the LH agonist may optionally comprise at least one peptide linker. In one embodiment, the linker is comprised of amino acids linked together by peptide bonds, wherein the amino acids are selected from the twenty naturally occurring amino acids. In various embodiments the linker can comprise 1-5 amino acids, 1-10 amino acids, 1-20 amino acids, 10-50 amino acids, 50-100 amino acids, or 100-200 amino acids. In one embodiment the amino acids are selected from glycine, alanine, proline, asparagine, glutamine, and lysine. In one embodiment a linker is made up of a majority of amino acids that are sterically unhindered, such as glycine and alanine. The linker in one embodiment can comprise the sequence Gn (equivalently, -(Gly)n-) (SEQ ID NO: 64). The linker can in one embodiment comprise the sequence (GGS)n SEQ ID NO: 65) or (GGGGS)n (SEQ ID NO: 66). In each instance, n is an integer, such as 1, 2, 3, 4, 5, 6, 7, 8, 9, or 10. Examples of linkers include, but are not limited to, GGG, SGGSGGS (SEQ ID NO: 58), GGSGGSGGSGGSGGG (SEQ ID NO: 59), GGSGGSGGSGGSGGSGGS (SEQ ID N0:60), and GGGGSGGGGSGGGGS (SEQ ID N0:57). In one embodiment the linker is an 8-amino acid linker EFAGAAAV (SEQ ID N0:56).

Different techniques for linking two or more molecules together, such as the LH agonist, e.g. the mammalian LH, and the pharmaceutically acceptable molecule, and optionally via a multifunctional linker, such as bifunctional linker, are available in the prior art, and a suitable reference here is WO0158493, including all relevant documents listed and cited therein.

In the present context, the term "a pharmaceutically acceptable molecule" as used herein means a molecule selected from any one of small organic molecules, peptides, oligopeptides, polypeptides, proteins, receptors, glycosylations, sugars, polymers (e.g. polyethylene glycols, PEG), nucleic acids (e.g. DNA and RNA), hormones, which when linked to the LH agonist, e.g. the mammalian LH, increases the serum half-life of the LH agonist, e.g. the mammalian LH, or the LH compound, e.g. the modified LH. Typically, pharmaceutically acceptable molecules are without limitation albumin, such as human albumin, recombinant albumin, or polymer, such as PEG, e.g. PEG of a molecular weight of at least 10 kDa, such as from 10 kDa to 150 kDa. Furthermore, pharmaceutically acceptable molecules may be selected from a Fc fragment of a mammalian antibody, transferrin, albumin, such as human albumin, recombinant albumin, variants of albumin, $CH_3(CH_2)_nCO$—, wherein n is 8 to 22, or polymer, such as PEG, e.g. PEG of a molecular weight of at least 5 kDa, such as from 10 kDa to 150 kDa, typically 10 to 40 kDa.

In the present context, the term "in vivo plasma half-life" is used in its normal meaning, i.e., the time required for the amount of the LH agonist, e.g. mammalian LH, or LH compound, e.g. modified LH, in a biological system to be reduced to one half of its value by biological processes.

The term "serum half-life", which may be used interchangeably with "plasma half-life" or "half-life" is used in its normal meaning, i.e., the time required for the amount of the LH agonist, e.g. mammalian LH, or LH compound, e.g. modified LH, recombinant or urinary hCG or LH or FSH or long-acting hCG, long-acting LH or long-acting FSH in a biological system to be reduced to one half of its concentration. Thus as used herein, the "serum half-life" means the serum half-life in vivo. Determination of serum half-life is often more simple than determining functional half-life and the magnitude of serum half-life is usually a good indication of the magnitude of functional in vivo half-life. Preferably the serum half-life is measured in a mammal, more preferably in a species of Homimidae, such as Orang-utan, Chimpanzee or Gorillas, more preferably in humans. The serum half-lives mentioned in the present application are half-lives as determined in humans. An indication of the half-life or any change in half-life can also be obtained in rodents, such as mouse or rat or hamster. Furthermore half-life can be measured in larger mammals having a body weight in the same range as human beings or closer to human being body weight than rodents: preferably monkey, dog, pig, or cattle (calf). Gonadotropins which have a longer half life than recombinant or urinary gonadotropins (FSH, LH or hCG) are considered "long-acting" according to the present invention.

The term "increased" as used in connection with the plasma half-life is used to indicate that the relevant half-life of the LH compound, e.g. the modified LH, is statistically significantly increased relative to that of the LH agonist, e.g. the mammalian LH, as determined under comparable conditions. For instance the relevant half-life may be increased by at least about 25%, such as by at least about 50%, e.g., by at least about 100%, 150%, 200%, 250%, or 500%. Measurement of in vivo plasma half-life can be carried out in a number of ways as described in the literature. An increase in in-vivo plasma half-life may be quantified as a decrease in clearance or as an increase in mean residence time (MRT). LH compound, e.g. modified LH, of the present invention for which the clearance is decreased to less than 70%, such as less than 50%, such as less than 20%, such as less than 10% of the clearance of the LH agonist, e.g. mammalian LH, as determined in a suitable assay is said to have an increased in-vivo plasma half-life. LH compound, e.g. modified LH, of the present invention for which MRT is increased to more than 130%, such as more than 150%, such as more than 200%, such as more than 500% of the MRT of the LH agonist, e.g. the mammalian LH, in a suitable assay is said to have an increased in vivo plasma half-life. Clearance and mean residence time can be assessed in standard pharmacokinetic studies using suitable test animals. It is within the capabilities of a person skilled in the art to choose a suitable test animal for a given protein. Tests in human, of course, represent the ultimate test. Suitable test animals include normal, Sprague-Dawley male rats, mice and cynomolgus monkeys. Typically the mice and rats are injected in a single subcutaneous bolus, while monkeys may be injected in a single subcutaneous bolus or in a single iv dose. The amount injected depends on the test animal. Subsequently, blood samples are taken over a period of one to ten days as appropriate (depending on the sensitivity of the assay it may be as long as 30 days) for the assessment of clearance and MRT. The blood samples are conveniently analysed by ELISA techniques or other immunological techniques.

In the present context, the term "mammalian origin" as used herein means obtained from a mammal, thus an LH agonist of mammalian origin may for instance be a human CG or human LH obtained from tissue or blood of a mammal, or may be obtained by recombinant means, such as recombinant proteins, recombinant polypeptides, for instance an LH agonist of mammalian origin may be a recombinant mammalian CG or recombinant mammalian LH, for instance recombinant human CG or LH.

In the present context, the term "non-mammalian origin" as used herein means obtained from a source which is not a mammal, such as synthetic peptides, oligo peptides and polypeptides or small organic molecules, for instance an LH agonist of non-mammalian origin may be a small organic molecule or short peptide of 5 to 20 amino acids that binds and activates the LH receptor.

In the present context, the term "plasma concentration" as used herein means the concentration that can be measured in circulation at any given time after injection of the LH agonist.

In the present context, the term "an injection" as used herein means administration by the parenteral route such as by subcutaneous, intramuscular, intraperitoneal or intravenous injection by means of a syringe or other administration device.

In the present context, the term "FSH treatment" as used herein means standard follicular stimulating hormone treatment. FSH is required for follicular recruitment (i.e., the early growth of ovarian follicles) at the beginning of the spontaneous menstrual cycle, and it also supports mid- and late-stage folliculogenesis. FSH is administered therapeutically to induce folliculogenesis in anovulatory women and women undergoing COS. In traditional ovulatory stimulation methods, FSH is administered throughout treatment until the time that oocytes are retrieved.

In the present context, the term "analog" or "analogue" (used interchangeably throughout the present description) as used herein means a polypeptide or protein wherein one or more amino acid residues of the polypeptide or protein have been substituted by other amino acid residues and/or wherein one or more amino acid residues have been deleted from the peptide and/or wherein one or more amino acid residues have been added to the polypeptide or protein. Such addition or deletion of amino acid residues can take e.g. place at the N-terminal of the peptide and/or at the C-terminal of the peptide. A simple system may be used to describe analogues: for example, an hCG analogue comprising the mutation R133c designates an analogue wherein the naturally occurring R at position 133 of hCG has been substituted with C. Another example, a hLH analogue comprising the mutation L121C designates an analogue wherein the naturally occurring L at position 121 of hLH beta chain has been substituted with C Formulae of polypeptide or protein analogs are drawn using standard single letter abbreviation for amino acids used according to IUPAC-IUB nomenclature.

In the present context, the term "identity" as used herein refers to a relationship between the sequences of two or more proteins, as determined by comparing the sequences. In the art, "identity" also means the degree of sequence relatedness between proteins, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related proteins can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM *J. Applied Math.*, 48, 1073, (1988). Preferred methods to determine identity are designed to give the largest match between the sequences tested. Methods to determine identity are described in publicly available computer programs. Preferred computer program methods to determine identity between two sequences include the GCG program package, including GAP (Devereux et al., *Nucl. Acid. Res.,* 12, 387, (1984); Genetics Computer Group, University of Wisconsin, Madison, Wis.), BLASTP, BLASTN, and FASTA (Altschul et al., *J. Mol. Biol.,* 215, 403-410, (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well known Smith Waterman algorithm may also be used to determine identity. For example, using the computer algorithm GAP (Genetics Computer Group, University of Wisconsin, Madison, Wis.), two proteins for which the percent sequence identity is to be determined are aligned for optimal matching of their respective amino acids (the "matched span", as determined by the algorithm). A gap opening penalty (which is calculated as 3 times the average diagonal; the "average diagonal" is the average of the diagonal of the comparison matrix being used; the "diagonal" is the score or number assigned to each perfect amino acid match by the particular comparison matrix) and a gap extension penalty (which is usually {fraction (1/10)} times the gap opening penalty), as well as a comparison matrix such as PAM 250 or BLOSUM 62 are used in conjunction with the algorithm. A standard comparison matrix (see Dayhoff et al., Atlas of Protein Sequence and Structure, vol. 5, supp. 3 (1978) for the PAM 250 comparison matrix; Henikoff et al., *Proc. Natl. Acad. Sci. USA,* 89, 10915-10919, (1992) for the BLOSUM 62 comparison matrix) is also used by the algorithm. Preferred parameters for a protein sequence comparison include the following: Algorithm: Needleman et al., *J. Mol. Biol,* 48, 443-453, (1970); Comparison matrix: BLOSUM 62 from Henikoff et al., *Proc. Natl. Acad. Sci. USA,* 89, 10915-10919, (1992); Gap Penalty: 12, Gap Length Penalty: 4, Threshold of Similarity: 0. The GAP program is useful with the above parameters. The aforementioned parameters are the default parameters for protein comparisons (along with no penalty for end gaps) using the GAP algorithm. Amino acid sequence homology/identity is conveniently determined from aligned sequences, using e.g. the ClustalW program, version 1.8, June 1999, using default parameters (Thompson et al., 1994, ClustalW: Improving the sensitivity of progressive multiple sequence alignment through sequence weighting, position-specific gap penalties and weight matrix choice, Nucleic Acids Res., 22:4673-4680) and analyzed by use of GENEDOC version 2.5 (Nicholas et al., 1997 GeneDoc: Analysis and Visualization of Genetic Variation, EMBNEW.NEWS 4:14; Nicholas, K. B. and Nicholas H. B. Jr. 1997 GeneDoc: Analysis and Visualization of Genetic Variation).

The most abundant protein component in circulating blood of mammalian species is serum albumin, which is normally present at a concentration of approximately 3 to 4.5 grams per 100 milliliters of whole blood. Serum albumin is a blood protein of approximately 70,000 Dalton (Da) which has several important functions in the circulatory system. It functions as a transporter of a variety of organic molecules found in the blood, as the main transporter of various metabolites such as fatty acids and bilirubin through the blood, and, owing to its abundance, as an osmotic regulator of the circulating blood. In the present context, the term "an albumin" as used herein means albumin of mammalian origin or non-mammalian origin, such as human serum albumin that is described in Peters, T., Jr. (1996) All about Albumin: Biochemistry, Genetics and Medical, Applications pp 10, Academic Press, Inc., Orlando (ISBN 0-12-5521 10-3), or recombinant human albumin, or modified albumin, such as human albumin modified as described in WO2011051489 and WO2010092135.

WO2011051489 the specification relates to variants of a parent albumin having altered plasma half-life compared with the parent albumin. The present invention also relates to fusion polypeptides and conjugates comprising said variant albumin.

WO2010092135 based on the three-dimensional structure of albumin, the inventors have designed variant polypeptides (muteins) which have one or more cysteine residues with a free thiol group (hereinafter referred to as "thio-albumin"). The variant polypeptide may be conjugated through the sulphur atom of the cysteine residue to a conjugation partner such as a bioactive compound.

WO2005054286 the specification relates to proteins comprising Interleukin 11 (IL-11) (including, but not limited to, fragments and variants thereof), which exhibit thrombopoietic or antiinflammatory properties, fused to albumin (including, but not limited to fragments or variants of albumin).

WO2004083245 describes an agent having a greater half-life than naturally produced albumin in a patient with NS, the agent comprising an albumin-like first polypeptide bound to a second polypeptide.

WO03066681 describes a composition comprising a non-albumin protein stabilised by the addition of a highly purified recombinant human serum albumin. The non-albumin protein may be Factor VIII.

In the present context, the term "a polymer" as used herein means a molecule formed by covalent linkage of two or more monomers, wherein none of the monomers is an amino acid residue, except where the polymer is human albumin or another abundant plasma protein. The term "polymer" may be used interchangeably with the term "polymer molecule". The term is intended to cover carbohydrate molecules attached by in vitro glycosylation. Carbohydrate molecules attached by in vivo glycosylation, such as N- or O-glycosylation (as further described below) are referred to herein as "an oligosaccharide moiety". Except where the number of polymer molecules is expressly indicated, every reference to "a polymer", "a polymer molecule", "the polymer" or "the polymer molecule" as used in the present invention shall be a reference to one or more polymer molecule(s). The polymer may be a water soluble or water insoluble polymer, such as a PEG moiety. The PEG moiety may have an average size selected from the range of 500 Da to 200,000 Da, such as from 500 Da to 100,000 Da, such as from 2000 Da to 50,000 Da. Such PEG molecules may be retrieved from i.a. Shearwater Inc.

In the present context, the term "a pharmaceutical composition" as used herein means a composition containing an LH compound, e.g. a modified LH, of the present invention, and/or a modified LH of the present invention and an FSH, and optionally one or more pharmaceutically acceptable carriers or excipients, and may be prepared by conventional techniques, e.g. as described in Remington: The Science and Practice of Pharmacy 1995, edited by E. W. Martin, Mack Publishing Company, 19th edition, Easton, Pa. The compositions may appear in conventional forms, for example capsules, tablets, aerosols, solutions, suspensions or topical applications. Typically, the pharmaceutical compositions of the present invention may be formulated for parenteral administration e.g., by i.v. or subcutaneous injection, and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water. Oils useful in parenteral formulations include petroleum, animal, vegetable, or synthetic oils. Specific examples of oils useful in such formulations include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. The parenteral formulations typically will contain from about 0.0001 to about 25%, such as from about 0.5 to about 25%, by weight of the active ingredient in solution. Preservatives and buffers may be used. In order to minimise or eliminate irritation at the site of injection, such compositions may contain one or more nonionic surfactants having a hydrophile-lipophile balance (HLB) of from about 12 to about 17. The quantity of surfactant in such formulations will typically range from about 0.000001 to about 15% by weight, such as from about 0.000001 to about 5% by weight or from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use.

In the present context, the term "assisted reproduction technologies" as used herein means methods that intent to enhance the possibility of conceiving either naturally or by retrieving an oocyte and spermatozoa and perform in vitro fertilization, this may either be through in vitro fertilization (IVF) or by intra cytoplasmatic sperm injection (ICSI), intra uterine insemination (IUD, in vitro maturation (IVM), or other forms derived thereof.

The term "recurrent pregnancy loss" or "habitual abortion" as used herein (used interchangeably) happens in about 1% of fertile women, who unsuccessfully tried to conceive in three or more pregnancies and the pregnancy terminated before 12 weeks of gestation. Because embryo attachment and early implantation in the uterus are exquisitely controlled by the local hormonal milieu, endocrine disorders are frequently linked to failures in early gestation although a multitude of factors may result in a similar clinical picture. The uterus undergoes essential developmental changes during the pre-implantation period, stimulated by estrogen and progesterone. Secreted by the CL, progesterone is important for the successful implantation and continuation of pregnancy. Therefore, conditions related to inadequate progesterone secretion by the CL are likely to negatively affect the outcome of the pregnancy.

The term "bolus" as used herein is the administration of a compound that is given to raise its concentration in blood, serum or plasma to an effective level. The administration can be given by any route of administration including oral, inhalation, intravenous administration, by intramuscular, intrathecal or subcutaneous injection.

The term "gonadotropin" as used herein is a naturally occurring hormone that belongs to a group of heterodimeric glycoproteins including follicle stimulating hormone (FSH), luteinising hormone (LH) and chorionic gonadotropin (CG), such as human chorionic gonadotropin. These hormones regulate gonadal function in the male and female. Each of these naturally occurring hormones is composed of two non-covalently linked subunits: an α-subunit, which is common to FSH, LH and hCG, and a β-subunit, which is unique to each of them, and which confers biological specificity to each hormone. In all of the naturally occurring gonadotropins, each subunit has asparagine-linked (N-linked) oligosaccharide side chains. In the common α-subunit of the human hormones, these are attached at positions 52 and 78 (SEQ ID NO: 1). In both human FSH and hCG, two N-linked oligosaccharide side chains are attached to the beta-subunit, at positions 7 and 24 in FSH (SEQ ID NO: 10).

The alpha chain of preferred gonadotropins of the present invention is selected from the group consisting of sequences having at least 80% sequence identity to SEQ ID NO 1, 2, or 3, more preferably 85%, more preferably 90%, more preferably 95%. Preferably, a variant comprises the conserved cysteine residues at the position and spacing of SEQ ID NO 1. In a particularly preferred embodiment, the gonadotropins comprise the human alpha-subunit having SEQ ID NO 1.

As with all glycoproteins, variations in oligosaccharide structure occur in the gonadotropins, resulting in an array of isoforms that are found within the pituitary gland and in circulation. Furthermore, there are differences in degree of terminal carbohydrate "capping" by sialic acid. The isoforms may be separated on the basis of their charge, which is largely determined by the number and distribution of sialylated N-linked oligosaccharides. Highly sialylated forms will have a more acidic pH and are termed "acidic". Less sialylated forms have comparatively higher pH's and are termed "basic".

As a consequence of their structural differences, gonadotropin isoforms differ in their capability to bind to target-cell receptors. The degree of sialylation affects their ability to survive in circulation. For example, in the case of FSH, highly acidic/sialylated isoforms have considerably longer plasma half-lives in animal models.

Days—the protocols of the present invention start at a certain point in the menstrual cycle. Day 1 of a menstrual cycle is the first day of menstruation. When reference is made to days of a stimulation protocol, day 1 is the day the first dosage of FSH is administered. Day 2 of a stimulation protocol is the day after etc. In the luteal phase, days are calculated either from the day of ovulation or from the day of oocyte pick up.

Follicle size—Ovarian function may be measured by gynecologic ultrasonography of follicular volume. Measurement of ovarian follicle diameter is routinely made using ultrasonography. Today, ovarian follicle volume can also be measured rapidly and automatically from three-dimensionally reconstructed ultrasound images (Salama S, Arbo E, Lamazou F, Levailllant J M, Frydman R, Fanchin R (April 2010).

Reproducibility and reliability of automated volumetric measurement of single preovulatory follicles using SonoAVC". *Fertil. Steril.* 93 (6): 2069-73).

Urine-derived or urinary. The terms are used interchangably. The term refers to the origin of gonadotropins purified from urine.

In the present context, the term "infertility treatment" as used herein means methods that help the woman of an infertile couple or a single woman to conceive.

In the present context, the term "promoting fertility" as used herein means methods that will enhance the fertility of a couple, a woman or a man.

In the present context, the term "mammalian subject", "mammal" or "mammalian" (these terms are used interchangeable throughout the specification) as used herein means any mammal, such as a human, a cow, a pig, a horse, a sheep, a dog, a cat and a goat.

The terms "a" and "an" and "the" and similar referents as used in the context of describing the invention are to be construed to cover both the singular and the plural, unless otherwise indicated herein or clearly contradicted by context.

An "effective amount" of an LH compound as used herein means an amount of the LH compound to be administered sufficient to promote fertility in a mammal or to treat infertility in a mammal in need thereof. An amount adequate to accomplish this is defined as "an effective amount". Effective amounts for each purpose will depend on the severity of the condition as well as the weight and general state of the subject. It will be understood that determining an appropriate dosage may be achieved using routine experimentation, by constructing a matrix of values and testing different points in the matrix, which is all within the ordinary skills of a trained physician or veterinarian. Typical dosages of hCG administration will be from 50-500 IU daily or dosages of an LH compound that will provide a similar biological effect.

An "effective amount" of a modified LH as used herein means an amount of the modified LH to be administered sufficient to assist in inducing follicular development, such as paucifolliculogenesis or unifolliculogenesis, in anovulatory treatment of a mammalian female subject or inducing COS in the follicular phase of the menstrual cycle of a mammalian female subject in need thereof. As the modified LH is intended to be used in combination with FSH as described herein, the modified LH will "assist" in this treatment together with FSH. An amount adequate to accomplish this is defined as "an effective amount". Effective amounts for each purpose will depend on the severity of the condition as well as the weight and general state of the subject. It will be understood that determining an appropriate dosage may be achieved using routine experimentation, by constructing a matrix of values and testing different points in the matrix, which is all within the ordinary skills of a trained physician or veterinarian. Typical dosages of hFSH administration will be from 50-500 IU daily or dosages of a molecule having FSH activity that will provide a similar biological effect.

The term "acylation group" as used herein means an R—(C=O)-group, wherein R is selected from straight-chain or branched, saturated or unsaturated carbon chains, optionally comprising one or more O, N, S, or P, such as a straight-chain or branched alkane carboxylic acid. Various examples of suitable acylation groups are described in WO2006/037810, WO00/34331, WO2006/097537, WO2011/080103. In particular examples of suitable acylation groups have the structure $CH_3(CH_2)_nCO$—, wherein n is 4 to 40, e.g. 8 to 22, such as an acylation group selected from the group comprising $CH_3(CH_2)_8CO$—, $CH_3(CH_2)_9CO$—, $CH_3(CH_2)_{10}CO$—, $CH_3(CH_2)_{11}CO$—, $CH_3(CH_2)_{12}CO$—, $CH_3(CH_2)_{13}CO$—, $CH_3(CH_2)_{14}CO$—, $CH_3(CH_2)_{15}CO$—, $CH_3(CH_2)_{16}CO$—, $CH_3(CH_2)_{17}CO$—, $CH_3(CH_2)_{18}CO$—, $CH_3(CH_2)_{19}CO$—, $CH_3(CH_2)_{20}CO$—, $CH_3(CH_2)_{21}CO$— and $CH_3(CH_2)_{22}CO$—. Further examples of suitable acylation groups has the structure $HOOC-(CH_2)_nCO$—, wherein n is 4 to 40, e.g. 12 to 20, typically, $HOOC-(CH_2)_{14}CO$—, $HOOC-(CH_2)_{15}CO$—, $HOOC-(CH_2)_{16}CO$—, $HOOC-(CH_2)_{17}CO$— and $HOOC-(CH_2)_{18}CO$—. See also U.S. Pat. No. 5,905,140 for further examples of acylation groups.

The term "treatment" and "treating" as used herein in relation to a modified LH means the management and care of a patient for the purpose of inducing follicular development in anovulatory treatment of a mammalian female subject or induce COS in the follicular phase of the menstrual cycle of a mammalian female subject.

The term "treatment" and "treating" as used herein in relation to an LH compound means the management and care of a patient for the purpose of treating infertility or promoting fertility. The patient to be treated is preferably a mammal; in particular a human being, but it may also include animals, such as dogs, cats, horses, cows, sheep and pigs.

DESCRIPTION OF THE INVENTION

Long Acting Biologically Active Luteinizing Hormone Compound

The present invention relates to a long acting biologically active LH compound comprising an LH agonist linked to a pharmaceutically acceptable molecule, wherein the administration of the LH compound can be done once or twice in connection with ART procedures, especially in the follicular phase. This is a considerable advantage over the current ART procedures, and leads to improved infertility treatments.

Moreover, the present invention relates to a long acting biologically active LH compound comprising an LH agonist linked to a pharmaceutically acceptable molecule, wherein the administration of the LH compound can be done at regular intervals in connection with ART procedures to sustain luteal and gestational phase support. This is a considerable advantage over the current ART procedures, and leads to improved infertility treatments.

In a broad aspect the present invention relates to a long acting biologically active LH compound comprising an LH agonist linked to a pharmaceutically acceptable molecule providing an in vivo plasma half-life of the LH agonist or LH compound which is increased substantially compared to the in vivo plasma half-life of an LH agonist administered in the same manner as the LH compound.

In another broad aspect the present invention relates to a long acting biologically active LH compound comprising an LH agonist linked to a pharmaceutically acceptable molecule providing an in vivo plasma half-life of the LH agonist or LH compound which is increased substantially compared to in vivo plasma half-life of endogenous CG.

In a still further aspect the present invention relates to a long acting biologically active luteinizing hormone (LH) compound comprising a mammal CG or analog thereof or a mammal LH or analog thereof linked to a pharmaceutically acceptable molecule selected from a molecule having binding to a mammal neonatal Fc receptor, transferrin and a $CH_3(CH_2)_nCO$—, wherein n is 8 to 22 and a polymer.

In one embodiment the pharmaceutically acceptable molecule is selected from a molecule having binding to a mammal neonatal Fc receptor.

In a further embodiment the pharmaceutically acceptable molecule is selected from an albumin, such as human albumin, recombinant human albumin, a modified human albumin with increased binding to a mammal FcRn, a modified recombinant albumin with increased binding to a mammal FcRn. Typically, the pharmaceutically acceptable molecule is selected from recombinant human albumin (SEQ ID NO 20). Typically, the pharmaceutically acceptable molecule is selected from recombinant K573P human albumin (SEQ ID NO 21).

In a still further embodiment the pharmaceutically acceptable molecule is selected from an Fc fragment of a mammalian antibody, such as a recombinant Fc fragment of a mammalian antibody. Typically, the pharmaceutically acceptable molecule is selected from SEQ ID NO 22.

In a further embodiment the pharmaceutically acceptable molecule is selected from a variant of an Fc fragment of a mammalian antibody, such as a recombinant variant of an Fc fragment of a mammalian antibody. Typically, the pharmaceutically acceptable molecule is selected from a sequence having at least 80% identity, such as at least 90% identity, such as at least 95% identity to SEQ ID NO 22, disclaiming SEQ ID NO. 22.

In a further embodiment the LH agonist may be selected from a small organic molecule, a peptide, a polypeptide, a protein, and may be produced by synthetic methods, recombinant means or be obtained from tissue or blood. In a particular embodiment the LH agonist is of non-mammalian origin. In another particular embodiment the LH agonist is of mammalian origin, such as a protein obtained by recombinant means.

In a still further embodiment the mammal CG or analog thereof or a mammal LH or analog thereof is selected from recombinant mammal CG or analog thereof or a recombinant mammal LH or analog thereof.

In a further embodiment the LH agonist is selected from a mammal CG or a mammal LH. When the LH agonist is a mammal CG it is typically a primate CG, e.g. a human CG or abe CG or monkey CG, but may also be selected from other mammalian species such as equine CG, e.g. horse CG. When the LH agonist is a mammal LH it is typically a primate LH, such as human LH, abe LH or monkey LH; the sequence of cow LH; the sequence pig LH; the sequence of equine LH, such as horse LH; the sequence of sheep LH; the sequence of dog LH; the sequence of cat LH; and the sequence of goat LH. Typically, the LH agonist is a human CG.

In a further embodiment the LH agonist is selected from an analog of a mammal CG or an analog of a mammal LH. When the LH agonist is an analog of a mammal CG the analog has at least 80% identity to the corresponding mammalian sequence of chorionic gonadotropin, such as 85% identity, 90% identity, 95% identity, 98% identity. Typically, the LH agonist is an analog of a human CG having at least 80% identity to the corresponding human sequence of chorionic gonadotropin, such as 85% identity, 90% identity, 95% identity, 98% identity. When the LH agonist is an analog of a mammal LH the analog has at least 80% identity to the corresponding mammalian sequence of luteinizing hormone, such as 85% identity, 90% identity, 95% identity, 98% identity. Typically, the LH agonist is an analog of a human LH having at least 80% identity to the corresponding human sequence of luteinizing hormone, such as 85% identity, 90% identity, 95% identity, 98% identity.

When the LH agonist is selected from a polypeptide or protein, such as an analog of a mammal CG or an analog of a mammal LH, it may be glycosylated. Typically, the LH agonist is an hCG which is glycosylated.

It may also be that the LH compound as such is glycosylated, and the glycosylation may be on the LH agonist or on the pharmaceutically acceptable molecule, when said molecule is selected from a polypeptide or protein, such as human albumin.

The LH agonist may be linked to the pharmaceutically acceptable molecule in various ways, such as directly through a valence bond, or indirectly through a linker, which linker typically is a bifunctional linker, although it may also be a multifunctional linker. In further embodiments, the linker is selected from a chemical linker, a sugar moiety, a disulphide bridge, a fused linker, a hydrophilic linker, a hydrolysable linker. In a further embodiment the LH agonist is fused to the pharmaceutically acceptable molecule through a peptide linker. In a still further embodiment the LH agonist is fused directly to the pharmaceutically acceptable molecule, so as to create one polypeptide or protein, by expressing the LH compound from a host cell, such as a CHO cell or yeast cell. In a further embodiment the LH agonist is linked to the pharmaceutically acceptable molecule through a stable linker. In another embodiment the LH agonist is linked to the pharmaceutically acceptable molecule through a labile linker.

Accordingly, the LH agonist may be linked to the pharmaceutically acceptable molecule in various ways using techniques that are well-known in the prior art, and the present invention also comprises the situation where one or more LH agonist(s) is linked to one or more pharmaceutically acceptable molecule(s), such as two LH agonist linked to one pharmaceutically acceptable molecule, or one LH agonist linked to two pharmaceutically acceptable molecules. In a further embodiment the LH agonist is linked to one or two pharmaceutically acceptable molecule(s), preferably one pharmaceutically acceptable molecule.

In a further embodiment the mammal CG or analog thereof or a mammal LH or analog thereof is linked to the pharmaceutically acceptable molecule and wherein the linker is selected from a chemical linker, optionally a bifunctional linker. Typically, the chemical linker is selected from a sugar moiety, a disulphide bridge, a hydrophilic linker, a hydrolysable linker, dicarboxylic acids, carboxylic acid hydrazides, maleimido hydrazides, PDPH, SPDP, LC-SPDP, GMBS, alkyl linkers, and PEG linkers. In a still further embodiment the chemical linker is selected from succinic acid, glutaric acid, adipic acid, N-[maleimidocaproic acid]hydrazide (EMCH), N-[maleimidopropionic acid]hydrazide (MPH or BMPH), 4-[N-maleimidomethyl]cyclohexan-1-carboxylhydrazide, N-[k-maleimidoundcanoic acid]hydrazide (KMUH), 4-(4-N-MaleimidoPhenyl)butyric acid Hydrazide (MPBH), NHS-3-maleimidopropionate Succinimide ester (MPS-EDA), (3-[2-pyridyldithio]propionyl hydrazide) conjugated to sulfurhydryl reactive protein, N-Succinimidyl 3-(2-pyridyldithio)-propionate (SPDP), Succinimidyl 6-(3-[2-pyridyldithio]-propionamido)hexanoate (LC-SPDP), N-(y-Maleimidobutyryloxy)succinimide ester (GMBS), carboxylic acid hydrazides having from 2-5 carbon atoms, —NH—(CH2)$_m$-C(O)—, wherein m is an integer from 2-20, optionally substituted with any non-sterically hindering group, such as $C_1$-$C_6$ alkyl, $C_1$-$C_6$ acyl, halogen (e.g., Cl, Br), CN, $NH_2$, or phenyl.

In a further embodiment the mammal CG or analog thereof or a mammal LH or analog thereof is directly chemically linked to the pharmaceutically acceptable molecule.

In a further embodiment the pharmaceutically acceptable molecule is linked to the alfa chain of the mammal CG or analog thereof or the mammal LH or analog thereof.

In a further embodiment the pharmaceutically acceptable molecule is linked to the beta chain of the mammal CG or analog thereof or the mammal LH or analog thereof.

In a still further embodiment the mammal CG or analog thereof or a mammal LH or analog thereof is fused to the pharmaceutically acceptable molecule selected from a molecule having binding to a mammal neonatal Fc receptor, such as an albumin, an Fc fragment of a mammalian antibody, or a variant of an Fc fragment of a mammalian antibody, optionally through a peptide linker.

In a further embodiment the peptide linker has at least 1 amino acid, such as from 1-200 amino acids, typically 1-50 amino acids wherein the amino acids are selected from the twenty naturally occurring amino acids. Typically, the peptide linker has from 1-40 amino acids, such as from 1-30, such as from 1-20, such as from 1-10 amino acids.

In a further embodiment the peptide linker is selected from a linker made up of amino acids selected from glycine, alanine, proline, asparagine, glutamine, and lysine. Typically, the peptide linker is made up of a majority of amino acids that are sterically unhindered, such as glycine and alanine. In particular, the peptide linker comprises a sequence selected from -(G)n- (SEQ ID NO: 67), (GGS)n (SEQ ID NO: 68) or (GGGGS)n (SEQ ID NO: 69) wherein n is an integer of from 1-50. Typically n is an integer selected from 1-10, such as 1, 2, 3, 4, 5, 6, 7, 8, 9, or 10.

In a further embodiment the peptide linker is selected from GGG, SGGSGGS (SEQ ID NO: 58), GGSGGSGGSGGSGGG (SEQ ID NO: 59), GGSGGSGGSGGSGGSGGS (SEQ ID NO:60), GGGGSGGGGSGGGGS (SEQ ID NO:57) and EFAGAAAV (SEQ ID NO:56).

In another embodiment the mammal CG or analog thereof or a mammal LH or analog thereof is directly fused to the pharmaceutically acceptable molecule.

In a further embodiment the pharmaceutically acceptable molecule is fused to an N-terminal of the mammal CG or analog thereof.

In a still further embodiment the pharmaceutically acceptable molecule is fused to an N-terminal of the mammal LH or analog thereof.

In a further embodiment the pharmaceutically acceptable molecule is fused to the N-terminal of the alfa chain of the mammal CG or analog thereof.

In a still further embodiment the pharmaceutically acceptable molecule is fused to the N-terminal of the alfa chain of the mammal LH or analog thereof.

In a further embodiment the pharmaceutically acceptable molecule is fused to the N-terminal of the beta chain of the mammal CG or analog thereof.

In a still further embodiment the pharmaceutically acceptable molecule is fused to the N-terminal of the beta chain of the mammal LH or analog thereof.

In a further embodiment the pharmaceutically acceptable molecule is fused to a C-terminal of the mammal CG or analog thereof.

In a still further embodiment the pharmaceutically acceptable molecule is fused to a C-terminal of mammal LH or analog thereof.

In a further embodiment the pharmaceutically acceptable molecule is fused to the C-terminal of the alfa chain of the mammal CG or analog thereof.

In a still further embodiment the pharmaceutically acceptable molecule is fused to the C-terminal of the alfa chain of the mammal LH or analog thereof.

In a further embodiment the pharmaceutically acceptable molecule is fused to the C-terminal of the beta chain of the mammal CG or analog thereof.

In a still further embodiment the pharmaceutically acceptable molecule is fused to the C-terminal of the beta chain of the mammal LH or analog thereof.

In a further embodiment the mammal CG or analog thereof or a mammal LH or analog thereof is selected from one mammal CG or analog thereof. Typically, one hCG.

In a still further embodiment the mammal CG or analog thereof or a mammal LH or analog thereof is selected from one mammal LH or analog thereof. Typically, one hLH.

In a further embodiment the mammal CG or analog thereof or a mammal LH or analog thereof is selected from two mammal CG or analog thereof. Typically, two hCG.

In a still further embodiment the mammal CG or analog thereof or a mammal LH or analog thereof is selected from two mammal LH or analog thereof. Typically, two hLH.

In a further embodiment the pharmaceutically acceptable molecule is selected from one pharmaceutically acceptable molecule. Typically, one albumin or one Fc fragment or one variant of an Fc fragment.

In a still further embodiment the pharmaceutically acceptable molecule is selected from two pharmaceutically acceptable molecules. Typically, two albumins or two Fc fragments or two variants of an Fc fragment, or combinations thereof.

Preferred LH compounds of the present invention are selected from Conjugate) (hCG-PDPH-rHA conjugate), Conjugate3 (hCG-SPDP-rHA conjugate), Conjugate4 (EDC activated hCG-PDPH-rHA conjugate), Conjugate3V1 (hCG-SPDP-rHA-K573P conjugate), and Conjugate4V1 (EDC activated hCG-PDPH-rHA-K573P conjugate).

Other preferred LH compounds of the present invention are selected from Product2 consisting of SEQ ID NO 9 and SEQ ID NO 26, Product3 consisting of SEQ ID NO 1 and SEQ ID NO 28, Product4 consisting of SEQ ID NO 9 and SEQ ID NO 27, Product5 consisting of SEQ ID NO 1 and SEQ ID NO 29, Product7 consisting of SEQ ID NO 4 and SEQ ID NO 26, Product8 consisting of SEQ ID NO 1 and SEQ ID NO 30, Product9 consisting of SEQ ID NO 4 and SEQ ID NO 27, Product10 consisting of SEQ ID NO 1 and SEQ ID NO 31, Product11 consisting of SEQ ID NO 32 and SEQ ID NO 33, Product12 consisting of SEQ ID NO 32 and SEQ ID NO 34, Product13 consisting of SEQ ID NO 32 and SEQ ID NO 61, and Product14 consisting of SEQ ID NO 32 and SEQ ID NO 62.

In order to produce the LH compound which can be administered once or twice in connection with ART procedures, such LH compound when administered to a mammal should result in the LH agonist or LH compound having in vivo plasma half-life augmented at least 1.5 times, at least 2 times, at least 3 times, at least 4 times, such as from 1.5 times to 25 times.

In a further embodiment the LH agonist has an in vivo plasma half-life of at least 2 days, 3 days, 4 days, 5 days, 6 days, 7 days, 8 days, 9 days, 10 days, 11 days, 12 days, 13 days, 14 days, 15 days, 16 days, 17 days, 18, days, 19 days, such as from 2 to 20 days. In a further embodiment the LH compound has an in vivo plasma half-life of at least 2 days, 3 days, 4 days, 5 days, 6 days, 7 days, 8 days, 9 days, 10 days, 11 days, 12 days, 13 days, 14 days, 15 days, 16 days, 17 days, 18, days, 19 days, such as from 2 to 20 days.

In a further embodiment the pharmaceutical acceptable molecule provides a biological body composition or concentration of the LH agonist or LH compound sufficient to drive an antral follicle from about 10 mm in diameter up to preovulatory stage at (i.e. about 15-30 mm in diameter) which a maturing oocyte can finalize the maturation to be ready for resumption of the meiosis.

In a still further embodiment the pharmaceutical acceptable molecule provides a biological body composition or concentration of the LH agonist or LH compound sufficient to drive androgen production in the early adolescent, about 1 year after birth of a male offspring or in puberty for both female and male subjects.

In a further embodiment the pharmaceutical acceptable molecule provides a biological body composition or concentration of the LH agonist or LH compound sufficient to support hypogonadothrophe hypogonade subjects.

In a still further embodiment the pharmaceutical acceptable molecule provides a biological body composition or concentration of the LH agonist or LH compound sufficient to sustain progesterone in the peri-, in the ovulatoric- and the post ovulatoric-phase of a mammalian subject with the object regulating the endometrium and womb for avoiding or allowing implantation of a mammalian blastocyst.

In a further embodiment the pharmaceutical acceptable molecule provides a biological body composition or concentration of the LH agonist or LH compound sufficient to sustain a progesterone in the pen, in the ovulatoric and the post ovulatoric phase of a mammalian subject with the object of preparing the endometrium and womb for implantation.

In a still further embodiment the pharmaceutically acceptable molecule provides a plasma concentration of the LH agonist or LH compound to support the formation and maintenance of CL, when an injection is given during the follicular phase of the menstrual cycle in connection with FSH treatment, preferably 5-10 days after initiation of FSH treatment.

In a further embodiment the pharmaceutically acceptable molecule provides a concentration of the LH agonist or LH compound to stimulate sufficient progesterone release from CL after an injection during the follicular phase of the menstrual cycle in connection with FSH treatment, preferably 5-10 days after initiation of FSH treatment.

In a still further embodiment the pharmaceutically acceptable molecule has binding to a neonatal Fc receptor (FcRn), such as a pH dependent binding allowing the LH compound to escape lysosomal degradation as described in Roopenian et. al., "FcRn: the neonatal Fc receptor comes of age", Nature reviews, Immunology, vol. 7, p. 715.725, September 2007.

A typical pharmaceutically acceptable molecule which has binding to the FcRn is selected from an albumin, such as modified albumin with increased binding to FcRn, human albumin, or recombinant human albumin.

In a further embodiment the pharmaceutically acceptable molecule is selected from any one of small organic molecules, peptides, oligopeptides, polypeptides, proteins, receptors, glycosylations, acylation groups, sugars, polymers (e.g. polyethylene glycols, PEG), nucleic acids (e.g. DNA and RNA), and hormones. Typically, the pharmaceutically acceptable molecule is without limitation selected from an Fc fragment of mammalian antibody, transferrin, albumin, such as human albumin, recombinant albumin, variants of albumin; an acylation group, such as $CH_3(CH_2)_nCO$—, wherein n is 8 to 22; or polymer, such as PEG, e.g. PEG of a molecular weight of at least 5 kDa, such as from 10 kDa to 150 kDa, typically 10 to 40 kDa.

In a further embodiment the pharmaceutically acceptable molecule is selected from a polymer, such as PEG. Typically, the PEG moiety may have an average size selected from the range of 500 Da to 200,000 Da, such as from 500 Da to 100,000 Da, such as from 2000 Da to 50,000 Da.

A further aspect of the present invention relates to a pharmaceutical composition comprising the LH compound of the present invention, and optionally a pharmaceutically acceptable carrier or excipient. Typically, the pharmaceutical composition is for injection, such as subcutaneous injection.

In connection with ART procedures more than one medicament in the infertility treatment or in promoting fertility may be administered, either concomitantly or sequentially. It is therefore within the scope of the present invention to use an LH compound of the present invention in ART procedures, such as IVF or ICSI, for infertility treatment or in promoting fertility in combination with one or more other therapeutically active compound(s) normally used in the infertility treatment or in promoting fertility. By analogy, it is also within the scope of the present invention to use an LH compound of the present invention in combination with other therapeutically active compounds normally used in the infertility treatment or in promoting fertility in the manufacture of a medicament for said infertility treatment or in promoting fertility.

A further aspect of the present invention relates to the LH compound of the present invention for use in infertility treatment or promoting fertility of a mammalian subject, such as assisted reproduction technologies treatment, e.g. IVF or ICSI treatment, or maldecensus of the testes.

A further aspect of the present invention relates to the LH compound of the present invention for use in a method for assisted reproductive therapy in a female mammal wherein the LH compound is administered in a dosage one time, two times, three times or four times during the follicular phase, the dosage being sufficient to support the follicle development. The LH compound may be administered as single bolus injection(s). In one embodiment the dosage is also sufficient to provide luteal support.

A still further aspect of the present invention relates to the LH compound of the present invention for use in a method for assisted reproductive therapy in a female mammal wherein the LH compound is administered in a dosage one time, two times, three times or four times during the luteal phase at least until 2 weeks after ovulation. The LH compound may be administered as single bolus injection(s). In one embodiment the LH compound is administered for the first time after ovulation.

A further aspect of the present invention relates to the LH compound of the present invention for use in a method for assisted reproductive therapy in a female mammal wherein the LH compound is administered in a dosage one time, two times, three times or four times, during the gestational phase at least until 2 weeks after ovulation. The LH compound may be administered as single bolus injection(s). In one embodiment the LH compound is administered for the first time after ovulation.

A still further aspect of the present invention relates to the LH compound of the present invention for use in a method for treatment of recurrent pregnancy loss in a female mammal wherein the LH compound is administered in a dosage one time, two times, three times or four or more times, during the early gestational period until 12 weeks after conception. The LH compound may be administered as single bolus injection(s). In one embodiment the LH compound is administered for the first time after ovulation.

A further aspect of the present invention relates to the LH compound of the present invention for use in a method for enhancing progesterone production and optimizing chances for a successful pregnancy wherein the LH compound is administered in a dosage one time, two times, three times or four or more times, during the first 12 weeks of gestation. The LH compound may be administered as single bolus injection(s). In one embodiment the LH compound is administered for the first time after ovulation.

A further aspect of the present invention relates to the LH compound of the present invention for use in a method for assisted reproductive therapy in a female mammal wherein the LH compound is administered in a dosage once or twice, in connection with ovulation induction. The LH compound may be administered as single bolus injection(s).

In connection with ovulation triggering various treatment regimens may be used. In one embodiment a GnRH agonist is used for ovulation triggering. In another embodiment an hCG is used for ovulation triggering.

A further aspect of the present invention relates to the LH compound of the present invention for use in promoting fertility or treatment of infertility of a hypogonadotropic hypogonadal male mammalian subject.

A still further aspect of the present invention relates to the LH compound of the present invention for use in promoting fertility or treatment of infertility of a young or adolescent male mammalian subject having cryptorchidism.

A still further aspect of the present invention relates to a method of infertility treatment of a mammalian subject comprising administering to a mammal in need thereof an effective amount of the LH compound of the present invention.

A further aspect of the present invention relates to a method of promoting fertility of a mammalian subject comprising administering to a mammal in need thereof an effective amount of the LH compound of the present invention.

In a further embodiment the mammalian subject is selected from a human, a cow, a pig, a horse, a sheep, a dog, a cat and a goat, typically a human subject.

In a further aspect the present invention relates to a method of preparing a long acting biologically active luteinizing hormone (LH) compound, such as any one of the herein disclosed conjugates of the present invention, comprising an LH agonist linked to a pharmaceutically acceptable molecule, the method comprising reacting an LH agonist with a linker attached to a pharmaceutically acceptable molecule, or reacting an LH agonist with a linker and then attaching said linker to a pharmaceutically acceptable molecule, or reacting a linker with a pharmaceutically acceptable molecule and then reacting an LH agonist with the linker attached to the pharmaceutically acceptable molecule, or by expressing the LH agonist and pharmaceutically acceptable molecule from a host cell.

Long-Acting Modified Mammalian LH

The present invention relates to a long-acting modified mammalian LH, e.g. human LH linked to e.g. fused to albumin, or conjugated to an acylation group or PEG, that agonize and activate the LH receptor in a mammal and provides an in vivo plasma half-life of the mammalian LH or analog thereof, or the modified LH which is from 2 to 48 hours in a mammal. The modified LH either given in the follicular phase or as a luteal phase support is believed to improve patient convenience and treatment outcome.

Furthermore, the use of a long acting modified mammalian LH will not interfere with the specific effects that the hyperglycosylated hCG secreted from the implanting embryo will exert and it will be possible for the patient at her earliest possible convenience to detect if she is pregnant by use of an ordinary pregnancy-test.

Collectively, these findings suggest that a long acting modified mammalian LH preparation, in which the specific effects of LH at the receptor level are maintained in combination with a constant presence in circulation will be able to optimise COS in the follicular phase of the menstrual cycle and thus final treatment outcome.

In a broad aspect the present invention relates to a modified LH comprising a mammalian LH or analog thereof linked to a pharmaceutically acceptable molecule providing an in vivo plasma half-life of the mammalian LH or analog thereof, or the modified LH which is from 2 to 48 hours in a mammal.

A further aspect of the present invention relates to a long acting biologically active luteinizing hormone (LH) compound comprising a mammal LH or analog thereof linked to a pharmaceutically acceptable molecule selected from a molecule having binding to a mammal neonatal Fc receptor, transferrin and a $CH_3(CH_2)_nCO—$, wherein n is 8 to 22 and a polymer for use in combination with an FSH or a molecule having FSH activity for simultaneous, sequential or separate use to induce follicular development, such as paucifolliculogenesis or unifolliculogenesis, in anovulatory treatment of a mammalian female subject or induce COS in the follicular phase of the menstrual cycle of a mammalian female subject.

In an embodiment the FSH is derived exogenously in the mammalian female subject. In another embodiment the FSH is produced endogenously in the mammalian female subject.

In a further embodiment the pharmaceutically acceptable molecule is selected from a molecule having binding to a mammal neonatal Fc receptor, such as an albumin, e.g. human albumin, recombinant human albumin, a modified human albumin with increased binding to a mammal FcRn, a modified recombinant albumin with increased binding to a mammal FcRn; an Fc fragment of a mammalian antibody, such as a recombinant Fc fragment of a mammalian antibody; and a variant of an Fc fragment of a mammalian antibody.

In a further embodiment the pharmaceutically acceptable molecule provides an in vivo plasma half-life of the mammal LH or analog thereof, or the modified LH which is from 2 to 48 hours in the mammalian female subject.

In a further embodiment the mammalian LH has an in vivo plasma half-life of at least 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, such as from 4 to 48 hours, 5 to 40 hours, 6 to 36 hours, 7 to 30 hours, 8 to 28 hours, 9 to 26 hours, or 10 to 24 hours, typically from 6 to 8 hours. In a further embodiment the modified LH has an in vivo plasma half-life of at least 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, such as from 4 to 48 hours, 5 to 40 hours, 6 to 36 hours, 7 to 30 hours, 8 to 28 hours, 9 to 26 hours, or 10 to 24 hours, typically from 6 to 8 hours.

Upon administration of the modified LH to a mammal it is important that a sufficient in vivo plasma concentration is reached and maintained for such time it takes to provide an effect in inducing follicular development in anovulatory treatment of a mammalian female subject or inducing COS in the follicular phase of the menstrual cycle of a mammalian female subject. In further embodiments the modified LH of the present invention provides an in vivo plasma concentration of the modified LH, the mammalian LH or a mixture thereof, in a mammal in the range of from 2 to 30 IU/L, such as 2 to 4 IU/L, 4 to 8 IU/L, 8 to 14 IU/L, 14 to 20 IU/L, or 20 to 30 IU/L.

The mammalian LH or analog thereof may be recombinant or synthetic, or a combination thereof and may be produced by synthetic methods, such as standard chemical methods, including synthesis by an automated procedure, or by recombinant means or be obtained from urine, tissue or blood. In a further embodiment the mammalian LH is a recombinant LH. In a still further embodiment the mammalian LH is recombinant human LH (rhLH).

In a further embodiment the mammalian LH may be selected from the sequence of human LH, the sequence of cow LH, the sequence of pig LH, the sequence of horse LH, the sequence of sheep LH, the sequence of dog LH, the sequence of cat LH, and the sequence of goat LH.

In a still further embodiment the mammalian LH analog is a recombinant LH. The mammalian LH analog which may be produced by recombinant means, is typically selected from an analog of the mammalian LH, wherein the analog has at least 80% identity to the corresponding mammalian sequence of LH, such as 85% identity, 90% identity, 95% identity, 98% identity. For instance, the mammalian LH analog is selected from an analog of the human LH, wherein the analog has at least 80% identity to the human sequence of LH, such as 85% identity, 90% identity, 95% identity, 98% identity. Or the mammalian LH analog is selected from an analog of the horse LH, wherein the analog has at least 80% identity to the horse sequence of LH, such as 85% identity, 90% identity, 95% identity, 98% identity.

The mammalian LH or analog of a mammalian LH, as used in accordance with the present invention may be glycosylated. Typically, the mammalian LH or analog is glycosylated, such as a hLH which is glycosylated.

It may also be that the modified LH as such is glycosylated, and the glycosylation may be on the mammalian LH or on the pharmaceutically acceptable molecule, when said molecule is selected from a polypeptide or protein, such as human albumin. The mammalian LH or analog thereof may be linked to the pharmaceutically acceptable molecule in various ways, such as directly through a valence bond, or indirectly through a linker, which linker typically is a bifunctional linker, although it may also be a multifunctional linker. In further embodiments, the linker is selected from a chemical linker, a sugar moiety, a disulphide bridge, a fused linker, a hydrophilic linker, a hydrolysable linker. In a further embodiment the mammalian LH or analog thereof is fused to the pharmaceutically acceptable molecule through a peptide linker. In a still further embodiment the mammalian LH or analog thereof is fused directly to the pharmaceutically acceptable molecule, so as to create one polypeptide or protein, by expressing the modified LH from a host cell, such as a CHO cell or yeast cell. In a further embodiment the mammalian LH or analog thereof is linked to the pharmaceutically acceptable molecule through a stable linker. In another embodiment the mammalian LH or analog thereof is linked to the pharmaceutically acceptable molecule through a labile linker.

Accordingly, the mammalian LH or analog thereof may be linked to the pharmaceutically acceptable molecule in various ways using techniques that are well-known in the prior art, and the present invention also comprises the situation where one or more mammalian LH or analog thereof is linked to one or more pharmaceutically acceptable molecule(s), such as two mammalian LH or analog thereof linked to one pharmaceutically acceptable molecule, or one mammalian LH or analog thereof linked to two pharmaceutically acceptable molecules. In a further embodiment the mammalian LH or analog thereof is linked to one or two pharmaceutically acceptable molecule(s), such as one pharmaceutically acceptable molecule.

In a still further embodiment the pharmaceutically acceptable molecule has binding to a neonatal Fc receptor (FcRn), such as a pH dependent binding allowing the modified LH to escape lysosomal degradation as described in Roopenian et. al., "FcRn: the neonatal Fc receptor comes of age", Nature reviews, Immunology, vol. 7, p. 715.725, sept. 2007.

A typical pharmaceutically acceptable molecule which has binding to the FcRn is selected from an albumin, such as modified albumin with increased or reduced binding to FcRn, human albumin, or recombinant human albumin.

In a further embodiment the pharmaceutically acceptable molecule is selected from any one of small organic molecules, peptides, oligopeptides, polypeptides, proteins, receptors, glycosylations, acylation groups, sugars, polymers (e.g. polyethylene glycols, PEG), nucleic acids (e.g. DNA and RNA), and hormones. Typically, the pharmaceutically acceptable molecule is without limitation selected from a Fc fragment of mammalian antibody, transferrin, albumin, such as human albumin, recombinant albumin, variants of albumin; an acylation group, such as $CH_3(CH_2)_nCO-$, wherein n is 8 to 22; or polymer, such as PEG, e.g. PEG of a molecular weight of at least 5 kDa, such as from 10 kDa to 150 kDa, typically 10 to 40 kDa.

A further aspect of the present invention relates to a pharmaceutical composition comprising the modified LH of the present invention, and optionally a pharmaceutically acceptable carrier or excipient.

In connection with ART procedures, and in particular with inducing follicular development or COS as explained herein, more than one medicament may be administered, either concomitantly or sequentially. It is therefore within the scope of the present invention to use a modified LH of the present invention in ART procedures, such as inducing COS, for infertility treatment or in promoting fertility in combination with one or more other therapeutically active compound(s) normally used in the infertility treatment or in promoting fertility.

In a further aspect the present invention relates to a modified LH comprising a mammalian LH or analog thereof linked to a pharmaceutically acceptable molecule providing an in vivo plasma half-life of the mammalian LH or analog thereof, or the modified LH which is from 2 to 48 hours in a mammal for use in combination with an FSH or a molecule having FSH activity for simultaneous, sequential or separate use to induce follicular development in anovulatory treatment of a mammalian female subject or induce COS in the follicular phase of the menstrual cycle of a mammalian female subject. In one embodiment the FSH is selected from mammalian FSH, such as human FSH, in particular recombinant FSH, e.g. rhFSH. In a particular embodiment the FSH is selected from Puregon, Gonal F, Elonva, Fostinorm, Bravelle, Menopur.

In a further embodiment the combination of a modified LH of the present invention and an FSH or a molecule having FSH activity is to induce follicular development, such as paucifolliculogenesis or unifolliculogenesis, in anovulatory treatment of a mammalian female subject. In a still further embodiment the combination of a modified LH of the present invention and an FSH or a molecule having FSH activity is to induce COS in the follicular phase of the menstrual cycle of a mammalian female subject. Typically, in inducing follicular development or COS, the modified LH of the present invention and an FSH or a molecule having FSH activity are administered in a IU ratio range (FSH:modified LH) from 20:1 to 1:20. In further embodiments the FSH:modified LH is administered in the IU ratios range from 18:1 to 1:18, 15:1 to 1:15, 12:1 to 1:12, 9:1 to 1:9, 5:1 to 1:5, such as 4:1 to 1:4.

Although as stated above the FSH and modified LH may be administered simultaneously, sequentially or separately the combination is typically administered together either as a kit of parts comprising the modified LH and FSH in separate dosage forms that may be the same, e.g. two separate injections in a kit, such as subcutaneous injections, or as a pharmaceutical composition comprising the modified LH of the present invention and an FSH or a molecule having FSH activity, and optionally a pharmaceutically acceptable carrier or excipient. It is preferred that the modified LH and FSH be administered subcutaneously, preferably into the anterior abdominal wall. Formulations for parenteral administration will usually be sterile. Pharmaceutical formulations adapted for parenteral administration include aqueous and non-aqueous sterile injection solutions which may contain anti-oxidants, buffers, bacteriostats and solutes which render the formulation isotonic with the blood of the intended mammalian subject; aqueous and non-aqueous sterile suspensions which may include suspending agents and thickening agents are also within the scope of the invention. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets. The formulations can be administered through a prefilled syringe, an auto-injector or a multidose auto-injector. Typically, LH compound and the FSH or the molecule having FSH activity are provided for simultaneous use in a pharmaceutical composition.

A still further aspect of the present invention relates to a method of inducing follicular development, such as paucifolliculogenesis or unifolliculogenesis, in anovulatory treatment of a mammalian female subject or induce COS in the follicular phase of the menstrual cycle of a mammalian female subject comprising administering to a mammal in need thereof an effective amount of the modified LH of the present invention simultaneous, sequential or separate in combination with an FSH or a molecule having FSH activity. In a further embodiment the FSH or the molecule having FSH activity is selected from mammalian FSH, such as human FSH, in particular recombinant FSH, e.g. rhFSH.

In a further embodiment the mammalian subject is selected from a human, a cow, a pig, a horse, a sheep, a dog, a cat and a goat, typically a human subject.

In a further aspect the present invention relates to a method of preparing a modified LH of the present invention, such as any one of the herein disclosed conjugates of the present invention, comprising a mammalian LH or analog thereof linked to a pharmaceutically acceptable molecule providing an in vivo plasma half-life of the mammalian LH or analog thereof, or the modified LH which is from 2 to 48 hours in a mammal, the method comprising reacting a mammalian LH or analog thereof with a linker attached to a pharmaceutically acceptable molecule, or reacting a mammalian LH or analog thereof with a linker and then attaching said linker to a pharmaceutically acceptable molecule, or reacting a linker with a pharmaceutically acceptable molecule and then reacting a mammalian LH or analog thereof with the linker attached to the pharmaceutically acceptable molecule, or by expressing the mammalian LH or analog thereof and pharmaceutically acceptable molecule from a host cell.

Methods of the Invention

FIGS. 1a and 1b describe protocols for controlled ovarian stimulation as known in the prior art. The protocol in FIG. 1a starts with administration of FSH, recombinant or urinary, on day 1-3 of a menstrual cycle. FSH is administered in daily dosages until ovulation induction. From about day 6, a GnRH antagonist is administered to avoid a premature surge in LH prior to ovulation induction. Ovulation is induced by administering a trigger shot of 5,000 to 10,000 IU of recombinant hCG. Ovulation may alternatively be induced by GnRH agonist triggering. This is typically done when one to three follicles have a size of 17 mm. In order to provide luteal support, progesterone is administered vaginally or intramuscularly starting on the day of embryo transfer. The progesterone administration is continued at least until day 28 of the stimulation protocol. In many cases progesterone is administered until week 5 or even until week 10 of the pregnancy.

In FIG. 1b, the daily dosages of FSH on days 1-6 are replaced by one dosage of long-acting FSH (corifollitropin). At around day 5-7 the serum level of corifollitropin is decreasing and daily dosages of recombinant or urinary FSH are given until ovulation triggering. The advantage of using corifollitropin is that the female does not need to visit the clinic and receive injections of FSH on days 2-5 or 6.

FIG. 2a is a schematic illustration of one embodiment of the stimulation protocol according to the present invention based on administration of long-acting gonadotropins. In this case, long-acting FSH, such as corifollitropin alpha, is administered on day 1-3 of a menstrual cycle. In case of corifollitropin the dosage may be 100 and 150 μg per female. The dosage and serum half-life is chosen so that the serum level of FSH decreases in the later stages of follicular phase so that further follicle recruitment is significantly reduced in the late phase of the follicular phase. This serves to reduce the number of follicles stimulated to develop and thereby reduce the risk of OHSS.

As in the known protocols, a GnRH antagonist is administered starting on day 4-7 of the stimulation protocol. Follicle development is stimulated by administering one dosage of a long-acting hCG on day 6 of the stimulation protocol or earlier. A long-acting LH can also be used. The dosage of long-acting hCG or LH is sufficient to stimulate follicle development and sufficiently low to reduce the risk of OHSS. The long acting hCG or LH is administered in a dosage giving a biological response similar to the response obtained with a serum level of 4-15 IU/liter. To further reduce the risk of OHSS, a GnRH agonist trigger shot is used to induce ovulation when at least one follicle has a diameter of at least 15 mm, preferably when 3 follicles have a diameter of 17 mm. Suitable dosages range between 0.1 and 1 mg when administered subcutaneously or intranasaly. Luteal phase support can be provided by administering either progesterone as in the known protocols (illustrated in FIG. 2a) or by administering an LH agonist as herein described and illustrated (FIGS. 4a and 4b).

FIG. 2b illustrates a protocol of the invention, wherein folliculogenesis is stimulated by administering recombinant or urine derived FSH as daily injections from day 1 until approximately day 6. Preferred daily dosages of FSH are 150-225 IU per day. The exact day of discontinuing FSH administration is determined by UV scanning and measurement of follicle diameter. When at least one follicle has reached a diameter of 12-14 mm, FSH administration is discontinued and a single dose of long-acting hCG or LH is administered to stimulate follicle development as described above. Oocyte induction and luteal support as described in FIG. 2a. In the regime of FIG. 2b, GnRH antagonist and agonist are administered as described for FIG. 2a.

FIG. 2c illustrates a protocol of the invention, wherein folliculogenesis and follicle development is stimulated by administering daily dosages of FSH as in FIG. 2b and daily dosages of hCG or LH starting from approximately day 6. Suitable dosages of hCG during the follicular phase include 25-400 IU per day, such as 50-300 IU per day, more preferably 100-300, such as 150-250, for example 175-225 IU per day. In the regime of FIG. 2c, the GnRH antagonist and agonist are administered as described for FIG. 2a. Luteal support is not illustrated here but may be either by progesterone administration or LH/hCG administration as illustrated in FIG. 4a or 4b.

In an alternative protocol based on administration of long-acting (long-lasting) hCG or LH illustrated in FIG. 3a, the FSH, GnRH antagonist and GnRH agonist are administered as described for the protocol in FIG. 2b. Follicle development and luteal support are provided by administering a long-acting hCG or LH at intervals of 2-7 days (illustrated by 5 days) starting e.g. from about day 6 in the follicular phase and continuing at least until pregnancy testing. In case of pregnancy, administration of long-acting LH or hCG can be continued until week 5, for example until week 10 of the pregnancy. A suitable dosage of long-acting hCG or LH during the follicular phase is a dosage giving a biological response similar to the response obtained with a serum level of 4-15 IU/liter.

In alternative protocols, recombinant or urinary hCG or LH is administered in daily dosages during the follicular phase and through the luteal phase (FIGS. 3b and 3c). The figures illustrate hCG administration, but it is likewise conceivable that LH is administered. Administration of hCG may commence on day 6 of the stimulation, but may likewise start earlier, such as on day 2 of the stimulation. Suitable dosages of urinary or recombinant hCG during the follicular phase include 25-400 IU per day, such as 50-300 IU per day, more preferably 100-300, such as 150-250, for example 175-225 IU per day. In the luteal phase it is preferred to use LH or an LH analogue or variant, as administration of recombinant or urinary hCG may result in a false detection of biochemical pregnancy. The majority of lateral flow device pregnancy tests rely on detection of urinary hCG. Suitable dosages of recombinant or urinary hCG in the luteal phase include 25-400 IU hCG per day, preferably 50-200 IU hCG per day, for example 75-200, such as 100-150 or 120-170 IU/day.

The protocol in FIG. 3c illustrates another protocol of the invention, in which hCG (or LH) is administered already from day 2 of the stimulation protocol. Otherwise the protocol is identical to the protocol of FIG. 3b. The follicle stimulation of the protocol in FIGS. 3b and 3c can also be performed with long-acting hCG or long-acting LH, which is administered as a single dosage on day 1, 2, or 3 of the stimulation protocol.

FIGS. 4a and 4b illustrate protocols for luteal support according to the invention. According to the illustrated embodiment (FIG. 4a), luteal support is provided by administering daily dosages of LH (or hCG) from around the time of oocyte harvest and continuing until day 28 of the protocol. A preferred dosage range of recombinant or urinary LH for luteal support includes daily dosages of 100-600 IU LH per day, preferably 150-450 IU LH per day, such as 200-400 IU LH per day, for example 250-350 IU/day. A preferred dosage range of recombinant or urinary hCG includes 25-400 IU hCG per day, preferably 50-200 IU hCG per day, for example 75-200, such as 100-150 or 120-170 IU/day.

Luteal support is continued until at least 2 weeks after ovulation, but may be continued until gestational week 5 or 10.

Similar results can be achieved by administering long-acting LH or long-acting hCG (FIG. 4b), one or more times during the luteal phase in a dosage giving a biological response similar to the response achieved by administering daily dosages of the preferred dosages of LH. The luteal support protocol can be used in conjunction with any type of ART.

The different protocols of the invention can be combined in many ways as long as they do not depart from the inventive concept of the invention as defined in the independent claims.

FSH

Follicle stimulating hormone (FSH) regulates the development, growth, pubertal maturation, and reproductive processes of the human body. In both males and females, FSH stimulates the maturation of germ cells. In males, FSH induces Sertoli cells to secrete inhibin and stimulates the formation of sertoli-sertoli tight junctions (zonula occludens). In females, FSH stimulates the growth and recruitment of immature Ovarian follicles in the ovary. In early (small) antral follicles, FSH is the major survival factor that rescues the follicles from apoptosis (programmed death of the somatic cells of the follicle and oocyte). In the luteal-follicle phase transition period the serum levels of progesterone and estrogen (primarily estradiol) decrease and no longer suppress the release of FSH, consequently FSH peaks at about day three (day one is the first day of menstrual cycle).

FSH is a heterodimeric glycoprotein. Each monomeric unit is a protein molecule with one or more oligosaccharide chains covalently linked to amino acid side chains; two of these monomeric units make the full, functional protein. The protein dimer contains 2 polypeptide units, labeled $\alpha$ and $\beta$ subunits. The $\alpha$ subunits of LH, FSH, TSH, and hCG are identical, and contain 92 amino acids (see FIG. 5). FSH has a $\beta$ subunit of 118 amino acids (FSHB), which confers its specific biologic action and is responsible for interaction with the FSH-receptor. The sugar part of the hormone is composed of fucose, galactose, mannose, galactosamine, glucosamine, and sialic acid, the latter being critical for its biologic half-life. The half-life of FSH is 3-4 hours.

The gene for the $\alpha$ subunit is located on chromosome 6p21.1-23. It is expressed in different cell types. The gene for the FSH $\beta$ subunit is located on chromosome 11p13, and is expressed in gonadotropes of the pituitary cells, controlled by GnRH, inhibited by inhibin, and enhanced by activin.

The beta-chain of preferred FSH of the present invention is selected from the group consisting of sequences having at least 80% sequence identity to SEQ ID NO 10, 11, 12, 13, or 15, more preferably 85%, more preferably 90%, more preferably 95%. Preferably, a variant comprises the conserved cysteine residues at the position and spacing of SEQ ID NO 10. In a particularly preferred embodiment, the FSH comprises the human alpha-subunit having SEQ ID NO 10.

It will be understood by one of skill in the art that FSH may be substituted by a biologically active analogue, or by a compound that stimulates endogenous FSH secretion. In this latter class are included aromatase inhibitors, and anti-oestrogens such as tamoxifen and clomiphene citrate (CC). These compounds stimulate endogenous FSH secretion by removing the negative feedback exerted by oestrogen on the hypothalamus (either by antagonising oestrogen receptors, as is the case with CC and tamoxifen, or by greatly decreasing oestrogen concentrations, as is the case with aromatase inhibitors). Other types of FSH analogues include, for example single chain FSH analogues in which the [beta]-subunit is fused to the CTP of hCG, which in turn is fused to FSH [alpha]-subunit, as described in WO 96/05224 (single chain FSH-CTP).

In a further embodiment the FSH is selected from an analogue of a mammal FSH or an analogue of a mammal FSH. When the FSH is an analogue of a mammal FSH the analogue has at least 80% identity to the corresponding mammalian sequence of FSH, such as 85% identity, 90% identity, 95% identity, 98% identity. The sequence identity applies both to the alpha and beta chains of FSH.

The two most common forms used are urinary human menopausal gonadotropin (containing FSH and LH activity) and recombinant FSH (containing FSH without any LH activity). Owing to the relatively short half-life of all currently used FSH preparations, clinical protocols for induction of multi follicular development in women stimulated for IVF require daily injections. The use of long-acting versions of FSH, exhibiting prolonged half-lives, can be used to replace the daily injections of FSH.

FSH activity is normally given in IU following the pharmacopeia. Now pure preparations of FSH may also be manufactured and the activity given in mass (e.g. µg per vial). In the present invention it is understood that activity given in IU correlates to FSH activity given with other units.

In one embodiment of the invention FSH is a long-acting FSH. By long-acting is intended a protein that has a serum half life which is at least 1.5 times the serum half-life of recombinant or urinary FSH, more preferably at least 2 times, more preferably at least 3 times, more preferably at least 4 times, more preferably at least 5 times, more preferably at least 7 times, more preferably at least 10 times, such as at least 15 times, for example at least 20 times, such as at least 25 times, for example at least 30 times, 40 times or 50 times or more.

Preferably the half-life of long-acting FSH is not longer than 72 hours, such as 48 hours. This makes it easier to control FSH administration in the later phases of folliculogenesis.

Long-acting FSH may for example be FSH-CTP, which is described in WO 93/06844, and has a wild type FSH [alpha]-subunit and a [beta]-subunit that consists of the wild type human FSH [beta]-subunit (SEQ ID NO 10) fused at its carboxyl terminal to the carboxy terminal peptide (CTP) of the [beta]-subunit of hCG (residues 118 to position 145 of the native hCG[beta] sequence, SEQ ID NO 9). The resulting beta-subunit has the sequence of SEQ ID NO 15.

Corifollitropin alfa is a glycoprotein produced in CHO cells by recombinant DNA technology. Corifollitropin alfa is designed as a sustained follicle stimulant with the same pharmacodynamic profile as (rec)FSH, but with a markedly prolonged duration of FSH activity. Due to its ability to initiate and sustain multiple follicular growth for up to a week, a single subcutaneous injection of the recommended dose of Corifollitropin (Elonva®) may replace some or all of the first seven injections of any daily (rec)FSH preparation in a COS treatment cycle. The long duration of FSH activity was achieved by adding the carboxyterminal peptide of the β-subunit of human chorionic gonadotropin (hCG) to the β-chain of human FSH (SEQ ID NO 10). Corifollitropin alfa does not display any intrinsic LH/hCG activity. Corifollitropin alfa has an average elimination half-life of 69 hours (59-79 hours).

Corifollitropin may preferably be administered as one bolus injection of 40-240 µg per female mammal such as for example 60-220 µg per female mammal, such as for example 80-200 µg per female mammal, such as for example 100-180 µg per female mammal or such as for example 100-150 µg per female. Corifollitropin may in another embodiment be administered as one bolus injection of 40-120 µg per female mammal, such as for example 60-100 µg per female mammal, or such as for example 70-90 µg per female mammal. In yet another embodiment corifollitropin is administered as one bolus injection of 120-240 µg per female mammal, such as for example 140-220 µg per female mammal, such as for example 160-200 µg per female mammal or such as for example 170-190 µg per female mammal. Corifollitropin is approved for dosages of 100 µg for females under 60 kg and 150 µg for females above 60 kg.

The administration of corifollitropin as one bolus injection is preferably on day 1-3 of the menstrual cycle, such as for example on day 1, day 2 or day 3 of the menstrual cycle.

Thus, in one preferred embodiment FSH is long-acting FSH, such as Corifollitropin, preferably administered as one bolus injection of 40-240 µg per female mammal on day 1-3 of the menstrual cycle.

In aspects of the invention where FSH (or an analogue) is used in conjunction with COS techniques or regimens, appropriate doses and administration regimes will be apparent to a person skilled in the art and any appropriate dose and administration regime may be used.

For example FSH may be administered in a dosage giving a serum level of 1-50 IU FSH per liter, such as for example 2-40 IU FSH per liter, such as for example 3-35 IU FSH per liter, for example 4-30 IU FSH per liter, such as for example 5-25 IU FSH per liter, for example 7-20 IU FSH per, such as for example 10-15 IU FSH per liter during the follicular phase.

It is preferred that FSH is administered in a dosage giving a serum level of 5-25 IU FSH per liter, preferably 10-15 IU per liter during the follicular phase.

FSH may in one embodiment be administered at daily dosages of 50-600 IU FSH per day, preferably 100-300 IU FSH per day, such as 150-225 IU/day. In some patients showing a decreased response to FSH it may be desirable to use doses of up to 600 IU FSH per day. A typical regimen is as follows: the patient is started on 150 IU FSH per day. If follicular development is adequate the dose of 150 IU FSH/day may be maintained. If follicular development is inadequate the dose may be increased to 225, 300, 375, 450, 525 or 600 IU FSH/day. Ideally, the cumulative dose of FSH should not exceed 6000 IU/cycle.

FSH used in the methods of the invention can be from any source. Such sources will be well known to a person skilled in the field of ovulation induction and COS procedures. A urinary preparation of FSH may be used, e.g. hMG which contains FSH and LH activity at a 1:1 ratio.

Thus, in one embodiment of the present invention FSH is recombinant or urine-derived FSH administered at daily dosages of 50-600 IU FSH per day, preferably 100-300 IU FSH per day, such as 150-225 IU/day.

FSH may be administered starting on cycle day 1-3 of the menstrual cycle, such as for example on cycle day 1, for example on cycle day 2 or for example on cycle day 3 of the menstrual cycle.

Administration of FSH is discontinued when at least one follicle has a diameter of 12-14 mm, such as for example 12-13 mm or for example 13-14 mm. Administration of FSH may for example be discontinued on cycle day 4, 5, 7 or 8 of the menstrual cycle. In typical cases of the invention the administration of FSH is discontinued on cycle day 6 of the menstrual cycle. The purpose of discontinuing FSH administration is to stop further folliculogenesis and allow the largest follicles to mature. It is known in the art that there is a correlation between the number of follicles and the risk of OHSS.

When the administered FSH is recombinant or urine derived FSH, discontinuing FSH administration merely requires that no further FSH is administered. The serum level of FSH will then fall over the next couple of days to a level which will no longer stimulate folliculogenesis. When long-acting FSH is administered, e.g. corifollitropin alpha, discontinuing FSH administration means that the administration should be discontinued so that the level of serum FSH activity no longer stimulate folliculogenesis one or two days after the first follicles have reached the diameters described above. In the case of administration of e.g. corifollitropin alpha, it is preferred to administer just one dosage of corrifollitropin alpha on the first day of the stimulation protocol. If there is a need for further folliculogenesis, recombinant or urine derived FSH can be administered later in the stimulation cycle but before the follicles reach a size of 12-14 mm. In this way the serum level of FSH can be more easily controlled.

Generally speaking, the level of serum FSH activity, measured in IU or µg per liter, should fall to a level which is below 50% of the serum level during the first 1-6 days of the stimulation protocol, more preferably below 25%, such as below 10%.

Luteinising Hormone (LH)

LH is a hormone produced by the anterior pituitary gland and is essential for reproduction both in males and females. In females, at the time of menstruation, FSH initiates follicular growth, specifically affecting granulosa cells. With the rise in oestrogens, LH receptors are also expressed on the maturing follicle that produces an increasing amount of estradiol. Eventually at the time of the maturation of the follicle, the oestrogen rise leads via the hypothalamic interface to the "positive feed-back" effect, a release of LH over a 24- to 48-hour period. This 'LH surge' triggers ovulation, thereby not only releasing the egg but also initiating the conversion of the residual follicle into a corpus luteum that, in turn, produces progesterone to prepare the endometrium for a possible implantation. LH is necessary to maintain luteal function for the first two weeks. In case of a pregnancy, luteal function will be further maintained by the action of hCG (a hormone very similar to LH) from the newly established pregnancy. LH supports theca cells in the ovary that provide androgens and hormonal precursors for estradiol production. LH is a heterodimeric glycoprotein. Each monomeric unit is a protein molecule with one or more oligosaccharide chains covalently linked to amino acid side chains; two of these monomeric units make the full, functional protein. The protein dimer contains 2 polypeptide units, labeled alpha and beta subunits. The alpha subunits of LH, FSH, TSH, and hCG are identical, and contain 92 amino acids. LH has a beta subunit of 141 amino acids (LHB), which confers its specific biologic action and is responsible for interaction with the LH-receptor. This beta subunit contains an amino acid sequence that exhibits homologies with that of the beta subunit of hCG and both stimulate the same receptor. However, the hCG beta subunit contains an additional 24 amino acids, and the two hormones differ in the composition of their sugar moieties.

The beta chain of LH of the present invention is selected from the group consisting of sequences having at least 80% sequence identity to SEQ ID NO 4, 5, 6, 7, and 8, more preferably 85%, more preferably 90%, more preferably 95%. Preferably, a variant comprises the conserved cysteine residues at the position and spacing of SEQ ID NO 4. In a particularly preferred embodiment, the LH comprises the human alpha-subunit having SEQ ID NO 4.

The different composition of these oligosaccharides affects bioactivity and speed of degradation and elimination. The biologic half-life of LH is 20 minutes, which is much shorter than that of FSH (3-4 hours) and hCG (24-30 hours).

It will be understood by one of skill in the art that LH may be substituted by a biologically active analogue, or by a compound that stimulates endogenous LH secretion. Analogues of LH include all molecules which exert the same physiological, biochemical or biological effects as LH, and/or bind to the same receptors as LH. Some analogues of LH may also include single chain LH. hCG is known to share some physiological actions with LH. Some examples of analogues of LH are as disclosed, for example in European patent no. EP 0 322 226 (Applied Research Systems), WO 92/22568 (University of Medicine & Dentistry of New Jersey), WO 96/05224 (Washington University), WO 90/09800 (Washington University), WO 93/06844 (Washington University), WO 98/43999 (Washington University), WO 99/25849 (Washington University), WO 00/61586 (Akzo Nobel).

LH and its analogues or the LH agonist may be selected from a small organic molecule, a peptide, a polypeptide, a protein, and may be produced by synthetic methods, recombinant means or be obtained from its natural sources, e.g. from urine, tissue or blood.

In one particular embodiment the LH agonist is recombinant or urine-derived LH. In another embodiment the LH agonist is of non-mammalian origin. In another particular embodiment the LH agonist is of mammalian origin, such as a protein obtained by recombinant means. In a further embodiment the LH agonist is selected from a mammal chorionic gonadotropin (CG) or a mammal LH. When the LH agonist is a mammal CG it is typically a primate CG, e.g. a human CG, but may also be selected from other mammalian species such as horse CG.

In a further embodiment the LH agonist is selected from an analogue of a mammal LH or an analogue of a mammal LH. When the LH agonist is an analogue of a mammal LH the analogue preferably has at least 80% identity to the corresponding mammalian sequence of luteinising hormone, such as 85% identity, 90% identity, 95% identity, 98% identity. The sequence variation can be in the alpha chain, in the beta chain or in both. The LH agonist may be an analogue of a human CG having at least 80% identity to the corresponding human sequence of chorionic gonadotropin, such as 85% identity, 90% identity, 95% identity, 98% identity. When the LH agonist is an analogue of a mammal LH the analogue has at least 80% identity to the corresponding mammalian sequence of luteinizing hormone, such as 85% identity, 90% identity, 95% identity, 98% identity. Typically, the LH agonist is an analogue of a human LH having at least 80% identity to the corresponding human sequence of luteinizing hormone, such as 85% identity, 90% identity, 95% identity, 98% identity.

When the LH agonist is selected from a polypeptide or protein, such as an analogue of a mammal CG or an analogue of a mammal LH, it may be glycosylated. Typically, the LH agonist is an hCG which is glycosylated. It may also be that the LH compound as such is glycosylated, and the glycosylation may be on the LH agonist or on the pharmaceutically acceptable molecule, when said molecule is selected from a polypeptide or protein, such as human albumin. The LH agonist may be linked to the pharmaceutically acceptable molecule in various ways, such as directly through a valence bond, or indirectly through a linker, which linker typically is a bifunctional linker, although it may also be a multifunctional linker. In further embodiments, the linker is selected from a chemical linker, a sugar moiety, a disulphide bridge, a fused linker, a hydrophilic linker, a hydrolysable linker. In a further embodiment the LH agonist is fused to the pharmaceutically acceptable molecule through a peptide linker. In a still further embodiment the LH agonist is fused directly to the pharmaceutically acceptable molecule, so as to create one polypeptide or protein, by expressing the LH compound from a host cell, such as a CHO cell or yeast cell. In a further embodiment the LH agonist is linked to the pharmaceutically acceptable molecule through a stable linker. In another embodiment the LH agonist is linked to the pharmaceutically acceptable molecule through a labile linker. Accordingly, the LH agonist may be linked to the pharmaceutically acceptable molecule in various ways using techniques that are well-known in the prior art, and the present invention also comprises the situation where one or more LH agonist(s) is linked to one or more pharmaceutically acceptable molecule(s), such as two LH agonist linked to one pharmaceutically acceptable molecule, or one LH agonist linked to two pharmaceutically acceptable molecules. In a further embodiment the LH agonist is linked to one or two pharmaceutically acceptable molecule(s), preferably one pharmaceutically acceptable molecule.

When the LH agonist is a mammal LH it is typically a human LH, but may also be selected from other mammalian species such as cow LH, pig LH, horse LH, sheep LH, dog LH, cat LH, and goat LH. Typically, the LH agonist is a human LH or human hCG. Normally, IVF involves daily luteal phase support treatment with progesterone during the first 2 weeks after embryo transfer. If gestation is confirmed on day 28 of the cycle daily luteal phase support treatment with progesterone may be extended for additional 5-10 weeks. In the present invention, administration of LH may however replace this daily treatment with progesterone. Providing luteal and gestational phase support by administering one or more dosages of an LH agonist may result in better development of oocytes, healthier oocytes, improved embryo implantation and retention, reduced biochemical pregnancy risk and may reduce the risk of OHSS.

In one embodiment the LH agonist used alone for luteal support is an LH analogue and not hCG or an hCG analogue. This is firstly because administration of hCG in the luteal phase may interfere with the biochemical pregnancy tests, which normally involve detection of urinary hCG secreted by the corpus luteum. Furthermore, administration of LH instead of hCG in the luteal phase is expected to reduce the risk of developing OHSS due to the different receptor affinities of the two proteins.

In another embodiment the LH agonist used alone for gestational support is an LH analogue and not hCG or an hCG analogue. This is firstly because administration of hCG in the gestational phase may interfere with the biochemical pregnancy tests, which normally involve detection of urinary hCG secreted by the corpus luteum. Furthermore, administration of LH instead of hCG in the gestational phase is expected to reduce the risk of developing OHSS due to the different receptor affinities of the two proteins.

Although both LH and hCG binds to and activate the LH-receptor, both hormones exist as a family of iso-hormones that differ in their oligosaccharide composition. Each of the different isoforms affects the receptor in a specific way and may elicit variable cellular responses (Burgon P G et al., Endocrinology, 1996; 137:4827; Stanton P G et al., Mol Cell Endocrinol. 1996; 125:133-141.), as have also been shown for the different FSH isoforms (Barrios-de-Tomasi J, et al. Mol Cell Endocrinol. 2002; 186:189-98, Yding Andersen C & Ezcurra D, Reproductive Biology Insights 2011:4, 1-10). Thus the more subtle and fine-tuned effects of LH and hCG may actually differ. Recent studies presented at the ESHRE conference in Stockholm (July 2011) actually showed that LH acted much faster than hCG, but less efficient overall at the receptor level (L. Casarini et al., ESHRE Stockholm 2011-P312, Universita degli Studi di Modena, Italy). In a presentation by professor Peter Humaindan (ESHRE Stockholm 2011), it was further shown that addition of recombinant LH to recombinant FSH during COS significantly increased the oocyte yield as compared to equivalent doses of hCG added, suggesting specific LH effects at the receptor level. hCG is a pregnancy associated protein which is secreted following the implantation of the embryo around 8 days after conception. hCG is capable of stimulating the corpus luteum to remain active and continue its secretion of progesterone and other substances necessary for the pregnancy to become established. When hCG starts to be secreted from the implanting embryo, LH is present in appreciable amounts, but these levels are insufficient to stimulate the corpus luteum further and unless the woman becomes pregnant the corpus luteum will regress, a menstrual bleeding will occur and a new menstrual cycle start. So at this stage hCG preferentially stimulates the corpus luteum. Although this difference between LH and hCG has puzzled science for some time, it has now been demonstrated that the LH-receptor (LH-R) changes during the luteal phase. The functional full-length receptor maintains its expression when hCG is present, whereas LH is unable to accomplish that (Dickinson R E et al., Endocrinology 150: 2873-2881, 2009). This demonstrates differences in the effect of LH and hCG during the luteal phase.

The method for assisted reproductive therapy in a female mammal as described herein may in one embodiment further comprise providing luteal phase support by administering one or more dosages of an LH agonist replacing the current progesterone luteal phase support.

LH activity is normally given in IU following the pharmacopeia. Now pure preparations of LH may also be manufactured and the activity given in mass (e.g. µg per vial). In the present invention it is understood that activity given in IU correlates to LH activity given with other units, such as molar units.

Urinary or recombinant or long-acting LH may be administered during the follicular phase instead of hCG (urinary or recombinant or long-acting) in dosages giving a response equivalent to the biological response provided by the dosages of urinary and recombinant hCG described herein.

The one or more dosages of LH agonist should be sufficient to provide a serum progesterone concentration of at least 5 nmol/L, such as at least 10 nmol/L, such as at least 15 nmol/L or such as at least 20 nmol/L at least until 5 days after ovulation or oocyte pick up, at least until 10 days after oocyte pick up, preferably at least until 14, more preferably at least until 21, more preferably at least until 28 days after ovulation or oocyte pick up. Preferably, the administration of an LH agonist may be continued beyond 28 days after ovulation or oocyte pickup such as up to 5 weeks, such as up to 6 weeks, for example up to 7 weeks, such as up to 8 weeks, for example up to 9 weeks, such as up to 10 weeks or more.

In one particular preferred embodiment, the method for assisted reproductive therapy further comprise providing luteal support by administering one or more dosages of an LH agonist sufficient to provide a serum progesterone concentration of at least 20 nmol/L at day 7 after oocyte pickup.

It is preferred that the one or more dosages in the luteal phase are sufficient to maintain a serum progesterone level of at least at 20 nmol/L at least until 10 days after oocyte pick up, preferably at least until 14, more preferably at least until 21, more preferably at least until 28 days after oocyte pick up.

It is preferred that the administered LH agonist is sufficient to provide a biological response similar to the response provided by a serum concentration of 4-12 IU recombinant or urinary LH per liter during the luteal phase, more preferably a serum concentration of 4-12 IU/L, such as 8-12 IU/L.

In a preferred embodiment recombinant or urine-derived LH is administered in the luteal phase at daily dosages of 100-600 IU LH per day, preferably 150-450 IU LH per day, such as 200-400 IU LH per day, for example 250-350 IU/day.

The LH agonist may in one embodiment be a long-acting LH exhibiting a prolonged serum half-life. The long-acting LH may comprise LH or an LH agonist linked to a chemical moiety such as a pharmaceutically acceptable molecule providing a serum half-life of the LH agonist or LH compound which is increased substantially when compared to the serum half-life of an LH agonist administered in the same manner as the LH compound or when compared to in vivo plasma half-life of endogenous chorionic gonadotropin (CG). The modified LH either given in the follicular phase or as a luteal phase support is believed to improve patient convenience and treatment outcome, when compared with conventional progesterone administration.

In one preferred embodiment the LH agonist is a long-acting LH comprising luteinizing hormone linked to a chemical moiety. In another preferred embodiment the LH agonist is a long-acting hCG comprising human chorionic gonadotropin linked to a chemical moiety.

In order to produce the long term LH compound which can be administered once or twice during the luteal phase in connection with assisted reproduction technology (ART) procedures, such long term LH compound when administered to a mammal should result in the LH agonist or LH compound having serum half-life of at least 1.5 times the half-life of LH, such as at least 2 times, at least 3 times, at least 4 times, preferably at least 5 times, more preferably at least 6 times or such as from 1.5 times to 25 times the half-life of LH.

In a preferred embodiment the LH agonist is a long-acting LH comprising luteinizing hormone linked to a chemical moiety, wherein the long-acting LH has a serum half-life of at least 6 times the half-life of LH.

When the long-acting LH comprises human chorionic gonadotropin linked to a chemical moiety, the serum half-life of the long term LH may for example be of at least 1.2 times the half-life of hCG, such as at least 1.3 times the half-life of hCG, at least 1.5 times the half-life of hCG, at least 2 times the half-life of hCG or such as at least 3 times the half-life of hCG.

The LH agonist may in one preferred embodiment be a long-acting hCG comprising human chorionic gonadotropin linked to a chemical moiety, wherein the long-acting hCG has a serum half-life of at least 1.5 times the half-life of hCG.

Luteal support is given to women before a biochemical pregnancy is detected, embryo implantation and pregnancy may be uncertain and the female might not get pregnant in a given cycle. Thus, the female mammal might have to undergo additional stimulation or ovulation cycles, and it is preferred that the half-life of the LH agonist administered during the luteal phase is no longer than 10 days, preferably no longer than 5 days, so that the level can fall below a level which can interfere with the subsequent ovulation or stimulation cycle in case the female mammal has to get a new treatment in the next cycle.

Examples of long-acting LH and hCG are found in the appended examples.

Human Chorionic Gonadotropin (hCG)

Human chorionic gonadotropin (hCG) is a glycoprotein hormone produced during pregnancy that is made by the developing embryo after conception and later by the syncytiotrophoblast (part of the placenta). Its role is to prevent the disintegration of the corpus luteum of the ovary and thereby maintain progesterone production that is critical during pregnancy in humans. hCG may have additional functions; for instance, it is thought that hCG affects the immune tolerance of the pregnancy. Early pregnancy testing, in general, is based on the detection or measurement of hCG.

Human chorionic gonadotropin interacts with the LHCG receptor and promotes the maintenance of the corpus luteum during the beginning of pregnancy, causing it to secrete the hormone progesterone. Progesterone enriches the uterus with a thick lining of blood vessels and capillaries so that it can sustain the growing fetus. Due to its highly-negative charge, hCG may repel the immune cells of the mother, protecting the fetus during the first trimester. It has also been hypothesized that hCG may be a placental link for the development of local maternal immunotolerance. For example, hCG-treated endometrial cells induce an increase in T cell apoptosis (dissolution of T-cells). These results suggest that hCG may be a link in the development of peritrophoblastic immune tolerance, and may facilitate the trophoblast invasion, which is known to expedite fetal development in the endometrium. It has also been suggested that hCG levels are linked to the severity of morning sickness in pregnant women.

Human chorionic gonadotropin is a glycoprotein composed of 244 amino acids with a molecular mass of 36.7 kDa. It is heterodimeric, with an alpha-subunit identical to that of luteinizing hormone (LH), follicle-stimulating hormone (FSH), thyroid-stimulating hormone (TSH), and beta-subunit that is unique to hCG (SEQ ID NO:9).

The alpha-subunit is 92 amino acids long. The beta-subunit of hCG contains 145 amino acids encoded by six highly-homologous genes that are arranged in tandem and inverted pairs on chromosome 19q13.3-CGB (1, 2, 3, 5, 7, 8). The two subunits create a small hydrophobic core surrounded by a high surface area-to-volume ratio: 2.8 times that of a sphere. The vast majority of the outer amino acids are hydrophilic.

The beta chain of preferred hCG of the present invention is selected from the group consisting of sequences having at least 80% sequence identity to SEQ ID NO 9, more preferably 85%, more preferably 90%, more preferably 95%. Preferably, a variant comprises the conserved cysteine residues at the position and spacing of SEQ ID NO 9. In a particularly preferred embodiment, the hCG comprise the human alpha-subunit having SEQ ID NO 9.

hCG can be distinguished from LH by the presence in the beta-subunit of the C terminal peptide, CTP, consisting of amino acids 112-145 of SEQ ID NO 9. A distinction can be done immunologically and by sequencing.

The hCG that is used may be from any source, provided it is not contaminated with any materials (particularly other gonadotropins) which will substantially affect its action. Urinary hCG may be used, although it is preferred to use recombinant hCG (rhCG), because of its high purity. Similar conditions apply to the source of hCG for use in the present invention.

hCG activity is normally given in IU following the pharmacopeia. Now pure preparations of hCG may also be manufactured and the activity given in mass (e.g. µg per vial). In the present invention it is understood that activity given in IU correlates to hCG activity given with other units, such as molar units.

Analogues of hCG include all molecules which exert the same physiological, biochemical or biological effects as hCG, and/or bind to the same receptors, as hCG. Luteinising hormone (LH) is known to share some physiological actions with hCG. Some analogues of hCG include single chain hCG, in which the C-terminus of the [beta]-subunit is fused to the N-terminus of the [alpha]-subunit (Sugahara et al., PNAS, 92, 1995, 2041-2045). Other examples of analogues are as is disclosed, for example in European patent no. EP 0 322 226 (Applied Research Systems), WO 92/22568 (University of Medicine & Dentistry of New Jersey), WO 96/05224 (Washington University), WO 90/09800 (Washington University), WO 93/06844 (Washington University), WO 98/43999 (Washington University), WO 99/25849 (Washington University).

In relation to fertility treatments, human chorionic gonadotropin is extensively used parentally as an ovulation inducer in lieu of luteinizing hormone. In the presence of one or more mature ovarian follicles, ovulation can be triggered by the administration of hCG. As ovulation will happen 24-36 hours after the injection of hCG, procedures can be scheduled to take advantage of this time sequence. Thus, patients that undergo IVF, in general, receive hCG to trigger the ovulation process, but have their eggs retrieved at about 36 hours after injection, a few hours before the eggs actually would be released from the ovary.

In the method of the present invention, at least one dosage of hCG is administered in the period from day 1-9 of the stimulation or of the menstrual cycle, the dosage being sufficient to stimulate follicle development until ovulation triggering.

It is preferred that the administered hCG is sufficient to provide a biological response similar to the response provided by a serum concentration of 4-15 IU LH per liter during the luteal phase, more preferably a serum concentration of 4-12, or 5-12, such as 5-8 IU/L.

As described above, hCG may be recombinant or urine-derived. Thus, in one embodiment hCG is administered as daily dosages of recombinant or urine-derived hCG. The daily administration of hCG may for example be carried out until follicle maturation is triggered or ovulation is induced/triggered with a conventional bolus of hCG.

For daily administration of hCG during the follicular phase the dosage should be in the range of 25-4000 IU hCG/day, preferably 25-1000 IU hCG/day, more preferably 30-1000 or 30-500 IU hCG/day, most preferably 25-400 IU per day, such as 50-300 IU per day, more preferably 100-300, such as 150-250, for example 175-225 IU per day. It is also possible to administer hCG on a less frequent basis, for example every two, three, or four days, preferably every two days, until ovulation is triggered. In such a regimen, doses such as those outlined above may be used, although a dose of 50-400 IU hCG is preferred.

Thus, in one preferred embodiment the daily dosage of hCG when administered in the luteal phase is 25-400 IU hCG per day, preferably 50-200 IU hCG per day, for example 75-200, such as 100-150 or 120-170 IU/day.

In one embodiment of the present invention, hCG is a long-acting hCG exhibiting a prolonged serum half-life. The long-acting hCG may comprise hCG linked to a chemical moiety such as a pharmaceutically acceptable molecule providing a serum half-life of the hCG compound which is increased substantially when compared to the serum half-life of an hCG administered in the same manner as the long-acting hCG.

The half-life of the long-acting hCG may for example be of at least 1.2 times the half-life of hCG, such as at least 1.3 times the half-life of hCG, at least 1.5 times the half-life of hCG, at least 2 times the half-life of hCG or such as at least 3 times the half-life of hCG.

In one preferred embodiment hCG is a long-acting hCG with a serum half-life of at least 1.5 times the half-life of hCG.

In one embodiment the long-acting hCG is administered every $2^{nd}$ day, such as every $3^{rd}$ day, for example every $4^{th}$ day, such as every $5^{th}$ day, for example every $6^{th}$ day, such as every $7^{th}$ day, for example every $8^{th}$ day, such as every $9^{th}$ day, for example every $10^{th}$ day during the ovulation induction phase and/or the subsequent luteal and/or gestational phases. In a further embodiment the long-acting hCG may be also administered every 14th day, such as every 21st, for example every month or even less frequently during the ovulation induction phase and/or the subsequent luteal phase and/or the subsequent gestational phase. As mentioned above, it is preferred to shift from hCG administration to LH administration in the luteal phase. The long-acting hCG is in one embodiment administered as a single bolus injection during the follicular phase, the dosage being sufficient to support the follicle development, and preferably also sufficient to provide luteal support.

In one embodiment of the present invention the long-acting hCG is administered as a single bolus injection when at least one follicle has a diameter of at least 8 mm, such as at least 9 mm, at least 10 mm, such as for example at least 11 mm, such as at least 13 mm, at least 14 mm or such as for example at least 15 mm.

In one preferred embodiment the long-acting hCG is administered as a single bolus injection when at least one follicle has a diameter of at least 12 mm.

The long-acting hCG is in one embodiment administered as a single bolus injection during FSH administration.

It is preferred that the hCG dosage in the follicular phase is sufficient to provide a biological response similar to the response provided by a serum concentration of 1-12 IU hCG per liter during the follicular phase.

It is further preferred that wherein hCG is recombinant or urine-derived hCG is administered at daily dosages of 25-300 IU hCG per day, preferably 50-200, such as 125-200 IU/day, for example 150-200 IU/day.

Preferably, hCG is administered daily from day 5 of the follicular phase and until ovulation triggering.

hCG may further be administered from day 2 of the follicular phase, so that hCG is administered from day 2 of the follicular phase and until ovulation.

Ovulation Triggering

The exact time of administration of the ovulation triggering treatment is determined by UV measurement of follicle diameter. Typically the triggering treatment is carried out when at least one follicle has a mean diameter of at least 15 mm. Preferably the triggering treatment is carried out when at least one follicle has a diameter of 16 mm, more preferably 17 mm. In many cases, the triggering treatment is carried out when at least 2 follicles have reached the indicated sizes, more preferably when at least 3 follicles have reached the indicated sizes. In a particularly preferred embodiment, ovulation triggering is induced when three or more follicles have a diameter of 17 mm.

In one aspect of the invention, the ovulation is triggered by administration of a therapeutically effective dosage of a GnRH agonist as herein described. In another aspect of the invention, ovulation is triggered by a relatively low dosage of hCG or an hCG analogue or variant or long-acting hCG. When recombinant or urinary hCG is used the triggering dosage is 2000 IU or less, such as 1500 IU or less, for example 1000 IU or less. A low dosage of hCG or analogue/variant/long-acting hCG can be supplemented with a dosage of a GnRH agonist.

Gonadotropin Releasing Hormone Agonist

A gonadotropin-releasing hormone agonist (GnRH agonist, GnRH-A) is a synthetic peptide modeled after the hypothalamic neuro hormone GnRH that interacts with the gonadotropin-releasing hormone receptor to elicit its biologic response, the release of the pituitary hormones FSH and LH. Agonists do not quickly dissociate from the GnRH receptor. As a result when administrating the GnRH agonist initially there is an increase in FSH and LH secretion (so-called "flare effect"). However after about ten days a profound hypogonadal effect (i.e. decrease in FSH and LH) is achieved through receptor down regulation by internalization of receptors. Generally this induced and reversible hypogonadism is the therapeutic goal.

In one aspect of the invention, a GnRH agonist is administered in order to trigger ovulation.

Examples of approved GnRH agonists include: leuprolide (Lupron, Eligard); buserelin (Suprefact, Suprecor); nafarelin (Synarel); histerelin (Supprelin); goserelin (Zoladex); deslorelin (Suprelorin, Ovuplant); Triptorelin.

Appropriate doses and administration regimes will be apparent to a person skilled in the art and any appropriate dose and administration regime may be used. The agonists can be administered subcutaneously or by initranasal spray.

By way of illustration, a commonly used and therapeutically effective dosage of Buserelin is 0.5 mg (subcutaneously) or 0.2 mg (intranasally). Triptorelin can be administered in a dosage of 0.2 mg subcutaneously and Leuprolide can be administered in a dosage of 1.0 mg subcutaneously.

Gonadotropin Releasing Hormone Antagonist

Gonadotropin-releasing hormone (GnRH) antagonists (receptor blockers) are a class of compounds that are similar in structure to natural GnRH (a hormone made by neurons in the hypothalamus) but that have an antagonistic effect. GnRH antagonists are peptide molecules that are made of multiple, often synthetically produced amino acids. GnRH antagonists compete with natural GnRH for binding to GnRH receptors, thus decreasing or blocking GnRH action in the body.

GnRH antagonists competitively and reversibly bind to GnRH receptors in the pituitary gland, blocking the release of luteinising hormone (LH) and follicle-stimulating hormone (FSH) from the pituitary. In women, the reduction in LH subsequently leads to suppression of estrogen release from the ovaries.

Unlike the GnRH agonists, which cause an initial stimulation of the hypothalamic-pituitary-gonadal axis (HPGA), leading to a surge in oestrogen levels, GnRH antagonists have an immediate onset of action, rapidly reducing sex hormone levels without an initial surge.

Currently approved GnRH antagonists suitable for use in the methods of the present invention include the following: Cetrorelix; Ganirelix; Abarelix; Degarelix. Appropriate doses and administration regimes will be apparent to a person skilled in the art and any appropriate dose and administration regime may be used.

The above embodiments as well as the embodiments to be described hereunder should be seen as referring to any one of the aspects described herein as well as any one of the embodiments described herein unless it is specified that an embodiment relates to a certain aspect or aspects of the present invention.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way.

Any combination of the above-described elements in all possible variations thereof is encompassed by the invention unless otherwise indicated herein or otherwise clearly contradicted by context.

Recitation of ranges of values herein are merely intended to serve as a shorth method of referring individually to each separate value falling within the range, unless other-wise indicated herein, and each separate value is incorporated into the specification as if it was individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

All methods described herein can be performed in any suitable order unless other-wise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

The present invention is further illustrated by the following examples which, however, are not to be construed as limiting the scope of protection. The features disclosed in the foregoing description and in the following examples may, both separately and in any combination thereof, be material for realizing the invention in diverse forms thereof.

LIST OF EMBODIMENTS

1. A long acting biologically active luteinizing hormone (LH) compound comprising an LH agonist linked to a pharmaceutically acceptable molecule providing an in vivo plasma half-life of the LH agonist or LH compound which is increased substantially compared to the in vivo plasma half-life of an LH agonist administered in the same manner as the LH compound.

2. The LH compound of embodiment 1 wherein the LH agonist is selected from a mammal CG or analog thereof or a mammal LH or analog thereof, such as recombinant hLH or hGH.

3. The LH compound of any one of the preceding embodiments wherein the LH agonist is chemically linked to the pharmaceutically acceptable molecule, optionally through a bifunctional linker.

4. The LH compound of any one of the preceding embodiments wherein the pharmaceutical acceptable molecule provides a biological body composition or concentration of the LH agonist or LH compound sufficient to drive an antral follicle from about 10 mm in diameter up to the preovulatory stage at about 15-30 mm in diameter in which a maturing oocyte can finalize the maturation to be ready for resumption of the meiosis.

5. The LH compound of any one of the preceding embodiments wherein the pharmaceutical acceptable molecule provides a biological body composition or concentration of the LH agonist or LH compound sufficient to support hypogonadothrophic hypogonadal subjects.

6. The LH compound of any one of the preceding embodiments wherein the pharmaceutical acceptable molecule provides a biological body composition or concentration of the LH agonist or LH compound sufficient to sustain progesterone in the peri-, in the ovulatoric- and the post ovulatoric-phase of a mammalian subject with the object regulating the endometrium and womb for avoiding or allowing implantation of a mammalian blastocyst.

7. The LH compound of any one of the preceding embodiments wherein the pharmaceutically acceptable molecule provides a plasma concentration of the LH agonist or LH compound to support the formation and maintenance of Corpus Luteum/corpora lutea (CL), when an injection is given during the follicular phase of the menstrual cycle in connection with follicle stimulating hormone (FSH) treatment, preferably 5-10 days after initiation of FSH treatment.

8. The LH compound of any one of the preceding embodiments wherein the LH agonist is selected from the sequence of human CG or human LH, the sequence of cow CG or cow LH, the sequence of pig CG or pig LH, the sequence of horse CG or horse LH, the sequence of sheep CG or sheep LH, the sequence of dog CG or dog LH, the sequence of cat CG or cat LH, and the sequence of goat CG or goat LH.

9. The LH compound of any one of the preceding embodiments wherein the analog has at least 80% identity to the corresponding mammalian sequence of chorionic gonadotropin or luteinizing hormone, such as 85% identity, 90% identity, 95% identity, 98% identity.

10. The LH compound of any one of the preceding embodiments wherein the LH agonist or LH compound having in vivo plasma half-life augmented at least 1.5 times, at least 2 times, at least 3 times, at least 4 times, such as from 1.5 times to 25 times.

11. The LH compound of any one of the preceding embodiments wherein the LH agonist or LH compound is glycosylated.

12. The LH compound of any one of the preceding embodiments wherein the pharmaceutically acceptable molecule is selected from an albumin or a polymer, such as modified albumin with increased binding to FcRn, human albumin, recombinant human albumin or PEG.

13. A pharmaceutical composition comprising the LH compound of any one of the preceding embodiments.

14. The LH compound of any one of the preceding embodiments for use in promoting fertility of a mammalian subject, such as assisted reproduction technologies treatment.

15. A modified luteinizing hormone comprising a mammalian LH or analog thereof linked to a pharmaceutically acceptable molecule providing an in vivo plasma half-life of the mammalian LH or analog thereof, or the modified LH which is from 2 to 48 hours in a mammal.

16. The modified LH of embodiment 15 for providing an in vivo plasma concentration of the modified LH, the mammalian LH or a mixture thereof, in a mammal in the range of from 2 to 30 IU/L.

17. The modified LH of any one of the preceding embodiments 15-16 wherein the mammalian LH or analog thereof is a recombinant LH, e.g. rhLH.

18. The modified LH of any one of the preceding embodiments 15-17 wherein the modified LH comprises an analog of the mammalian LH, wherein the analog has at least 80% identity to the corresponding mammalian sequence of LH.

19. The modified LH of any one of the preceding embodiments 15-18 wherein the mammalian LH is selected from the sequence of human LH, and the sequence of horse LH.

20. The modified LH of any one of the preceding embodiments 15-19 wherein the pharmaceutically acceptable molecule is selected from any one of small organic molecules, peptides, oligopeptides, polypeptides, proteins, receptors, glycosylations, acylation groups, sugars, polymers (e.g. polyethylene glycols, PEG), nucleic acids (e.g. DNA and RNA), hormones, typically, pharmaceutically acceptable molecules are without limitation albumin, such as human albumin, recombinant albumin, variants of albumin, $CH_3(CH_2)_nCO-$, wherein n is 4 to 40, or polymer, such as PEG, e.g. PEG of a molecular weight of at least 5 kDa, such as from 10 kDa to 150 kDa, typically 10 to 40 kDa.

21. The modified LH of any one of the preceding embodiments 15-20 wherein the mammalian LH or analog thereof is chemically linked to the pharmaceutically acceptable molecule, optionally through a bifunctional linker, or is fused to the pharmaceutically acceptable molecule, optionally through a peptide linker.

22. The modified LH of any one of the preceding embodiments 15-21 wherein the mammalian LH or analog thereof, or modified LH is glycosylated.

23. The modified LH of any one of the preceding embodiments 15-22 wherein the mammalian LH or analog thereof is linked to one or two pharmaceutically acceptable molecule(s), preferably one pharmaceutically acceptable molecule.

24. A pharmaceutical composition comprising the modified LH of any one of the preceding embodiments 15-23.

25. A pharmaceutical composition comprising the modified LH of any one of the preceding embodiments 15-23 and an FSH or a molecule having FSH activity.

26. The modified LH of any one of the preceding embodiments 15-23 for use in combination with an FSH or a molecule having FSH activity for simultaneous, sequential or separate use to induce follicular development, such as paucifolliculogenesis or unifolliculogenesis, in anovulatory treatment of a mammalian female subject or induce COS in the follicular phase of the menstrual cycle of a mammalian female subject.

27. The modified LH of embodiment 26 wherein administration of FSH:LH the IU ratios range from 20:1 to 1:20.

28. The modified LH of any one of embodiments 25-27 wherein the FSH is selected from mammalian FSH, such as human FSH, in particular recombinant FSH, e.g. rhFSH.

EXAMPLES

Example 1

Method Producing Long Acting hCG

A long acting hCG is produced by chemical conjugation of hCG to human serum albumin or a variant of human serum albumin with selected improved or reduced affinity for the neonatal Fc receptor.

Chemical conjugation can be performed using a multitude of different chemistries and linkers known in the art, including linkers with a high covalent stability and linkers with lower covalent stability having the potential of releasing the active component from the albumin molecule typically by hydrolysation of a labile chemical bond.

Suitable attachment groups on the albumin molecule are apparent from the table below

| Attachment group | Amino acid | Examples of non-peptide moiety | Conjugation method/-Activated PEG | Reference |
|---|---|---|---|---|
| —NH2 | N-terminal, Lys, His, Arg | Polymer, e.g. PEG, with amide or imine group | mPEG-SPA Tresylated mPEG | Shearwater Inc. Delgado et al., critical reviews in Therapeutic Drug Carrier Systems 9(3, 4): 249-304 (1992) |
| —COOH | C-term, Asp, Glu | Polymer, e.g, PEG, with ester or amide group Oligosaccharide moiety | mPEG-Hz In vitro coupling | Shearwater Inc. |
| —SH | Cys | Polymer, e.g. PEG, with disulfide, critimaleimide or vinyl sulfone group Oligosaccharide moiety | PEG-Vinylsulphone PEG-maleimide In vitro coupling | Shearwater Inc. Delgado et al., critical reviews in Therapeutic Drug Carrier Systems 9(3, 4): 249-304 (1992) |
| —OH | Ser, Thr, —OH, Lys | Oligosaccharide moiety PEG with ester, ether, carbamate, carbonate | In vivo O-linked glycosylation | |
| —CONH2 | Asn as part of an N-glycosylation site | Oligosaccharide moiety Polymer, e.g. PEG | In vivo N-glycosylation | |
| Aromatic residue | Phe, Tyr, Trp | Oligosaccharide moiety | In vitro coupling | |
| —CONH2 | Gln | Oligosaccharide moiety | In vitro coupling | Yan and Wold, Biochemistry, 1984, Jul. 31; 23(16): 3759-65 |
| Aldehyde Ketone | Oxidized oligosaccharide | Polymer, e.g. PEG, PEG-hydrazide | PEGylation | Andresz et al., 1978, Makromol. Chem. 179: 301, WO92/16555, WO00/23114 |
| Guanidino | | Oligosaccharide moiety | In vitro coupling | Lundblad and Noyes, Chemical Reagents for Protein Modification, CRC Press Inc., Florida, USA |
| Imidazole ring | His | Oligosaccharide moiety | In vitro coupling | As for guanidine |

Especially suitable is coupling to the free cysteine residue on the albumin molecule (Cys 34), e.g. by methods described in WO2010092135, especially the methods using PDPH (3-(2-pyridyldithio)propionyl hydrazide) to link albumin to hCG via a hydrazone link to hCG. In another aspect the method in WO2010092135 using EMCH ((3,3"-N-(ε-maleimidocaproic acid) hydrazide) to link albumin to hCG via a hydrazone link to hCG is used.

Suitable attachment groups on the hCG molecule include those in the table above, and include chemistries for coupling to the glycosylation moieties of the hCG molecule. Coupling to the glycosylation moieties is preferred as these are expected not to have direct interaction with the hCG receptor and thereby the coupling will not interfere with the function.

Yet another coupling technology is described by Neose (see eg US2004/0126838) using enzymatic glycoconjugation. This technology can be used to link e.g. albumin to hCG using a suitable linker.

In the special case where chemical conjugation to the hCG molecule strongly reduce the functional activity it will be preferable to use a labile linker that can release a functional hCG. It is preferable to attach only one albumin molecule pr. hCG molecule.

In another instance the coupling of the hCG and the albumin molecule can be performed by genetic fusion of the two molecules. As the hCG molecule has two chains there are four different orientation possibilities:

Albumin-hCG(alpha chain)
Albumin-hCG(beta chain)
hCG(alpha chain)-albumin
hCG(beta chain)-albumin Recombinant hCG packaged in a prefilled syringe in the product Ovitrelle® produced by Merck Serono are available containing 0.5 mL solution with 250 μg recombinant hCG. The formulation excipients can be removed by dialysis and gel filtration. Albumin or albumin variants can be produced as described in WO2010092135. The hCG and the albumin can be conjugated using the PDPH or EMCH chemistry as described in WO2010092135.

Example 2

List of Sequences and their UniProt (www.uniprot.org) ID (Name) and AC (Accession)

Glycoprotein Hormones Alpha Chain:

| Human | GLHA_HUMAN | P01215 | SEQ ID NO 1 |
| Mouse | GLHA_MOUSE | P01216 | SEQ ID NO 2 |
| Rat   | GLHA_RAT   | P11962 | SEQ ID NO 3 |

```
>GLHA_HUMAN P01215_Mature25-116
APDVQDCPECTLQENPFFSQPGAPILQCMGCCFSRAYPTPLRSKKTMLVQKNVTSESTCC
VAKSYNRVTVMGGFKVENHTACHCSTCYYHKS >GLHA_MOUSE P01216_Mature 25-120
LPDGDFIIQGCPECKLKENKYFSKLGAPIYQCMGCCFSRAYPTPARSKKTMLVPKNITSE
ATCCVAKAFTKATVMGNARVENHTECHCSTCYYHKS >GLHA_RAT P11962_Mature 25-120
LPDGDLIIQGCPECKLKENKYFSKLGAPIYQCMGCCFSRAYPTPARSKKTMLVPKNITSE
ATCCVAKSFTKATVMGNARVENHTDCHCSTCYYHKS
```

Luteinizing Hormone Beta Chain:

| Human:      | LSHB_HUMAN | P01229 | SEQ ID NO 4 |
| Mouse:      | LSHB_MOUSE | O09108 | SEQ ID NO 5 |
| Rat:        | LSHB_RAT   | P01230 | SEQ ID NO 6 |
| Gorilla:    | LSHB_GORGO | Q2Q1P1 | SEQ ID NO 7 |
| Chimpanzee: | LSHB_PANTR | Q2Q1P2 | SEQ ID NO 8 |

```
>LSHB_HUMAN P01229_Mature 21-141
SREPLRPWCHPINAILAVEKEGCPVCITVNTTICAGYCPTMMRVLQAVLPPLPQVVCTYR
DVRFESIRLPGCPRGVDPVVSFPVALSCRCGPCRRSTSDCGGPKDHPLTCDHPQLSGLLF
L >LSHB_PANTR Q2Q1P2_Mature 21-141
SREPLRPWCHPINATLAVEKEGCPVCITVNTTICAGYCPTMMRVLQAVLPPLPQVVCTYR
DVRFESIRLPGCPRGVDPVVSFPVALSCRCGPCRRSTSDCGGPKDHPLTCDHPQLSGLLF
L >LSHB_GORGO Q2Q1P1_Mature 21-141
SREPLRPRCRPINATLAVEKEGCPVCITVNTTICAGYCPTMMRVLQGVLPPLPQVVCTYR
DVRFESIXLPGCPRGVDPMVSFPVALSCRCGPCHRSTSDCGGPNDHPLTCDHPQLSGLLF
L
```

```
>LSHB_MOUSE O09108_Mature 21-141
SRGPLRPLCRPVNATLAAENEFCPVCITFTTSICAGYCPSMVRVLPAALPPVPQPVCTYR
ELAFASVRLPGCPPGVDPIVSFPVALSCRCGPCRLSSSDCGGPRTQPMACDLPHLPGLLL
L >LSHB_RAT P01230_Mature 21-141
SRGPLRPLCRPVNATLAAENEFCPVCITFTTSICAGYCPSMVRVLPAALPPVPQPVCTYR
ELRFASVRLPGCPPGVDPIVSFPVALSCRCGPCRLSSSDCGGPRTQPMTCDLPHLPGLLL
F
```

Choriogonadotropin Beta (hCG-B):

```
Human:        CGHB_HUMAN        P01233        SEQ ID NO 9

>CGHB_HUMAN P01233_Mature 21-165
SKEPLRPRCRPINATLAVEKEGCPVCITVNTTICAGYCPTMTRVLQGVLPALPQVVCNYR
DVRFESIRLPGCPRGVNPVVSYAVALSCQCALCRRSTTDCGGPKDHPLTCDDPRFQDSSS
SKAPPPSLPSPSRLPGPSDTPILPQ
```

Follicle Stimulating Hormone

```
              Follitropin subunit beta
Human:        FSHB_HUMAN        P01225        SEQ ID NO 10

Mouse:        FSNB_MOUSE        Q60687        SEQ ID NO 11

Rat:          FSHB_RAT          P18427        SEQ ID NO 12

Gorilla:      FSHB_GORGO        A1BN60        SEQ ID NO 13

Chimpanzee:   FSHB_PANTR        Q2PUH2        SEQ ID NO 14

>FSHB_HUMAN P01225_Mature 19-129
NSCELTNITIAIEKEECRFCISINTTWCAGYCYTRDLVYKDPARPKIQKTCTFKELVYET
VRVPGCAHHADSLYTYPVATQCHCGKCDSDSTDCTVRGLGPSYCSFGEMKE >FSNB_MOUSE Q60687_Mature 21-130
SCELTNITISVEKEECRFCISINTTWCAGYCYTRDLVYKDPARPNTQKVCTFKELVYETV
RLPGCARHSDSLYTYPVATECHCGKCDSDSTDCTVRGLGPSYCSFSEMKE >FSHB_RAT P18427_Mature 21-130
SCELTNITISVEKEECRFCISINTTWCEGYCYTRDLVYKDPARPNTQKVCTFKELVYETI
RLPGCARHSDSLYTYPVATECHCGKCDSDSTDCTVRGLGPSYCSFGEMKE >FSHB_GORGO A1BN60_Mature 21-129
CELTNITIAIEKEECRFCISINTTWCAGYCYTRDLVYKDPARPNIQKTCTFKELVYETVR
VPGCAHHADSLYTYPVATQCHCGKCDSDSTDCTVRGLGPSYCSFGEMKE >FSHB_PANTR Q2PUH2_Mature 21-129
CELTNITIAIEKEECRFCISINTTWCAGHCYTRDLVYKDPARPNIQKTCTFKELVYETVR
VPGCAHHADSLYTYPVATQCHCGKCDSDSTDCTVRGLGPSYCSFGEMKE
```

Corifollitropin Alpha

Corifollitropin alpha consists of the gonadotropin alpha chain (SEQ ID NO 1) and the beta chain of FSH+the C-terminal 28 amino acids of hCG (marked in bold). SEQ ID NO: 15

```
NSCELTNITIAIEKEECRFCISINTTWCAGYCYTRDLVYKDPARPKIQKT

CTFKELVYETVRVPGCAHHADSLYTYPVATQCHCGKCDSDSTDCTVRGLG

PSYCSFGEMKESSSSKAPPPSLPSPSRLPGPSDTPILPQ
```

Example 3

Method Producing Long Acting hLH

A long acting hLH is produced by chemical conjugation of hLH to human serum albumin or a variant of human serum albumin with selected improved or reduced affinity for the neonatal Fc receptor.

Chemical conjugation can be performed using a multitude of different chemistries and linkers known in the art, including linkers with a high covalent stability and linkers with lower covalent stability having the potential of releasing the active component from the albumin molecule typically by hydrolysation of a labile chemical bond.

Suitable attachment groups on the albumin molecule are apparent from the table below

| Attachment group | Amino acid | Examples of non-peptide moiety | Conjugation method/-Activated PEG | Reference |
|---|---|---|---|---|
| —NH2 | N-terminal, Lys, His, Arg | Polymer, e.g. PEG, with amide or imine group | mPEG-SPA Tresylated mPEG | Shearwater Inc. Delgado et al., critical reviews in Therapeutic Drug Carrier Systems 9(3, 4): 249-304 (1992) |
| —COOH | C-term, Asp, Glu | Polymer, e.g, PEG, with ester or amide group Oligosaccharide moiety | mPEG-Hz In vitro coupling | Shearwater Inc. |
| —SH | Cys | Polymer, e.g. PEG, with disulfide, critimaleimide or vinyl sulfone group Oligosaccharide moiety | PEG-Vinylsulphone PEG-maleimide In vitro coupling | Shearwater Inc. Delgado et al., critical reviews in Therapeutic Drug Carrier Systems 9(3, 4): 249-304 (1992) |
| —OH | Ser, Thr, —OH, Lys | Oligosaccharide moiety PEG with ester, ether, carbamate, carbonate | In vivo O-linked glycosylation | |
| —CONH2 | Asn as part of an N-glycosylation site | Oligosaccharide moiety Polymer, e.g. PEG | In vivo N-glycosylation | |
| Aromatic residue | Phe, Tyr, Trp | Oligosaccharide moiety | In vitro coupling | |
| —CONH2 | Gln | Oligosaccharide moiety | In vitro coupling | Yan and Wold, Biochemistry, 1984, Jul. 31; 23(16): 3759-65 |
| Aldehyde Ketone | Oxidized oligosaccharide | Polymer, e.g. PEG, PEG-hydrazide | PEGylation | Andresz et al., 1978, Makromol. Chem. 179: 301, WO92/16555, WO00/23114 |
| Guanidino | | Oligosaccharide moiety | In vitro coupling | Lundblad and Noyes, Chemical Reagents for Protein Modification, CRC Press Inc., Florida, USA |
| Imidazole ring | His | Oligosaccharide moiety | In vitro coupling | As for guanidine |

Especially suitable is coupling to the free cysteine residue on the albumin molecule (Cys 34), e.g. by methods described in WO2010092135, especially the methods using PDPH (3-(2-pyridyldithio)propionyl hydrazide) to link albumin to hCG via a hydrazone link to hCG. In another aspect the method in WO2010092135 using EMCH ((3,3'-N-(ε-maleimidocaproic acid) hydrazide) to link albumin to hCG via a hydrazone link to hLH is used.

Suitable attachment groups on the hLH molecule include those in the table above, and include chemistries for coupling to the glycosylation moieties of the hLH molecule. Coupling to the glycosylation moieties is preferred as these are expected not to have direct interaction with the hLH receptor and thereby the coupling will not interfere with the function.

Yet another coupling technology is described by Neose (see eg US2004/0126838) using enzymatic glycoconjugation. This technology can be used to link e.g. albumin to hLH using a suitable linker.

In the special case where chemical conjugation to the hLH molecule strongly reduce the functional activity it will be preferable to use a labile linker that can release a functional hLHCG. It is preferable to attach only one albumin molecule pr. hLH molecule.

In another instance the coupling of the hLH and the albumin molecule can be performed by genetic fusion of the two molecules. As the hLH molecule has two chains there are four different orientation possibilities:
 Albumin-hLH(alpha chain)
 Albumin-hLH(beta chain)
 hLH(alpha chain)-albumin
 hLH(beta chain)-albumin Recombinant hLH packaged as lyophilized powder in the product Luveris® produced by EMD Serono are available and can be reconstituted in 1.0 mL solution containing 82.5 IU recombinant hLH. The formulation excipients can be removed by dialysis and gel filtration. Albumin or albumin variants can be produced as described in WO2010092135. The recombinant hLH and the albumin can be conjugated using the PDPH or EMCH chemistry as described in WO2010092135.

Example 4

Covalent Attachment of SPA-PEG to hLH or Variants Thereof

Human LH and variants thereof are covalently linked to SPA-PEG 5000, SPA-PEG 12000 and SPA-PEG 20000 (NOF Corporation) as described below ("PEGylation of hLH and variants thereof in solution").

PEGylation of hLH and Variants Thereof in Solution

Human LH and variants thereof are PEGylated at a concentration of 250 µg/ml in 50 mM sodium phosphate, 100 mM NaCl, pH 8.5. The molar surplus of PEG is 5-100 times with respect to PEGylation sites on the protein. The reaction mixture is placed in a thermo mixer for 30 minutes at 37° C. 10 at 1200 rpm. After 30 minutes, quenching of the reaction is obtained by adding a molar excess of glycine.

Cation exchange chromatography is applied to remove excess PEG, glycine and other by-products from the reaction mixture. The PEGylation reaction mixture is diluted with 20 mM sodium citrate pH 2.5 until the ionic strength is less than 7 mS/cm. pH is adjusted to 2.5 using 5 N HCl. The mixture is applied to a SP-sepharose FF column equilibrated with 20 mM sodium citrate pH 2.5. Unbound material is washed off the column using 4 column volumes of equilibration buffer. PEGylated protein is eluted in three column volumes by adding 20 mM sodium citrate, 750 mM sodium chloride. Pure PEGylated hLH is concentrated and buffer exchange is performed using VivaSpin concentration devices, molecular weight cut-off (mwco): 10 kDa.

Example 5

Production and Characterization of 1:1 Conjugates Between hCG and Recombinant Human Albumin or K573P Variant of Human Albumin Materials Recombinant Human Albumin (Recombumin, Novozymes Biopharma) was supplied as a 200 mg/ml solution. The original vial was aliquoted into 50×1 ml aliquots in a laminar flow cabinet. Aliquots were stored refrigerated.

Recombinant Human Albumin variant K573P may be produced as described in WO2011051489. The compound (112 mg/ml) was stored refrigerated.

Recombinant hCG was produced from the product Ovitrelle (Merck Serono), and formulation excipients were removed by a buffer change using GE Healthcare, disposable PD-10 desalting columns as described for each conjugate.

PDPH ((3-[2-pyridyldithio]propionyl hydrazide), EMCH (N-[maleimidocaproic acid]hydrazide)), SPDP (N-Succinimidyl 3-(2-pyridyldithio)-propionate) and EDC (1-Ethyl-3-[3-dimethylaminopropyl]carbodiimide hydrochloride) was purchased from Thermo Fisher Scientific Inc.

All other chemicals and materials was standard laboratory quality.

Methods

Size Exclusion HPLC (SEC-HPLC):

Analytical SEC-HPLC was undertaken using an Agilent HP1100 machine fitted with a multi-wavelength detector. Analytical columns used were:

TSK g3000 SWXL (7.8 mm id×30 cm length) with TSK-SWXL guard column

TSK g3000 SWXL (7.5 mm id×60 cm length) with TSK-SWXL guard column

Prep-scale HPLC was undertaken using a Waters HPLC system. Prep columns used were:
 Superdex 200 26/600 Hiload
 Superdex 200 10/300 GL All columns were run in 0.2 µm filtered PBS at pH 7.4 unless described otherwise.

Detection was at 280 nm.

Typical run conditions/analysis times are shown in the Table below.

| Column | Method | Flow rate (ml/min) | Analysis time (min) |
|---|---|---|---|
| Superdex 200 26/600 Hiload | Manual | 2.6 | 120 |
| Superdex 200 10/300 GL | SPRDX200.M | 0.5 | 60 |
| TSK g3000 30 cm | hCG.M | 1 | 15 |
| TSK g3000 60 cm | TSK60.M | 1 | 30 |

SDS Non-Reducing Gels:

Optimal separation/resolution for SDS non-reducing gels was achieved using Novex 4-12% Tris-glycine gels. Running Buffer was Tris acetate SDS running buffer. Sample preparation was as follows:

5 µl LDS sample buffer was added to 15 µl sample. Incubate 5 minutes at room temperature 10 µl sample loaded onto gel All gels were run at a constant voltage of 150V, run time ~60 minutes.

Gels were washed for 5 minutes with deionised water, stained with Gel Code Blue Safe-Stain (ThermoFisher) and de-stained using deionised water.

SDS Reducing Gels:

Optimal separation/resolution for SDS non-reducing gels was achieved using Novex 4-12% Tris-glycine gels. Running Buffer was Tris-glycine SDS running buffer. Sample preparation was as follows:

5 µl LDS sample buffer
2 µl NuPAGE reducing agent
15 µl sample.

Samples were heated to 85 deg. C. for two minutes and 10 µl sample was loaded onto the gel. All gels were run at a constant voltage of 150V, run time ~60 minutes. Gels were washed and stained/de-stained as for non-reducing gels.

Spectrophotometric Methods (A280):

Measurement was performed using a Shimadzu UV-160 spectrophotometer with 1 cm quartz microcuvette over the range 220-320 nm, following baseline correction against the sample buffer.

Endotoxin Measurements:

Endotoxin measurements were taken using a Charles River Portable Test System (PTS) with a 1-0.01 EU/mL. Samples were analysed after dilution with 1/10 ratio of dispersal reagent (0.05 mL sample+0.1 mL dispersal agent+0.35 mL LAL water). A PTS endotoxin cartridge was used to analyse the samples post dilution.

A: Production of Conjugate 1

Conjugate 1 is a 1:1:1 hCG-PDPH-Albumin conjugation produced by conjugation of PDPH linker to oxidized sialic acids on hCG and further coupling of hCG-PDPH to rHA via formation of a disulphide bond to the free cysteine at rHA as described for PDPH by the manufacturer.

Preparation of hCG:

Thirty syringes of Ovitrelle were pooled (totaling 15 ml, 7.5 mg hCG) and concentrated to ~5 mg/ml using vivaspin 500 centrifugal concentrators in a bench top centrifuge at 13,000 rpm. The concentrated solution was buffer changed using three PD-10 desalting columns, equilibrated in phosphate buffered saline at pH 7.4. 500 µl solution was loaded onto each column and washed in with 2.5 ml PBS. hCG was eluted in 1 ml PBS. The buffer changed hCG concentration was determined by A280 measurement using an extinction coefficient of 0.459 for a 1 mg/ml solution.

Periodate Oxidation of hCG:

A 1 mg/ml solution of sodium periodate in H2O was prepared. This was added to chilled hCG solution (44 µl per mg hCG), wrapped in foil to protect from light, and placed on ice for 35 minutes. Unreacted periodate was removed from the reaction mixture using two PD-10 desalting columns, equilibrated in phosphate buffered saline at pH 7.4. The reaction mixture was divided into two equal aliquots, loaded onto columns, and washed in to a total volume of 2.5 ml with PBS. Oxidised hCG was eluted in 500 µl aliquots of PBS. Protein containing peak fractions were identified by A280 measurement and pooled. The hCG concentration was determined by A280 measurement. The oxidised hCG solution was concentrated to ~8 mg/ml hCG using vivaspin 500 centrifugal concentrator.

Reaction of Oxidised hCG with PDPH:

A 100 mg/ml solution of PDPH in dimethyl sulphoxide (DMSO) was prepared. This was added to the oxidised hCG solution to give a 32.5 fold molar excess of PDPH (3 µl PDPH solution per mg hCG), mixed gently and placed in a water bath at 25 deg. C. for 3 hours. To remove unreacted crosslinker, the reaction mixture was loaded onto a PD-10 column equilibrated in PBS, and washed in to a total volume of 2.5 ml with PBS. The hCG-PDPH was eluted in 500 µl aliquots of PBS. Peak fractions were identified by A280 measurement and pooled.

Preparation of rHA:

Recombumin rHA was purified to remove rHA dimer, prior to reaction with hCG-PDPH. The rHA (500 µl) was loaded onto a Superdex 200 10/300 GL column and eluted in PBS as described in above. The monomer peak was collected. rHA concentration was determined by A280 measurement using a 1 mg/ml extinction coefficient of 0.51. The purified rHA was concentrated to ~200 mg/ml using a vivaspin 500 centrifugal concentrator in a benchtop centrifuge at 13,000 rpm.

Reaction of hCG-PDPH with rHA:

Purified rHA was added to the hCG-PDPH solution to give a 5 fold molar excess of rHA (12.8 mg rHA per mg hCG), mixed gently and placed in a waterbath at 25 deg. C. for 3 hours.

Purification of 1:1:1 Conjugate:

The reaction mixture was divided into two 500 µl aliquots. The first aliquot was loaded onto a Superdex 200 10/300 GL column and eluted in PBS as described above. The conjugate peak was collected. This was repeated with the second aliquot of reaction mixture. Conjugate peaks were pooled and conjugate concentration was determined by A280 measurement using a 1 mg/ml extinction coefficient of 0.496.

The conjugate solution was re-concentrated tenfold, to a volume of 700 µl, using vivaspin500 centrifugal concentrators. This concentrated conjugate solution was purified in 100 µl aliquots using a Superdex 200 10/300 GL column as before.

The purified conjugate solution was filtered through a 0.2 µm filter, pipetted into 50 µl aliquots in sterile 500 µl eppendorf tubes, and frozen.

The samples were analyzed by reducing and non-reducing SDS-PAGE (FIGS. 8a and 8b) and by SEC-HPLC (FIG. 8c).

Conjugate 1 stability was analyzed for 96 hours at four different conditions; 5 deg. C. (pH 7.4), 37 deg. C. (pH 7.4), 37 deg. C. (pH 6.4), and 37 deg. C. (pH 5.4). The samples were analyzed by SEC-HPLC

| Storage Conditions | | 5 deg. C. pH 7.4 | 37 deg. C. pH 7.4 | 37 deg. C. pH 6.4 | 37 deg. C. pH 5.4 |
|---|---|---|---|---|---|
| t = 0 | conjugate | 89.9% | — | — | — |
|  | monomer | 7.5% | — | — | — |
| t = 12 h | conjugate | 92% | 70.4% | 75.6% | 69.9% |
|  | monomer | 8% | 29.6% | 24.4% | 30.1% |
| t = 24 | conjugate | 90% | 53.2% | 70.4% | 65.6.1% |
|  | monomer | 10% | 46.8% | 29.6% | 34.4% |
| t = 48 | conjugate | 90.4% | 32.5% | 63.3% | 57.0% |
|  | monomer | 9.6% | 67.5% | 36.7% | 43.0% |
| t = 96 | conjugate | 89.7% | 20.4% | 45.8% | 46.6% |
|  | monomer | 10.3% | 79.6% | 54.2% | 53.4% |

The result of the stability analysis it that non-conjugated hCG is released at an initial speed of app. 40% per day.

B: Production of Conjugate3

Conjugate3 is a 1:1:1 hCG-SPDH-Albumin conjugation produced by conjugation of SPDP linker to free amines (on N-termini or on lysine side chains) on hCG and further coupling of hCG-SPDP to rHA via formation of a disulphide bond to the free cysteine at rHA as described by the SPDP manufacturer.

Preparation of hCG:

Twenty syringes of Ovitrelle were pooled (10 ml, 5 mg hCG) and concentrated to app. 2 ml using 6 Vivaspin500 centrifugal concentrators in a benchtop centrifuge at 13,000 rpm. The concentrated solution was buffer changed using 2 PD-10 desalting columns, equilibrated in citrate buffer at pH 5.9. Half of the solution was loaded onto each column and washed in to a total volume of 2.5 ml with citrate buffer. The hCG was eluted in 500 µl aliquots of citrate buffer. Peak fractions were identified by A280 measurement and pooled. The hCG concentration was determined by A280 measurement using an extinction coefficient of 0.459 and diluted to a concentration of 1 mg/ml with citrate buffer.

Reaction of hCG with SPDP:

A 2.5 mg/ml solution of SPDP in DMSO was prepared. This was added to the hCG solution to give a 10 fold molar excess of SPDP (50 µl SPDP solution per mg hCG), mixed gently and placed in a water bath at 25 deg. C. for 1 hour. To remove unreacted crosslinker, half of the reaction mixture was loaded onto each of two PD10 columns equilibrated in phosphate buffered saline at pH 7.4, and washed in to a total volume of 2.5 ml with PBS. The hCG-SPDP conjugate was eluted in 500 µl aliquots of PBS. Protein containing peak fractions were identified by A280 measurement and pooled.

Preparation of rHA:

The rHA was purified using a Superdex 200 26/600 Hiload column. The rHA (3 ml) was loaded onto the column and eluted in PBS as described above. The monomer peak was collected. The rHA concentration was determined by A280 measurement as before.

Reaction of hCG-SPDP with rHA:

Purified rHA was added to the hCG-SPDP solution to give a 5 fold molar excess of rHA (12.8 mg rHA per mg hCG), mixed gently and placed in a water bath at 25 deg. C. overnight. The reaction mixture (3 ml) was loaded onto a Superdex 200 26/600 Hiload column and eluted in PBS as described above. The conjugate peak was collected. The solution was sterile filtered, and placed in an incubator at 37 deg. C. for 48 hours, for hydrolysis of weakly bound crosslinker.

Final Purification of 1:1:1 Conjugate:

After hydrolysis the solution was concentrated to a volume of app. 3 ml, using vivaspin500 centrifugal concentrators. Concentrated solution was loaded onto a Superdex 200 26/600 Hiload column and eluted in PBS. The conjugate peak was collected. Conjugate concentration was determined by A280 measurement using a 1 mg/ml extinction coefficient of 0.496. The purified conjugate solution was concentrated to app. 1 mg/ml as before, filtered through 0.2 micom filter, pipetted into 50 µl aliquots in sterile 500 µl eppendorf tubes, and frozen.

The samples were analyzed by reducing and non-reducing SDS-PAGE (FIGS. 9a and 9b) and by SEC-HPLC (FIG. 9c).

Conjugate 3 stability was analyzed for 96 hours at 37 deg. C. (pH 7.4). The samples were analyzed by SEC-HPLC:

| Time | High MW (%) | Conjugate (%) | rHA + hCG monomer (%) |
|---|---|---|---|
| 0 (start) | 4.5 | 95.5 | 0 |
| 24 hours | 2.5 | 95.2 | 2.3 |
| 48 hours | 2.2 | 94.5 | 3.3 |
| 72 hours | 4.7 | 91.0 | 4.3 |
| 96 hours | 3.4 | 91.0 | 5.7 |

The result of the stability analysis was that conjugate 3 is reasonable stable and that non-conjugated hCG is released at an initial speed of app. 2% pr. day.

C: Production of Conjugate4

Conjugate4 is a 1:1:1 hCG-PDPH-Albumin conjugation produced by conjugation of PDPH linker to hCG activated with EDC whereby carboxylic acid groups in hCG will react with PDPH. hCG-PDPH is further coupled to rHA via formation of a disulphide bond to the free cysteine at rHA as described by the PDPH and EDC manufacturer.

Preparation of hCG:

Twenty syringes of Ovitrelle were pooled (10 ml, 5 mg hCG) and concentrated to a volume of app. 1.5 ml using 6 Vivaspin500 centrifugal concentrators in a benchtop centrifuge at 13,000 rpm. The concentrated hCG solution was buffer changed using 3 PD-10 columns, equilibrated in MES buffer at pH 5.3. Approximately 500 μl solution was loaded onto each column and washed into a total volume of 3 ml with MES buffer. hCG was eluted in 1.0 ml MES buffer. The hCG concentration was determined by A280 measurement using an extinction coefficient of 0.459.

Reaction of hCG with EDC and PDPH:

A 50 mg/ml solution of PDPH in DMSO was prepared. This was added to the hCG solution to give 5 mM PDPH in the reaction mixture (1.15 mg/ml PDPH) and mixed gently. A 50 mg/ml solution of EDC in MES buffer was prepared and immediately added to the hCG/PDPH solution to give 2.5 mM EDC in the reaction mixture (0.48 mg/ml EDC). The reaction mixture was mixed gently and placed in a water bath at 25 deg. C. for 30 minutes. To remove unreacted crosslinker, half of the reaction mixture was loaded onto each of two PD-10 columns equilibrated in phosphate buffered saline at pH 7.4, and washed in to a total volume of 2.5 ml with PBS. The hCG-PDPH was eluted in 500 μl aliquots of PBS. Protein containing peak fractions were identified by A280 measurement and pooled.

Preparation of rHA:

rHA was purified using a Superdex 200 26/600 Hiload column. The rHA (3 ml) was loaded onto the column and eluted in PBS. The monomer peak was collected. The rHA concentration was determined by A280 measurement as before.

Reaction of hCG-PDPH with rHA:

Purified rHA was added to the hCG-PDPH solution to give a 5 fold molar excess of rHA (12.8 mg rHA per mg hCG), mixed gently and placed in a water bath at 25 deg. C. for three hours. Half of the reaction mixture was loaded onto a Superdex 200 26/600 Hiload column after three hours. The second half was loaded two hours later, on completion of the first cycle. The conjugate solution was concentrated to a volume of app. 3 ml using vivaspin500 centrifugal concentrators. The solution was sterile filtered, and placed in an incubator at 37 deg. C. for 36 hours, for hydrolysis of weakly bound crosslinker.

Final Purification of 1:1 Conjugate:

The hydrolysed conjugate solution (3 ml) was loaded onto a Superdex 200 26/600 Hiload column and eluted in PBS as described above. The conjugate peak was collected. Conjugate concentration was determined by A280 measurement using a 1 mg/ml extinction coefficient of 0.496. The purified conjugate solution was concentrated to app. 1 mg/ml as before, filtered through 02 μm filter, pipetted into 50 μl aliquots in sterile 500 μl eppendorf tubes, and frozen.

The samples were analyzed by reducing and non-reducing SDS-PAGE (FIGS. 10*a* and 10*b*) and by SEC-HPLC (FIG. 10*c*)

Conjugate 4 stability was analyzed for 96 hours at 37 deg. C. (pH 7.4). The samples were analyzed by SEC-HPLC:

| Incubation time (h) | % monomer |
|---|---|
| 0 (start) | 0 |
| 24 | 2.7 |
| 48 | 3.7 |
| 72 | 4.6 |
| 96 | 4.5 |

The result of the stability analysis was that conjugate 3 is reasonable stable and that non-conjugated hCG is released at an initial speed of app. 2% per day.

D: Production of Conjugate3V1

Conjugate3V1 is rhCG-SPDP-rHA(K573P).

A conjugate of hCG and rHA variant (K573P) was prepared using SPDP crosslinker, using the method used to produce Conjugate3 as described above. The samples were analyzed by reducing and non-reducing SDS-PAGE (FIGS. 11*a* and 11*b*) and by SEC-HPLC (FIG. 11*c*).

Conjugate 3V1 stability was analyzed for 96 hours at 37 deg. C. (pH 7.4). The samples were analyzed by SEC-HPLC:

| Incubation time (h) | % monomer |
|---|---|
| 0 (start) | 0 |
| 24 | 3.7 |
| 48 | 4.8 |
| 72 | 5.5 |
| 96 | 6.2 |

The result of the stability analysis was that conjugate 3V1 is reasonable stable and that non-conjugated hCG is released at an initial speed of app. 2% per day.

E: Production of Conjugate4V1

Conjugate4V1 is rhCG-PDPH-rHA(K573P).

A conjugate of hCG and rHA variant (K573P) was prepared using EDC and PDPH crosslinkers, using the method used to produce Conjugate4 as described above. The samples were analyzed by reducing and non-reducing SDS-PAGE (FIGS. 12a and 12b) and by SEC-HPLC (FIG. 12c).

| Incubation time (h) | % monomer |
|---|---|
| 0 (start) | 0 |
| 24 | 2.8 |
| 48 | 3.3 |
| 72 | 4.3 |
| 96 | 5.7 |

The result of the stability analysis was that conjugate 4V1 is reasonable stable and that non-conjugated hCG is released at an initial speed of app. 2% pr day Example 6

Production of hCG-Albumin Fusions and hLH-Albumin Fusions

Construction of Expression Plasmids

Genes encoding the gonadotropin common α-subunit, the hCG β-subunit and the hLH β-subunit and fusions of these three with the gene of human serum albumin at either the 3'-end or at the 5'-end was constructed by assembly of synthetic oligonucleotides using polymerase chain reaction (PCR). The sequence encoding for the natural human signal sequences of the relevant genes was included, and for human serum albumin the gene encoding for the natural pro-peptide was included. The codon usage of the genes was optimized for high expression in mammalian cells. The relevant genes are:

| Gene# | Sequence ID | Gene encoding |
|---|---|---|
| Gene1 | SEQ ID NO 44 | α-chain (348 bases) |
| Gene2 | SEQ ID NO 45 | hCG β-chain (495 bases) |
| Gene3 | SEQ ID NO 46 | LH β-chain (423 bases) |
| Gene4 | SEQ ID NO 47 | Wt Albumin + α-chain (2103 bases) |
| Gene5 | SEQ ID NO 48 | α-chain + wt Albumin (2103 bases) |
| Gene6 | SEQ ID NO 49 | Wt Albumin + hCG β-chain (2262 bases) |
| Gene7 | SEQ ID NO 50 | hCG β-chain + wt Albumin (2250 bases) |
| Gene8 | SEQ ID NO 51 | Wt Albumin + LH β-chain (2190 bases) |
| Gene9 | SEQ ID NO 52 | LH + β-chain + wt Albumin (2178 bases) |

The gene sequences were synthesised by GeneArt AG and sub-cloned into pEE12.4 and pEE6.4 vectors respectively as shown in Tables below

| Product Number | Product name | First Gene | Second Gene |
|---|---|---|---|
| 1 | hCG | Gene1 | Gene2 |
| 2 | hCG-wtA-α-N | Gene4 | Gene2 |
| 3 | hCG-wtA-β-N | Gene1 | Gene6 |
| 4 | hCG-wtA-α-C | Gene5 | Gene2 |
| 5 | hCG-wtA-β-C | Gene1 | Gene7 |
| 6 | LH | Gene1 | Gene3 |
| 7 | LH-wtA-α-N | Gene4 | Gene3 |
| 8 | LH-wtA-β-N | Gene1 | Gene8 |
| 9 | LH-wtA-α-C | Gene5 | Gene3 |
| 10 | LH-wtA-β-C | Gene1 | Gene9 |

N-terminal restriction site Hind III and the C-terminal restriction site EcoRI were used. In short, 5 µg of lyophilised shuttle vector as produced by GeneArt was resuspended in 50 µl endotoxin free, sterile water. 10 µl of the generated 100 ng/ml DNA solution was mixed with 2.5 µl each of EcoRI and HindIII high-fidelity restriction enzymes, 5 µl of 10×NEB buffer and 30 µl endotoxin free, sterile water on ice. Samples were then incubated at 37° C. for 2 hours. 8.3 µl of 6×DNA loading buffer was added and samples electrophoresed at 120 V for 40-60 min on a 1% w/v agarose gel stained with ethidium bromide. 10 µl Lonza SimplyLoad Tandem DNA ladder was used as reference ladder. The agarose gel was imaged using a BioSpectrum Imaging System (UVP).

The relevant fragments were gel-extracted using a QIAquick gel extraction kit according to manufacturer's instructions. Ligations were set-up using a 1:6 and a 1:12 ratio of vector backbone to insert DNA, 1 µl T4 quick ligase, 20 µl of 2× T4 quick ligation buffer, reaction volume adjusted to 20 µl with endotoxin-free, sterile water when necessary and samples incubated at room temperature for 15 minutes. 10 µl aliquots of the ligation reaction were used to transform One Shot Top 10 Chemically Competent *Escherichia coli* cells using the heat-shock method according to manufacturer's instructions. Cells were spread onto ampicillin-containing (50 µg/ml) Luria Bertani agar plates and incubated overnight at 37° C. until bacterial colonies were evident. To screen for recombinants, single bacterial colonies were picked into 15 ml Luria Bertani (LB) medium containing 50 µg/ml ampicillin and incubated at 37° C. for 6 hours with shaking. Vector DNA was isolated from 10 ml of these growth cultures using the QIAGEN miniprep system and eluted in 30 µl EB buffer. Positive recombinants were identified by digestion with Hind III and EcoRI. Aliquots of generated vectors were sent for gene sequencing by 3rd party using vector specific forward (GCTGACAGACTAACAGACTGTTCC SEQ ID NO: MD and reverse (CAAATGTGGTATGGCTGA (SEQ ID NO: 71)) primers. The Table below shows the GS vectors used for each gene.

| Gene | Sub-cloned into |
|---|---|
| 1 | pEE12.4 |
| 2 | pEE6.4 |
| 3 | pEE6.4 |
| 4 | pEE12.4 |
| 5 | pEE12.4 |
| 6 | pEE6.4 |
| 7 | pEE6.4 |
| 8 | pEE6.4 |
| 9 | pEE6.4 |

DNA Amplification:

For DNA amplification, 5 ml of the growth cultures produced during the colony screening were used to inoculate 1.5 L Luria Bertani (LB) medium containing 50 µg/ml ampicillin, and incubated 37° C. overnight with shaking at 220 rpm. Vector DNA was isolated using the QIAGEN Plasmid Plus Gigaprep system. In all instances, DNA concentration was measured using a Nanodrop 1000 spectrophotometer (Thermo-Scientific) and adjusted to 1 mg/ml with endotoxin-free, sterile water. FIG. 13 show confirmation of the gene sizes.

Routine Culture of CHOK1SV Cells:

CHOK1SV cells were cultured in CD-CHO media supplemented with 6 mM glutamine. Cells were incubated in a shaking incubator at 36.5° C., 10% CO2, 85% humidity, 140 rpm. Cells were routinely sub-cultured every 3-4 days, seeding at 2×105 cells/ml and were propagated in order to have sufficient cells available for transfection. Cells were discarded by passage 20.

Transient Transfections of CHOK1SV Cells:

Transient transfections were performed using CHOK1SV cells which had been in culture a minimum two weeks. Cells were sub-cultured 24 h prior to transfection and cell viability was >99% at the time of transfection. All transfections were carried out via electroporation using the Gene Pulse MXCell (Bio-Rad), a plate based system for electroporation. For each transfection, viable cells were resuspended in pre-warmed media to 2.86×107 cells/ml. 80 µg DNA (40 µg per single gene vector) was aliquotted into each well and 700 µl cell suspension added. Cells were electroporated at 300 V, 1300 µF. Transfected cells were transferred to pre-warmed media in Erlenmeyer flasks and the wells rinsed twice with pre-warmed media which was also transferred to the flasks. Transfected cell cultures were incubated in a shaking incubator at 36.5° C., 10% CO2, 85% humidity, 140 rpm for 6 days. Cell viability was measured at the time of harvest using a Cedex HiRes automated cell counter (Roche).

Purification of Albumin Linked Products:

For all purifications, culture supernatant was harvested and clarified by centrifugation at 2000 rpm, 10 mins. Clarified supernatant was concentrated approximately 10 times to approximately 100-150 ml using Tangential-Flow-Filtration (TFF) with a 30 kDa MWCO filter. The concentrated supernatant was purified using 5 ml of CaptureSelect HSA resin (BAC, 191.2970.05) which was packed into a 10/50 Tricorn column (GE Healthcare, 28-4064-14) at a flow rate of 2 ml/min. The column was equilibrated and washed with 50 mM sodium phosphate, 125 mM sodium chloride (PBS buffer), pH 7.4 after loading of cell culture supernatant. Elution was initiated with 20 mM Tris, 2 M magnesium chloride, pH 7.4. After each run the column was cleaned in place with PBS buffer, pH 2.0.

Purification of Wild Type hCG and LH:

Clarified supernatant was concentrated approximately 10 times to approximately 100-150 ml using Tangential-Flow-Filtration (TFF) with a 10 kDa MWCO filter. The concentrated supernatant was purified using a HiTrap Capto Q column (5 ml, GE Healthcare, 11-0013-03) at a flow of 5 ml/min. The column was equilibrated and washed with 20 mM Tris, pH 8.0 after loading of cell culture supernatant. Elution was initiated by applying a linear elution gradient to 20 mM Tris, 1 M sodium chloride, pH 8.0 over 20 column volumes. After each run the column was cleaned in place with 0.5 M NaOH.

Analysis of Products 1-10 by SDS PAGE

Reduced samples were prepared for analysis by mixing with NuPage 4×LDS sample buffer (Invitrogen, NP0007) and NuPage 10× sample reducing agent (Invitrogen, NP0009), and incubated at 70° C., 10 min. For non-reduced samples, the reducing agent and heat incubation were omitted. Samples were electrophoresed on 1.5 mm NuPage 4-12% Bis-Tris Novex pre-cast gels (Invitrogen, NP0315) with NuPage MES SDS running buffer under denaturing conditions. 10 µl aliquots of SeeBlue Plus 2 pre-stained molecular weight standard (Invitrogen, LC5925) and of a control antibody or hCG protein at 1 mg/ml were included on the gel. 10 µl of each sample at 1 mg/ml were loaded onto the gel. Once electrophoresed, gels were stained with InstantBlue (TripleRed, ISB01 L) for 30 min at room temperature. Images of the stained gels were analysed on a BioSpectrum Imaging System (UVP) (see FIG. 17).

Analysis of Products 1-10 by Western Blot Methods

Gels, prepared as described for SDS PAGE with the inclusion of an appropriate control (Human Serum Albumin (Abcam, ab7473) or hCG (Ovitrelle, Serono), were transferred onto nitrocellulose membrane (0.2 µm pore size) using X-Cell II Blot module (Invitrogen) in NuPAGE transfer buffer (Invitrogen) over 1.5 hours at 25 V, 100-125 mA. The Western Blot was performed using Western Breeze Chromogenic Western Blot Immunodetection kits (Invitrogen), according to manufacturers instructions. Briefly, membranes were blocked for 30 min, room temperature and washed 2×20 ml H2O. Membranes were incubated with primary antibody solution, for 1 hour at room temperature. The membrane was washed with 4×20 ml wash solution and incubated with secondary antibody solution for 30 min at room temperature. The membrane was once again washed with 4×20 ml of wash solution followed by 2×20 ml H2O, incubated in 5 ml Chromogenic substrate until bands developed, then rinsed 2×20 ml H2O and dried. Images of the dried membranes were analysed on a BioSpectrum Imaging System (UVP).

Anti-HSA Western Blot:

This Western Blot used a goat anti-Human Serum Albumin antibody (Abcam, ab19180) as primary antibody. It was used at 1:2000 dilution (0.5 µg/ml final concentration). A Goat Western Breeze Chromogenic Western Blot Immunodetection kit was used (Invitrogen, WB7107) See FIG. 14.

Anti-hCG Alpha Chain Western Blot:

This Western Blot used a polyclonal goat anti-hCG alpha chain (Abcam, ab20712) as primary antibody. It was used at 1:10000 dilution (0.6 µg/ml final concentration). A Goat Western Breeze Chromogenic Western Blot Immunodetection kit was used (Invitrogen, WB7107), see FIG. 15.

Anti-hCG Beta Chain Western Blot:

This Western Blot used a monoclonal mouse anti-hCG beta chain antibody (Abcam, ab9582) as primary antibody. It was used at 1:333.33 dilution (0.6 µg/ml final concentration). A Mouse Western Breeze Chromogenic Western Blot Immunodetection kit was used (Invitrogen, WB7103), see FIG. 16.

The western blot analysis identified and confirmed successfully the individual building blocks of the products.

Analysis by SEC

Duplicate samples were analysed by SE-HPLC on an Agilent 1200 series HPLC system, using a Zorbax GF-250 4 µm 4.6 mm ID×25 cm column (Agilent) or a Zorbax GF-250 4 µm 9.2 mm ID×25 cm column (Agilent). Aliquots of sample at a concentration of 1 mg/ml were filtered through a 0.2 µm filter prior to injection. 20 or 100 µl aliquots were injected respectively and run at 1 ml/min for 5 to 15 minutes. Soluble aggregate levels were analysed using Chemstation software.

Example 7

Production of hCG-Fc Fusion and LH-Fc Fusion

Construction of Expression Plasmids

Genes encoding fusion of the gonadotropin common a-subunit and a linker (GGGGSGGGGSGGGGS (SEQ ID NO: 57)) with the Fc of a human IgG1, fusion of the hCG β-subunit and a linker (GGGGSGGGGSGGGGS (SEQ ID NO: 57)) with the Fc of a human IgG1 and fusion of the hLH β-subunit and a linker (GGGGSGGGGSGGGGS (SEQ ID NO: 57)) with the Fc of a human IgG1 was constructed by assembly of synthetic oligonucleotides using polymerase chain reaction (PCR). The sequence encoding for the natural human signal sequences of the relevant genes was included. The codon usage of the genes was optimized for high expression in mammalian cells. The relevant genes are:

| Gene # | Sequence ID | Protein chain |
|---|---|---|
| Gene10 | SEQ ID NO 53 | α-chain + link + Fc (1074 bases) |
| Gene11 | SEQ ID NO 54 | hCG β-chain + link + Fc + His-tag (1239 bases) |
| Gene12 | SEQ ID NO 55 | LH β-chain + link + Fc + His-tag (1167 bases) |

The gene sequences were synthesised by GeneArt AG and sub-cloned into pEE12.4 and pEE6.4 vectors respectively as shown in Tables below. All work was performed as described in Example 6.

| Product Number | Product name | First Gene | Second Gene |
|---|---|---|---|
| 11 | hCG-Fc | Gene10 | Gene11 |
| 12 | LH-Fc | Gene10 | Gene12 |

| Gene | Sub-cloned into |
|---|---|
| 10 | pEE12.4 |
| 11 | pEE6.4 |
| 12 | pEE6.4 |

FIG. 13 show confirmation of the gene sizes.

DNA amplification, culture and transfection of CHOK1SV cells were performed as described in Example 6.

Purification:

Protein A purification was used to purify the Fc-fusion products. Clarified supernatant was purified using a pre-packed 5 ml HiTrap MabSelect SuRE column (GE Healthcare, 11-0034-94) on an AKTA purifier (10 ml/min). The column was equilibrated with 50 mM sodium phosphate, 125 mM sodium chloride, pH 7.3, washed with 50 mM sodium phosphate and 1 M sodium chloride pH 7.3 and eluted with 10 mM sodium formate, pH 3.5. Eluted fractions were immediately pH adjusted to pH 7.3.

Analysis of Products 11 and 12 by SDS PAGE

The purified materials were analyzed by reduced and non-reduced SDS PAGE as described in example 6 (see FIG. 18).

Analysis by SEC-HPLC

The purified materials were further analyzed by Size Exclusion Chromatography as described in Example 6 confirming purity and identity.

Example 8

Measurement of In Vitro Activity of hCG and LH Variants

The MLTC-1 line (murine leydig tumor cell line MLTC-1 (ATCC-CRL-2065)), expressing the LH/hCG receptors was seeded at an appropriate cell density and challenged with LH/hCG variants on day 1 of culture. In response to this challenge the steroidogenic pathway was activated in the cells and progesterone and testosterone produced and secreted.

Cells were propagated in RPMI medium and for the assay seeded at a concentration of 80000 c/ml or 8000 c/well.

Cell Culture:

Day 0: seeding of the MLTC cells
Day 1—T=0 h:
  Exposure according to experimental setup
Day 1—T=4 h:
  Collection of the spent medium for progesterone and/or testosterone quantification.
  Spent medium of the duplo wells is pooled and stored at −20° C.
Day 2—T=24 h:
  Collection of the spent medium for progesterone and/or testosterone quantification.
  Spent medium of the duplo wells is pooled and stored at −20° C.

Steroid Quantification in Spent Medium:

The levels of steroid hormone was measured using the Meso Scale Discovery Multi-Spot Assay System:

The spent medium are added to a MULTI-SPOT 96-well Human Progesterone or Testosterone Plate.

1. Add 25 μL/well of Detection Reagent (solution of Diluent 22 containing diluted SULFO-TAG progesterone).
2. Add 25 μL/well Calibrator or sample and incubate at room temperature with shaking for 1 hour.
3. Prepare SECTOR® instrument such that the plate can be read immediately following Read Buffer addition.
4. Wash plates 3 times with PBS.
5. Add 150 μL/well 1× Read Buffer T. Avoid bubbles. The use of an electronic multi-pipettor at moderate speed setting is recommended.
6. Read the plate on the SECTOR instrument.

All buffers and reference standards provided by the vendor.

EC-50 is calculated for all compounds using Prism software from Graphpad Software, Inc. Graphs are fitted using non-linear regression with or without fixed slopes and/or max and min values.

The method was applied to the compounds from example 5 and the products from example 6 and example 7. The results are shown in FIGS. 19a-d.

Example 9

In Vivo Potency of LH/hCG Variants

The objective of the study was to determine the potency of hCG/LH test material with respect to its HCG stimulating activities in the LH assay. The effect on growth stimulation of the seminal vesicles in immature male rats was assessed. Different dosing regimens, e.g. daily dosing, dosing every other day or dosing at day one, two, three or four were employed. The LH compounds produced in example 5 and the products produced in example 6 and example 7 were compared to the reference material Ovitrelle. The results were presented as weights of seminal vesicles after dosing of Ovitrelle, and the LH compounds at varying levels over four days.

Both reference and test material were reconstituted daily in PBS-albumin buffer (0.1% albumin) and concentrations adjusted prior to administration. Administration was subcutaneously at the neck at 0.2 ml/rat.

Male SPF Wistar rats at 21 to 23 days of age at arrival were used. Rats within a weight range of no more than 10 g on the first day of dose administration were used in the study. On day 5, 24 hours after last dosing, the rats were euthanised by an overdose of CO2/O2 anaesthesia.

Seminal vesicles were removed and trimmed and blot-dried. The weight of the seminal vesicles were determined and recorded.

The method was applied to the compounds from example 5 and the products from example 6 and example 7. The results are shown in FIGS. 20a-j.

Example 10

Measurement of hCG Content in Rat Serum

Serum collected from rats exposed to LH containing products were sent to Bioscientia GmbH, Institut für Medizinische Diagnostik GmbH, Konrad-Adenauer-Str. 17, 55218 Ingelheim, Germany for analysis, using the ADVIA Centaur Total hCG (ThCG) assay.

The ADVIA Centaur Total hCG (ThCG) assay is a two-site sandwich immunoassay using direct chemiluminometric technology, which uses constant amounts of two antibodies. The first antibody, in the Lite Reagent, is a polyclonal goat anti-hCG antibody that has been affinity purified and labeled with acridinium ester. The second antibody, in the Solid Phase, is a purified monoclonal mouse anti-hCG antibody, which is covalently coupled to paramagnetic particles. These two antibodies are specific for different epitopes that are present on both the free β subunit and the β subunit of intact hCG.

The system automatically performs the following actions:
dispenses 50 µL of sample into a cuvette
dispenses 100 µL of Lite Reagent and 450 µL of Solid Phase and incubates for 7.5 minutes at 37° C.
separates, aspirates, and washes the cuvettes with reagent water 3
dispenses 300 µL each of Acid Reagent and Base Reagent to initiate the chemiluminescent reaction
reports results according to the selected option, as described in the system operating instructions or in the online help system A direct relationship exists between the amount of hCG present in the serum sample and the amount of relative light units (RLUs) detected by the system.

Dilution curves of the respective hCG containing products were used for calibration of the data obtained.

Example 11

Measurement of Content of LH Like Immunoreactivity in Rat Serum

Serum collected from rats exposed to LH containing products were sent to Bioscientia GmbH, Institut für Medizinische Diagnostik GmbH, Konrad-Adenauer-Str. 17, 55218 Ingelheim, Germany for analysis, using the Cobas® Luteinizing Hormone ECLIA (Elecsys) assay.

The Elecsys LH assay employs two monoclonal antibodies specifically directed against human LH. The two specific antibodies used recognize particular conformations, with the biotinylated antibodies detecting an epitope constructed from both subunits whereas the antibody with the ruthenium complexa label detects an epitope from the β-subunit. As a result, the Elecsys LH assay shows negligible cross-reactivity with FSH, TSH, hCG, hGH, and hPL.

Test Principle
1st incubation: 20 µL of sample, a biotinylated monoclonal LH-specific antibody, and a monoclonal LH-specific antibody labeled with a ruthenium complex form a sandwich complex.
2nd incubation: After addition of streptavidin-coated microparticles, the complex becomes bound to the solid phase via interaction of biotin and streptavidin.
The reaction mixture is aspirated into the measuring cell where the microparticles are magnetically captured onto the surface of the electrode. Unbound substances are then removed with ProCell/ProCell M. Application of a voltage to the electrode then induces chemiluminescent emission which is measured by a photomultiplier.
Results are determined via a calibration curve which is instrument-specifically generated by 2-point calibration and a master curve provided via the reagent barcode.

Dilution curves of the respective LH containing products were used for calibration of the data obtained.

Example 12

PK Data in Hypophysectomized Male Wistar Rats

The pharmacokinetic profiles of the LH compounds were measured in hypophysectomized male Wistar rats.

The LH compounds were administered subcutaneously at varying dosages at time 0 hours. Blood was sampled from the rats at varying time points—the first 4 blood samples from each rat was collected by sublingual bleeding using 19 G single use needles. The 5th and terminal blood sample was collected under anaesthesia.

Serum was prepared according to following instruction:
The blood samples were collected in SST tubes with clotting activator, Sarstedt RefNo. 41.1500.005. The samples were inverted 5× and then allowed to clot for 30 minutes at ambient temperature. The samples were centrifuged immediately after clotting for 10 minutes at 2500 G, 20° C. The serum was split into two storage vials −50 µl in each vial. 300 µl PBS/BSA is added to one of the vials.

The serum samples were frozen at ≤−15° C. within 60 minutes after centrifugation.

The serum labels of the LH compounds were measured as described in example 10 for hCG containing compounds and as described in example 11 for LH containing compounds. The method was applied to the compounds from example 5 and to the products from example 6 and example 7. The results are shown in FIG. 21a-d and FIG. 22a-h.

Example 13

PK Data in Normal Adult Male Rats

The pharmacokinetic profiles of the LH compounds were measured in normal Sprague Dawley male rats.

The LH compounds were administered subcutaneously at varying dosages at time 0 hours. Blood was sampled from the rats at varying time points—the first 4 blood samples from each rat was collected by sublingual bleeding using 19 G single use needles. The 5th and terminal blood sample was collected under anaesthesia.

Serum was prepared according to following instruction:
The blood samples were collected in SST tubes with clotting activator, Sarstedt RefNo. 41.1500.005. The samples were inverted 5× and then allowed to clot for 30 minutes at ambient temperature. The samples were centrifuged immediately after clotting for 10 minutes at 2500 G, 20° C. The serum was split into two storage vials—100 µl in each vial. 250 µl PBS/BSA was added to one of the vials.

The serum samples were frozen at ≤−15° C. within 60 minutes after centrifugation.

The serum levels of the LH compounds were measured as described in example 10 for hCG containing compounds and as described in example 11 for LH containing compounds. The method was applied to the compounds from example 5 and to the products from example 6. The results are shown in FIG. 23a-d.

Example 14

Comparison of hCG given in the late follicular phase as a substitute for FSH and luteal phase support given as daily injections of low dose r-hCG or r-LH as compared to a standard GnRH antagonist protocol supplemented with luteal phase progesterone administration.

Background

It is becoming increasingly clear that the current method of supporting the luteal phase for optimizing chances of implantation and establishment of a pregnancy is poorly defined. Further the current regimes of administering luteal phase support do not appear to provide sufficient progesterone concentrations in all patients to secure optimal results. In addition, the mode of administration of the most commonly used luteal phase support products have a number of side effects that reduce patients' compliance and acceptance.

The aim of the present study is to determine whether it is possible to develop new stimulation protocols in which no luteal phase progesterone administration is required by combining follicular phase administration of low-dose hCG (i.e. 150-200 IU per day) as a substitute for FSH stimulation in the late follicular phase, while using a GnRH agonist injection for ovulation induction. The use of a GnRH agonist for ovulation induction is known to reduce pituitary output of gonadotropins resulting in an insufficient corpus luteum function. However, the risk of ovarian hyper stimulation syndrome (OHSS) is simultaneously reduced to a near negligible level. In order to secure a proper luteal phase sustaining the establishment of a pregnancy, as well as maintaining the risk of OHSS at low levels, the present study will either administer daily injections of r-hCG (125 IU per day) or r-LH (i.e. 300 IU per day) from the day of oocyte pickup to stimulate the corpus luteum function and augment the endogenous production of progesterone without administration of exogenous progesterone in connection with a GnRH agonist ovulation trigger.

Material and Methods

It is planned to perform two studies, one on each of two clinics, including a total of 90 women per clinic in a randomized clinical evaluation.

Inclusion Criteria:
1. Female age between 25 and 40 years
2. Baseline FSH and LH<12 IU/l
3. Menstrual cycle length between 25-34 days
4. Body Mass Index (BMI) between 18 and 30
5. Both ovaries present and absence of uterine abnormalities Exclusion Criteria
1. The presence of only one ovary.
2. Uterine abnormalities
3. Polycystic ovarian syndrome
4. Diabetes, epilepsy, lever, kidney, heart disease including metabolic diseases as judged by the treating doctor
5. Allergy towards any substance present in the drugs used for administration.
6. Earlier participation in the study Hormonal Treatment Treatment Group-I:

From cycle day two recombinant FSH (r-hFSH; Gonal-F, Merck-Serono, Hellerup, Denmark) is administered in a fixed dose for the first 4 days. The dose is either 150 or 225 IU per day depending on age, BMI, basal FSH, antral follicle count and the ovarian volume. After 4 days, doses can be adjusted depending on the ovarian response.

When at least four follicles reach a diameter of 12 mm, the daily FSH dose (irrespective of which specific dose was used initially) is exchanged with 200 IU hCG daily (r-hCG, Ovitrelle, Merck-Serono, Hellerup, Denmark)—see instructions for dilution below. To prevent a premature LH rise, a fixed GnRH antagonist protocol is used commencing on stimulation day 5 in the morning. On this day, 0.25 mg/day GnRH antagonist (Cetrotide, Merck-Serono, Hellerup, Denmark) is given s.c. daily and will be continued until and including the day of ovulation induction. When three or more follicles reach a diameter of 17 mm ovulation is induced in all patients by the administration of a single bolus of GnRH agonist, such as 0.5 mg buserelin s.c. (Suprefact; Sanofi-Aventis, Hørsholm, Denmark) followed by oocyte pick up (OPU) 34 hours later. In connection with the OPU, at around hours after the buserelin injection, administration of 125 IU IU r-hCG (r-hCG, Ovitrelle, Merck-Serono, Hellerup, Denmark)(see instructions for dilution below) daily will be initiated for luteal phase support and stimulation of endogenous progesterone production. Administration of r-hCG will be continued until the pregnancy test is performed. No exogenous progesterone is administered.

Treatment Group-II:

From cycle day two recombinant FSH (r-hFSH; Gonal-F, Merck-Serono, Hellerup, Denmark) is administered in a fixed dose of 225 IU daily. Also from cycle day two a fixed dose of 150 IU of hCG daily (r-hCG, Ovitrelle, Merck-Serono, Hellerup, Denmark) will be administered—see instructions for dilution below. To prevent a premature LH rise, a fixed GnRH antagonist protocol is used commencing on stimulation day 5 in the morning. On this day, 0.25 mg/day GnRH antagonist (Cetrotide, Merck-Serono, Hellerup, Denmark) is given s.c. daily and will be continued until and including the day of ovulation induction.

When at least four follicles reach a diameter of 12-13 mm, the daily FSH dose is discontinued while the dose of hCG will continue with 150 IU daily until ovulation induction.

When three or more follicles reach a diameter of 17 mm ovulation is induced in all patients by the administration of a single bolus GnRH antagonist of 0.5 mg buserelin s.c. (Suprefact; Sanofi-Aventis, Hørsholm, Denmark) followed by oocyte pick up (OPU) 34 hours later. In connection with the OPU, at around 35 hours after the buserelin injection, administration of 125 IU IU r-hCG (r-hCG, Ovitrelle, Merck-Serono, Hellerup, Denmark)(see instructions for dilution below) daily will be initiated for luteal phase support and stimulation of endogenous progesterone production. Administration of r-hCG will be continued until the pregnancy test is performed. No exogenous progesterone is administered.

Treatment Group-III:

From cycle day two recombinant FSH (r-hFSH; Gonal-F, Merck-Serono, Hellerup, Denmark) is administered in a fixed dose for the first 4 days. The dose is either 150 or 225 IU per day depending on age, BMI, basal FSH, antral follicle count and the ovarian volume. After 4 days, doses can be adjusted depending on the ovarian response. To prevent a premature LH rise, a fixed GnRH antagonist protocol is used commencing on stimulation day 5 in the morning. On this day, 0.25 mg/day GnRH antagonist (Cetrotide, Merck-Serono, Hellerup, Denmark) is given s.c. daily and will be continued until and including the day of ovulation induction. When three or more follicles reach a diameter of 17 mm ovulation is induced in all patients by administration of a single bolus of 0.5 mg buserelin s.c. (Suprefact; Sanofi-Aventis, Hørsholm, Denmark) followed by oocyte pick up (OPU) 34 hours later. In connection with the OPU, at around 35 hours after the buserelin injection, administration of 300 IU r-LH (r-LH, Luveris, Merck-Serono, Hellerup, Denmark) daily will be initiated for luteal phase support and stimulation of endogenous progesterone production. Administration of r-LH will be continued until the pregnancy test is performed. No exogenous progesterone is administered.

Control Group:

From cycle day two recombinant FSH (r-hFSH; Gonal-F, Merck-Serono, Hellerup, Denmark) is administered in a fixed dose for the first 4 days. The dose is either 150 or 225 IU per day depending of age, BMI, basal FSH, antral follicle count and the ovarian volume. After 4 days, doses can be adjusted depending on the ovarian response. To prevent a premature LH rise, a fixed GnRH antagonist protocol is used commencing on stimulation day 5 in the morning. On this day, 0.25 mg/day GnRH antagonist (Cetrotide, Merck-Serono, Hellerup, Denmark) is given s.c. daily and will be continued until and including the day of ovulation induction. When three or more follicles reach a diameter of 17 mm ovulation will be induced in all patients by administration of a single bolus of 250 μg r-hCG (r-hCG, Ovitrelle, Merck-Serono, Hellerup, Denmark) followed by oocyte pick up (OPU) 34-35 hours later. For luteal phase support daily micronized progesterone vaginally, 90 mg per day (Crinone; Merck-Serono, Hellerup, Denmark) and oestradiol 4 mg per day orally (Estrofem; Novo Nordisk, Copenhagen, Denmark) will be administered, commencing the day after OPU and continuing until the day of the pregnancy test.

For all for Groups:

Laboratory procedures will follow the participating clinics normal procedures and will be independent of the randomization. A maximum of two embryos will be transferred on day 2 after retrieval. All laboratory parameters including fertilization rate, cleavage rate will be monitored. A biochemical pregnancy is defined by a plasma β-hCG concentration ≥10 IU/l on day 12 after ET. Clinical pregnancy is defined as an intrauterine gestational sac with a heartbeat 3 weeks after a positive hCG-test.

Randomization

Participating patients will be randomized to one of four groups on stimulation day 1.

Blood Samples and Hormone Assays

Blood samples will be collected on 1) the day of ovulation induction, 2) the day of OPU 3) the day of OPU plus seven and 4) on day 14 after OPU. Serum aliquots (the sample is divided into two equal ampoules) are kept frozen at −20° C. for subsequent analysis of LH, progesterone and hCG. The hormones will be measured using each participating laboratory's in house assay.

Outcome Measures

The primary outcome is the mid-luteal phase progesterone level. Secondary outcome measures include ongoing pregnancy rate, the rate of early pregnancy loss and the OHSS rate.

Dilution of r-hCG for Stimulation

One ampoule of r-hCG (r-hCG, Ovitrelle, Merck-Serono, Hellerup, Denmark) contains 250 μg r-hCG corresponding to approximately 6,500 IU. Using a sterile 2 ml syringe with an injection needle 1 ml of liquid should be drawn from a bottle with 10 ml sterile physiological saline by penetrating the rubber stopper. The content of the ampoule should subsequently be injected into the remaining 9 ml saline in the bottle. The concentration of hCG will now constitute 650 IU/ml in the bottle. In order to provide the patient stimulation with 200 IU hCG 0.3 ml (or precisely 195 IU) from the bottle should be redrawn and injected via a sterile 1 ml syringe.

In order to retrieve a total of 125 IU hCG, 0.19 ml from the bottle should be redrawn and injected via a sterile 1 ml syringe.

In order to retrieve a total of 150 IU hCG, 0.23 ml from the bottle should be redrawn and injected via a sterile 1 ml syringe.

The r-hCG for stimulation should be prepared fresh every day.

Participants and Clinical Activity

Two fertility clinics participate in the study. One fertility clinic undertakes a trial comprising treatment group I and treatment group II and a control group including a total of 90 patients (3 groups of 30 patients). The other fertility clinic undertakes a trial comprising treatment group I, treatment group III and a control group including a total of 90 patients (3 groups of 30 patients).

Example 15 hCG administered in the late follicular phase as a substitute for FSH and luteal phase support administered as daily injections of low dose r-hCG or r-LH were compared to a standard GnRH antagonist protocol supplemented with luteal phase progesterone administration. Thus wild-type hCG was administered as daily small doses to illustrate the effect of S-hCG as described in this patent application.

Background

It has become increasingly clear that the current method of supporting the luteal phase to optimize chances of implantation and establishment of pregnancy is poorly defined. Further the current regimes of administering luteal phase support do not appear to provide sufficient progesterone concentrations in all patients to secure optimal results. In addition, the mode of administration of the most commonly used luteal phase support products have a number of side effects that reduce patients' compliance and acceptance.

The aim of the present study was to determine whether it would be possible to develop a new stimulation protocol in which no luteal phase progesterone administration was required by combining follicular phase administration of low-dose hCG (i.e. 150-200 IU per day) as a substitute for FSH stimulation in the late follicular phase, while using a GnRH agonist injection for ovulation induction. The use of a GnRH agonist for ovulation induction is known to reduce pituitary output of gonadotropins resulting in an insufficient corpus luteum function. However, the risk of ovarian hyper stimulation syndrome (OHSS) is simultaneously reduced to a near negligible level. In order to secure a proper luteal phase sustaining the establishment of a pregnancy, as well as maintaining the risk of OHSS at low levels, patients in the present study were either administered daily injections of r-hCG (125 IU per day) or r-LH (i.e. 300 IU per day) from the day of oocyte pickup to stimulate the corpus luteum function and augment the endogenous production of progesterone without administration of exogenous progesterone in connection with a GnRH agonist ovulation trigger.

Material and Methods

A total of 32 women were included in this prospective randomized trial, which is detailed below:

Inclusion Criteria:
1. Female age between 25 and 40 years
2. Baseline FSH and LH<12 IU/l
3. Menstrual cycle length between 25-34 days
4. Body Mass Index (BMI) between 18 and 30
5. Both ovaries present and absence of uterine abnormalities Exclusion Criteria
1. The presence of only one ovary.
2. Uterine abnormalities
3. Polycystic ovarian syndrome
4. Diabetes, epilepsy, liver, kidney, heart disease including metabolic diseases as judged by the treating doctor
5. Allergy towards any substance present in the drugs used for administration.
6. Earlier participation in the study Hormonal Treatment
Treatment Group-I:
From cycle day two recombinant FSH (r-hFSH; Gonal-F, Merck-Serono, Hellerup, Denmark) was administered in a fixed dose for the first 4 days. The dose was either 150 or 225 IU per day depending on age, BMI, basal FSH, antral follicle count and the ovarian volume. After 4 days, doses were adjusted depending on the ovarian response.

When at least four follicles had reached a diameter of 12 mm, the daily FSH dose (irrespective of which specific dose was used initially) was exchanged with 200 IU hCG daily (r-hCG, Ovitrelle, Merck-Serono, Hellerup, Denmark)—see instructions for dilution below. To prevent a premature LH rise, a fixed GnRH antagonist protocol was used commencing on stimulation day 5 in the morning. On this day, 0.25 mg GnRH antagonist (Cetrotide, Merck-Serono, Hellerup, Denmark) was adminstered s.c. daily and continued until and including the day of ovulation induction. When three or more follicles had reached a diameter of 17 mm ovulation was induced in all patients by the administration of a single bolus of a GnRH agonist, such as 0.5 mg buserelin s.c. (Suprefact; Sanofi-Aventis, Hørsholm, Denmark) followed by oocyte pick up (OPU) 34 hours later. In connection with the OPU, at around 35 hours after the buserelin injection, administration of 125 IU r-hCG (r-hCG, Ovitrelle, Merck-Serono, Hellerup, Denmark)(see instructions for dilution below) daily was initiated for luteal phase support and stimulation of endogenous progesterone production. Administration of r-hCG was continued until the pregnancy test was performed. No exogenous progesterone was administered.

Treatment Group-II:
From cycle day two recombinant FSH (r-hFSH; Gonal-F, Merck-Serono, Hellerup, Denmark) was administered in a fixed dose of 225 IU daily. Also from cycle day two a fixed dose of 150 IU of hCG daily (r-hCG, Ovitrelle, Merck-Serono, Hellerup, Denmark) was administered—see instructions for dilution below. To prevent a premature LH rise, a fixed GnRH antagonist protocol was used commencing on stimulation day 5 in the morning. On this day, 0.25 mg GnRH antagonist (Cetrotide, Merck-Serono, Hellerup, Denmark) was given s.c. daily and continued until and including the day of ovulation induction.

When at least four follicles had reached a diameter of 12-13 mm, the daily FSH dose was discontinued while the dose of hCG was continued with 150 IU daily until ovulation induction.

When three or more follicles had reached a diameter of 17 mm ovulation was induced in all patients by the administration of a single bolus GnRH antagonist of 0.5 mg buserelin s.c. (Suprefact; Sanofi-Aventis, Hørsholm, Denmark) followed by oocyte pick up (OPU) 34 hours later. In connection with the OPU, at around 35 hours after the buserelin injection, administration of 125 IU r-hCG (r-hCG, Ovitrelle, Merck-Serono, Hellerup, Denmark) (see instructions for dilution below) daily was initiated for luteal phase support and stimulation of endogenous progesterone production. Administration of r-hCG was continued until the pregnancy test was performed. No exogenous progesterone was administered.

Treatment Group-III:
From cycle day two recombinant FSH (r-hFSH; Gonal-F, Merck-Serono, Hellerup, Denmark) was administered in a fixed dose for the first 4 days. The dose was either 150 or 225 IU per day depending on age, BMI, basal FSH, antral follicle count and the ovarian volume. After 4 days, doses were adjusted depending on the ovarian response. To prevent a premature LH rise, a fixed GnRH antagonist protocol was used commencing on stimulation day 5 in the morning. On this day, 0.25 mg GnRH antagonist (Cetrotide, Merck-Serono, Hellerup, Denmark) was given s.c. daily and continued until and including the day of ovulation induction. When three or more follicles had reached a diameter of 17 mm ovulation was induced in all patients by administration of a single bolus of 0.5 mg buserelin s.c. (Suprefact; Sanofi-Aventis, Hørsholm, Denmark) followed by oocyte pick up (OPU) 34 hours later. In connection with the OPU, at around 35 hours after the buserelin injection, administration of 300 IU r-LH (r-LH, Luveris, Merck-Serono, Hellerup, Denmark) daily was initiated for luteal phase support and stimulation of endogenous progesterone production. Administration of r-LH was continued until the pregnancy test was performed. No exogenous progesterone was administered.

Control Group (Treatment Group 4):
From cycle day two recombinant FSH (r-hFSH; Gonal-F, Merck-Serono, Hellerup, Denmark) was administered in a fixed dose for the first 4 days. The dose was either 150 or 225 IU per day depending of age, BMI, basal FSH, antral follicle count and the ovarian volume. After 4 days, doses were adjusted depending on the ovarian response. To prevent a premature LH rise, a fixed GnRH antagonist protocol was used commencing on stimulation day 5 in the morning. On this day, 0.25 mg GnRH antagonist (Cetrotide, Merck-Serono, Hellerup, Denmark) was given s.c. daily and continued until and including the day of ovulation induction. When three or more follicles had reached a diameter of 17 mm ovulation was induced in all patients by administration of a single bolus of 250 µg r-hCG (r-hCG, Ovitrelle, Merck-Serono, Hellerup, Denmark) followed by oocyte pick up (OPU) 34-35 hours later. For luteal phase support daily micronized progesterone vaginally, 90 mg per day (Crinone; Merck-Serono, Hellerup, Denmark) and estradiol 4 mg per day orally (Estrofem; Novo Nordisk, Copenhagen, Denmark) was administered, commencing the day after OPU and continued until the day of the pregnancy test.

For all for Groups:
Laboratory procedures followed the participating clinics normal procedures and were independent of the randomization. A maximum of two embryos were transferred on day 2 after retrieval. All laboratory parameters including fertilization rate and cleavage rate were monitored. A biochemical pregnancy was defined by a plasma β-hCG concentration ≥10 IU/l on day 12 after ET. Clinical pregnancy was defined as an intrauterine gestational sac with a heartbeat 3 weeks after a positive hCG-test.

Randomization
Participating patients were randomized to one of four groups on stimulation day 1.

Blood Samples and Hormone Assays
Blood samples were collected on 1) the day of ovulation induction, 2) the day of OPU 3) the day of OPU plus seven and 4) on day 14 after OPU. Serum aliquots (the sample was divided into two equal ampoules) were kept frozen at −20° C. for subsequent analysis of LH, progesterone and hCG. The hormones were measured using each participating laboratory's in house assay.

Outcome Measures
The primary outcome was the mid-luteal phase progesterone level.

Dilution of r-hCG for Stimulation
One ampoule of r-hCG (r-hCG, Ovitrelle, Merck-Serono, Hellerup, Denmark) contains 250 µg r-hCG corresponding to approximately 6,500 IU. Using a sterile 2 ml syringe with an injection needle 1 ml of liquid was drawn from a bottle with 10 ml sterile physiological saline by penetrating the rubber stopper. The content of the ampoule was subsequently injected into the remaining 9 ml saline in the bottle. The concentration of hCG did now constitute 650 IU/ml in the bottle. In order to provide the patient stimulation with 200 IU hCG 0.3 ml (or precisely 195 IU) from the bottle was redrawn and injected via a sterile 1 ml syringe.

In order to retrieve a total of 125 IU hCG, 0.19 ml from the bottle was redrawn and injected via a sterile 1 ml syringe.

In order to retrieve a total of 150 IU hCG, 0.23 ml from the bottle was redrawn and injected via a sterile 1 ml syringe.

The r-hCG for stimulation was prepared fresh every day.

Results

|  | Progesterone concentration (nmol/l) (mean ± SEM) | | | |
| --- | --- | --- | --- | --- |
|  | Treatment group 1 | Treatment group 2 | Treatment group 3 | Treatment group 4 |
| No. of patients | 11 | 6 | 4 | 11 |
| Day of ovulation induction | 5.3 ± 1.8 | 6.5 ± 3.1 | 2.7 ± 1.6 | 4.4 ± 1.9 |
| Day of oocyte pickup (OPU) | 10 ± 3 | 18 ± 11 | 37 ± 24 | 19 ± 6 |
| OPU + 7 | 351 ± 118 | 448 ± 91 | 448 ± 294 | 211 ± 52 |
| Day of hCG testing | 88 ± 33 | 168 ± 72 | 126 ± 124 | 49 ± 23 |

The data clearly demonstrate that the proposed dosing regiments of rhCG in the follicular phase and in the luteal phase and the proposed dosing regimen for stimulation progesterone production by rhLH in the luteal phase show a pronounced positive effect on the mid-luteal phase progesterone production.

Pharmacological Methods

Example 16

How to Determine the Biopotency of a Long Acting LH Compound, Such as hCG Linked to Human Albumin (SUS-hCG)

The biopotency of SUS-hCG will be determined using one of two established in vivo assays. The pharmacopaeia and authorities ask for the Van Hell bioassay. (Van Hell et al., Acta Endocrin. 47: 409 (1964) which determine the LH biological activity of LH-containing gonadotropin products measuring the seminal vesicle weight gain. The ovarian ascorbic acid depletion assay, which measures the decrease in ovarian ascorbic acid in response to exogenous LH treatments ministered to pseudo-pregnant rats (Parlow AF: Bioassay of pituitary luteinizing hormone by depletion of ovarian ascorbic acid. In Human Pituitary Gonadotropins Edited by: Albert A. Springfield; C C Thomas; 1961:300-320). This latter assay shows greater sensitivity for detecting LH bioactivity compared to the first mentioned pharmacopaeia described assay being almost one order of magnitude more sensitive.

Further the in vitro bioactivity of SUS-hCG will be determined using standard cell assays such as the MA10 Leydig cell bioassay disclosed Ascoli, Endocrinology 108: 88 (1981) or the mouse Leydig cell assay in which LH induced increase in testosterone in vitro by mouse Leydig cells is measured by standard immunological techniques such as RIA assay (Van Damme et al., Acta Endocrinol. (Copenh.) 1974:77; 655).

For all assays the bioactivity of SUS-hCG will be compared to recombinant hCG and human urine derived hCG and by using The National Institute of Biological Standards and Controls (NIBSC Herts, UK) appropriate standards.

The amount hCG protein in a given composition will be determined using standard immunological techniques such as ELISA assay or RIA assay and characterized by Western blotting and measurement of total protein content using Bradford and/or Lowry assays.

Example 17

How to Determine the Biopotency of a Long Acting Modified LH (S-LH), Such as hLH Linked to an Acylation Group, PEG or Human Albumin in Combination with FSH The biopotency of S-LH will be determined using one of two established in vivo assays. The pharmacopaeia and authorities ask for the Van Hell bioassay. (Van Hell 30 et al., Acta Endocrin. 47: 409 (1964) which determine the LH biological activity of LH-containing gonadotropin products measuring the seminal vesicle weight gain. The ovarian ascorbic acid depletion assay, which measures the decrease in ovarian ascorbic acid in response to exogenous LH treatments ministered to pseudo-pregnant rats (Parlow 32 AF: Bioassay of pituitary luteinizing hormone by depletion of ovarian ascorbic acid. In Human Pituitary Gonadotropins Edited by: Albert A. Springfield; CC Thomas; 1961:300-320). This latter assay shows greater sensitivity for detecting LH bioactivity compared to the first mentioned pharmacopaeia described assay being almost one order of magnitude more sensitive.

Further the in vitro bioactivity of S-LH will be determined using standard cell assays such as the MA10 Leydig cell bioassay disclosed Ascoli, Endocrinology 108: 88 (1981) or the mouse Leydig cell assay in which LH induced increase in testosterone in vitro by mouse Leydig cells is measured by standard immunological techniques such as RIA assay (Van Damme et al., Acta Endocrinol. (Copenh.) 1974:77; 655).

For all assays the bioactivity of S-LH will be compared to recombinant hCG, recombinant LH and human urine derived hCG and by using The National Institute of Biological Standards and Controls (NIBSC Herts, UK) appropriate standards.

The amount LH protein in a given composition will be determined using standard immunological techniques such as ELISA assay or RIA assay and characterized by Western blotting and measurement of total protein content using Bradford and/or Lowry assays.

The effect of S-LH in combination with FSH to sustain multiple follicular development and embryo development in vivo will be performed in mice as described by Yding Andersen C et al., Requirements for human chorionic gonadotropin and recombinant human luteinizing hormone for follicular development and maturation. J. Assist. Reprod. Gen., 1999, 16, 536-541, in relation to the native LH and hCG hormones. Mice will be stimulated with a fixed dose of FSH to induce multiple follicular development and in combination with varying amounts of LH/hCG activity. The mice will be induced to ovulate and be mated to a male. Later the mice will be killed and the oviduct will be recovered and flushed to determine the number of blastocysts present. The number of blastocysts will in a semi quantitative way express the potency of the LH component.

Example 18

How to Determine the Bio Potency of a Long-Acting Modified LH, Such as hLH Linked to an Acylation Group, PEG or Human Albumin in Combination with FSH The bio potency of long-acting LH may be determined using one of two established in vivo assays. The pharmacopaeia and authorities ask for the Van Hell bioassay. (Van Hell et al., Acta Endocrin. 47: 409 (1964) which determine the LH biological activity of LH containing gonadotropin products measuring the seminal vesicle weight gain. The ovarian ascorbic acid depletion assay, which measures the decrease in ovarian ascorbic acid in response to exogenous LH treatments ministered to pseudo-pregnant rats (Parlow A F: Bioassay of pituitary luteinizing hormone by depletion of ovarian ascorbic acid. In Human Pituitary Gonadotropins Edited by: Albert A. Springfield; C C Thomas; 1961:300-320). This latter assay shows greater sensitivity for detecting LH bioactivity compared to the first mentioned pharmacopaeia described assay being almost one order of magnitude more sensitive.

Further the in vitro bioactivity of long-acting LH will be determined using standard cell assays such as the MA10 Leydig cell bioassay disclosed Ascoli, Endocrinology 108: 88 (1981) or the mouse Leydig cell assay in which LH induced increase in testosterone in vitro by mouse Leydig cells is measured by standard immunological techniques such as RIA assay (Van Damme et al., Acta Endocrinol. (Copenh.) 1974:77; 655).

For all assays the bioactivity of long-acting LH will be compared to recombinant hCG, recombinant LH and human urine derived hCG and by using The National Institute of Biological Standards and Controls (NIBSC Herts, UK) appropriate standards. The amount of LH protein in a given composition will be determined using standard immunological techniques such as ELISA assay or RIA assay and characterized by Western blotting and measurement of total protein content using Bradford and/or Lowry assays.

Example 19

Combined PK/PD Study Data in Normal and Hypophysectomized Male Rats

The LH compounds are administered subcutaneously at varying dosages at time 0 hours. Blood is sampled from the rats at varying time points but at least daily for up to four week. The first blood samples from each rat are collected by sublingual bleeding using 19 G single use needles. The terminal blood sample is collected under anaesthesia. Both reference and test material are reconstituted daily in PBS-albumin buffer (0.1% albumin) and concentrations adjusted prior to administration. Administration was subcutaneously at the neck at 0.2 ml/rat.

For the study in hypophysectimised rats, male Wistar rats, 95-110 g, are purchased from Taconic-M&B and hypophysectomised using a trans auricular procedure. For the study in normal rats, male Sprague Dawley rats weighing approximately 250 g are used. Serum is prepared according to following instruction:

The blood samples are collected in SST tubes with clotting activator, Sarstedt RefNo. 41.1500.005. The samples are inverted 5× and then allowed to clot for 30 minutes at ambient temperature. The samples are centrifuged immediately after clotting for 10 minutes at 2500 G, 20° C. The serum is split into two storage vials—50 μl in each vial. 300 μl PBS/BSA is added to one of the vials.

The serum samples are frozen at 5-15° C. within 60 minutes after centrifugation.

The serum levels of the LH compounds are measured as described in example X and Z.

The serum levels of testosterone are measured as described in example Y

On the last day the rats are euthanized by an overdose of $CO_2/O_2$ anaesthesia. Seminal vesicles are removed and trimmed and blot-dried. The weight of the seminal vesicles are determined and recorded

We claim:

1. A long acting biologically active luteinizing hormone (LH) compound comprising a mammal chorionic gonadotropin (CG) or a mammal LH fused to an albumin, wherein the albumin is fused to an N-terminal or a C-terminal of the mammal CG or an N-terminal or a C-terminal of the mammal LH, wherein the LH compound is selected from Product 2 consisting of SEQ ID NO: 9 and SEQ ID NO 26, Product 3 consisting of SEQ ID NO: 1 and SEQ ID NO: 28, Product 4 consisting of SEQ ID NO: 9 and SEQ ID NO: 27, Product 5 consisting of SEQ ID NO: 1 and SEQ ID NO: 29, Product 7 consisting of SEQ ID NO: 4 and SEQ ID NO: 26, Product 8 consisting of SEQ ID NO: 1 and SEQ ID NO: 30, Product 9 consisting of SEQ ID NO: 4 and SEQ ID NO: 27, or Product 10 consisting of SEQ ID NO: 1 and SEQ ID NO: 31.

2. A composition comprising the LH compound of claim 1 for subcutaneous injection.

3. A method for assisted reproductive therapy in a female mammal in need thereof comprising administering a dosage of the LH compound of claim 1 as a single bolus injection 1-4 times: (i) during the follicular phase, the dosage effective to support follicle development, or (ii) during the luteal phase for at least 2 weeks after ovulation.

4. A method for assisted reproductive therapy in a female mammal in need thereof comprising administering a dosage of the LH compound of claim 1 as a single bolus injection 1-2 times, effective to induce ovulation.

5. A method for promoting fertility of a mammalian subject in need thereof, comprising administering a dosage of the LH compound of claim 1 as a single bolus injection 1-2 times, effective to promote fertility.

* * * * *